(12) United States Patent
Aoyagi et al.

(10) Patent No.: US 8,030,469 B2
(45) Date of Patent: Oct. 4, 2011

(54) ANTI-CD26 ANTIBODIES AND METHODS OF USE THEREOF

(75) Inventors: Teikichi Aoyagi, Saitama (JP); Peter Peizhi Luo, Lansdale, PA (US); Pingyu Zhong, Blue Bell, PA (US); Mark Hsieh, Jenkintown, PA (US); Yan Li, San Jose, CA (US); Kevin Caili Wang, Lansdale, PA (US); Chikao Morimoto, Setagaya-ku (JP)

(73) Assignee: SBI Incubation Co., Ltd., Tokyo (JP)

( * ) Notice: Subject to any disclaimer, the term of this patent is extended or adjusted under 35 U.S.C. 154(b) by 12 days.

(21) Appl. No.: 12/263,919

(22) Filed: Nov. 3, 2008

(65) Prior Publication Data
US 2009/0136523 A1    May 28, 2009

Related U.S. Application Data

(63) Continuation of application No. 11/492,498, filed on Jul. 24, 2006, now Pat. No. 7,462,698.

(60) Provisional application No. 60/701,802, filed on Jul. 22, 2005.

(51) Int. Cl.
C07H 21/02 (2006.01)
C07H 21/04 (2006.01)
A61K 39/395 (2006.01)
A61K 39/00 (2006.01)

(52) U.S. Cl. ............ 536/23.53; 536/23.1; 424/130.1; 424/133.1; 424/158.1; 424/172.1

(58) Field of Classification Search .................. None
See application file for complete search history.

(56) References Cited

U.S. PATENT DOCUMENTS

| | | |
|---|---|---|
| 4,485,045 A | 11/1984 | Regen |
| 4,544,545 A | 10/1985 | Ryan et al. |
| 4,603,112 A | 7/1986 | Paoletti et al. |
| 4,676,980 A | 6/1987 | Segal et al. |
| 4,769,330 A | 9/1988 | Paoletti et al. |
| 4,777,127 A | 10/1988 | Suni et al. |
| 4,816,567 A | 3/1989 | Cabilly et al. |
| 4,897,268 A | 1/1990 | Tice et al. |
| 5,013,556 A | 5/1991 | Woodle et al. |
| 5,017,487 A | 5/1991 | Stunnenberg et al. |
| 5,047,335 A | 9/1991 | Paulson et al. |
| 5,075,109 A | 12/1991 | Tice et al. |
| 5,120,642 A | 6/1992 | Schlossman et al. |
| 5,219,740 A | 6/1993 | Miller et al. |
| 5,278,299 A | 1/1994 | Wong et al. |
| 5,422,120 A | 6/1995 | Kim |
| 5,510,261 A | 4/1996 | Goochee et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,733,743 A | 3/1998 | Johnson et al. |
| 5,739,277 A | 4/1998 | Presta et al. |
| 5,750,373 A | 5/1998 | Garrard et al. |
| 5,814,482 A | 9/1998 | Dubensky, Jr. et al. |
| 5,866,692 A | 2/1999 | Shitara et al. |
| 5,997,867 A | 12/1999 | Waldmann et al. |
| 6,054,297 A | 4/2000 | Carter et al. |
| 6,180,377 B1 | 1/2001 | Morgan et al. |
| 6,210,671 B1 | 4/2001 | Co |
| 6,265,150 B1 | 7/2001 | Terstappen et al. |
| 6,265,551 B1 | 7/2001 | Duke-Cohan et al. |
| 6,325,989 B1 | 12/2001 | Duke-Cohan et al. |
| 6,350,861 B1 | 2/2002 | Co et al. |
| 6,376,471 B1 | 4/2002 | Lawrence, III et al. |
| 6,413,942 B1 | 7/2002 | Felgner et al. |
| 6,436,908 B1 | 8/2002 | Koch et al. |
| 6,573,096 B1 | 6/2003 | Chen et al. |
| 7,117,096 B2 | 10/2006 | Luo et al. |
| 7,198,788 B2 | 4/2007 | Dang et al. |
| 2002/0132979 A1 | 9/2002 | Chen |
| 2002/0177170 A1 | 11/2002 | Luo et al. |
| 2003/0022240 A1 | 1/2003 | Luo et al. |
| 2003/0031665 A1 | 2/2003 | Dang et al. |

(Continued)

FOREIGN PATENT DOCUMENTS

EP    0 345 242 A2    12/1989

(Continued)

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Mac Callum, Martin, and Thornton. Antibody-antigen interactions: contact analysis and binding site topography. Journal of Molecular Biology, 1996. vol. 262, pp. 732-745.*

(Continued)

Primary Examiner — Anne M. Gussow

(74) Attorney, Agent, or Firm — Wenderoth, Lind & Ponack, LLP

(57) ABSTRACT

The present invention provides novel anti-CD26 antibodies and other, related polypeptides, as well as novel polynucleotides encoding the antibodies and polypeptides. The invention also provides methods of making the antibodies and polypeptides. Compositions and cells comprising the antibodies or polypeptides are further provided. Methods of using the antibodies and/or polypeptides, such as to inhibit cell proliferation and in the treatment of conditions associated with CD26, are also provided.

2 Claims, 41 Drawing Sheets

U.S. PATENT DOCUMENTS

| | | | |
|---|---|---|---|
| 2004/0010376 A1 | 1/2004 | Luo et al. |
| 2004/0115202 A1 | 6/2004 | Chen |
| 2004/0133357 A1 | 7/2004 | Zhong et al. |
| 2005/0084928 A1 | 4/2005 | Birch et al. |
| 2005/0170454 A1 | 8/2005 | Mainwaring et al. |
| 2006/0003405 A1 | 1/2006 | Kallmeier et al. |
| 2006/0093553 A1 | 5/2006 | Dang et al. |
| 2007/0009526 A1 | 1/2007 | Benson et al. |
| 2007/0037214 A1 | 2/2007 | Luo et al. |
| 2007/0060528 A1 | 3/2007 | Christopher et al. |
| 2007/0105771 A1 | 5/2007 | Aoyagi et al. |
| 2007/0207143 A1 | 9/2007 | Dang et al. |
| 2007/0259824 A1 | 11/2007 | Morimoto et al. |

FOREIGN PATENT DOCUMENTS

| | | |
|---|---|---|
| EP | 0 345 242 A3 | 12/1989 |
| EP | 0 519 596 A1 | 12/1992 |
| EP | 0 524 968 A1 | 2/1993 |
| EP | 0 524 968 A4 | 2/1993 |
| EP | 0 524 968 B1 | 2/1993 |
| GB | 2200651 A | 8/1988 |
| WO | WO-89/01973 A2 | 3/1989 |
| WO | WO-89/01973 A3 | 3/1989 |
| WO | WO-90/07936 A1 | 7/1990 |
| WO | WO-90/11092 A1 | 10/1990 |
| WO | WO-91/00360 A1 | 1/1991 |
| WO | WO-91/02805 A2 | 3/1991 |
| WO | WO-91/07985 A1 | 6/1991 |
| WO | WO-91/14445 A1 | 10/1991 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/16102 A1 | 8/1993 |
| WO | WO-93/19191 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/09132 A1 | 4/1994 |
| WO | WO-94/12649 A2 | 6/1994 |
| WO | WO-94/12649 A3 | 6/1994 |
| WO | WO-94/23697 A1 | 10/1994 |
| WO | WO-94-28938 A1 | 12/1994 |
| WO | WO-95/00655 A1 | 1/1995 |
| WO | WO-95/07944 A1 | 3/1995 |
| WO | WO-95/11984 A2 | 5/1995 |
| WO | WO-95/11984 A3 | 5/1995 |
| WO | WO-95/13796 A1 | 5/1995 |
| WO | WO-95/30763 A2 | 11/1995 |
| WO | WO-95/30763 A3 | 11/1995 |
| WO | WO-96/17072 A2 | 6/1996 |
| WO | WO-96/17072 A3 | 6/1996 |
| WO | WO-96/38550 A1 | 12/1996 |
| WO | WO-97/42338 A1 | 11/1997 |
| WO | WO-99/58572 A1 | 11/1999 |
| WO | WO-01/27160 A1 | 4/2001 |
| WO | WO-01/74299 A2 | 10/2001 |
| WO | WO-01/74299 A3 | 10/2001 |
| WO | WO-02/084277 A1 | 10/2002 |
| WO | WO-02/092127 A1 | 11/2002 |
| WO | WO-03/035696 A2 | 5/2003 |
| WO | WO-03/035696 A3 | 5/2003 |
| WO | WO-03/054172 A2 | 7/2003 |
| WO | WO-03/054172 A3 | 7/2003 |
| WO | WO-03/064630 A2 | 8/2003 |
| WO | WO-03/064630 A3 | 8/2003 |
| WO | WO-03/099999 A2 | 12/2003 |
| WO | WO-03/099999 A3 | 12/2003 |
| WO | WO-2004/009823 A1 | 1/2004 |
| WO | WO-2004/045497 A2 | 6/2004 |
| WO | WO-2004/045497 A3 | 6/2004 |
| WO | WO-2004/058184 A2 | 7/2004 |
| WO | WO-2004/058184 A3 | 7/2004 |
| WO | WO-2005/054273 A2 | 6/2005 |
| WO | WO-2005/054273 A3 | 6/2005 |
| WO | WO-2005/063170 A2 | 7/2005 |
| WO | WO-2005/063170 A3 | 7/2005 |
| WO | WO-2007/005955 A2 | 1/2007 |
| WO | WO-2007/014169 A2 | 2/2007 |
| WO | WO-2007/014169 A3 | 2/2007 |

OTHER PUBLICATIONS

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Wu, Nie, Huse, and Watkins. Humanization of a murine monoclonal antibody by simultaneous optimization of framework and CDR residues. Journal of Molecular Biology, 1999. vol. 294, pp. 151-162.*

Adelman, J.P. et al. (1983). "In Vitro Deletional Mutagenesis for Bacterial Production of the 20,000-Dalton Form of Human Pituitary Growth Hormone," *DNA* 2(3):183-193.

Aertgeerts, K. et al. (2004). "Crystal Structure of Human Dipeptidyl Peptidase IV in Complex with a Decapeptide Reveals Details on Substrate Specificity and Tetrahedral Intermediate Formation," *Protein Sci.* 13(2):412-421.

Al-Lazikani, B. et al. (Nov. 7, 1997). "Standard Conformations for the Canonical Structures of Immunoglobulins," *J. Molec. Biol.* 273(4):927-948.

Altschul, S.F. et al. (Oct. 5, 1990). "Basic Local Alignment Search Tool," *J. Mol. Biol.* 215(3):403-410.

Altschul, S.F. et al. (1996). "Local Alignment Statistics" Chapter 27 In *Methods in Enzymology*, Doolittle, R.F. ed., Academic Press, Inc.: San Diego, CA 266:460-480.

Altschul, S.F. et al. (Sep. 1, 1997). "Gapped BLAST and PSI-BLAST: A New Generation of Protein Database Search Programs," *Nucleic Acids Res.* 25(17):3389-3402.

Aratake, Y. et al. (Sep. 1991). "Dipeptidyl Aminopeptidase IV Staining of Cytologic Preparations to Distinguish Benign from Malignant Thyroid Diseases," *Am. J. Clin. Pathol.* 96(3):306-310.

Aratake, Y. et al. (2002). "Diagnostic Utility of Galectin-3 and CD26/DPPIV as Preoperative Diagnostic Markers for Thyroid Nodules," *Diagnostic Cytopathology* 26(6):366-372.

Asada, Y. et al. (1993). "Expression of Dipeptidyl Aminopeptidase IV Activity in Human Lung Carcinoma," *Histopathology* 23:265-270.

Aytac, U. et al. (Oct. 1, 2001). "Expression of CD26 and Its Associated Dipeptidyl Peptidase IV Enzyme Activity Enhances Sensitivity to Doxorubicin-Induced Cell Cycle Arrest at the $G_2$/M Checkpoint," *Cancer Res.* 61(19):7204-7210.

Aytac, U. et al. (Feb. 10, 2003). "Effect of CD26/Dipeptidyl Peptidase IV on Jurkat Sensitivity to $G_2$/M Arrest Induced by Topoisimerase II Inhibitors," *British Journal of Cancer* 88(3):455-462.

Aytac, U. et al. (2004). "CD26/Dipeptidyl Peptidase IV: A Regulator of Immune Function and a Potential Molecular Target for Therapy," *Current Drug Targets—Immune, Endocrine & Metabolic Disorders* 4(1):11-18.

Bach, J-F. et al. (1985). "Monoclonal Antibodies as Therapeutic Tools in Medicine" Chapter 22 In *Handbook of Monoclonal Antibodies*, Ferrone, S. et al. eds., Noyes Publications: Park Ridge, NJ, pp. 419-435.

Bacigalupo, A. et al. (Aug. 1985). "Intravenous Monoclonal Antibody (BT 5/9) for the Treatment of Acute Graft-Versus-Host Disease," *Acta Haemat.* 73(3):185-186.

Barbas III, C.F. et al. (Apr. 26, 1994). "In Vitro Evolution of a Neutralizing Human Antibody to Human Immunodeficiency Virus Type 1 to Enhance Affinity and Broaden Strain Cross-Reactivity," *Proc. Natl. Acad. Sci.* USA 91(9):3809-3813.

Bauvois, B. et al. (Mar. 1999). "Constitutive Expression of CD26/ Dipeptidylpeptidase IV on Peripheral Blood B Lymphocytes of Patients with B Chronic Lumphocytic Leukaemia," *Br. J. Cancer* 79(7/8):1042-1048.

Bénard, J. et al. (Oct. 1985). "Characterization of a Human Ovarian Adenocarcinoma Line, IGROV1, in Tissue Culture and in Nude Mice," *Cancer Res.* 45:4970-4979.

Berkner, K.L. (Jul./Aug. 1988). "Development of Adenovirus Vectors for the Expression of Heterologous Genes," *Biotechniques* 6(7):616-629.

Bernengo, M.G. et al. (2001). "The Relevance of the CD4+ CD26—Subset in the Identification of Circulating Sézary Cells," *Br. J. Dermatol.* 144:125-135.

Bird, R.E. et al. (Oct. 21, 1988). "Single-Chain Antigen-Binding Proteins," *Science* 242(4877):423-426.

Boerner, P. et al. (Jul. 1, 1991). "Production of Antigen-Specific Human Monoclonal Antibodies From In Vitro-Primed Human Splenocytes," *J. Immunol.* 147(1):86-95.

Boyd, P.N. et al. (Dec. 1995). "The Effect of the Removal of Sialic Acid, Galactose and Total Carbohydrate on the Functional Activity of Campath-1H," *Mol. Immunol.* 32(17/18):1311-1318.

Brennan, M. et al. (Jul. 5, 1985). "Preparation of Bispecific Antibodies by Chemical Recombination of Monoclonal Immunoglobulin $G_1$ Fragments," *Science* 229(4708):81-83.

Brown, B.A. et al. (Jul. 1, 1987). "Tumor-Specific Genetically Engineered Murine/Human Chimeric Monoclonal Antibody," *Cancer Res.* 47(13):3577-3583.

Carbone, A. et al. (Dec. 1994). "CD26/Dipeptidyl Peptidase IV Expression in Human Lymphomas Is Restricted to CD30-Positive Anaplastic Large Cell and a Subset of T-Cell Non-Hodgkin's Lymphomas," *Hum. Pathol.* 25(12):1360-1365.

Carbone, A. et al. (Dec. 15, 1995). "The Expression of CD26 and CD40 Ligand Is Mutually Exclusive in Human T-Cell Non-Hodgkin's Lymphomas/Leukemias," *Blood* 86(12):4617-4626.

Carter, P. et al. (Feb. 1992). "High Level *Escherichia coli* Expression and Production of a Bivalent Humanized Antibody Fragment," *Bio/Technology* 10(2):163-167.

Chen, Y. et al. (Nov. 5, 1999). "Selection and Analysis of an Optimized Anti-VEGF Antibody: Crystal Structure of an Affinity-Matured Fab in Complex with Antigen," *J. Mol. Biol.* 293(4):865-881.

Chothia, C. et al. (Aug. 20, 1987). "Canonical Structures for the Hypervariable Regions of Immunoglobulins," *J. Mol. Biol.* 196(4):901-917.

Clackson, T. et al. (Aug. 15, 1991). "Making Antibody Fragments Using Phage Display Libraries," *Nature* 352(6336):624-628.

Cohen, J. (Mar. 19, 1993). "Naked DNA Points Way to Vaccines," *Science* 259:1691-1692.

Cole, S.P.C. et al. (1985). "The EBV-Hybridoma Technique and Its Application to Human Lung Cancer" In *Monoclonal Antibodies and Cancer Therapy*, Reisfeld, R. et al. eds., Alan R. Liss, Inc.: New York, NY, pp. 77-96.

Connelly, S. et al. (Feb. 1995). "In Vivo Gene Delivery and Expression of Physiological Levels of Functional Human Factor VIII in Mice," *Human Gene Therapy* 6:185-193.

Cordero, O.J. et al. (2000). "Preoperative Serum CD26 Levels: Diagnostic Efficiency and Predictive Value for Colorectal Cancer," *Br. J. Cancer* 83(9):1139-1146.

Curiel, D.T. et al. (Apr. 1992). "High-Efficiency Gene Transfer Mediated by Adenovirus Coupled to DNA-Polylysine Complexes," *Hum. Gene Ther.* 3(2):147-154.

Dang, N.H. et al. (Jun. 1, 1990). "Comitogenic Effect of Solid-Phase Immobilized Anti-1F7 on Human CD4 T Cell Activation via CD3 and CD2 Pathways," *J. Immunol.* 144(11):4092-4100.

Dang, N.H. et al. (Aug. 1, 1990). "Human CD4 Helper T Cell Activation: Functional Involvement of Two Distinct Collagen Receptors, 1F7 and VLA Integrin Family," *J. Exp. Med.* 172(2):649-652.

Dang, N.H. et al. (Dec. 15, 1990). "Cell Surface Modulation of CD26 by Anti-1F7 Monoclonal Antibody. Analysis of Surface Expression and Human T Cell Activation," *J. Immunol.* 145(12):3963-3971.

Dang, N.H. et al. (Nov. 1, 1991). "1F7 (CD26): A Marker of Thymic Maturation Involved in the Differential Regulation of the CD3 and CD2 Pathways of Human Thymocyte Activation," *J. Immunol.* 147(9):2825-2832.

Dang, N.H. (Oct. 2002). "CD26: An Expanding Role in Immune Regulation and Cancer," *Histol. Histopathol.* 17(4):1213-1226.

Darmoul, D. et al. (Mar. 5, 1992). "Dipeptidyl Peptidase IV (CD 26) Gene Expression in Enterocyte-like Colon Cancer Cell Lines HT-29 and Caco-2. Cloning of the Complete Human Coding Sequence and Changes of Dipeptidyl Peptidase IV mRNA Levels During Cell Differentiation," *J. Biol. Chem.* 267(7):4824-4833.

Daugherty, B.L. et al. (May 11, 1991). "Polymerase Chain Reaction Facilitates the Cloning, CDR-Grafting, and Rapid Expression of a Murine Monoclonal Antibody Directed Against the CD18 Component of Leukocyte Integrins," *Nucl. Acids Res.* 19(9):2471-2476.

Dayhoff, M.O. et al. (1978). "A Model of Evolutionary Change in Proteins" Chapter 22 In *Atlas of Protein Sequence and Structure*, National Biomedical Research Foundation, Washington D.C., 5(Supp.3-1978):345-352.

De Meester, I. et al. (Aug. 1999). "CD26, Let It Cut or Cut It Down," *Immunology Today* 20(8):367-375.

Dixon, J. et al. (1994). "Expression of Aminopeptidase-n (CD 13) in Normal Tissues and Malignant Neoplasms of Epithelial and Lymphoid Origin," *J. Clin. Pathol.* 47:43-47.

Dong, R-P. et al. (Feb. 15, 1996). "Characterization of Adenosine Deaminase Binding to Human CD26 on T Cells and Its Biologic Role in Immune Response," *J. Immunol.* 156(4):1349-1355.

Dong, R-P. et al. (Jan. 1998). "Correlation of the Epitopes Defined by Anti-CD26 mAbs and CD26 Function," *Molecular Immunology* 35(1):13-21.

Duke-Cohan, J.S. et al. (Oct. 1, 1993). "Targeting of an Activated T-Cell Subset Using a Bispecific Antibody-Toxin Conjugate Directed Against CD4 and CD26," *Blood* 82(7):2224-2234.

Eppstein, D.A. et al. (Jun. 1985). "Biological Activity of Liposome-Encapsulated Murine Interferon γ is Mediated by a Cell Membrane Receptor," *Proc. Natl. Acad. Sci.* USA 82(11):3688-3692.

Falcioni, F. et al. (Oct. 1996). "Influence of CD26 and Integrins on the Antigen Sensitivity of Human-Memory T-Cells," *Human Immunology* 50(2):79-90.

Fan, H. et al. (2003). "Dipeptidyl Peptidase IV/CD26 in T Cell Activation, Cytokine Secretion and Immunoglobulin Production," *Dipeptidyl Aminopeptidases in Health and Disease*, Hildebrandt, H. ed et_al., Kluwer Academic/Plenum Publishers: New York, NY, pp. 165-174.

Findeis, M.A. et al. (May 1993). "Targeted Delivery of DNA for Gene Therapy Via Receptors," *Trends Biotechnol.* 11:202-205.

Fisher-Hoch, S.P. et al. (Jan. 1989). "Protection of Rhesus Monkeys from Fatal Lassa Fever by Vaccination with a Recombinant Vaccinia Virus Containing the Lassa Virus Glycoprotein Gene," *Proc. Natl. Acad. Sci.* USA 86(1):317-321.

Fleischer, B. (1987). "Activation Pathways for Human T-Lymphocytes Defined by Monoclonal Antibodies against T-Cell Surface Structures," *Arzneimittelforschung* 37(5):585-586.

Fleischer, B. (Mar. 1, 1987). "A Novel Pathway of Human T Cell Activation Via a 103 kD T Cell Activation Antigen," *J. Immunol.* 138(5):1346-1350.

Fleischer, B. (Apr. 1994). "CD26: A Surface Protease Involved in T-Cell Activation," *Immunol.* Today 15(4):180-184.

Flexner, C. et al. (Feb. 1990). "Attenuation and Immunogenicity in Primates of Vaccinia Virus Recombinants Expressing Human Interleukin-2," *Vaccine* 8(1):17-21.

Fox, D.A. et al. (Sep. 1984). "$Ta_1$, A Novel 105 KD Human T Cell Activation Antigen Defined by a Monoclonal Antibody," *J. Immunol.* 133(3):1250-1256.

Ghersi, G. et al. (Aug. 9, 2002). "Regulation of Fibroblast Migration on Collagenous Matrix by a Cell Surface Peptidase Complex," *J. Biological Chemistry* 277(32):29231-29241.

Gines, S. et al. (Jan. 15, 2002). "Regulation of Epithelial and Lymphocyte Cell Adhesion by Adenosine Deaminase-CD26 Interaction," *Biochem J.* 361(Pt. 2):203-209.

Griffiths, A.D. et al. (Feb. 1993). "Human Anti-Self Antibodies with High Specificity From Phage Display Libraries," *EMBO J.* 12(2):725-734.

Gonzalez-Gronow, M. et al. (May 14, 2004). "Cell Surface Adenosine Deaminase Binds and Stimulates Plasminogen Activation on 1-LN Human Prostate Cancer Cells," *J Biol Chem* 279(20):20993-20998.

Guzman, R.J. et al. (Dec. 1993). "Efficient Gene Transfer Into Myocardium by Direct Injection of Adenovirus Vectors," *Cir. Res.* 73(6):1202-1207.

Guzman, R.J. et al. (Dec. 1993). "Efficient and Selective Adenovirus-Mediated Gene Transfer Into Vascular Neointima," *Circulation* 88(6):2838-2848.

Hansen, M.B. et al. (1989). "Re-Examination and Further Development of a Precise and Rapid Dye Method for Measuring Cell Growth/Cell Kill," *J. Immunol. Methods* 119(2):203-210.

Hawkins, R.E. et al. (1992). "Selection of Phage Antibodies by Binding Affinity: Mimicking Affinity Maturation," *J. Mol. Biol.* 226:889-896.

Hegen, M. et al. (Apr. 15, 1990). "The T Cell Triggering Molecule Tp103 Is Associated with Dipeptidyl Aminopeptidase IV Activity," *J. Immunol.* 144(8):2908-2914.

Hegen, M. et al. (1997). "Structure of CD26 (Dipeptidyl Peptidase IV) and Function in Human T Cell Activation," Chapter 15, in *Cellular Peptidases in Immune Functions and Diseases*, Ansorge, S. ed., Plenum Press, New York, NY, pp. 109-116.

Hegen, M. et al. (Feb. 1997). "Cross-Linking of CD26 by Antibody Induces Tyrosine Phosphorylation and Activation of Mitogen-Activated Protein Kinase," *Immunology* 90(2):257-264.

Hein, J. (1990). "Unified Approach to Alignment and Phylogenies" Chapter 39 in *Methods in Enzymology*, Doolittle, R.F. ed., Academic Press, Inc.: San Diego, CA, 183:626-645.

Higgins, D.G. et al. (Apr. 1989). "Fast and Sensitive Multiple Sequence Alignments on a Microcomputer," *CABIOS* 5(2):151-153.

Ho, L. et al. (Jul. 2001). "In Vitro and in Vivo Antitumor Effect of the Anti-CD26 Monoclonal Antibody 1F7 on Human CD30+ Anaplastic Large Cell T-Cell Lymphoma Karpas 299," *Clinical Cancer Research* 7(7):2031-2040.

Holliger, P. et al. (Jul. 15, 1993). "'Diabodies': Small Bivalent and Bispecific Antibody Fragments," *Proc. Natl. Acad. Sci.* USA 90(14):6444-6448.

Hoogenboom, H. R. et al. (Sep. 20, 1992). "By-Passing Immunisation: Human Antibodies From Synthetic Repertoires of Germline $V_H$ Gene Segments Rearranged in Vitro," *J. Mol. Biol.* 227(2):381-388.

Hsu, T-A. et al. (Apr. 4, 1997). "Differential N-Glycan Patterns of Secreted and Intracellular IgG Produced in *Trichoplusia ni* Cells," *J. Biol. Chem.* 272(14):9062-9070.

Hwang, K.J. et al. (Jul. 1980). "Hepatic Uptake and Degradation of Unilamellar Sphingomyelin/Cholesterol Liposomes: A Kinetic Study," *Proc. Natl. Acad. Sci.* USA 77(7):4030-4034.

Ikushima, H. et al. (Jul. 18, 2000). "Internalization of CD26 by Mannose 6-Phosphate/Insulin-Like Growth Factor II Receptor Contributes to T Cell Activation," *Proc. Natl. Acad. Sci.* USA 97(15):8439-8444.

Iliades, P. et al. (1997). "Triabodies: Single Chain Fv Fragments Without a Linker Form Trivalent Trimers," *FEBS Letters* 409:437-441.

Inamoto, T. et al. (Jun. 1, 2006). "Anti-CD26 Monoclonal Antibody-Mediated $G_1$-S Arrest of Human Renal Clear Cell Carcinoma Caki-2 is Associated with Retinoblastoma Substrate Dephosphorylation, Cyclin-Dependent Kinase 2 Reduction, $p27^{kip1}$ Enhancement, and Disruption of Binding to the Extracellular Matrix," *Clin. Cancer Res.* 12(11):3470-3477.

Inamoto, T. et al. (Jul. 15, 2007). "Humanized Anti-CD26 Monoclonal Antibody as a Treatment for Malignant Mesothelioma Tumors," *Clin. Cancer Res.* 13(14):4191-4200.

International Search Report mailed Mar. 16, 2007, for PCT Patent Application No. PCT/US2006/028702, filed Jul. 24, 2006, six pages.

Jackson, J.R. et al. (Apr. 1, 1995). "In Vitro Antibody Maturation: Improvement of a High Affinity, Neutralizing Antibody Against IL-1β," *J. Immunol.* 154(7):3310-3319.

Jefferis, R. et al. (1997). "Glycosylation of Antibody Molecules: Structural and Functional Significance," *Chem. Immunol.* 65:111-128.

Johnson, J.P. et al. (1985). "Monoclonal Antibodies and Melanomas" Chapter 18 in *Handbook of Monoclonal Antibodies: Applications in Biology and Medicine*, Ferrone, S. et al., eds., Noyes Publications: Park Ridge: NJ, pp. 347-359.

Johnson, K.S. et al. (1993). "Human Antibody Engineering," *Current Opinion in Structural Biology* 3:564-571.

Jolly, D. (1994). "Viral Vector Systems for Gene Therapy," *Cancer Gene Therapy* 1(1):51-64.

Jones, P.T. et al. (May 29, 1986). "Replacing the Complementarity-Determining Regions in a Human Antibody with Those from a Mouse," *Nature* 321:522-525.

Jones, D. et al. (Jun. 2001). "Absence of CD26 Expression Is a Useful Marker for Diagnosis of T-Cell Lymphoma in Peripheral Blood," *Am. J. Clin. Pathol.* 115(6):885-892.

Kabat, E.A. et al. (1987). *Sequences of Proteins of Immunological Interest*, Fourth Edition, National Institutes of Health: Bethesda, MD pp. iii-v, (Table of Contents Only.).

Kabat, E.A. et al. (1991). *Sequences of Proteins of Immunological Interest*, Fifth Edition, National Institutes of Health: Bethesda, MD pp. iii-xi (Table of Contents Only.).

Kabawat, S.E. et al. (1985). "Monoclonal Antibodies in Diagnostic Pathology" Chapter 16 in *Handbook of Monoclonal Antibodies: Applications in Biology and Medicine*, Ferrone, S. et al eds., Noyes Publications: Park Ridge, NJ, pp. 293-328.

Kajiyama, H. et al. (May 1, 2003). "Dipeptidyl Peptidase IV Overexpression Induces Up-Regulation of Ecadherin and Tissue Inhibitors of matrix Metalloproteinases, Resulting in Decreased Invasive Potential in Ovarian Carcinoma Cells," *Cancer Res* 63:2278-2283.

Kameoka, J. et al. (Jul. 23, 1993). "Direct Association of Adenosine Deaminase with a T Cell Activation Antigen, CD26," *Science* 261(5120):466-469.

Kameoka, J. et al. (Feb. 15, 1995). "Differential CD26-Mediated Activation of the CD3 and CD2 Pathways after CD6-Depleted Allogeneic Bone Marrow Transplantation," *Blood* 85(4):1132-1137.

Kaplitt, M.G. et al. (Oct. 1994). "Long-Term Gene Expression and Phenotypic Correction Using Adeno-Associated Virus Vectors in the Mammalian Brain," *Nature Genetics* 8(2):148-153.

Karlin, S. et al. (Mar. 1990). "Methods for Assessing the Statistical Significance of Molecular Sequence Features by Using General Scoring Schemes," *Proc. Natl. Acad. Sci.* USA 87(6):2264-2268.

Karlin, S. et al. (Jun. 15, 1993). "Applications and Statistics for Multiple High-Scoring Segments in Molecular Sequences," *Proc. Natl. Acad. Sci.* USA 90(12):5873-5877.

Kass-Eisler, A. et al. (Dec. 15, 1993). "Quantitative Determination of Adenovirus-Mediated Gene Delivery to Rat Cardiac Myocytes In Vitro and In Vivo," *Proc. Natl. Acad. Sci.* USA 90(24):11498-11502.

Kimura, O. et al. (Jul. 1994). "Retroviral Delivery of DNA into the Livers of Transgenic Mice Bearing Premalignant and Malignant Hepatocellular Carcinomas," *Human Gene Therapy* 5(7):845-852.

Klobušická, M. et al. (1999). "CD26 and DPP IV Expression in T Acute Lymphoblastic Leukemia Cells: Immunocytochemistry and Enzyme Cytochemistry," *Gen. Physiol. Biophys*.1 18(Supp. 1): 34-37.

Klobušická, M. et al. (1999). "Expression of CD26 and DPP IV in T-Acute Lymphoblastic Leukemia: Comparison of Immunocytochemistry with Enzyme Cytochemistry," *Neoplasma* 46(5):299-303.

Köhler, G. et al. (Aug. 7, 1975). "Continuous Cultures of Fused Cells Secreting Antibody of Predefined Specificity," *Nature* 256(5517):495-497.

Kolls, J. et al. (Jan. 4, 1994). "Prolonged and Effective Blockade of Tumor Necrosis Factor Activity Through Adenovirus-Mediated Gene Transfer," *Proc. Natl. Acad. Sci.* USA 91(1):215-219.

Kortt, A.A. et al. (Apr. 1997). "Single-Chain Fv Fragments of Anti-Neuraminidase Antibody NC10 Containing Five- and Ten-Residue Linkers Form Dimers and With Zero-Residue Linker a Trimer," *Protein Engineering* 10(4):423-433.

Lambeir, A-M. et al. (2003). "Dipeptidyl-Peptidase IV from Bench to Bedside: An Update on Structural Properties, Functions, and Clinical Aspects of the Enzyme DPP IV," *Crit. Rev. Clin. Lab. Sci.* 40(3):209-294.

Lin, Y.S. et al. (1999). "Preclinical Pharmacokinetics, Interspecies Scaling, and Tissue Distribution of a Humanized Monoclonal Antibody against Vascular Endothelial Growth Vascular Endothelial Growth Factor," *J. Pharmacol. Exp. Ther.* 288(1):371-378.

Lobuglio, A.F. et al. (Jun. 1989). "Mouse/Human Chimeric Monoclonal Antibody in Man: Kinetics and Immune Response," *Proc. Natl. Acad. Sci.* USA 86(11):4220-4224.

Löfås, S. et al. (1990). "A Novel Hydrogel Matrix on Gold Surfaces in Surface Plasmon Resonance Sensors for Fast and Efficient Covalent Immobilization of Ligands," *J. Chem. Soc. Chem. Commun.* 21:1526-1528.

Luo, G.X. et al. (Apr. 1, 2003). "Humanization of an Anti-ICAM-1 Antibody with Over 50-Fold Affinity and Functional Improvement," *J. Immunol. Methods* 275(1-2):31-40. (Luo humanized antibody pubmed listing.).

Marguet, D. et al. (Feb. 5, 1992). "cDNA Cloning for Mouse Thymocyte-activating Molecule. A Multifunctional Ecto-Dipeptidyl Peptidase IV (CD26) Included in a Subgroup of Serine Proteases," *J. Biol. Chem.* 267(4):2200-2208.

Marguet, D. et al. (Jun. 6, 2000). "Enhanced Insulin Secretion and Improved Glucose Tolerance in Mice Lacking CD26," *Proc. Natl. Acad. Sci. .U.S.A.* 97(12):6874-6879.

Marks, J.D. et al. (1991). "By-Passing Immunization: Human Antibodies From V-Gene Libraries Displayed on Phage," *J. Mol. Biol.* 222:581-597.

Marks, J.D. et al. (Jul. 1992). "By-Passing Immunization: Building High Affinity Human Antibodies by Chain Shuffling," *Bio/Technol.* 10(7):779-783.

Martin, F.J. et al. (Jan. 10, 1982). "Irreversible Coupling of Immunoglobulin Fragments to Preformed Vesicles: An Improved Method for Liposome Targeting," *J. Biol. Chem.* 257(1):286-288.

McCafferty, J. et al. (Dec. 6, 1990). "Phage Antibodies: Filamentous Phage Displaying Antibody Variable Domains," *Nature* 348(6301):552-554.

Milstein, C. et al. (Oct. 6, 1983). "Hybrid Hydridomas and Their Use in Immunohistochemistry," *Nature* 305:537-540.

Mizokami, A. et al. (Dec. 1996). "Increased Population of High Fluorescence 1F7 (CD26) Antigen on T Cells in Synovial Fluid of Patients with Rheumatoid Arthritis," *J. Rheumatol.* 23(12):2022-2026.

Moehrle, M.C. et al. (Jun. 1995). "Aminopeptidase M and Dipeptidyl Peptidase IV Activity in Epithelial Skin Tumors: a Histochemical Study," *J. Cutan. Pathol.* 22(3):241-247.

Morikawa, K. et al. (Dec. 1, 1988). "Influence of Organ Environment on the Growth, Selection, and Metastasis of Human Colon Carcinoma Cells in Nude Mice," *Cancer Res.* 48(23):6863-6871.

Morimoto, C. et al. (Dec. 1, 1989). "1F7, A Novel Cell Surface Molecule, Involved in Helper Function of CD4 Cells," *J. Immunol.* 143(11):3430-3439.

Morimoto, C. et al. (Jan./Feb. 1994). "CD26: A Key Costimulary Molecule on CD4 Memory T Cells," *Immunologist* 2(1):4-7.

Morimoto, C. et al. (Oct. 11, 1994). "Role of CD26/Dipeptidyl Peptidase IV in Human Immunodeficiency Virus Type 1 Infection and Apoptosis," *Proc. Natl. Acad. Sci.* USA 91(21):9960-9964.

Morimoto, C. et al. (1998). "The Structure and Function of CD26 in the T-Cell Immune Response," *Immunol. Rev.* 161:55-70.

Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *J. Biochem. Biophys. Methods* 24:107-117.

Morrison, M.E. et al. (Apr. 1, 1993). "A Marker for Neoplastic Progression of Human Melanocytes Is a Cell Surface Ectopeptidase," *J. Exp. Med.* 177(4):1135-1143.

Moss, B. et al. (1989). "Vaccinia Virus Expression Vectors," *Ann. NY Acad. Sci.* 569:86-103.

Muller, Y.A. et al. (Sep. 15, 1998). "VEGF and the Fab Fragment of a Humanized Neutralizing Antibody: Crystal Structure of the Complex at 2.4 Å Resolution and Mutational Analysis of the Interface," *Structure* 6(9):1153-1167.

Myers, E.W. et al. (1988). "Optimal Alignments in Linear Space," *CABIOS* 4(1):11-17.

Nori, M. et al. (Nov. 2003). "Ebastine Inhibits T Cell Migration, Production of Th2-type Cytokines and Proinflammatory Cytokines," *Clin. Exp. Allergy* 33(11):1544-1554.

Ogata, S. et al. (Feb. 25, 1989). "Primary Structure of Rat Liver Dipeptidyl Peptidase IV Deduced from its cDNA and Identification of the $NH_2$-Terminal Signal Sequence as the Membrane-anchoring Domain," *J. Biol. Chem.* 264(6):3596-3601.

Ohnuma, K. et al. (Dec. 15, 2001). "Soluble CD26/Dipeptidyl Peptidase IV Induces T Cell Proliferation Through CD86 Up-Regulation on APCs," *J. Immunol.* 167(12):6745-6755.

Ohnuma, K. et al. (Nov. 2002). "G1/S Cell Cycle Arrest Provoked in Human T Cells by Antibody to CD26," *Immunology* 107(3):325-333.

Ohnuma, K. et al. (2006). "T-Cell Activation via CD26 and Caveolin-1 in Rheumatoid Synovium," *Mod. Rheumatol.* 16(1):3-13.

Philip, R. et al. (Apr. 1994). "Efficient and Sustained Gene Expression in Primary T Lymphocytes and Primary and Cultured Tumor Cells Mediated by Adeno-Associated Virus Plasmid DNA Complexed to Cationic Liposomes," *Mol. Cell Biol.* 14(4):2411-2418.

Poljak, R.J. (Dec. 15, 1994). "Production and Structure of Diabodies," *Structure* 2(12):1121-1123.

Riechmann, L. et al. (Mar. 24, 1988). "Reshaping Human Antibodies for Therapy," *Nature* 332(6162):323-327.

Robinson, D.F. (Oct. 1971). "Comparison of Labeled Trees with Valency Three," *J. Comb. Theor.* 11(2):105-119.

Rolland, A.P. (1998). "From Genes to Gene Medicines: Recent Advances in Nonviral Gene Delivery," *Crit. Rev. Therap. Drug Carrier Systems* 15(2):143-198.

Rosenfeld, M.A. et al. (Apr. 19, 1991). "Adenovirus-Mediated Transfer of a Recombinant α1-Antitrypsin Gene to the Lung Epithelium in Vivo," *Science* 252(5004):431-434.

Rudikoff, S. et al. (Mar. 1982). "Single Amino Acid Substitution Altering Antigen-Binding Specificity," *Proc. Natl. Acad. Sci.* USA 79(6):1979-1983.

Ruiz, P. et al. (Feb. 15, 1998). "CD26 Expression and Dipeptidyl Peptidase IV Activity in an Aggressive Hepatosplenic T-Cell Lymphoma," *Cytometry* 34(1):30-35.

Saitou, N. et al. (Jul. 1987). "The Neighbor-Joining Method: A New Method for Reconstructing Phylogenetic Trees," *Mol. Biol. Evol.* 4(4):406-425.

Sakamoto, J. et al. (1993). "Distribution of Adenosine Deaminase Binding Protein in Normal and Malignant Tissues of the Gastrointestinal Tract Studied by Monoclonal Antibodies," *J. Surg. Oncol.* 52:124-134.

Sato, K. et al. (2003). "CD26: A Novel Treatment Target for T-Cell Lymphoid Malignancies? (Review)," *Int. J. Oncol.* 22:481-497.

Sato, T. et al. (Aug. 1, 2005). "CD26 Regulates p38 Mitogen-Activated Protein Kinase-Dependent Phosphorylation of Integrin β1, Adhesion to Extracellular Matrix, and Tumorigenicity of T-Anaplastic Large Cell Lymphoma Karpas 299," *Cancer. Res.* 65(15):6950-6956.

Schier, R. et al. (1996). "Identification of Functional and Structural Amino-Acid Residues by Parsimonious Mutagenesis," *Gene* 169:147-155.

Schultz, D.R. (1985). "Monoclonal Antibodies and Detection of Malignancies" Chapter 17 in *Handbook of Monoclonal Antibodies: Applications in Biology and Medicine*, Ferrone, S. et al. eds., Noyes Publications: Park Ridge: NJ, pp. 329-346.

Sedo, A. et al. (1991). "Dipeptidyl Peptidase IV in the Human Lung and Spinocellular Lung Cancer," *Physiol. Res.* 40(3):359-362.

Sevarino, K.A. et al. (Jan. 15, 1988). "Biosynthesis of Thyrotropin-Releasing Hormone by a Rat Medullary Thyroid Carcinoma Cell Line," *J. Biol. Chem.* 263(2):620-623.

Shaw, D.R. et al. (Jun. 15, 1987). "Characterization of a Mouse/Human Chimeric Monoclonal Antibody (17-1A) to a Colon Cancer Tumor-Associated Antigen," *J. Immunol.* 138(12):4534-4538.

Sheets, M.D. et al. (May 26, 1998). "Efficient Construction of a Large Nonimmune Phage Antibody Library: The Production of High-Affinity Human Single-Chain Antibodies to Protein Antigens," *Proc. Natl. Acad. Sci.* USA 95(11):6157-6162.

Smith, T.W. et al. (1977). "Cardiac Glycoside-Specific Antibodies in the Treatment of Digitalis Intoxication," In *Antibodies in Human Diagnosis and Therapy*, Haber, E. et al. eds., Raven Press: New York, NY, pp. 365-389.

Stecca, B.A. et al. (Aug. 1997). "Aberrant Dipeptidyl Peptidase IV (DPP IV/CD26) Expression in Human Hepatocellular Carcinoma," *J. Hepatol.* 27(2):337-345.

Suresh, M.R. et al. (1986). "Bispecific Monoclonal Antibodies from Hybrid Hybridomas," Chapter 16 In *Methods in Enzymology*, Langone, J.J. et al. eds., Academic Press, Inc.:Orlando, FL, 121(Pt. 1):210-228.

Tanaka, T. et al. (May 15, 1993). "The Costimulatory Activity of the CD26 Antigen Requires Dipeptidyl Peptidase IV Enzymatic Activity," *Proc. Natl. Acad. Sci.* USA 90(10):4586-4590.

Tanaka, T. et al. (1995). "CD26 (Dipeptidyl Peptidase IV/DPP IV) as a Novel Molecular Marker for Differentiated Thyroid Carcinoma," *Int. J. Cancer* 64:326-331.

Thompson, M.A. et al. (Mar. 2007). "CD26/Dipeptidyl Peptidase IV as a Novel Therapeutic Target for Cancer and Immune Disorders," *Mini Rev. Med. Chem.* 7(3):253-273.

Torimoto, Y. et al. (Feb. 1992). "Biochemical Characterization of CD26 (Dipeptidyl Peptidase IV): Functional Comparison of Distinct Epitopes Recognized by Various Anti-CD26 Monoclonal Antibodies," *Mol. Immunol.* 29(2):183-192.

Ulmer, A.J. et al. (1990). "CD26 Antigen is a Surface Dipeptidyl Peptidase IV (DPPIV) as Characterized by Monoclonal Antibodies Clone TII-19-4-7 and 4EL1C7," *Scand. J. Immunol.* 31(4):429-435.

Ulmer, J.B. et al. (Mar. 19, 1993). "Heterologous Protection Against Influenza by Injection of DNA Encoding a Viral Protein," *Science* 259:1745-1749.

Umaña, P. et al. (Feb. 1999). "Engineered Glycoforms of an Antineuroblastoma IgG1 with Optimized Antibody-Dependent Cellular Cytotoxic Activity," *Nature Biotech.* 17(2):176-180.

Vaughan, T.J. et al. (Mar. 1996). "Human Antibodies with Sub-Nanomolar Affinities Isolated from a Large Non-Immunized Phage Display Library," *Nature Biotechnology* 14:309-314.

Verhoeyen, M. et al. (Mar. 25, 1988). "Reshaping Human Antibodies: Grafting an Antilysozyme Activity," *Science* 239:1534-1536.

Waterhouse, P. et al. (May 11, 1993). "Combinatorial Infection and In Vivo Recombination: A Strategy for Making Large Phage Antibody Repertoires," *Nucl. Acids Res.* 21(9):2265-2266.

Wesley, U.V. et al. (Aug. 2, 1999). "A Role for Dipeptidyl Peptidase IV in Suppressing the Malignant Phenotype of Melanocytic Cells," *J. Exp. Med.* 190(3):311-322.

Wilbur, W.J. et al. (Feb. 1983). "Rapid Similarity Searches of Nucleic Acid and Protein Data Banks," *Proc. Natl. Acad. Sci.* USA 80(3):726-730.

Winter, G. et al. (Jan. 24, 1991). "Man-Made Antibodies," *Nature* 349(6307):293-299.

Winter, G. et al. (1994). "Making Antibodies by Phage Display Technology," *Annu. Rev. Immunol.* 12:433-455.

Wittwer, A.J. et al. (May 1, 1990). "Glycosylation at Asn-184 Inhibits the Conversion of Single-Chain to Two-Chain Tissue-Type Plasminogen Activator by Plasmin," *Biochem.* 29(17):4175-4180.

Woffendin, C. et al. (Nov. 22, 1994). "Nonviral and Viral Delivery of a Human Immunodeficiency Virus Protective Gene into Primary Human T Cells," *Proc. Natl. Acad. Sci.* USA 91(24):11581-11585.

Wolff, J.A. ed. (1994). *Gene Therapeutics: Methods and Applications of Direct Gene Transfer*, Birkhäuser: Boston, MA, pp. vii-ix, (Table of Contents Only.).

Wright, A. et al. (Jan. 1997). "Effect of Glycosylation on Antibody Function: Implications for Genetic Engineering," *TibTECH* 15:26-32.

Written Opinion mailed Mar. 16, 2007, for PCT Patent Application No. PCT/US2006/028702, filed Jul. 24, 2006, 10 pages.

Wu, C.H. et al. (Oct. 15, 1989). "Targeting Genes: Delivery and Persistent Expression of a Foreign Gene Driven by Mammalian Regulatory Elements in Vivo," *J. Biol. Chem.* 264(29):16985-16987.

Wu, G.Y. et al. (Aug. 5, 1991). "Receptor-Mediated Gene Delivery in Vivo: Partial Correction of Genetic Analbuminemia in Nagase Rats," *J. Biol. Chem.* 266(22):14338-14342.

Wu, G.Y. et al. (Apr. 15, 1994). "Incorporation of Adenovirus into a Ligand-Based DNA Carrier System Results in Retention of Original Receptor Specificity and Enhances Targeted Gene Expression," *J. Biol. Chem.* 269(15):11542-11546.

Wyss, D.F. et al. (Aug. 1996). "The Structural Role of Sugars in Glycoproteins," *Current Opin. Biotech* 7(4):409-416.

Y's Therapeutics Co., Ltd. (Feb. 23, 2004). "Y's Therapeutics Raises 2.4 Billion Yen (US $22 Million) in Series B Financing—One of the Largest Private Equity Financings in Japanese Biotech Industry," Press Release from Y's Therapeutics, Tokyo, Japan, located at <http://www.ysthera.com/news/040223_p.html>, last visited May 28, 2007, two pages.

Y's Therapeutics Co., Ltd. (Mar. 2, 2004). "Y's Therapeutics and Abmaxis Announce Antibody Collaboration—Therapeutics Focus on Tumors," Press Release from Y's Therapeutics, Mountain View, CA, and Tokyo, Japan, located at <http://www.ysthera.com/news/040302_p.html>, last visited May 28, 2007, two pages.

Y's Therapeutics Co., Ltd. (Sep. 27, 2004). "Kissei Pharmaceutical Options Antibody from Y's Therapeutics," Press Release from Y's Therapeutics, Tokyo, Japan, located at <http://www.ysthera.com/news/040927_p.html>, last visited May 28, 2007, two pages.

Yamochi, T. et al. (Mar. 1, 2005). "Regulation of p38 Phosphorylation and Topoisomerase IIα Expression in the B-Cell Lymphoma Line Jiyoye by CD26/Dipeptidyl Peptidase IV Is Associated with Enhanced In Vitro and In Vivo Sensitivity to Doxorubicin," *Cancer Research* 65(5): 1973-1983.

Yelton, D.E. et al. (Aug. 15, 1995). "Affinity Maturation of the BR96 Anti-Carcinoma Antibody by Codon-Based Mutagenesis," *The Journal of Immunology* 155(4):1994-2004.

Yeung, P. et al. (2007). "The In Vivo Anti-Tumor Activity of YS110: A Humanized Anti-CD26 Monoclonal Antibody," Poster 668, Y's Therapeutics, Inc., Burlingame, California, one page.

Zenke, M. et al. (May 1990). "Receptor-Mediated Endocytosis of Transferrin-Polycation Conjugates: An Efficient Way to Introduce DNA Into Hematopoietic Cells," *Proc. Natl. Acad. Sci.* USA 87(10):3655-3659.

Zola, H. (1987). "Using Monoclonal Antibodies: Soluble Antigens" Chapter 6 in *Monocolonal Antibodies: A Manual of Techniques*, CRC Press, Inc.: Boca Raton, FL, pp. 147-158.

* cited by examiner

Figure 1

VH
Murine CM03    QVKLQESGPGLVQPSQTLSITCTVSGFSLTTYGVHWVRQSPGKGLEWLGVIWGGGRTDYDAAFIS
RLSISKDNSKSQVFFKMNSLQANDTAIYYCVRNRHDWFDYWGQGTTVTVSS

VL
Murine CM03    DIQMTQSPSSLSASLGDRVTITCSASQGIRNSLNWYQQKPDGAVKLLIYYSSNLHSGVPSRFSGS
GSGTDFSLTISNLEPEDIATYYCQQSIKLPFTFGSGTKLEIK

Figure 2

```
X376VL
GACATCCTGATGACCCAGTCTCCATCTTCTCTGTCTGCTTCTCCTGGCGACCGTGTTACCATCTCCTGTCGTGCCTCTCAGGACATCCGTAACAACCTGAACTGGTATCAGCAGAAACCAGGTCAGGCCCCA
CGTCTGCTGATCTACTACTCTTCTAATTTGCACTCCGGTGTGCCAGACCGTGTTCTCCGGATCTGGTTCTGGCACCGACTTCACCCTGACCATCTCTAGACTGGAACCTGAAGACTTTGCCGCCTACTACTGC
CAGCAGTCTATCAAGCTGCCACTTACCTTCGGTTCTGGTACCAAAGTGGAGATCAAA
X377VL
GAAATCGAGCTGACCCAGTCTCCATCTTCTCTGTCTGTTTCTCTTGGCGACCGTGTTACCATCTCCTGTAGTGCCTCTCAGGACATGGTTACAACAACCTGAACTGGTATCAGCAGAAACAGGTCAGGCCCCA
CGTCTGCTGATCTACTACTCTTCTAATTTGCAGACCGGTGTGCCAGCCCGTGTTCTCCGGATCTGGTTCTGGCACCGACTTCACCCTGACCATCTCTAGACTGGAACCTGAAGACTTGCCGCCTACTACTGC
CAGCAGTCTATCAAGCTGCCATTTACCTTCGGTTCTGGTACCAAAGTGGAGATCAAA
X378VL
GACATCGAGATGACCCAGTCTCCATCTTCTCTGTCTGCTTCTCTGGGCGAACGTGTTACCATCCGTGAACAGCCTGAACTGGTATCAGCAGAAACCAGGTCAGGCCCCA
CGTCTGCTGATCTACTACTCTTCTAATTTGCAGACCGGTGTGCCATCCCGTGTTCTCCGGATCTGGTTCTGGCACCGACTTCACCCTGACCATCTCTAGACTGGAACCTGCAAGCTGAAGACTTTGCCACCTACTACTGC
CAGCAGTCTAACAAGCTGCCATTTACCTTCGGTTCTGGTACCAAAGTGGAGATCAAA
X379VL
GACATCCTGACCCAGTCTCCATCTTCTCTGTCTGCTACCCAGTCTCCATCATCCTGTCGTGCCTCTCAGGCGAACGTGCTACCACCATCACCTGTCGTGCCTCTCAGGGACATCGTCGTGCCTCTCAGGGCAACGTGTTACCATCCGTAACAACCTGAACTGGTATCAGCAGAAACAGGTCAGGCCCCA
CGTCTGCTGATCTACTACTCTTCTAATTTGCAGTCCGGTGTCCGTTTCTCCGGATCTGGTTCTGGCACCGACTTCACCCTGACCATCTCTAGACTGGAACCTGCAACCTGAAGACTTGCCGCCTACTACTGC
CAGCAGTCTATCAAGCTGCCATTTACCTTCGGTTCTGGTACCAAAGTGGAGATCAAA
X380VL
GAAATCGAGATGACCCAGTCTCCATCTTCTCTGTCTGTTTCTGCTGGCGAACGTGCTACCATCTCCTGTAGTGCCTCTCAGGACATCCGTAACAGCCTGAACTGGTATCAGCAGAAACCAGGTCAGGCCCCA
CGTCTGCTGATCTACTACTCTTCTAATTTGCACACCGGTGTGCCAGCCCGTGTTCTCCGGATCTGGTTCTGGCACCGACTTCACCCTGACCATCTCTAGACTGGAACCTGGAACCTGAAGACGTTGCCATCTACTACTGC
CAGCAGTCTAACAAGCTGCCACTTACCTTCGGTTCTGGTACCAAAGTGGAGATCAAA
X381VL
GAAATCGAGCTGACCCAGTCTCCATCTTCTCTGTCTGTTTCTGCTGGCGACCGTGTTACCATCTCCTGTAGTGCCTCTCAGGGCATCCGTAACAGCCTGAACTGGTATCAGCAGAAACAGGTCAGGCCCCA
CGTCTGCTGATCTACTACTCTTCTAATTTGCACACCGGTGTGCCAGCCCGTGTTCTCCGGATCTGGTTCTGGCACCGACTTCACCCTGACCATCTCTAGACTGGAACCTGCAAGCTGAAGACTTGCCACCTACTACTGC
CAGCAGTCTATCAAGCTGCCACTTACCTTCGGTTCTGGTACCAAAGTGGAGATCAAA
X394VL
GACATCCTGATGACCCAGTCTCCATCTTCTCTGTCTGCTTCTCCTGGCGACCGTGTTACCATCTCCTGTCGTGCCTCTCAGGACATCCGTAACAACCTGAACTGGTATCAGCAGAAACCAGGTCAGGCCCCA
CGTCTGCTGATCTACTACTCTTCTAATTTGCAGACCGGTGTGCCAGCCCGTGTTCTCCGGATCTGGTTCTGGCACCGACTTCACCCTGACCATCTCTAGACTGGAACCTGGAACCTGAAGACTTTGCCGCCTACTACTGC
CAGCAGTCTATCAAGCTGCCACTTACCTTCGGTTCTGGTACCAAAGTGGAGATCAAA
```

Figure 3

```
Sequential
Numbering           10        20        30        40        50        60        70        80        90       100
           1234567890123456789012345678901234567890123456789012345678901234567890123456789012345678901234567
           <------FR1------><--CDR1---><----FR2-----><-CDR2-><---------FR3-------------><--CDR3--><--FR4--->

CM03 VL    DIQMTQSPSSLSASLGDRVTITCSASQGIRNSLNWYQQKPDGAVKLLIYYSSNLHSGVPSRFSGSGSGTDFSLTISNLEPEDIATYYCQQSIKLPFTFGSGTKLEIK
X376       DILMTQSPSSLSASPGDRVTISCRASQDIRNNLNWYQQKPGQAPRLLIYYSSNLHSGVPDRFSGSGSGTDFTLTISRLEPEDFAAYYCQQSIKLPLTFGSGTKVEIK
X377       EIELTQSPSSLSVSLGDRVTISCSASQDIRNNLNWYQQKPGQAPRLLIYYSSNLQTGVPARFSGSGSGTDFTLTISRLEPEDVAAYYCQQSIKLPFTFGSGTKVEIK
X378       DIEMTQSPSSLSASAGERVTISCRASQGIRNNLNWYQQKPGQAPRLLIYYSSNLQTGVPSRFSGSGSGTDFTLTISRLQAEDFATYYCQQSNKLPFTFGSGTKVEIK
X379       DILLTQSPSSLSATPGERATTCRASQGIRNNLNWYQQKPGQAPRLLIYYSSNLQSGVPSRFSGSGSGTDFTLTISRLQPEDVAAYYCQQSIKLPFTFGSGTKVEIK
X380       EIEMTQSPSSLSVSAGERATISCSASQGIRNSLNWYQQKPGQAPRLLIYYSSNLHTGVPARFSGSGSGTDFTLTISRLEPEDVAIYYCQQSNKLPLTFGSGTKVEIK
X381       EIELTQSPSSLSVSPGDRVTISCSASQGIRNSLNWYQQKPGQAPRLLIYYSSNLHTGVPARFSGSGSGTDFTLTISRLQAEDFATYYCQQSIKLPLTFGSGTKVEIK
X394       DILMTQSPSSLSASPGDRVTISCRASQDIRNNLNWYQQKPGQAPRLLIYYSSNLQTGVPARFSGSGSGTDFTLTISRLEPEDFAAYYCQQSIKLPLTFGSGTKVEIK

Kabat Numbering              24       34                50   56                                 89      97
(same as sequential numbering; no insertion)
```

Figure 4

X384VH
GAAGTGCAGCTGGTGGAAAGCGGTGGTCTGGAGTGAAGCAGCCCGGGTGGAGTGAAGCAGCCCGGGTGGAACCCTGCGTCTGACCTGCACGGCTAGCGGTTTCAGCCTGACCATACGGTGTGCACTGGGTGCGTCAGGCGCCCGGGAAAGG
TCTGGAATGGGTGGGTGTAATCTGGGGCGATGGCGATTACGATGCTCGTCTTCATGAGCCGGGTGACCATCAGCAAAGATACCAGCAAAGATACCAGCAAAGCACCGTGTACTTGCAGATGAACAGCCTGCGTGCGG
AAGATACTGCAGTTGCAGTGTACTACTGCAGTCGTCATGCGTAATCGTCGATTACTGGGGCCAAGGAACCACCGTGACCGTCTCGAGC

X385VH
GAAGTGCAGCTGGTGGAAAGCGGTGGTCTGGAGTGAAGCAGCCCGGGTGGAGTGAAGCAGCCCGGGTGAAACCCTGCGTCTGACCTGCACGGCTAGCGGTTTCAGCCTGACCATACGGTGTGCACTGGGTGCGTCAGGCGCCCGGGAAAGG
TCTGGAATGGGTGGGTGTAATCTGGGCGATGTGTAATCTGGGGCGATGGCGATTACGATGCTGCTTTCATGAGCCGGGTGACCATCAGCCGGGTGACCATCAGCAAAGATACCAGCAAAGATACCAGCAAAGCACCGTGTACTTGCAGATGAACAGCCTGCGTGCGG
AAGATACTGCAGTTGCAGTGTACTACTGCAGTCGTCATGCGTAATCGTCGATTACTGGGGCCAAGGAACCACCGTGACCGTCTCGAGC

X386VH
GAAGTGCAGCTGGTGGAAAGCGGTGGTCTGGAGTGAAGCAGCCCGGGTGGAGAGCAGCCCGGGTGAAACCCTGCGTCTGACCTGCACGGCTAGCGGTTTCAGCCTGACCATACGGTGTGCACTGGGTGCGTCAGGCGCCCGGGAAAGG
TCTGGAATGGATGGGTGTAATCTGGGGCGATGGTCGTACCGATTACGATGCTGTCTTTCATGAGCCGGGTGACCATCAGAGAGATACCAGCAAAGATACCAGCAAAGCACCGTGTACTTGCAGATGAACAGCCTGCGTGCGG
AAGATACTGCAGTTGCAGTGTACTACTGCGTCGTAATCGTCATGATTGGTTCATGATTGGTTCGATTACTGGGGCCAAGGAACCACCGTGACCGTCTCGAGC

X387VH
GAAGTGCAGCTGGTGGAAAGCGGTGGTCTGGAGTGAAGCAGCCCGGGTGAAGCAGCCCGGGTGAAACCCTGCGTCTGACCTGCACGGCTAGCGGTTTCACCCTGAACACATACGGTGTGCACTGGGTGCGTCAGGCGCCCGGGAAAGG
TCTGGAATGGATGGGTGTAATCTGGGGCCGTGGTTCGTGGCGTACCGATTACGATGCTCTTTCATGAGCCGGGTGACCATCAGCCGGGTGACCATCAGCAAAGATAACAGCAAAGATAACAGCAAAACACCCGCTACTTGCAGCTGAACAGCCTGCGTGCGG
AAGATACTGCAGTTGCAGTGTACTACTGCGTCCACGCGTAGTCGTAGTCGTCATGATTGGTTCGATTACTGGGGCCAAGGAACCACCGTGACCGTCTCGAGC

X388VH
GAAGTGCAGCTGGTGCAAAGCGGTGGTCTGGAGTGAAGCAGCCCGGGTGAAGCAGCCCGGGTGACTGAAACCCTGCGTCTGAGCTGCACGGTGACCGGTTACAGCCTGACCATACGGTGTGCACTGGGTGCGTCAGGCGCCCGGGAAAGG
TCTGGAATGGATGGGTGTAATCTGGGGCGATGGTGTAATCTGGGGCGATGGTGTAATCGTACGCGTAGTGTCGTACCGATTACGATTCGTACCGATTACGATTGTCTTTCATGATTCGTACCGATTCGTACCGATTCGTACCGATTCGTACCGATTACAGCAAAGATACCAGCAAAGATACCAGCAAAGATACCAGCAAAGCACCGTACTTGCAGCTGAACAGCCTGCGTGCGG
AAGATACTGCAGTTGCAGTGTACTACTGCGTCGTAATCGTCATGATTGGTTCGATTACTGGGGCCAAGGAACCACCGTGACCGTCTCGAGC

X399VH
GAAGTGCAGCTGGTGCAAAGCGGTGGTCTGGAGTGAAGCAGCCCGGGTGAAGCAGCCCGGGTGAAACCCTGCGTCTGACCTGCACGGCTAGCGGTTTCAGCCTGAGCACTGCACGGCTGAGCACTGAGCCATACGGTGTGCACTGGGTGCGTCAGGCGCCCGGGAAAGG
TCTGGAATGGATGGGTGTAATCTGGGGCGATGCGGTGTAATCTGGGGCGATGCGTACCGATTACGATGCTGTCTTTCATGAGCCGGGTGACCATCAGCCGGGTGACCATCAGCAAAGATACCAGCAAAGATACCAGCAAAGCACCGTACTTGCAGATGAACAGCCTGCGTGCGG
AAGATACTGCAGTTGCAGTGTACTACTGCGTCGTAATCGTCATGATTGGTTCGATTACTGGGGCCAAGGAACCACCGTGACCGTCTCGAGC

X420VH
GAAGTGCAGCTGGTGGAAAGCGGTGGTCTGGAGTGAAGCAGCCCGGGTGGAGAGCAGCCCGGGTGAAACCCTGCGTCTGACCTGCACGGCTAGCGGTTTCAGCCTGAGCACATACGGTGTGCACTGGGTGCGTCAGGCGCCCGGGAAAGG
TCTGGAATGGGTGGGTGTAATCTGGGGCGATGCGGTGTAATCTGGGGCGATGTCGTACCGATTACGATGCTGTCTTTCATGAGCCGGGTGACCATCAGCCGGGTGACCATCAGCAAAGATACCAGCAAAGATACCAGCAAAGCACCGTACTTGCAGATGAACAGCCTGCGTGCGG
AAGATACTGCAGTTGCAGTGTACTACTGCGTCGTAATCGTCATGATTGGTTCGATTACTGGGGCCAAGGAACCACCGTGACCGTCTCGAGC

Figure 5

```
Sequential
Numbering          10        20        30        40        50        60        70        80        90        100       110
          1234567890123456789012345678901234567890123456789012345678901234567890123456789012345678901234567890123456
          <------FR1------><--CDR1--><----FR2-----><----CDR2----><-------------FR3--------------><--CDR3--><--FR4---->

CM03 VH   QVKLQESGPGLVQPSQTLSITCTVSGFSLTTYGVHWLRQSPGKGLEWLGVIWGGGDTDYDAAFISRLSISKDNSKSQVFFKMNSLQANDTAIYYCVRNRHDWFDYWGQGTTVTVSS
X384      EVQLVESGAGVKQPGGTLRLTCTASGFSLTTYGVHWVRQAPGKGLEWVGVIWGDGRTDYDAAFMSRVTISKDTSKSTVYLQMNSLRAEDTAVYYCMRNRHDWFDYWGQGTTVTVSS
X385      EVQLVESGGGVKQPGETLRLTCTASGFSLTTYGVHWVRQAPGKGLEWVGVIWGDGRTDYDAAFMSRVTISKDTSKSTVYLQMNSLRAEDTAVYYCMRNRHDWFDYWGQGTTVTVSS
X386      EVQLVESGAGVEQPGGTLRLTCTASGFSLTTYGVHWVRQAPGKGLEWMGVIWGGGRTDYDAAFMSRVTISRDTSKSTAYLQLNSLRAEDTAVYYCVRNRHDWFDYWGQGTTVTVSS
X387      EVQLVESGAELVQPGGSLRLTCKASGFTLNTYGVHWVRQAPGKGLEWMGVIWGGGRTDYDASFMSRVTISKDNSKNTAYLQLNSLRAEDTAVYYCTRSRHDWFDYWGQGTTVTVSS
X388      EVQLVQSGGGLKQPGETLRLSCTASGYSLTTYGVHWVRQAPGKGLEWMGVIWGDGRTDYDSSFMSRVTISKDTSKSTAYLQLNSLRAEDTAVYYCTRNRHDWFDYWGQGTTVTVSS
X399      EVQLVQSGGGVKQPGETLRLTCTASGFSLSTYGVHWVRQAPGKGLEWVGVIWGDGRTDYDAAFMSRVTISKDTSKSTVYLQMNSLRAEDTAVYYCMRNRHDWFDYWGQGTTVTVSS
X420      EVQLVESGGGVKQPGETLRLTCTASGFSLSTYGVHWVRQAPGKGLEWVGVIWGDGRTDYDAAFMSRVTISKDTSKSTVYLQMNSLRAEDTAVYYCMRNRHDWFDYWGQGTTVTVSS

Kabat Numbering
                          26        35            50         65                  82  abc345678901234567890123
                                                                                  90      95      100  102
                                                                                                   110
```

Figure 6

```
X389
X384VH   EVQLVESGAGVKQPGGTLRLTCTASGFSLTTYGVHWVRQAPGKGLEWVGVIWGDRTDYDAAFMSRVTISKDTSKSTVYLQMNSLRAEDTAVYYCMRNRHDWFDYWGQGTTVTVSS
X376VL   DILMTQSPSSLSASPGDRVTISCRASQDIRNNLNWYQQKPGQAPRLLIYYSSNLHSGVPDRFSGSGSGTDFTLTISRLEPEDFAAYYCQQSIKLPLTFGSGTKVEIK
X390
X385VH   EVQLVQSGGGVKQPGETLRLTCTASGFSLTTYGVHWVRQAPGKGLEWVGVIWGDRTDYDAAFMSRVTISKDTSKSTAYLQMNSLRAEDTAVYYCMRNRHDWFDYWGQGTTVTVSS
X376VL   DILMTQSPSSLSASPGDRVTISCRASQDIRNNLNWYQQKPGQAPRLLIYYSSNLHSGVPDRFSGSGSGTDFTLTISRLEPEDFAAYYCQQSIKLPLTFGSGTKVEIK
X391
X388VH   EVQLVQSGGGLKQPGETLRLSCTASGYSLTTYGVHWVRQAPGKGLEWMGVIWGDRTDYDSSFMSRVTISKDTSKSTAYLQLNSLRAEDTAVYYCTRNRHDWFDYWGQGTTVTVSS
X376VL   DILMTQSPSSLSASPGDRVTISCRASQDIRNNLNWYQQKPGQAPRLLIYYSSNLHSGVPDRFSGSGSGTDFTLTISRLEPEDFAAYYCQQSIKLPLTFGSGTKVEIK
X392
X384VH   EVQLVESGAGVKQPGGTLRLTCTASGFSLTTYGVHWVRQAPGKGLEWVGVIWGDRTDYDAAFMSRVTISKDTSKSTVYLQMNSLRAEDTAVYYCMRNRHDWFDYWGQGTTVTVSS
X379VL   DILLTQSPSSLSATPGERATITCRASQGIRNNLNWYQQKPGQAPRLLIYYSSNLQSGVPSRFSGSGSGTDFTLTISRLQPEDVAAYYCQQSIKLPFTFGSGTKVEIK
X393
X385VH   EVQLVQSGGGVKQPGETLRLTCTASGFSLTTYGVHWVRQAPGKGLEWVGVIWGDRTDYDAAFMSRVTISKDTSKSTAYLQMNSLRAEDTAVYYCMRNRHDWFDYWGQGTTVTVSS
X379VL   DILLTQSPSSLSATPGERATITCRASQGIRNNLNWYQQKPGQAPRLLIYYSSNLQSGVPSRFSGSGSGTDFTLTISRLQPEDVAAYYCQQSIKLPFTFGSGTKVEIK
X394
X384VH   EVQLVESGAGVKQPGGTLRLTCTASGFSLTTYGVHWVRQAPGKGLEWVGVIWGDRTDYDAAFMSRVTISKDTSKSTVYLQMNSLRAEDTAVYYCMRNRHDWFDYWGQGTTVTVSS
X394VL   DILMTQSPSSLSASPGDRVTISCRASQDIRNNLNWYQQKPGQAPRLLIYYSSNLQTGVPARFSGSGSGTDFTLTISRLEPEDFAAYYCQQSIKLPLTFGSGTKVEIK
X395
X384VH   EVQLVESGAGVKQPGGTLRLTCTASGFSLTTYGVHWVRQAPGKGLEWVGVIWGDRTDYDAAFMSRVTISKDTSKSTVYLQMNSLRAEDTAVYYCMRNRHDWFDYWGQGTTVTVSS
X380VL   EIEMTQSPSSLSVSAGERATISCASQDIRNSLNWYQQKPGQAPRLLIYYSSNLHTGVPARFSGSGSGTDFTLTISRLEPEDVAIYYCQQSNKLPLTFGSGTKVEIK
X396
X385VH   EVQLVQSGGGVKQPGETLRLTCTASGFSLTTYGVHWVRQAPGKGLEWVGVIWGDRTDYDAAFMSRVTISKDTSKSTAYLQMNSLRAEDTAVYYCMRNRHDWFDYWGQGTTVTVSS
X380VL   EIEMTQSPSSLSVSAGERATISCASQDIRNSLNWYQQKPGQAPRLLIYYSSNLHTGVPARFSGSGSGTDFTLTISRLEPEDVAIYYCQQSNKLPLTFGSGTKVEIK
X399
X399VH   EVQLVQSGGGVKQPGETLRLTCTASGFSLSTYGVHWVRQAPGKGLEWVGVIWGDRTDYDAAFMSRVTISKDTSKSTVYLQMNSLRAEDTAVYYCMRNRHDWFDYWGQGTTVTVSS
X380VL   EIEMTQSPSSLSVSAGERATISCASQDIRNSLNWYQQKPGQAPRLLIYYSSNLHTGVPARFSGSGSGTDFTLTISRLEPEDVAIYYCQQSNKLPLTFGSGTKVEIK
X420
X420VH   EVQLVQSGGGVKQPGETLRLTCTASGFSLSTYGVHWVRQAPGKGLEWVGVIWGDRTDYDAAFMSRVTISKDTSKSTVYLQMNSLRAEDTAVYYCMRNRHDWFDYWGQGTTVTVSS
X380VL   EIEMTQSPSSLSVSAGERATISCASQDIRNSLNWYQQKPGQAPRLLIYYSSNLHTGVPARFSGSGSGTDFTLTISRLEPEDVAIYYCQQSNKLPLTFGSGTKVEIK
X429
X399VH   EVQLVQSGGGVKQPGETLRLTCTASGFSLSTYGVHWVRQAPGKGLEWVGVIWGDRTDYDAAFMSRVTISKDTSKSTVYLQMNSLRAEDTAVYYCMRNRHDWFDYWGQGTTVTVSS
X394VL   DILMTQSPSSLSASPGDRVTISCRASQDIRNNLNWYQQKPGQAPRLLIYYSSNLQTGVPARFSGSGSGTDFTLTISRLEPEDFAAYYCQQSIKLPLTFGSGTKVEIK
```

Figure 17A

Leader Sequence------- [VH variant] TVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVMHEALH
NHYTQKSLSLSPGK

Figure 17B

Leader Sequence------[VL variant] RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

SEQUENCE LISTING

<160> NUMBER OF SEQ ID NOS: 220

<210> SEQ ID NO 1
<211> LENGTH: 321
<212> TYPE: DNA
<213> ORGANISM: Artificial Sequence
<220> FEATURE:
<223> OTHER INFORMATION: Synthetic Construct

<400> SEQUENCE: 1
gacatcctga tgacccagtc tccatcttct ctgtctgctt ctcctggcga ccgtgttacc      60
atctcctgtc gtgcctctca ggacatccgt aacaacctga actggtatca gcagaaacca     120
ggtcaggccc cacgtctgct gatctactac tcttctaatt tgcactccgg tgtgccagac     180
cgtttctccg gatctggttc tggcaccgac ttcaccctga ccatctctag actggaacct     240
gaagactttg ccgcctacta ctgccagcag tctatcaagc tgccacttac cttcggttct     300
ggtaccaaag tggagatcaa a                                                321

<210> SEQ ID NO 2
<211> LENGTH: 321
<212> TYPE: DNA
<213> ORGANISM: Artificial Sequence
<220> FEATURE:
<223> OTHER INFORMATION: Synthetic Construct

<400> SEQUENCE: 2
gaaatcgagc tgacccagtc tccatcttct ctgtctgttt ctcttggcga ccgtgttacc      60
atctcctgta gtgcctctca ggacatccgt aacaacctga actggtatca gcagaaacca     120
ggtcaggccc cacgtctgct gatctactac tcttctaatt tgcagaccgg tgtgccagcc     180
cgtttctccg gatctggttc tggcaccgac ttcaccctga ccatctctag actggaacct     240
gaagacgttg ccgcctacta ctgccagcag tctatcaagc tgccatttac cttcggttct     300
ggtaccaaag tggagatcaa a                                                321

<210> SEQ ID NO 3
<211> LENGTH: 321
<212> TYPE: DNA
<213> ORGANISM: Artificial Sequence
<220> FEATURE:
<223> OTHER INFORMATION: Synthetic Construct

<400> SEQUENCE: 3
gacatcgaga tgacccagtc tccatcttct ctgtctgctt ctgctggcga acgtgttacc      60
atctcctgtc gtgcctctca gggcatccgt aacagcctga actggtatca gcagaaacca     120
ggtcaggccc cacgtctgct gatctactac tcttctaatt tgcagaccgg tgtgccatcc     180
cgtttctccg gatctggttc tggcaccgac ttcaccctga ccatctctag actgcaagct     240
gaagactttg ccacctacta ctgccagcag tctaacaagc tgccatttac cttcggttct     300
ggtaccaaag tggagatcaa a                                                321

<210> SEQ ID NO 4
<211> LENGTH: 321
<212> TYPE: DNA
<213> ORGANISM: Artificial Sequence
<220> FEATURE:
<223> OTHER INFORMATION: Synthetic Construct

<400> SEQUENCE: 4

```
gacatcctgc tgacccagtc tccatcttct ctgtctgcta ctcctggcga acgtgctacc    60
atcacctgtc gtgcctctca gggcatccgt aacaacctga actggtatca gcagaaacca   120
ggtcaggccc cacgtctgct gatctactac tcttctaatt tgcagtccgg tgtgccatcc   180
cgtttctccg gatctggttc tggcaccgac ttcaccctga ccatctctag actgcaacct   240
gaagacgttg ccgcctacta ctgccagcag tctatcaagc tgccatttac cttcggttct   300
ggtaccaaag tggagatcaa a                                             321

<210> SEQ ID NO 5
<211> LENGTH: 321
<212> TYPE: DNA
<213> ORGANISM: Artificial Sequence
<220> FEATURE:
<223> OTHER INFORMATION: Synthetic Construct

<400> SEQUENCE: 5
gaaatcgaga tgacccagtc tccatcttct ctgtctgttt ctgctggcga acgtgctacc    60
atctcctgta gtgcctctca ggacatccgt aacagcctga actggtatca gcagaaacca   120
ggtcaggccc cacgtctgct gatctactac tcttctaatt tgcacaccgg tgtgccagcc   180
cgtttctccg gatctggttc tggcaccgac ttcaccctga ccatctctag actggaacct   240
gaagacgttg ccatctacta ctgccagcag tctaacaagc tgccacttac cttcggttct   300
ggtaccaaag tggagatcaa a                                             321

<210> SEQ ID NO 6
<211> LENGTH: 321
<212> TYPE: DNA
<213> ORGANISM: Artificial Sequence
<220> FEATURE:
<223> OTHER INFORMATION: Synthetic Construct

<400> SEQUENCE: 6
gaaatcgagc tgacccagtc tccatcttct ctgtctgttt ctcctggcga ccgtgttacc    60
atctcctgta gtgcctctca gggcatccgt aacagcctga actggtatca gcagaaacca   120
ggtcaggccc cacgtctgct gatctactac tcttctaatt tgcacaccgg tgtgccagcc   180
cgtttctccg gatctggttc tggcaccgac ttcaccctga ccatctctag actgcaagct   240
gaagactttg ccacctacta ctgccagcag tctatcaagc tgccacttac cttcggttct   300
ggtaccaaag tggagatcaa a                                             321

<210> SEQ ID NO 7
<211> LENGTH: 321
<212> TYPE: DNA
<213> ORGANISM: Artificial Sequence
<220> FEATURE:
<223> OTHER INFORMATION: Synthetic Construct

<400> SEQUENCE: 7
gacatcctga tgacccagtc tccatcttct ctgtctgctt ctcctggcga ccgtgttacc    60
atctcctgtc gtgcctctca ggacatccgt aacaacctga actggtatca gcagaaacca   120
ggtcaggccc cacgtctgct gatctactac tcttctaatt tgcagaccgg tgtgccagcc   180
cgtttctccg gatctggttc tggcaccgac ttcaccctga ccatctctag actggaacct   240
gaagactttg ccgcctacta ctgccagcag tctatcaagc tgccacttac cttcggttct   300
ggtaccaaag tggagatcaa a                                             321

<210> SEQ ID NO 8
```

<211> LENGTH: 348
<212> TYPE: DNA
<213> ORGANISM: Artificial Sequence
<220> FEATURE:
<223> OTHER INFORMATION: Synthetic Construct

<400> SEQUENCE: 8

```
gaagtgcagc tggtggaaag cggtgctgga gtgaagcagc cgggtggaac cctgcgtctg    60
acctgcacgg ctagcggttt cagcctgacc acatacggtg tgcactgggt gcgtcaggcg   120
cccgggaaag gtctggaatg ggtgggtgta atctggggcg atggtcgtac cgattacgat   180
gctgctttca tgagccgggt gaccatcagc aaagatacca gcaaaagcac cgtgtacttg   240
cagatgaaca gcctgcgtgc ggaagatact gcagtgtact actgcatgcg taatcgtcat   300
gattggttcg attactgggg ccaaggaacc accgtgaccg tctcgagc              348
```

<210> SEQ ID NO 9
<211> LENGTH: 348
<212> TYPE: DNA
<213> ORGANISM: Artificial Sequence
<220> FEATURE:
<223> OTHER INFORMATION: Synthetic Construct

<400> SEQUENCE: 9

```
gaagtgcagc tggtgcaaag cggtggtgga gtgaagcagc cgggtgaaac cctgcgtctg    60
acctgcacgg ctagcggttt cagcctgacc acatacggtg tgcactgggt gcgtcaggcg   120
cccgggaaag gtctggaatg ggtgggtgta atctggggcg atggtcgtac cgattacgat   180
gctgctttca tgagccgggt gaccatcagc aaagatacca gcaaaagcac cgcgtacttg   240
cagatgaaca gcctgcgtgc ggaagatact gcagtgtact actgcatgcg taatcgtcat   300
gattggttcg attactgggg ccaaggaacc accgtgaccg tctcgagc              348
```

<210> SEQ ID NO 10
<211> LENGTH: 348
<212> TYPE: DNA
<213> ORGANISM: Artificial Sequence
<220> FEATURE:
<223> OTHER INFORMATION: Synthetic Construct

<400> SEQUENCE: 10

```
gaagtgcagc tggtggaaag cggtgctgga gtggagcagc cgggtggaac cctgcgtctg    60
acctgcacgg ctagcggttt cagcctgacc acatacggtg tgcactgggt gcgtcaggcg   120
cccgggaaag gtctggaatg gatgggtgta atctggggcg atggtcgtac cgattacgat   180
gctgctttca tgagccgggt gaccatcagc agagatacca gcaaaagcac cgcgtacttg   240
cagctgaaca gcctgcgtgc ggaagatact gcagtgtact actgcgtgcg taatcgtcat   300
gattggttcg attactgggg ccaaggaacc accgtgaccg tctcgagc              348
```

<210> SEQ ID NO 11
<211> LENGTH: 348
<212> TYPE: DNA
<213> ORGANISM: Artificial Sequence
<220> FEATURE:
<223> OTHER INFORMATION: Synthetic Construct

<400> SEQUENCE: 11

```
gaagtgcagc tggtggaaag cggtgctgaa ctggtgcagc cgggtggaag cctgcgtctg    60
acctgcaagg ctagcggttt caccctgaac acatacggtg tgcactgggt gcgtcaggcg   120
cccgggaaag gtctggaatg gatgggtgta atctggggcg gtggtcgtac cgattacgat   180
```

```
gcttctttca tgagccgggt gaccatcagc aaagataaca gcaaaaacac cgcgtacttg    240
cagctgaaca gcctgcgtgc ggaagatact gcagtgtact actgcacgcg tagtcgtcat    300
gattggttcg attactgggg ccaaggaacc accgtgaccg tctcgagc                 348
```

<210> SEQ ID NO 12
<211> LENGTH: 348
<212> TYPE: DNA
<213> ORGANISM: Artificial Sequence
<220> FEATURE:
<223> OTHER INFORMATION: Synthetic Construct

<400> SEQUENCE: 12

```
gaagtgcagc tggtgcaaag cggtggtgga ctgaagcagc cgggtgaaac cctgcgtctg     60
agctgcacgg ctagcggtta cagcctgacc acatacggtg tgcactgggt gcgtcaggcg    120
cccgggaaag gtctggaatg gatgggtgta atctggggcg atggtcgtac cgattacgat    180
tcttctttca tgagccgggt gaccatcagc aaagatacca gcaaaagcac cgcgtacttg    240
cagctgaaca gcctgcgtgc ggaagatact gcagtgtact actgcacgcg taatcgtcat    300
gattggttcg attactgggg ccaaggaacc accgtgaccg tctcgagc                 348
```

<210> SEQ ID NO 13
<211> LENGTH: 348
<212> TYPE: DNA
<213> ORGANISM: Artificial Sequence
<220> FEATURE:
<223> OTHER INFORMATION: Synthetic Construct

<400> SEQUENCE: 13

```
gaagtgcagc tggtgcaaag cggtggtgga gtgaagcagc cgggtgaaac cctgcgtctg     60
acctgcacgg ctagcggttt cagcctgagc acatacggtg tgcactgggt gcgtcaggcg    120
cccgggaaag gtctggaatg ggtggtgta atctggggcg atggtcgtac cgattacgat    180
gctgctttca tgagccgggt gaccatcagc aaagatacca gcaaaagcac cgtgtacttg    240
cagatgaaca gcctgcgtgc ggaagatact gcagtgtact actgcatgcg taatcgtcat    300
gattggttcg attactgggg ccaaggaacc accgtgaccg tctcgagc                 348
```

<210> SEQ ID NO 14
<211> LENGTH: 348
<212> TYPE: DNA
<213> ORGANISM: Artificial Sequence
<220> FEATURE:
<223> OTHER INFORMATION: Synthetic Construct

<400> SEQUENCE: 14

```
gaagtgcagc tggtggaaag cggtggtgga gtgaagcagc cgggtgaaac cctgcgtctg     60
acctgcacgg ctagcggttt cagcctgagc acatacggtg tgcactgggt gcgtcaggcg    120
cccgggaaag gtctggaatg ggtggtgta atctggggcg atggtcgtac cgattacgat    180
gctgctttca tgagccgggt gaccatcagc aaagatacca gcaaaagcac cgtgtacttg    240
cagatgaaca gcctgcgtgc ggaagatact gcagtgtact actgcatgcg taatcgtcat    300
gattggttcg attactgggg ccaaggaacc accgtgaccg tctcgagc                 348
```

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct -continued

```
<400> SEQUENCE: 15

Asp Ile Leu Met Thr Gln Ser Pro Ser Ser Leu Ser Ala Ser Pro Gly
 1               5                  10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Ser Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Ala Tyr Tyr Cys Gln Gln Ser Ile Lys Leu Pro Leu
                85                  90                  95

Thr Phe Gly Ser Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Glu Ile Glu Leu Thr Gln Ser Pro Ser Ser Leu Ser Val Ser Leu Gly
 1               5                  10                  15

Asp Arg Val Thr Ile Ser Cys Ser Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

Asp Ile Glu Met Thr Gln Ser Pro Ser Ser Leu Ser Ala Ser Ala Gly
 1               5                  10                  15

Glu Arg Val Thr Ile Ser Cys Arg Ala Ser Gln Gly Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ser Arg Phe Ser Gly
    50                  55                  60

Ser Gly Ser Gly Thr Asp Phe Thr Leu Thr Ile Ser Arg Leu Gln Ala
65                  70                  75                  80

Glu Asp Phe Ala Thr Tyr Tyr Cys Gln Gln Ser Asn Lys Leu Pro Phe
```

```
                     85                  90                  95

Thr Phe Gly Ser Gly Thr Lys Val Glu Ile Lys
                100                 105

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Ile Leu Leu Thr Gln Ser Pro Ser Ser Leu Ser Ala Thr Pro Gly
  1               5                  10                  15

Glu Arg Ala Thr Ile Thr Cys Arg Ala Ser Gln Gly Ile Arg Asn Asn
                 20                  25                  30

Leu Asn Trp Tyr Gln Gln Lys Pro Gly Gln Ala Pro Arg Leu Leu Ile
             35                  40                  45

Tyr Tyr Ser Ser Asn Leu Gln Ser Gly Val Pro Ser Arg Phe Ser Gly
     50                  55                  60

Ser Gly Ser Gly Thr Asp Phe Thr Leu Thr Ile Ser Arg Leu Gln Pro
 65                  70                  75                  80

Glu Asp Val Ala Ala Tyr Tyr Cys Gln Gln Ser Ile Lys Leu Pro Phe
                 85                  90                  95

Thr Phe Gly Ser Gly Thr Lys Val Glu Ile Lys
                100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

Glu Ile Glu Met Thr Gln Ser Pro Ser Ser Leu Ser Val Ser Ala Gly
  1               5                  10                  15

Glu Arg Ala Thr Ile Ser Cys Ser Ala Ser Gln Asp Ile Arg Asn Ser
                 20                  25                  30

Leu Asn Trp Tyr Gln Gln Lys Pro Gly Gln Ala Pro Arg Leu Leu Ile
             35                  40                  45

Tyr Tyr Ser Ser Asn Leu His Thr Gly Val Pro Ala Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Val Ala Ile Tyr Tyr Cys Gln Gln Ser Asn Lys Leu Pro Leu
                 85                  90                  95

Thr Phe Gly Ser Gly Thr Lys Val Glu Ile Lys
                100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic Construct

<400> SEQUENCE: 20

Glu Ile Glu Leu Thr Gln Ser Pro Ser Ser Leu Ser Val Ser Pro Gly
  1               5                  10                  15
```

```
Asp Arg Val Thr Ile Ser Cys Ser Ala Ser Gln Gly Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Thr Gly Val Pro Ala Arg Phe Ser Gly
 50                  55                  60

Ser Gly Ser Gly Thr Asp Phe Thr Leu Thr Ile Ser Arg Leu Gln Ala
 65                  70                  75                  80

Glu Asp Phe Ala Thr Tyr Tyr Cys Gln Gln Ser Ile Lys Leu Pro Leu
                85                  90                  95

Thr Phe Gly Ser Gly Thr Lys Val Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

```
Asp Ile Leu Met Thr Gln Ser Pro Ser Ser Leu Ser Ala Ser Pro Gly
 1               5                  10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ala Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Ala Tyr Tyr Cys Gln Gln Ser Ile Lys Leu Pro Leu
                85                  90                  95

Thr Phe Gly Ser Gly Thr Lys Val Glu Ile Lys
            100                 105
```

<210> SEQ ID NO 22
<211> LENGTH: 116
<212> TYPE: PRT
<213> ORGANISM: Artificial Sequence
<220> FEATURE:
<223> OTHER INFORMATION: Synthetic Construct

<400> SEQUENCE: 22

```
Glu Val Gln Leu Val Glu Ser Gly Ala Gly Val Lys Gln Pro Gly Gly
 1               5                  10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
 50                  55                  60

Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110
```

<210> SEQ ID NO 23
<211> LENGTH: 116
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Gln Ser Gly Gly Gly Val Lys Gln Pro Gly Glu
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Ala Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 24
<211> LENGTH: 116
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Ala Gly Val Glu Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Met
        35                  40                  45

Gly Val Ile Trp Gly Asp Gly Arg Thr Asp Tyr Asp Ala Ala Phe Met
    50                  55                  60

Ser Arg Val Thr Ile Ser Arg Asp Thr Ser Lys Ser Thr Ala Tyr Leu
65                  70                  75                  80

Gln Leu Asn Ser Leu Arg Ala Glu Asp Thr Ala Val Tyr Tyr Cys Val
                85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Synthetic Construct

<400> SEQUENCE: 25

```
Glu Val Gln Leu Val Glu Ser Gly Ala Glu Leu Val Gln Pro Gly Gly
  1               5                  10                  15

Ser Leu Arg Leu Thr Cys Lys Ala Ser Gly Phe Thr Leu Asn Thr Tyr
             20                  25                  30

Gly Val His Trp Val Arg Gln Ala Pro Gly Lys Gly Leu Glu Trp Met
             35                  40                  45

Gly Val Ile Trp Gly Gly Gly Arg Thr Asp Tyr Asp Ala Ser Phe Met
 50                  55                  60

Ser Arg Val Thr Ile Ser Lys Asp Asn Ser Lys Asn Thr Ala Tyr Leu
 65                  70                  75                  80

Gln Leu Asn Ser Leu Arg Ala Glu Asp Thr Ala Val Tyr Tyr Cys Thr
             85                  90                  95

Arg Ser Arg His Asp Trp Phe Asp Tyr Trp Gly Gln Gly Thr Thr Val
            100                 105                 110

Thr Val Ser Ser
            115

<210> SEQ ID NO 26
<211> LENGTH: 116
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Gln Ser Gly Gly Gly Leu Lys Gln Pro Gly Glu
  1               5                  10                  15

Thr Leu Arg Leu Ser Cys Thr Ala Ser Gly Tyr Ser Leu Thr Thr Tyr
             20                  25                  30

Gly Val His Trp Val Arg Gln Ala Pro Gly Lys Gly Leu Glu Trp Met
             35                  40                  45

Gly Val Ile Trp Gly Asp Gly Arg Thr Asp Tyr Asp Ser Ser Phe Met
 50                  55                  60

Ser Arg Val Thr Ile Ser Lys Asp Thr Ser Lys Ser Thr Ala Tyr Leu
 65                  70                  75                  80

Gln Leu Asn Ser Leu Arg Ala Glu Asp Thr Ala Val Tyr Tyr Cys Thr
             85                  90                  95

Arg Asn Arg His Asp Trp Phe Asp Tyr Trp Gly Gln Gly Thr Thr Val
            100                 105                 110

Thr Val Ser Ser
            115

<210> SEQ ID NO 27
<211> LENGTH: 116
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Gln Ser Gly Gly Gly Val Lys Gln Pro Gly Glu
  1               5                  10                  15

Thr Leu Arg Leu Thr Cys Thr Ala Ser Gly Phe Ser Leu Ser Thr Tyr
             20                  25                  30

Gly Val His Trp Val Arg Gln Ala Pro Gly Lys Gly Leu Glu Trp Val
             35                  40                  45

Gly Val Ile Trp Gly Asp Gly Arg Thr Asp Tyr Asp Ala Ala Phe Met
 50                  55                  60
```

```
Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Val Lys Gln Pro Gly Glu
 1               5                  10                  15

Thr Leu Arg Leu Thr Cys Thr Ala Ser Gly Phe Ser Leu Ser Thr Tyr
                 20                  25                  30

Gly Val His Trp Val Arg Gln Ala Pro Gly Lys Gly Leu Glu Trp Val
             35                  40                  45

Gly Val Ile Trp Gly Asp Gly Arg Thr Asp Tyr Asp Ala Ala Phe Met
 50                  55                  60

Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser
        115

<210> SEQ ID NO 29
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Glu or Gln
<220> FEATURE:
<221> NAME/KEY: VARIANT
<222> LOCATION: 9
<223> OTHER INFORMATION: Xaa = Ala or Gly
<220> FEATURE:
<221> NAME/KEY: VARIANT
<222> LOCATION: 10, 16
<223> OTHER INFORMATION: Xaa = Gly or Glu
<220> FEATURE:
<221> NAME/KEY: VARIANT
<222> LOCATION: 11
<223> OTHER INFORMATION: Xaa = Leu or Val
<220> FEATURE:
<221> NAME/KEY: VARIANT
<222> LOCATION: 12
<223> OTHER INFORMATION: Xaa = Val, Lys or Glu
<220> FEATURE:
<221> NAME/KEY: VARIANT
<222> LOCATION: 17
<223> OTHER INFORMATION: Xaa = Thr or Ser
<220> FEATURE:
<221> NAME/KEY: VARIANT
```

```
<222> LOCATION: 21
<223> OTHER INFORMATION: Xaa = Thr or Ser
<220> FEATURE:
<221> NAME/KEY: VARIANT
<222> LOCATION: 23
<223> OTHER INFORMATION: Xaa = Thr or Lys
<220> FEATURE:
<221> NAME/KEY: VARIANT
<222> LOCATION: 27
<223> OTHER INFORMATION: Xaa = Phe or Tyr
<220> FEATURE:
<221> NAME/KEY: VARIANT
<222> LOCATION: 28
<223> OTHER INFORMATION: Xaa = Ser or Thr
<220> FEATURE:
<221> NAME/KEY: VARIANT
<222> LOCATION: 30
<223> OTHER INFORMATION: Xaa = Thr, Asn or Ser
<220> FEATURE:
<221> NAME/KEY: VARIANT
<222> LOCATION: 48
<223> OTHER INFORMATION: Xaa = Val or Met
<220> FEATURE:
<221> NAME/KEY: VARIANT
<222> LOCATION: 54
<223> OTHER INFORMATION: Xaa = Gly or Asp
<220> FEATURE:
<221> NAME/KEY: VARIANT
<222> LOCATION: (61)...(62)
<223> OTHER INFORMATION: Xaa = Ala or Ser
<220> FEATURE:
<221> NAME/KEY: VARIANT
<222> LOCATION: 71
<223> OTHER INFORMATION: Xaa = Lys or Arg
<220> FEATURE:
<221> NAME/KEY: VARIANT
<222> LOCATION: 73
<223> OTHER INFORMATION: Xaa = Asn or Thr
<220> FEATURE:
<221> NAME/KEY: VARIANT
<222> LOCATION: 76
<223> OTHER INFORMATION: Xaa = Ser or Asn
<220> FEATURE:
<221> NAME/KEY: VARIANT
<222> LOCATION: 78
<223> OTHER INFORMATION: Xaa = Val or Ala
<220> FEATURE:
<221> NAME/KEY: VARIANT
<222> LOCATION: 82
<223> OTHER INFORMATION: Xaa = Met or Leu
<220> FEATURE:
<221> NAME/KEY: VARIANT
<222> LOCATION: 96
<223> OTHER INFORMATION: Xaa = Val, Met or Thr
<220> FEATURE:
<221> NAME/KEY: VARIANT
<222> LOCATION: 98
<223> OTHER INFORMATION: Xaa = Asn or Ser

<400> SEQUENCE: 29

Glu Val Gln Leu Val Xaa Ser Gly Xaa Xaa Xaa Xaa Gln Pro Gly Xaa
 1               5                  10                  15

Xaa Leu Arg Leu Xaa Cys Xaa Ala Ser Gly Xaa Xaa Leu Xaa Thr Tyr
                20                  25                  30

Gly Val His Trp Val Arg Gln Ala Pro Gly Lys Gly Leu Glu Trp Xaa
            35                  40                  45

Gly Val Ile Trp Gly Xaa Gly Arg Thr Asp Tyr Asp Xaa Xaa Phe Met
        50                  55                  60

Ser Arg Val Thr Ile Ser Xaa Asp Xaa Ser Lys Xaa Thr Xaa Tyr Leu
 65                 70                  75                  80

Gln Xaa Asn Ser Leu Arg Ala Glu Asp Thr Ala Val Tyr Tyr Cys Xaa
                85                  90                  95

Arg Xaa Arg His Asp Trp Phe Asp Tyr Trp Gly Gln Gly Thr Thr Val
```

-continued

```
                100                 105                 110
Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 3
<223> OTHER INFORMATION: Xaa = Leu or Glu
<220> FEATURE:
<221> NAME/KEY: VARIANT
<222> LOCATION: 4
<223> OTHER INFORMATION: Xaa = Met or Leu
<220> FEATURE:
<221> NAME/KEY: VARIANT
<222> LOCATION: 13
<223> OTHER INFORMATION: Xaa = Ala or Val
<220> FEATURE:
<221> NAME/KEY: VARIANT
<222> LOCATION: 14
<223> OTHER INFORMATION: Xaa = Ser or Thr
<220> FEATURE:
<221> NAME/KEY: VARIANT
<222> LOCATION: 15
<223> OTHER INFORMATION: Xaa = Leu, Pro or Ala
<220> FEATURE:
<221> NAME/KEY: VARIANT
<222> LOCATION: 17
<223> OTHER INFORMATION: Xaa = Asp or Glu
<220> FEATURE:
<221> NAME/KEY: VARIANT
<222> LOCATION: 19
<223> OTHER INFORMATION: Xaa = Val or Ala
<220> FEATURE:
<221> NAME/KEY: VARIANT
<222> LOCATION: 22
<223> OTHER INFORMATION: Xaa = Thr or Ser
<220> FEATURE:
<221> NAME/KEY: VARIANT
<222> LOCATION: 24
<223> OTHER INFORMATION: Xaa = Ser or Arg
<220> FEATURE:
<221> NAME/KEY: VARIANT
<222> LOCATION: 28
<223> OTHER INFORMATION: Xaa = Gly or Asp
<220> FEATURE:
<221> NAME/KEY: VARIANT
<222> LOCATION: 33
<223> OTHER INFORMATION: Xaa = Ser or Asn
<220> FEATURE:
<221> NAME/KEY: VARIANT
<222> LOCATION: 55
<223> OTHER INFORMATION: Xaa = His or Gln
<220> FEATURE:
<221> NAME/KEY: VARIANT
<222> LOCATION: 56
<223> OTHER INFORMATION: Xaa = Ser or Thr
<220> FEATURE:
<221> NAME/KEY: VARIANT
<222> LOCATION: 60
<223> OTHER INFORMATION: Xaa = Ser, Asp or Ala
<220> FEATURE:
<221> NAME/KEY: VARIANT
<222> LOCATION: 79
<223> OTHER INFORMATION: Xaa = Glu or Gln
<220> FEATURE:
<221> NAME/KEY: VARIANT
<222> LOCATION: 80
<223> OTHER INFORMATION: Xaa = Pro or Ala
```

```
<220> FEATURE:
<221> NAME/KEY: VARIANT
<222> LOCATION: 83
<223> OTHER INFORMATION: Xaa = Phe or Val
<220> FEATURE:
<221> NAME/KEY: VARIANT
<222> LOCATION: 85
<223> OTHER INFORMATION: Xaa = Thr, Ala or Ile
<220> FEATURE:
<221> NAME/KEY: VARIANT
<222> LOCATION: 92
<223> OTHER INFORMATION: Xaa = Ile or Asn
<220> FEATURE:
<221> NAME/KEY: VARIANT
<222> LOCATION: 96
<223> OTHER INFORMATION: Xaa = Phe or Leu

<400> SEQUENCE: 30

Xaa Ile Xaa Xaa Thr Gln Ser Pro Ser Ser Leu Ser Xaa Xaa Xaa Gly
 1               5                  10                  15

Xaa Arg Xaa Thr Ile Xaa Cys Xaa Ala Ser Gln Xaa Ile Arg Asn Xaa
            20                  25                  30

Leu Asn Trp Tyr Gln Gln Lys Pro Gly Gln Ala Pro Arg Leu Leu Ile
         35                  40                  45

Tyr Tyr Ser Ser Asn Leu Xaa Xaa Gly Val Pro Xaa Arg Phe Ser Gly
 50                  55                  60

Ser Gly Ser Gly Thr Asp Phe Thr Leu Thr Ile Ser Arg Leu Xaa Xaa
 65                  70                  75                  80

Glu Asp Xaa Ala Xaa Tyr Tyr Cys Gln Gln Ser Xaa Lys Leu Pro Xaa
             85                  90                  95

Thr Phe Gly Ser Gly Thr Lys Val Glu Ile Lys
            100                 105

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Phe or Tyr
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 5
<223> OTHER INFORMATION: Xaa = Thr, Asn or Ser

<400> SEQUENCE: 31

Gly Xaa Xaa Leu Xaa Thr Tyr Gly Val His
 1               5                  10

<210> SEQ ID NO 32
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Gly or Asp
<220> FEATURE:
<221> NAME/KEY: VARIANT
<222> LOCATION: 12
<223> OTHER INFORMATION: Xaa = Ala or Ser
```

```
<220> FEATURE:
<221> NAME/KEY: VARIANT
<222> LOCATION: 13
<223> OTHER INFORMATION: Xaa = Ala or Ser

<400> SEQUENCE: 32

Val Ile Trp Gly Xaa Gly Arg Thr Asp Tyr Asp Xaa Xaa Phe Met Ser
 1               5                  10                  15

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asn or Ser

<400> SEQUENCE: 33

Xaa Arg His Asp Trp Phe Asp Tyr
 1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser or Arg
<220> FEATURE:
<221> NAME/KEY: VARIANT
<222> LOCATION: 5
<223> OTHER INFORMATION: Xaa = Gly or Asp
<220> FEATURE:
<221> NAME/KEY: VARIANT
<222> LOCATION: 9
<223> OTHER INFORMATION: Xaa = Ser or Asn

<400> SEQUENCE: 34

Xaa Ala Ser Gln Xaa Ile Arg Asn Xaa Leu Asn
 1               5                  10

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = His or Gln
<220> FEATURE:
<221> NAME/KEY: VARIANT
<222> LOCATION: 7
<223> OTHER INFORMATION: Xaa = Ser or Thr

<400> SEQUENCE: 35

Tyr Ser Ser Asn Leu Xaa Xaa
 1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 4
<223> OTHER INFORMATION: Xaa = Ile or Asn
<220> FEATURE:
<221> NAME/KEY: VARIANT
<222> LOCATION: 8
<223> OTHER INFORMATION: Xaa = Phe or Leu

<400> SEQUENCE: 36

Gln Gln Ser Xaa Lys Leu Pro Xaa Thr
 1               5

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Glu or Gln
<220> FEATURE:
<221> NAME/KEY: VARIANT
<222> LOCATION: 9
<223> OTHER INFORMATION: Xaa = Ala or Gly
<220> FEATURE:
<221> NAME/KEY: VARIANT
<222> LOCATION: 10
<223> OTHER INFORMATION: Xaa = Gly or Glu
<220> FEATURE:
<221> NAME/KEY: VARIANT
<222> LOCATION: 11
<223> OTHER INFORMATION: Xaa = Leu or Val
<220> FEATURE:
<221> NAME/KEY: VARIANT
<222> LOCATION: 12
<223> OTHER INFORMATION: Xaa = Val, Lys or Glu
<220> FEATURE:
<221> NAME/KEY: VARIANT
<222> LOCATION: 16
<223> OTHER INFORMATION: Xaa = Gly or Glu
<220> FEATURE:
<221> NAME/KEY: VARIANT
<222> LOCATION: 17
<223> OTHER INFORMATION: Xaa = Thr or Ser
<220> FEATURE:
<221> NAME/KEY: VARIANT
<222> LOCATION: 21
<223> OTHER INFORMATION: Xaa = Thr or Ser
<220> FEATURE:
<221> NAME/KEY: VARIANT
<222> LOCATION: 23
<223> OTHER INFORMATION: Xaa = Thr or Lys

<400> SEQUENCE: 37

Glu Val Gln Leu Val Xaa Ser Gly Xaa Xaa Xaa Xaa Gln Pro Gly Xaa
 1               5                  10                  15

Xaa Leu Arg Leu Xaa Cys Xaa Ala Ser
             20                  25

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 13
<223> OTHER INFORMATION: Xaa = Val or Met

<400> SEQUENCE: 38
```

Trp Val Arg Gln Ala Pro Gly Lys Gly Leu Glu Trp Xaa Gly
1               5                   10

<210> SEQ ID NO 39
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Lys or Arg
<220> FEATURE:
<221> NAME/KEY: VARIANT
<222> LOCATION: 8
<223> OTHER INFORMATION: Xaa = Asn or Thr
<220> FEATURE:
<221> NAME/KEY: VARIANT
<222> LOCATION: 11
<223> OTHER INFORMATION: Xaa = Ser or Asn
<220> FEATURE:
<221> NAME/KEY: VARIANT
<222> LOCATION: 13
<223> OTHER INFORMATION: Xaa = Val or Ala
<220> FEATURE:
<221> NAME/KEY: VARIANT
<222> LOCATION: 17
<223> OTHER INFORMATION: Xaa = Met or Leu
<220> FEATURE:
<221> NAME/KEY: VARIANT
<222> LOCATION: 31
<223> OTHER INFORMATION: Xaa = Val, Met or Thr

<400> SEQUENCE: 39

Arg Val Thr Ile Ser Xaa Asp Xaa Ser Lys Xaa Thr Xaa Tyr Leu Gln
1               5                   10                  15

Xaa Asn Ser Leu Arg Ala Glu Asp Thr Ala Val Tyr Tyr Cys Xaa Arg
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Trp Gly Gln Gly Thr Thr Val Thr Val Ser Ser
1               5                   10

<210> SEQ ID NO 41
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 3
<223> OTHER INFORMATION: Xaa = Leu or Glu
<220> FEATURE:
<221> NAME/KEY: VARIANT
<222> LOCATION: 4
<223> OTHER INFORMATION: Xaa = Met or Leu
<220> FEATURE:
<221> NAME/KEY: VARIANT
<222> LOCATION: 13
<223> OTHER INFORMATION: Xaa = Ala or Val
<220> FEATURE:

```
<221> NAME/KEY: VARIANT
<222> LOCATION: 14
<223> OTHER INFORMATION: Xaa = Ser or Thr
<220> FEATURE:
<221> NAME/KEY: VARIANT
<222> LOCATION: 15
<223> OTHER INFORMATION: Xaa = Leu, Pro or Ala
<220> FEATURE:
<221> NAME/KEY: VARIANT
<222> LOCATION: 17
<223> OTHER INFORMATION: Xaa = Asp or Glu
<220> FEATURE:
<221> NAME/KEY: VARIANT
<222> LOCATION: 19
<223> OTHER INFORMATION: Xaa = Val or Ala
<220> FEATURE:
<221> NAME/KEY: VARIANT
<222> LOCATION: 22
<223> OTHER INFORMATION: Xaa = Thr or Ser

<400> SEQUENCE: 41

Xaa Ile Xaa Xaa Thr Gln Ser Pro Ser Ser Leu Ser Xaa Xaa Xaa Gly
 1               5                   10                  15

Xaa Arg Xaa Thr Ile Xaa Cys
            20

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42

Trp Tyr Gln Gln Lys Pro Gly Gln Ala Pro Arg Leu Leu Ile Tyr
 1               5                   10                  15

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser, Asp or Ala
<220> FEATURE:
<221> NAME/KEY: VARIANT
<222> LOCATION: 23
<223> OTHER INFORMATION: Xaa = Glu or Gln
<220> FEATURE:
<221> NAME/KEY: VARIANT
<222> LOCATION: 24
<223> OTHER INFORMATION: Xaa = Pro or Ala
<220> FEATURE:
<221> NAME/KEY: VARIANT
<222> LOCATION: 27
<223> OTHER INFORMATION: Xaa = Phe or Val
<220> FEATURE:
<221> NAME/KEY: VARIANT
<222> LOCATION: 29
<223> OTHER INFORMATION: Xaa = Thr, Ala or Ile

<400> SEQUENCE: 43

Gly Val Pro Xaa Arg Phe Ser Gly Ser Gly Ser Gly Thr Asp Phe Thr
 1               5                   10                  15

Leu Thr Ile Ser Arg Leu Xaa Xaa Glu Asp Xaa Ala Xaa Tyr Tyr Cys
            20                  25                  30

<210> SEQ ID NO 44
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 44

Phe Gly Ser Gly Thr Lys Val Glu Ile Lys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Construct

<400> SEQUENCE: 45

Tyr Ser Leu Arg Trp Ile Ser Asp His Glu Tyr Leu Tyr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Leu Glu Tyr Asn Tyr Val Lys Gln Trp Arg His Ser Tyr
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Thr Trp Ser Pro Val Gly His Lys Leu Ala Tyr Val Trp
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Construct

<400> SEQUENCE: 48

Leu Trp Trp Ser Pro Asn Gly Thr Phe Leu Ala Tyr Ala
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Construct

<400> SEQUENCE: 49

Arg Ile Ser Leu Gln Trp Leu Arg Arg Ile Gln Asn Tyr
1               5                   10

<210> SEQ ID NO 50
<211> LENGTH: 13
<212> TYPE: PRT
<213> ORGANISM: Artificial Sequence
```

```
<220> FEATURE:
<223> OTHER INFORMATION: Synthetic Construct

<400> SEQUENCE: 50

Tyr Val Lys Gln Trp Arg His Ser Tyr Thr Ala Ser Tyr
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Construct

<400> SEQUENCE: 51

Glu Glu Glu Val Phe Ser Ala Tyr Ser Ala Leu Trp Trp
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic Construct

<400> SEQUENCE: 52

Asp Tyr Ser Ile Ser Pro Asp Gly Gln Phe Ile Leu Leu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic Construct

<400> SEQUENCE: 53

Ser Ile Ser Pro Asp Gly Gln Phe Ile Leu Leu Glu Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic Construct

<400> SEQUENCE: 54

Ile Tyr Val Lys Ile Glu Pro Asn Leu Pro Ser Tyr Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Phe Ser Leu Thr Thr Tyr Gly Val His
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 56

Gly Phe Ser Leu Ser Thr Tyr Gly Val His
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Gly Tyr Ser Leu Thr Thr Tyr Gly Val His
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Synthetic Construct

<400> SEQUENCE: 58

Val Ile Trp Gly Asp Gly Arg Thr Asp Tyr Asp Ala Ala Phe Met Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct

<400> SEQUENCE: 59

Val Ile Trp Gly Asp Gly Arg Thr Asp Tyr Asp Ser Ser Phe Met Ser
1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Asn Arg His Asp Trp Phe Asp Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: Synthetic Construct

<400> SEQUENCE: 61

Arg Ala Ser Gln Asp Ile Arg Asn Asn Leu Asn
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62
```

```
Arg Ala Ser Gln Gly Ile Arg Asn Asn Leu Asn
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Construct

<400> SEQUENCE: 63

Ser Ala Ser Gln Asp Ile Arg Asn Ser Leu Asn
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct

<400> SEQUENCE: 64

Tyr Ser Ser Asn Leu His Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Tyr Ser Ser Asn Leu Gln Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct

<400> SEQUENCE: 66

Tyr Ser Ser Asn Leu His Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Gln Gln Ser Ile Lys Leu Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Gln Ser Ile Lys Leu Pro Phe Thr
```

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Gln Gln Ser Asn Lys Leu Pro Leu Thr
1               5

<210> SEQ ID NO 70
<211> LENGTH: 25
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Ala Gly Val Lys Gln Pro Gly Gly
1               5                   10                  15

Thr Leu Arg Leu Thr Cys Thr Ala Ser
            20                  25

<210> SEQ ID NO 71
<211> LENGTH: 25
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Gln Ser Gly Gly Gly Val Lys Gln Pro Gly Glu
1               5                   10                  15

Thr Leu Arg Leu Thr Cys Thr Ala Ser
            20                  25

<210> SEQ ID NO 72
<211> LENGTH: 25
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Gln Ser Gly Gly Gly Leu Lys Gln Pro Gly Glu
1               5                   10                  15

Thr Leu Arg Leu Ser Cys Thr Ala Ser
            20                  25

<210> SEQ ID NO 73
<211> LENGTH: 25
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Val Lys Gln Pro Gly Glu
1               5                   10                  15

Thr Leu Arg Leu Thr Cys Thr Ala Ser
            20                  25

```
<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Trp Val Arg Gln Ala Pro Gly Lys Gly Leu Glu Trp Val Gly
 1               5                  10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Trp Val Arg Gln Ala Pro Gly Lys Gly Leu Glu Trp Met Gly
 1               5                  10

<210> SEQ ID NO 76
<211> LENGTH: 32
<212> TYPE: PRT
<213> ORGANISM: Artificial Sequence
<220> FEATURE:
<223> OTHER INFORMATION: Synthetic Construct

<400> SEQUENCE: 76

Arg Val Thr Ile Ser Lys Asp Thr Ser Lys Ser Thr Val Tyr Leu Gln
 1               5                  10                  15

Met Asn Ser Leu Arg Ala Glu Asp Thr Ala Val Tyr Tyr Cys Met Arg
                20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Synthetic Construct

<400> SEQUENCE: 77

Arg Val Thr Ile Ser Lys Asp Thr Ser Lys Ser Thr Ala Tyr Leu Gln
 1               5                  10                  15

Met Asn Ser Leu Arg Ala Glu Asp Thr Ala Val Tyr Tyr Cys Met Arg
                20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Synthetic Construct

<400> SEQUENCE: 78

Arg Val Thr Ile Ser Lys Asp Thr Ser Lys Ser Thr Ala Tyr Leu Gln
 1               5                  10                  15

Leu Asn Ser Leu Arg Ala Glu Asp Thr Ala Val Tyr Tyr Cys Thr Arg
                20                  25                  30

<210> SEQ ID NO 79
<211> LENGTH: 23
<212> TYPE: PRT
<213> ORGANISM: Artificial Sequence
<220> FEATURE:
<223> OTHER INFORMATION: Synthetic Construct
```

<400> SEQUENCE: 79

Asp Ile Leu Met Thr Gln Ser Pro Ser Ser Leu Ser Ala Ser Pro Gly
1               5                   10                  15

Asp Arg Val Thr Ile Ser Cys
            20

<210> SEQ ID NO 80
<211> LENGTH: 23
<212> TYPE: PRT
<213> ORGANISM: Artificial Sequence
<220> FEATURE:
<223> OTHER INFORMATION: Synthetic Construct

<400> SEQUENCE: 80

Asp Ile Leu Leu Thr Gln Ser Pro Ser Ser Leu Ser Ala Thr Pro Gly
1               5                   10                  15

Glu Arg Ala Thr Ile Thr Cys
            20

<210> SEQ ID NO 81
<211> LENGTH: 23
<212> TYPE: PRT
<213> ORGANISM: Artificial Sequence
<220> FEATURE:
<223> OTHER INFORMATION: Synthetic Construct

<400> SEQUENCE: 81

Glu Ile Glu Met Thr Gln Ser Pro Ser Ser Leu Ser Val Ser Ala Gly
1               5                   10                  15

Glu Arg Ala Thr Ile Ser Cys
            20

<210> SEQ ID NO 82
<211> LENGTH: 32
<212> TYPE: PRT
<213> ORGANISM: Artificial Sequence
<220> FEATURE:
<223> OTHER INFORMATION: Synthetic Construct

<400> SEQUENCE: 82

Gly Val Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Ala Tyr Tyr Cys
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Synthetic Construct

<400> SEQUENCE: 83

Gly Val Pro Ser Arg Phe Ser Gly Ser Gly Ser Gly Thr Asp Phe Thr
1               5                   10                  15

Leu Thr Ile Ser Arg Leu Gln Pro Glu Asp Val Ala Ala Tyr Tyr Cys
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Synthetic Construct

<400> SEQUENCE: 84

Gly Val Pro Ala Arg Phe Ser Gly Ser Gly Ser Gly Thr Asp Phe Thr
1               5                   10                  15

Leu Thr Ile Ser Arg Leu Glu Pro Glu Asp Val Ala Ile Tyr Tyr Cys
            20                  25                  30

<210> SEQ ID NO 85
<211> LENGTH: 15
<212> TYPE: PRT
<213> ORGANISM: Artificial Sequence
<220> FEATURE:
<223> OTHER INFORMATION: Synthetic Construct

<400> SEQUENCE: 85

Gly Gly Gly Gly Ser Gly Gly Gly Gly Ser Gly Gly Gly Gly Ser
1               5                   10                  15

<210> SEQ ID NO 86
<211> LENGTH: 15
<212> TYPE: PRT
<213> ORGANISM: Homo sapiens

<400> SEQUENCE: 86

Glu Pro Lys Ser Cys Asp Lys Thr His Thr Cys Pro Pro Cys Pro
1               5                   10                  15

<210> SEQ ID NO 87
<211> LENGTH: 334
<212> TYPE: PRT
<213> ORGANISM: Homo sapiens

<400> SEQUENCE: 87

Thr Val Ser Ser Ala Ser Thr Lys Gly Pro Ser Val Phe Pro Leu Ala
1               5                   10                  15

Pro Ser Ser Lys Ser Thr Ser Gly Gly Thr Ala Ala Leu Gly Cys Leu
            20                  25                  30

Val Lys Asp Tyr Phe Pro Glu Pro Val Thr Val Ser Trp Asn Ser Gly
        35                  40                  45

Ala Leu Thr Ser Gly Val His Thr Phe Pro Ala Val Leu Gln Ser Ser
    50                  55                  60

Gly Leu Tyr Ser Leu Ser Ser Val Val Thr Val Pro Ser Ser Ser Leu
65                  70                  75                  80

Gly Thr Gln Thr Tyr Ile Cys Asn Val Asn His Lys Pro Ser Asn Thr
                85                  90                  95

Lys Val Asp Lys Lys Val Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

-continued

Lys Val Ser Asn Lys Ala Leu Pro Ala Pro Ile Glu Lys Thr Ile Ser
            210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 88
<211> LENGTH: 107
<212> TYPE: PRT
<213> ORGANISM: Homo sapiens

<400> SEQUENCE: 88

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 89
<211> LENGTH: 766
<212> TYPE: PRT
<213> ORGANISM: Homo sapiens

<400> SEQUENCE: 89

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln

```
                    100                 105                 110
Phe Ile Leu Leu Glu Tyr Asn Tyr Val Lys Gln Trp Arg His Ser Tyr
            115                 120                 125
Thr Ala Ser Tyr Asp Ile Tyr Asp Leu Asn Lys Arg Gln Leu Ile Thr
            130                 135                 140
Glu Glu Arg Ile Pro Asn Asn Thr Gln Trp Val Thr Trp Ser Pro Val
145                 150                 155                 160
Gly His Lys Leu Ala Tyr Val Trp Asn Asn Asp Ile Tyr Val Lys Ile
            165                 170                 175
Glu Pro Asn Leu Pro Ser Tyr Arg Ile Thr Trp Thr Gly Lys Glu Asp
            180                 185                 190
Ile Ile Tyr Asn Gly Ile Thr Asp Trp Val Tyr Glu Glu Val Phe
            195                 200                 205
Ser Ala Tyr Ser Ala Leu Trp Trp Ser Pro Asn Gly Thr Phe Leu Ala
            210                 215                 220
Tyr Ala Gln Phe Asn Asp Thr Glu Val Pro Leu Ile Glu Tyr Ser Phe
225                 230                 235                 240
Tyr Ser Asp Glu Ser Leu Gln Tyr Pro Lys Thr Val Arg Val Pro Tyr
            245                 250                 255
Pro Lys Ala Gly Ala Val Asn Pro Thr Val Lys Phe Phe Val Val Asn
            260                 265                 270
Thr Asp Ser Leu Ser Ser Val Thr Asn Ala Thr Ser Ile Gln Ile Thr
            275                 280                 285
Ala Pro Ala Ser Met Leu Ile Gly Asp His Tyr Leu Cys Asp Val Thr
            290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
            325                 330                 335
Trp Asn Cys Leu Val Ala Arg Gln His Ile Glu Met Ser Thr Thr Gly
            340                 345                 350
Trp Val Gly Arg Phe Arg Pro Ser Glu Pro His Phe Thr Leu Asp Gly
            355                 360                 365
Asn Ser Phe Tyr Lys Ile Ile Ser Asn Glu Glu Gly Tyr Arg His Ile
            370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
            405                 410                 415
Tyr Ile Ser Asn Glu Tyr Lys Gly Met Pro Gly Gly Arg Asn Leu Tyr
            420                 425                 430
Lys Ile Gln Leu Ser Asp Tyr Thr Lys Val Thr Cys Leu Ser Cys Glu
            435                 440                 445
Leu Asn Pro Glu Arg Cys Gln Tyr Tyr Ser Val Ser Phe Ser Lys Glu
            450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
            485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
            515                 520                 525
```

```
Ile Leu Pro Pro His Phe Asp Lys Ser Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
                660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
                740                 745                 750

Thr His Met Ser His Phe Ile Lys Gln Cys Phe Ser Leu Pro
            755                 760                 765

<210> SEQ ID NO 90
<211> LENGTH: 116
<212> TYPE: PRT
<213> ORGANISM: Artificial Sequence
<220> FEATURE:
<223> OTHER INFORMATION: Synthetic Construct

<400> SEQUENCE: 90

Gln Val Lys Leu Gln Glu Ser Gly Pro Gly Leu Val Gln Pro Ser Gln
 1                5                  10                  15

Thr Leu Ser Ile Thr Cys Thr Val Ser Gly Phe Ser Leu Thr Thr Tyr
                20                  25                  30

Gly Val His Trp Val Arg Gln Ser Pro Gly Lys Gly Leu Glu Trp Leu
            35                  40                  45

Gly Val Ile Trp Gly Gly Gly Arg Thr Asp Tyr Asp Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Val
                85                  90                  95

Arg Asn Arg His Asp Trp Phe Asp Tyr Trp Gly Gln Gly Thr Thr Val
                100                 105                 110

Thr Val Ser Ser
            115
```

```
<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Leu Gly
 1               5                  10                  15

Asp Arg Val Thr Ile Thr Cys Ser Ala Ser Gln Gly Ile Arg Asn Ser
            20                  25                  30

Leu Asn Trp Tyr Gln Gln Lys Pro Asp Gly Ala Val Lys Leu Leu Ile
        35                  40                  45

Tyr Tyr Ser Ser Asn Leu His Ser Gly Val Pro Ser Arg Phe Ser Gly
    50                  55                  60

Ser Gly Ser Gly Thr Asp Phe Ser Leu Thr Ile Ser Asn Leu Glu Pro
65                  70                  75                  80

Glu Asp Ile Ala Thr Tyr Tyr Cys Gln Gln Ser Ile Lys Leu Pro Phe
                85                  90                  95

Thr Phe Gly Ser Gly Thr Lys Leu Glu Ile Lys
            100                 105

<210> SEQ ID NO 92
<211> LENGTH: 13
<212> TYPE: PRT
<213> ORGANISM: Artificial Sequence
<220> FEATURE:
<223> OTHER INFORMATION: Synthetic Construct

<400> SEQUENCE: 92

Tyr Leu Lys Asn Thr Tyr Arg Leu Lys Leu Tyr Ser Leu
 1               5                  10

<210> SEQ ID NO 93
<211> LENGTH: 13
<212> TYPE: PRT
<213> ORGANISM: Artificial Sequence
<220> FEATURE:
<223> OTHER INFORMATION: Synthetic Construct

<400> SEQUENCE: 93

Lys Asn Thr Tyr Arg Leu Lys Leu Tyr Ser Leu Arg Trp
 1               5                  10

<210> SEQ ID NO 94
<211> LENGTH: 13
<212> TYPE: PRT
<213> ORGANISM: Artificial Sequence
<220> FEATURE:
<223> OTHER INFORMATION: Synthetic Construct

<400> SEQUENCE: 94

Thr Tyr Arg Leu Lys Leu Tyr Ser Leu Arg Trp Ile Ser
 1               5                  10

<210> SEQ ID NO 95
<211> LENGTH: 13
<212> TYPE: PRT
<213> ORGANISM: Artificial Sequence
<220> FEATURE:
<223> OTHER INFORMATION: Synthetic Construct

<400> SEQUENCE: 95

Arg Leu Lys Leu Tyr Ser Leu Arg Trp Ile Ser Asp His
```

<210> SEQ ID NO 96
<211> LENGTH: 13
<212> TYPE: PRT
<213> ORGANISM: Artificial Sequence
<220> FEATURE:
<223> OTHER INFORMATION: Synthetic Construct

<400> SEQUENCE: 96

Lys Leu Tyr Ser Leu Arg Trp Ile Ser Asp His Glu Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Leu Arg Trp Ile Ser Asp His Glu Tyr Leu Tyr Lys Gln
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic Construct

<400> SEQUENCE: 98

Trp Ile Ser Asp His Glu Tyr Leu Tyr Lys Gln Glu Asn
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic Construct

<400> SEQUENCE: 99

Ser Asp His Glu Tyr Leu Tyr Lys Gln Glu Asn Asn Ile
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic Construct

<400> SEQUENCE: 100

His Glu Tyr Leu Tyr Lys Gln Glu Asn Asn Ile Leu Val
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic Construct

<400> SEQUENCE: 101

Tyr Leu Tyr Lys Gln Glu Asn Asn Ile Leu Val Phe Asn
1               5                   10

```
<210> SEQ ID NO 102
<211> LENGTH: 13
<212> TYPE: PRT
<213> ORGANISM: Artificial Sequence
<220> FEATURE:
<223> OTHER INFORMATION: Synthetic Construct

<400> SEQUENCE: 102

Tyr Lys Gln Glu Asn Asn Ile Leu Val Phe Asn Ala Glu
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Synthetic Construct

<400> SEQUENCE: 103

Gln Glu Asn Asn Ile Leu Val Phe Asn Ala Glu Tyr Gly
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic Construct

<400> SEQUENCE: 104

Asn Asn Ile Leu Val Phe Asn Ala Glu Tyr Gly Asn Ser
 1               5                  10

<210> SEQ ID NO 105
<211> LENGTH: 13
<212> TYPE: PRT
<213> ORGANISM: Artificial Sequence
<220> FEATURE:
<223> OTHER INFORMATION: Synthetic Construct

<400> SEQUENCE: 105

Ile Leu Val Phe Asn Ala Glu Tyr Gly Asn Ser Ser Val
 1               5                  10

<210> SEQ ID NO 106
<211> LENGTH: 13
<212> TYPE: PRT
<213> ORGANISM: Artificial Sequence
<220> FEATURE:
<223> OTHER INFORMATION: Synthetic Construct

<400> SEQUENCE: 106

Val Phe Asn Ala Glu Tyr Gly Asn Ser Ser Val Phe Leu
 1               5                  10

<210> SEQ ID NO 107
<211> LENGTH: 13
<212> TYPE: PRT
<213> ORGANISM: Artificial Sequence
<220> FEATURE:
<223> OTHER INFORMATION: Synthetic Construct

<400> SEQUENCE: 107

Asn Ala Glu Tyr Gly Asn Ser Ser Val Phe Leu Glu Asn
 1               5                  10

<210> SEQ ID NO 108
```

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 108

Glu Tyr Gly Asn Ser Ser Val Phe Leu Glu Asn Ser Thr
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic Construct

<400> SEQUENCE: 109

Gly Asn Ser Ser Val Phe Leu Glu Asn Ser Thr Phe Asp
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic Construct

<400> SEQUENCE: 110

Ser Ser Val Phe Leu Glu Asn Ser Thr Phe Asp Glu Phe
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic Construct

<400> SEQUENCE: 111

Val Phe Leu Glu Asn Ser Thr Phe Asp Glu Phe Gly His
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic Construct

<400> SEQUENCE: 112

Leu Glu Asn Ser Thr Phe Asp Glu Phe Gly His Ser Ile
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic Construct

<400> SEQUENCE: 113

Asn Ser Thr Phe Asp Glu Phe Gly His Ser Ile Asn Asp
1               5                   10

<210> SEQ ID NO 114
<211> LENGTH: 13
<212> TYPE: PRT
```

<213> ORGANISM: Artificial Sequence
<220> FEATURE:
<223> OTHER INFORMATION: Synthetic Construct

<400> SEQUENCE: 114

Thr Phe Asp Glu Phe Gly His Ser Ile Asn Asp Tyr Ser
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic Construct

<400> SEQUENCE: 115

Asp Glu Phe Gly His Ser Ile Asn Asp Tyr Ser Ile Ser
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic Construct

<400> SEQUENCE: 116

Phe Gly His Ser Ile Asn Asp Tyr Ser Ile Ser Pro Asp
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic Construct

<400> SEQUENCE: 117

His Ser Ile Asn Asp Tyr Ser Ile Ser Pro Asp Gly Gln
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic Construct

<400> SEQUENCE: 118

Ile Asn Asp Tyr Ser Ile Ser Pro Asp Gly Gln Phe Ile
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Synthetic Construct

<400> SEQUENCE: 119

Ser Pro Asp Gly Gln Phe Ile Leu Leu Glu Tyr Asn Tyr
1               5                   10

<210> SEQ ID NO 120
<211> LENGTH: 13
<212> TYPE: PRT
<213> ORGANISM: Artificial Sequence
<220> FEATURE:

<223> OTHER INFORMATION: Synthetic Construct

<400> SEQUENCE: 120

Asp Gly Gln Phe Ile Leu Leu Glu Tyr Asn Tyr Val Lys
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Synthetic Construct

<400> SEQUENCE: 121

Gln Phe Ile Leu Leu Glu Tyr Asn Tyr Val Lys Gln Trp
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic Construct

<400> SEQUENCE: 122

Ile Leu Leu Glu Tyr Asn Tyr Val Lys Gln Trp Arg His
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic Construct

<400> SEQUENCE: 123

Tyr Asn Tyr Val Lys Gln Trp Arg His Ser Tyr Thr Ala
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic Construct

<400> SEQUENCE: 124

Ser Leu Gln Trp Leu Arg Arg Ile Gln Asn Tyr Ser Val
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Synthetic Construct

<400> SEQUENCE: 125

Lys Gln Trp Arg His Ser Tyr Thr Ala Ser Tyr Asp Ile
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 126

Trp Arg His Ser Tyr Thr Ala Ser Tyr Asp Ile Tyr Asp
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Synthetic Construct

<400> SEQUENCE: 127

His Ser Tyr Thr Ala Ser Tyr Asp Ile Tyr Asp Leu Asn
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Synthetic Construct

<400> SEQUENCE: 128

Tyr Thr Ala Ser Tyr Asp Ile Tyr Asp Leu Asn Lys Arg
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthetic Construct

<400> SEQUENCE: 129

Ala Ser Tyr Asp Ile Tyr Asp Leu Asn Lys Arg Gln Leu
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic Construct

<400> SEQUENCE: 130

Tyr Asp Ile Tyr Asp Leu Asn Lys Arg Gln Leu Ile Thr
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic Construct

<400> SEQUENCE: 131

Ile Tyr Asp Leu Asn Lys Arg Gln Leu Ile Thr Glu Glu
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Synthetic Construct

<400> SEQUENCE: 132
```

```
Asp Leu Asn Lys Arg Gln Leu Ile Thr Glu Glu Arg Ile
1               5                   10
```

<210> SEQ ID NO 133
<211> LENGTH: 13
<212> TYPE: PRT
<213> ORGANISM: Artificial Sequence
<220> FEATURE:
<223> OTHER INFORMATION: Synthetic Construct

<400> SEQUENCE: 133

```
Asn Lys Arg Gln Leu Ile Thr Glu Glu Arg Ile Pro Asn
1               5                   10
```

<210> SEQ ID NO 134
<211> LENGTH: 13
<212> TYPE: PRT
<213> ORGANISM: Artificial Sequence
<220> FEATURE:
<223> OTHER INFORMATION: Synthetic Construct

<400> SEQUENCE: 134

```
Arg Gln Leu Ile Thr Glu Glu Arg Ile Pro Asn Asn Thr
1               5                   10
```

<210> SEQ ID NO 135
<211> LENGTH: 13
<212> TYPE: PRT
<213> ORGANISM: Artificial Sequence
<220> FEATURE:
<223> OTHER INFORMATION: Synthetic Construct

<400> SEQUENCE: 135

```
Leu Ile Thr Glu Glu Arg Ile Pro Asn Asn Thr Gln Trp
1               5                   10
```

<210> SEQ ID NO 136
<211> LENGTH: 13
<212> TYPE: PRT
<213> ORGANISM: Artificial Sequence
<220> FEATURE:
<223> OTHER INFORMATION: Synthetic Construct

<400> SEQUENCE: 136

```
Thr Glu Glu Arg Ile Pro Asn Asn Thr Gln Trp Val Thr
1               5                   10
```

<210> SEQ ID NO 137
<211> LENGTH: 13
<212> TYPE: PRT
<213> ORGANISM: Artificial Sequence
<220> FEATURE:
<223> OTHER INFORMATION: Synthetic Construct

<400> SEQUENCE: 137

```
Glu Arg Ile Pro Asn Asn Thr Gln Trp Val Thr Trp Ser
1               5                   10
```

<210> SEQ ID NO 138
<211> LENGTH: 13
<212> TYPE: PRT
<213> ORGANISM: Artificial Sequence
<220> FEATURE:
<223> OTHER INFORMATION: Synthetic Construct

<400> SEQUENCE: 138

```
Ile Pro Asn Asn Thr Gln Trp Val Thr Trp Ser Pro Val
1               5                   10
```

<210> SEQ ID NO 139
<211> LENGTH: 13
<212> TYPE: PRT
<213> ORGANISM: Artificial Sequence
<220> FEATURE:
<223> OTHER INFORMATION: Synthetic Construct

<400> SEQUENCE: 139

Asn Asn Thr Gln Trp Val Thr Trp Ser Pro Val Gly His
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic Construct

<400> SEQUENCE: 140

Thr Gln Trp Val Thr Trp Ser Pro Val Gly His Lys Leu
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic Construct

<400> SEQUENCE: 141

Trp Val Thr Trp Ser Pro Val Gly His Lys Leu Ala Tyr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic Construct

<400> SEQUENCE: 142

Ser Pro Val Gly His Lys Leu Ala Tyr Val Trp Asn Asn
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Synthetic Construct

<400> SEQUENCE: 143

Val Gly His Lys Leu Ala Tyr Val Trp Asn Asn Asp Ile
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic Construct

<400> SEQUENCE: 144

His Lys Leu Ala Tyr Val Trp Asn Asn Asp Ile Tyr Val
1               5                   10

```
<210> SEQ ID NO 145
<211> LENGTH: 13
<212> TYPE: PRT
<213> ORGANISM: Artificial Sequence
<220> FEATURE:
<223> OTHER INFORMATION: Synthetic Construct

<400> SEQUENCE: 145

Leu Ala Tyr Val Trp Asn Asn Asp Ile Tyr Val Lys Ile
 1               5                  10

<210> SEQ ID NO 146
<211> LENGTH: 13
<212> TYPE: PRT
<213> ORGANISM: Artificial Sequence
<220> FEATURE:
<223> OTHER INFORMATION: Synthetic Construct

<400> SEQUENCE: 146

Tyr Val Trp Asn Asn Asp Ile Tyr Val Lys Ile Glu Pro
 1               5                  10

<210> SEQ ID NO 147
<211> LENGTH: 13
<212> TYPE: PRT
<213> ORGANISM: Artificial Sequence
<220> FEATURE:
<223> OTHER INFORMATION: Synthetic Construct

<400> SEQUENCE: 147

Trp Asn Asn Asp Ile Tyr Val Lys Ile Glu Pro Asn Leu
 1               5                  10

<210> SEQ ID NO 148
<211> LENGTH: 13
<212> TYPE: PRT
<213> ORGANISM: Artificial Sequence
<220> FEATURE:
<223> OTHER INFORMATION: Synthetic Construct

<400> SEQUENCE: 148

Asn Asp Ile Tyr Val Lys Ile Glu Pro Asn Leu Pro Ser
 1               5                  10

<210> SEQ ID NO 149
<211> LENGTH: 13
<212> TYPE: PRT
<213> ORGANISM: Artificial Sequence
<220> FEATURE:
<223> OTHER INFORMATION: Synthetic Construct

<400> SEQUENCE: 149

Val Lys Ile Glu Pro Asn Leu Pro Ser Tyr Arg Ile Thr
 1               5                  10

<210> SEQ ID NO 150
<211> LENGTH: 13
<212> TYPE: PRT
<213> ORGANISM: Artificial Sequence
<220> FEATURE:
<223> OTHER INFORMATION: Synthetic Construct

<400> SEQUENCE: 150

Ile Glu Pro Asn Leu Pro Ser Tyr Arg Ile Thr Trp Thr
 1               5                  10

<210> SEQ ID NO 151
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 151

Pro Asn Leu Pro Ser Tyr Arg Ile Thr Trp Thr Gly Lys
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic Construct

<400> SEQUENCE: 152

Leu Pro Ser Tyr Arg Ile Thr Trp Thr Gly Lys Glu Asp
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic Construct

<400> SEQUENCE: 153

Ser Tyr Arg Ile Thr Trp Thr Gly Lys Glu Asp Ile Ile
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Synthetic Construct

<400> SEQUENCE: 154

Arg Ile Thr Trp Thr Gly Lys Glu Asp Ile Ile Tyr Asn
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Synthetic Construct

<400> SEQUENCE: 155

Thr Trp Thr Gly Lys Glu Asp Ile Ile Tyr Asn Gly Ile
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Synthetic Construct

<400> SEQUENCE: 156

Thr Gly Lys Glu Asp Ile Ile Tyr Asn Gly Ile Thr Asp
1               5                   10

<210> SEQ ID NO 157
<211> LENGTH: 13
<212> TYPE: PRT
<213> ORGANISM: Artificial Sequence
```

<220> FEATURE:
<223> OTHER INFORMATION: Synthetic Construct

<400> SEQUENCE: 157

Lys Glu Asp Ile Ile Tyr Asn Gly Ile Thr Asp Trp Val
1               5                   10

<210> SEQ ID NO 158
<211> LENGTH: 13
<212> TYPE: PRT
<213> ORGANISM: Artificial Sequence
<220> FEATURE:
<223> OTHER INFORMATION: Synthetic Construct

<400> SEQUENCE: 158

Asp Ile Ile Tyr Asn Gly Ile Thr Asp Trp Val Tyr Glu
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic Construct

<400> SEQUENCE: 159

Ile Tyr Asn Gly Ile Thr Asp Trp Val Tyr Glu Glu Glu
1               5                   10

<210> SEQ ID NO 160
<211> LENGTH: 13
<212> TYPE: PRT
<213> ORGANISM: Artificial Sequence
<220> FEATURE:
<223> OTHER INFORMATION: Synthetic Construct

<400> SEQUENCE: 160

Asn Gly Ile Thr Asp Trp Val Tyr Glu Glu Glu Val Phe
1               5                   10

<210> SEQ ID NO 161
<211> LENGTH: 13
<212> TYPE: PRT
<213> ORGANISM: Artificial Sequence
<220> FEATURE:
<223> OTHER INFORMATION: Synthetic Construct

<400> SEQUENCE: 161

Ile Thr Asp Trp Val Tyr Glu Glu Glu Val Phe Ser Ala
1               5                   10

<210> SEQ ID NO 162
<211> LENGTH: 13
<212> TYPE: PRT
<213> ORGANISM: Artificial Sequence
<220> FEATURE:
<223> OTHER INFORMATION: Synthetic Construct

<400> SEQUENCE: 162

Asp Trp Val Tyr Glu Glu Glu Val Phe Ser Ala Tyr Ser
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 163

Val Tyr Glu Glu Val Phe Ser Ala Tyr Ser Ala Leu
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Synthetic Construct

<400> SEQUENCE: 164

Glu Val Phe Ser Ala Tyr Ser Ala Leu Trp Trp Ser Pro
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Synthetic Construct

<400> SEQUENCE: 165

Phe Ser Ala Tyr Ser Ala Leu Trp Trp Ser Pro Asn Gly
1               5                   10

<210> SEQ ID NO 166
<211> LENGTH: 13
<212> TYPE: PRT
<213> ORGANISM: Artificial Sequence
<220> FEATURE:
<223> OTHER INFORMATION: Synthetic Construct

<400> SEQUENCE: 166

Ala Tyr Ser Ala Leu Trp Trp Ser Pro Asn Gly Thr Phe
1               5                   10

<210> SEQ ID NO 167
<211> LENGTH: 13
<212> TYPE: PRT
<213> ORGANISM: Artificial Sequence
<220> FEATURE:
<223> OTHER INFORMATION: Synthetic Construct

<400> SEQUENCE: 167

Ser Ala Leu Trp Trp Ser Pro Asn Gly Thr Phe Leu Ala
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Synthetic Construct

<400> SEQUENCE: 168

Trp Ser Pro Asn Gly Thr Phe Leu Ala Tyr Ala Gln Phe
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Synthetic Construct

<400> SEQUENCE: 169
```

-continued

```
Pro Asn Gly Thr Phe Leu Ala Tyr Ala Gln Phe Asn Asp
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Synthetic Construct

<400> SEQUENCE: 170

Gly Thr Phe Leu Ala Tyr Ala Gln Phe Asn Asp Thr Glu
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Synthetic Construct

<400> SEQUENCE: 171

Phe Leu Ala Tyr Ala Gln Phe Asn Asp Thr Glu Val Pro
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Synthetic Construct

<400> SEQUENCE: 172

Ala Tyr Ala Gln Phe Asn Asp Thr Glu Val Pro Leu Ile
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Synthetic Construct

<400> SEQUENCE: 173

Ala Gln Phe Asn Asp Thr Glu Val Pro Leu Ile Glu Tyr
1               5                   10

<210> SEQ ID NO 174
<211> LENGTH: 13
<212> TYPE: PRT
<213> ORGANISM: Artificial Sequence
<220> FEATURE:
<223> OTHER INFORMATION: Synthetic Construct

<400> SEQUENCE: 174

Phe Asn Asp Thr Glu Val Pro Leu Ile Glu Tyr Ser Phe
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthetic Construct

<400> SEQUENCE: 175

Asp Thr Glu Val Pro Leu Ile Glu Tyr Ser Phe Tyr Ser
```

```
                1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: Synthetic Construct

<400> SEQUENCE: 176

```
Glu Val Pro Leu Ile Glu Tyr Ser Phe Tyr Ser Asp Glu
 1               5                   10
```

<210> SEQ ID NO 177
<211> LENGTH: 13
<212> TYPE: PRT
<213> ORGANISM: Artificial Sequence
<220> FEATURE:
<223> OTHER INFORMATION: Synthetic Construct

<400> SEQUENCE: 177

```
Pro Leu Ile Glu Tyr Ser Phe Tyr Ser Asp Glu Ser Leu
 1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: Synthetic Construct

<400> SEQUENCE: 178

```
Ile Glu Tyr Ser Phe Tyr Ser Asp Glu Ser Leu Gln Tyr
 1               5                   10
```

<210> SEQ ID NO 179
<211> LENGTH: 13
<212> TYPE: PRT
<213> ORGANISM: Artificial Sequence
<220> FEATURE:
<223> OTHER INFORMATION: Synthetic Construct

<400> SEQUENCE: 179

```
Tyr Ser Phe Tyr Ser Asp Glu Ser Leu Gln Tyr Pro Lys
 1               5                   10
```

<210> SEQ ID NO 180
<211> LENGTH: 13
<212> TYPE: PRT
<213> ORGANISM: Artificial Sequence
<220> FEATURE:
<223> OTHER INFORMATION: Synthetic Construct

<400> SEQUENCE: 180

```
Phe Tyr Ser Asp Glu Ser Leu Gln Tyr Pro Lys Thr Val
 1               5                   10
```

<210> SEQ ID NO 181
<211> LENGTH: 13
<212> TYPE: PRT
<213> ORGANISM: Artificial Sequence
<220> FEATURE:
<223> OTHER INFORMATION: Synthetic Construct

<400> SEQUENCE: 181

```
Ser Asp Glu Ser Leu Gln Tyr Pro Lys Thr Val Arg Val
 1               5                   10
```

<210> SEQ ID NO 182
<211> LENGTH: 13
<212> TYPE: PRT
<213> ORGANISM: Artificial Sequence
<220> FEATURE:
<223> OTHER INFORMATION: Synthetic Construct

<400> SEQUENCE: 182

Glu Ser Leu Gln Tyr Pro Lys Thr Val Arg Val Pro Tyr
 1               5                  10

<210> SEQ ID NO 183
<211> LENGTH: 13
<212> TYPE: PRT
<213> ORGANISM: Artificial Sequence
<220> FEATURE:
<223> OTHER INFORMATION: Synthetic Construct

<400> SEQUENCE: 183

Leu Gln Tyr Pro Lys Thr Val Arg Val Pro Tyr Pro Lys
 1               5                  10

<210> SEQ ID NO 184
<211> LENGTH: 13
<212> TYPE: PRT
<213> ORGANISM: Artificial Sequence
<220> FEATURE:
<223> OTHER INFORMATION: Synthetic Construct

<400> SEQUENCE: 184

Tyr Pro Lys Thr Val Arg Val Pro Tyr Pro Lys Ala Gly
 1               5                  10

<210> SEQ ID NO 185
<211> LENGTH: 13
<212> TYPE: PRT
<213> ORGANISM: Artificial Sequence
<220> FEATURE:
<223> OTHER INFORMATION: Synthetic Construct

<400> SEQUENCE: 185

Lys Thr Val Arg Val Pro Tyr Pro Lys Ala Gly Ala Val
 1               5                  10

<210> SEQ ID NO 186
<211> LENGTH: 13
<212> TYPE: PRT
<213> ORGANISM: Artificial Sequence
<220> FEATURE:
<223> OTHER INFORMATION: Synthetic Construct

<400> SEQUENCE: 186

Val Arg Val Pro Tyr Pro Lys Ala Gly Ala Val Asn Pro
 1               5                  10

<210> SEQ ID NO 187
<211> LENGTH: 13
<212> TYPE: PRT
<213> ORGANISM: Artificial Sequence
<220> FEATURE:
<223> OTHER INFORMATION: Synthetic Construct

<400> SEQUENCE: 187

Val Pro Tyr Pro Lys Ala Gly Ala Val Asn Pro Thr Val
 1               5                  10

<210> SEQ ID NO 188

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 188

Tyr Pro Lys Ala Gly Ala Val Asn Pro Thr Val Lys Phe
 1               5                  10

<210> SEQ ID NO 189
<211> LENGTH: 13
<212> TYPE: PRT
<213> ORGANISM: Artificial Sequence
<220> FEATURE:
<223> OTHER INFORMATION: Synthetic Construct

<400> SEQUENCE: 189

Lys Ala Gly Ala Val Asn Pro Thr Val Lys Phe Phe Val
 1               5                  10

<210> SEQ ID NO 190
<211> LENGTH: 13
<212> TYPE: PRT
<213> ORGANISM: Artificial Sequence
<220> FEATURE:
<223> OTHER INFORMATION: Synthetic Construct

<400> SEQUENCE: 190

Gly Ala Val Asn Pro Thr Val Lys Phe Phe Val Val Asn
 1               5                  10

<210> SEQ ID NO 191
<211> LENGTH: 13
<212> TYPE: PRT
<213> ORGANISM: Artificial Sequence
<220> FEATURE:
<223> OTHER INFORMATION: Synthetic Construct

<400> SEQUENCE: 191

Val Asn Pro Thr Val Lys Phe Phe Val Val Asn Thr Asp
 1               5                  10

<210> SEQ ID NO 192
<211> LENGTH: 13
<212> TYPE: PRT
<213> ORGANISM: Artificial Sequence
<220> FEATURE:
<223> OTHER INFORMATION: Synthetic Construct

<400> SEQUENCE: 192

Pro Thr Val Lys Phe Phe Val Val Asn Thr Asp Ser Leu
 1               5                  10

<210> SEQ ID NO 193
<211> LENGTH: 13
<212> TYPE: PRT
<213> ORGANISM: Artificial Sequence
<220> FEATURE:
<223> OTHER INFORMATION: Synthetic Construct

<400> SEQUENCE: 193

Val Lys Phe Phe Val Val Asn Thr Asp Ser Leu Ser Ser
 1               5                  10

<210> SEQ ID NO 194
<211> LENGTH: 13
<212> TYPE: PRT
```

<213> ORGANISM: Artificial Sequence
<220> FEATURE:
<223> OTHER INFORMATION: Synthetic Construct

<400> SEQUENCE: 194

Phe Phe Val Val Asn Thr Asp Ser Leu Ser Ser Val Thr
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Synthetic Construct

<400> SEQUENCE: 195

Val Val Asn Thr Asp Ser Leu Ser Ser Val Thr Asn Ala
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthetic Construct

<400> SEQUENCE: 196

Asn Thr Asp Ser Leu Ser Ser Val Thr Asn Ala Thr Ser
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Synthetic Construct

<400> SEQUENCE: 197

Asp Ser Leu Ser Ser Val Thr Asn Ala Thr Ser Ile Gln
1               5                   10

<210> SEQ ID NO 198
<211> LENGTH: 13
<212> TYPE: PRT
<213> ORGANISM: Artificial Sequence
<220> FEATURE:
<223> OTHER INFORMATION: Synthetic Construct

<400> SEQUENCE: 198

Leu Ser Ser Val Thr Asn Ala Thr Ser Ile Gln Ile Thr
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Synthetic Construct

<400> SEQUENCE: 199

Ser Val Thr Asn Ala Thr Ser Ile Gln Ile Thr Ala Pro
1               5                   10

<210> SEQ ID NO 200
<211> LENGTH: 13
<212> TYPE: PRT
<213> ORGANISM: Artificial Sequence
<220> FEATURE:

<223> OTHER INFORMATION: Synthetic Construct

<400> SEQUENCE: 200

Thr Asn Ala Thr Ser Ile Gln Ile Thr Ala Pro Ala Ser
1               5                   10

<210> SEQ ID NO 201
<211> LENGTH: 13
<212> TYPE: PRT
<213> ORGANISM: Artificial Sequence
<220> FEATURE:
<223> OTHER INFORMATION: Synthetic Construct

<400> SEQUENCE: 201

Ala Thr Ser Ile Gln Ile Thr Ala Pro Ala Ser Met Leu
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Synthetic Construct

<400> SEQUENCE: 202

Ser Ile Gln Ile Thr Ala Pro Ala Ser Met Leu Ile Gly
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Synthetic Construct

<400> SEQUENCE: 203

Gln Ile Thr Ala Pro Ala Ser Met Leu Ile Gly Asp His
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Synthetic Construct

<400> SEQUENCE: 204

Thr Ala Pro Ala Ser Met Leu Ile Gly Asp His Tyr Leu
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Synthetic Construct

<400> SEQUENCE: 205

Pro Ala Ser Met Leu Ile Gly Asp His Tyr Leu Cys Asp
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 206

Ser Met Leu Ile Gly Asp His Tyr Leu Cys Asp Val Thr
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Synthetic Construct

<400> SEQUENCE: 207

Leu Ile Gly Asp His Tyr Leu Cys Asp Val Thr Trp Ala
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic Construct

<400> SEQUENCE: 208

Gly Asp His Tyr Leu Cys Asp Val Thr Trp Ala Thr Gln
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthetic Construct

<400> SEQUENCE: 209

His Tyr Leu Cys Asp Val Thr Trp Ala Thr Gln Glu Arg
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Synthetic Construct

<400> SEQUENCE: 210

Leu Cys Asp Val Thr Trp Ala Thr Gln Glu Arg Ile Ser
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetic Construct

<400> SEQUENCE: 211

Asp Val Thr Trp Ala Thr Gln Glu Arg Ile Ser Leu Gln
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Synthetic Construct

<400> SEQUENCE: 212
```

Thr Trp Ala Thr Gln Glu Arg Ile Ser Leu Gln Trp Leu
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Synthetic Construct

<400> SEQUENCE: 213

Ala Thr Gln Glu Arg Ile Ser Leu Gln Trp Leu Arg Arg
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Synthetic Construct

<400> SEQUENCE: 214

Gln Glu Arg Ile Ser Leu Gln Trp Leu Arg Arg Ile Gln
1               5                   10

<210> SEQ ID NO 215
<211> LENGTH: 1398
<212> TYPE: DNA
<213> ORGANISM: Artificial Sequence
<220> FEATURE:
<223> OTHER INFORMATION: Synthetic Construct

<400> SEQUENCE: 215

```
atggaatgga gctgggtctt tctcttcttc ctgtcagtaa ctacaggtgt ccactccgaa      60
gtgcagctgg tggaaagcgg tgctggagtg aagcagccgg tggaaccct gcgtctgacc     120
tgcacggcta gcggtttcag cctgaccaca tacggtgtgc actgggtgcg tcaggcgccc     180
gggaaaggtc tggaatgggt gggtgtaatc tggggcgatg gtcgtaccga ttacgatgct    240
gctttcatga gccgggtgac catcagcaaa gataccagca aaagcaccgt gtacttgcag    300
atgaacagcc tgcgtgcgga agatactgca gtgtactact gcatgcgtaa tcgtcatgat    360
tggttcgatt actggggcca aggaaccacc gtgaccgtct cgagcgcaag caccaaaggc    420
ccatcggtat tccccctggc accctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
```

```
tccttcttcc tctacagcaa gctcaccgtg acaagagca ggtggcagca ggggaacgtc    1320
ttctcatgct ccgtgatgca tgaggctctg cacaaccact acacgcagaa gagcctctcc    1380
ctgtctccgg gtaaatga                                                  1398

<210> SEQ ID NO 216
<211> LENGTH: 705
<212> TYPE: DNA
<213> ORGANISM: Artificial Sequence
<220> FEATURE:
<223> OTHER INFORMATION: Synthetic Construct

<400> SEQUENCE: 216
atgagtgtgc ccactcaggt cctggggttg ctgctgctgt ggcttacaga tgccagatgt      60
gacatcctgc tgacccagtc tccatcttct ctgtctgcta ctcctggcga acgtgctacc     120
atcacctgtc gtgcctctca gggcatccgt aacaacctga actggtatca gcagaaacca     180
ggtcaggccc cacgtctgct gatctactac tcttctaatt tgcagtccgg tgtgccatcc     240
cgtttctccg gatctggttc tggcaccgac ttcaccctga ccatctctag actgcaacct     300
gaagacgttg ccgcctacta ctgccagcag tctatcaagc tgccatttac cttcggttct     360
ggtaccaaag tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg ataacgccc tccaatcggg taactcccag      540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                    705

<210> SEQ ID NO 217
<211> LENGTH: 465
<212> TYPE: PRT
<213> ORGANISM: Artificial Sequence
<220> FEATURE:
<223> OTHER INFORMATION: Synthetic Construct

<400> SEQUENCE: 217

Met Glu Trp Ser Trp Val Phe Leu Phe Phe Leu Ser Val Thr Thr Gly
  1               5                  10                  15

Val His Ser Glu Val Gln Leu Val Glu Ser Gly Ala Gly Val Lys Gln
             20                  25                  30

Pro Gly Gly Thr Leu Arg Leu Thr Cys Thr Ala Ser Gly Phe Ser Leu
         35                  40                  45

Thr Thr Tyr Gly Val His Trp Val Arg Gln Ala Pro Gly Lys Gly Leu
     50                  55                  60

Glu Trp Val Gly Val Ile Trp Gly Asp Gly Arg Thr Asp Tyr Asp Ala
 65                  70                  75                  80

Ala Phe Met Ser Arg Val Thr Ile Ser Lys Asp Thr Ser Lys Ser Thr
                 85                  90                  95

Val Tyr Leu Gln Met Asn Ser Leu Arg Ala Glu Asp Thr Ala Val Tyr
            100                 105                 110

Tyr Cys Met Arg Asn Arg His Asp Trp Phe Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160
```

```
Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 218
<211> LENGTH: 234
<212> TYPE: PRT
<213> ORGANISM: Artificial Sequence
<220> FEATURE:
<223> OTHER INFORMATION: Synthetic Construct

<400> SEQUENCE: 218

Met Ser Val Pro Thr Gln Val Leu Gly Leu Leu Leu Leu Trp Leu Thr
  1               5                  10                  15

Asp Ala Arg Cys Asp Ile Leu Leu Thr Gln Ser Pro Ser Ser Leu Ser
             20                  25                  30

Ala Thr Pro Gly Glu Arg Ala Thr Ile Thr Cys Arg Ala Ser Gln Gly
         35                  40                  45
```

```
Ile Arg Asn Asn Leu Asn Trp Tyr Gln Gln Lys Pro Gly Gln Ala Pro
 50                  55                  60

Arg Leu Leu Ile Tyr Tyr Ser Ser Asn Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Arg Leu Gln Pro Glu Asp Val Ala Ala Tyr Tyr Cys Gln Gln Ser Ile
                100                 105                 110

Lys Leu Pro Phe Thr Phe Gly Ser Gly Thr Lys Val Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 219
<211> LENGTH: 446
<212> TYPE: PRT
<213> ORGANISM: Artificial Sequence
<220> FEATURE:
<223> OTHER INFORMATION: Synthetic Construct

<400> SEQUENCE: 219

```
Glu Val Gln Leu Val Glu Ser Gly Ala Gly Val Lys Gln Pro Gly Gly
  1               5                  10                  15

Thr Leu Arg Leu Thr Cys Thr Ala Ser Gly Phe Ser Leu Thr Thr Tyr
                 20                  25                  30

Gly Val His Trp Val Arg Gln Ala Pro Gly Lys Gly Leu Glu Trp Val
                 35                  40                  45

Gly Val Ile Trp Gly Asp Gly Arg Thr Asp Tyr Asp Ala Ala Phe Met
 50                  55                  60

Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

```
                180                 185                 190
Gly Thr Gln Thr Tyr Ile Cys Asn Val Asn His Lys Pro Ser Asn Thr
                    195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 220
<211> LENGTH: 214
<212> TYPE: PRT
<213> ORGANISM: Artificial Sequence
<220> FEATURE:
<223> OTHER INFORMATION: Synthetic Construct

<400> SEQUENCE: 220

Asp Ile Leu Leu Thr Gln Ser Pro Ser Ser Leu Ser Ala Thr Pro Gly
1               5                   10                  15
Glu Arg Ala Thr Ile Thr Cys Arg Ala Ser Gln Gly Ile Arg Asn Asn
            20                  25                  30
Leu Asn Trp Tyr Gln Gln Lys Pro Gly Gln Ala Pro Arg Leu Leu Ile
        35                  40                  45
Tyr Tyr Ser Ser Asn Leu Gln Ser Gly Val Pro Ser Arg Phe Ser Gly
    50                  55                  60
Ser Gly Ser Gly Thr Asp Phe Thr Leu Thr Ile Ser Arg Leu Gln Pro
65                  70                  75                  80
Glu Asp Val Ala Ala Tyr Tyr Cys Gln Gln Ser Ile Lys Leu Pro Phe
                85                  90                  95
Thr Phe Gly Ser Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-CD26 ANTIBODIES AND METHODS OF USE THEREOF

CROSS REFERENCE TO RELATED APPLICATIONS

This application is a continuation of U.S. patent application Ser. No. 11/492,498, filed Jul. 24, 2006; which claims priority to U.S. Provisional Patent Application No. 60/701,802; the disclosures of each of which are herein incorporated by references in their entirety.

FIELD OF THE INVENTION

The field of this invention relates generally to anti-CD26 antibodies and other polypeptides, and, in particular, to humanized anti-CD26 antibodies, as well as to methods of using the antibodies and other polypeptides for the treatment of diseases associated with expression of CD26.

BACKGROUND OF THE INVENTION

CD26 is a widely distributed 110 kDa cell surface glycoprotein. CD26 was initially defined as a T-cell activation antigen (Fox et al. (1984) J. Immunol. 133, 1250-1256, Fleischer (1987) J. Immunol. 138, 1346-1350, and Morimoto et al. (1989) J. Immunol. 143, 3430-3439). This molecule has been shown to have dipeptidyl peptidase IV (DPPIV; EC3.4.14.5) activity in its extracellular domain, and wide tissue distribution (Hegen et al. (1990) J. Immunol. 144, 2908-2914 and Ulmer et al. (1990) J. Immunol. 31, 429-435). CD26 has multiple functions in human T-cell physiology. For instance, evidence suggests that CD26 can deliver a costimulatory signal for T-cell activation (Morimoto et al. (1994) Immunologist 2: 4-7 and Fleischer (1994) Immunol. Today 15: 180-184). Further, CD26 has been identified as the ADA binding protein, and the CD26/ADA complex may play a key role in regulating immune system function (Dong et al. (1996) J Immunol. 156(4):1349-55, Kameoka et al. (1993) Science. 261(5120):466-9, and Morrison et al. (1993) J Exp Med. 177(4):1135-43). A functional association between CD26 and the cellular protein topoisomerase II α has also been reported (Aytac et al. (2003) British Journal of Cancer 88:455-462).

CD26 may also have a role in development of some tumors. For instance, CD26 is expressed on the surface of some aggressive T-cell malignancies such as T-cell lymphoblastic lymphomas/acute lymphoblastic leukaemias, as well as T cell CD30+ anaplastic large cell lymphomas (Carbone et al. (1995) Blood 86(12):4617-26 and Jones et al. (2001) Am J Clin Pathol. 115(6):885-92).

A variety of murine antibodies that bind to CD26 have been reported. (See, e.g., Morimoto et al. (1989) J. Immunol. 143: 3430-39, Nam Hong Dang et al. (1990) J. Immunol. 145(12): 3963-71, Nam Hong Dang et al. (1990) J. Immunol. 144(11): 4092-100, PCT Publication No. WO 91/07985 (Schlossman et al.), PCT Publication No. WO 02/092127 (Nam Hong Dang et al.), and U.S. Pat. No. 6,573,096 (Chen et al.).)

One mouse monoclonal antibody against CD26 which has been produced is known as the 1F7 antibody. (See, e.g., U.S. Pat. No. 5,120,642, PCT Publication No. WO 91/07985 (Schlossman et al.), and Morimoto et al. (1989) J. Immunology, 143:3430-3439.) The 1F7 antibody was identified as binding to an antigen comprised of a 110,000 dalton molecular weight glycoprotein on human CD4 and CD8 lymphocytes and later identified as CD26, which was present on helper inducer cells but not suppressor inducer cells. Thus, the 1F7 monoclonal antibody has been reported as being able to distinguish between helper inducer and suppressor inducer cells in human CD4 lymphocyte populations.

In addition, the 1F7 antibody and other anti-CD26 monoclonal antibodies have been proposed to be useful in the treatment of some diseases associated with cells expressing CD26, such as some cancers. (See, e.g., U.S. Patent Publication No. 2003/0031665 and PCT Publication No. WO 02/092127 (Nam Hoang Dang et al.).) Binding of the anti-CD26 monoclonal antibody 1F7 to CD26 reportedly led to cell cycle arrest at the G1/S checkpoint, and engagement of CD26 induced G1 arrest on CD26 Jurkat transfectants through enhanced expression of the cell cycle regulatory protein p21. Treatment with the 1F7 antibody has also been reported to inhibit CD26+ tumor formation and enhance survival in a mouse model (Ho et al. (2001) Clinical Cancer Research, 7:2031-2040).

Other anti-CD26 murine monoclonal antibodies that have been identified include rat anti-CD26 antibodies E19 and E26. (See, e.g., U.S. Pat. No. 6,573,096, US Patent Publication No. 2002/0132979, U.S. Patent Publication No. 2002/0132979, U.S. Patent Publication No. 2004/0115202, PCT Publication No. WO 01/74299 (Chen et al.), and Ghersi et al. (2002) J. Biological Chemistry, 32:29231-29241.) These antibodies reportedly exhibit inhibitory effects on cell migration of fibroblasts and wounded cells from a monolayer, and inhibitory effects on blood vessel tube formation, and inhibitory effect on invasion and capillary sprout formation of human dermal microvascular endothelial cells. Use of the antibodies in treatments to inhibit cancer invasion and angiogenesis has been proposed.

Another mouse anti-CD26 monoclonal antibody which has been generated is 14D10 (also referred to herein as CM03). (See, e.g., Dong et al. (1998) Mol. Immunol. 35(1): 13-21 and U.S. Pat. Pub. No. 2003/0031665.)

Modifying the activity of CD26 should prove helpful in treating a variety of ailments. Anti-CD26 monoclonal antibodies are one means of modifying the effects of CD26.

Murine monoclonal antibodies have been tried in human therapy. However, when murine antibodies are used therapeutically in humans, a human anti-murine antibody ("HAMA") response develops in a significant number of treated individuals. In the HAMA response, treated subjects develop antibodies against mouse antibodies. This not only limits the effectiveness of the murine monoclonal antibody therapy, it also leads to allergic reactions which can result in anaphylaxis. In addition, even chimeric antibodies comprising human Fc regions and mouse Fv regions can potentially trigger HAMA responses.

To minimize the HAMA response, some researchers have tried to make antibodies that are not recognized as foreign by the human immune system. One method used is the "humanization" of antibodies. These humanized antibodies may contain sequences which are substantially of human origin but also generally contain some complementarity-determining region ("CDR") residues and/or framework region residues originating from a different species, such as a rodent species, or which are purely artificial. A variety of different ways to humanize antibodies are known in the art. One form of humanization is by "grafting" antigen-specific murine complementarity-determining regions ("CDRs") onto the framework of a human immunoglobulin molecule. Another level of humanization may include genetic engineering of murine CDR or other variable region sequences to be "more human," thereby reducing the HAMA response. For instance, another form of humanization is by grafting the heavy and light variable chain regions from one species, such as mouse, onto human heavy and light chain constant regions and then replacing individual residues in the framework regions ("FRs") and/or complementarity determining regions with residues derived from human antibodies and/or residues designed to lower the immunogenicity of the antibody in humans. All of these techniques may include further genetic engineering of the antibody sequences to increase the effectiveness of binding or biological effect of the antibody.

All publications, patents, patent applications, internet sites, and accession numbers/database sequences (including both polynucleotide and polypeptide sequences) cited herein are hereby incorporated by reference herein in their entirety for all purposes to the same extent as if each individual publication, patent, patent application, internet site, or accession number/database sequence were specifically and individually indicated to be so incorporated by reference.

BRIEF SUMMARY OF THE INVENTION

The present invention provides novel polypeptides such as anti-CD26 antibodies, fragments of anti-CD26 antibodies, and other polypeptides related to anti-CD26 antibodies. In some embodiments, the anti-CD26 antibodies are humanized anti-CD26 antibodies. Polynucleotides comprising nucleic acid sequences encoding the polypeptides are also provided. Vectors and host cells comprising the polynucleotides are also provided. Compositions, such as pharmaceutical compositions, comprising the polypeptides of the invention are also provided. Methods of making the polypeptides are also provided. In addition, methods of using the polypeptides or compositions comprising the polypeptides to inhibit proliferation of cells expressing CD26 or in the treatment or diagnosis of conditions associated with CD26 expression are further provided.

In one aspect, the invention provides a polypeptide comprising: (a) a heavy chain CDR1 comprising the sequence $GX_1X_2LX_3TYGVH$ (SEQ ID NO:31), wherein $X_1$ is F or Y, $X_2$ is S or T, and $X_3$ is T, N, or S; (b) a heavy chain CDR2 comprising the sequence $VIWGX_1GRTDYDX_2X_3FMS$ (SEQ ID NO:32), wherein $X_1$ is G or D, $X_2$ is A or S, and $X_3$ is A or S; and/or (c) a heavy chain CDR3 comprising the sequence $X_1RHDWFDY$ (SEQ ID NO:33), wherein $X_1$ is N or S. In some embodiments, the polypeptide is an antibody.

In another aspect, the invention provides a polypeptide comprising: (a) a light chain CDR1 comprising the sequence $X_1ASQX_2IRNX_3LN$ (SEQ ID NO:34), wherein $X_1$ is S or R, $X_2$ is G or D, and $X_3$ is S or N; (b) a light chain CDR2 comprising the sequence $YSSNLX_1X_2$ (SEQ ID NO:35), wherein $X_1$ is H or Q and $X_2$ is S or T; and/or (c) a light chain CDR3 comprising the sequence $QQSX_1KLPX_2T$ (SEQ ID NO:36), wherein $X_1$ is I or N and $X_2$ is F or L. In some embodiments, the polypeptide is an antibody.

In another aspect, the invention provides a polypeptide, such as an antibody, comprising: (a) one or more (e.g., one, two, or three) heavy chain CDRs selected from the group consisting of (i) a heavy chain CDR1 comprising the sequence $GX_1X_2LX_3TYGVH$ (SEQ ID NO:31), wherein $X_1$ is F or Y, $X_2$ is S or T, and $X_3$ is T, N, or S, (ii) a heavy chain CDR2 comprising the sequence $VIWGX_1GRTDYDX_2X_3FMS$ (SEQ ID NO:32), wherein $X_1$ is G or D, $X_2$ is A or S, and $X_3$ is A or S, and (iii) a heavy chain CDR3 comprising the sequence $X_1RHDWFDY$ (SEQ ID NO:33), wherein $X_1$ is N or S; and/or (b) one or more (e.g., one, two, or three) light chain CDRs selected from the group consisting of (i) a light chain CDR1 comprising the sequence $X_1ASQX_2IRNX_3LN$ (SEQ ID NO:34), wherein $X_1$ is S or R, $X_2$ is G or D, and $X_3$ is S or N, (ii) a light chain CDR2 comprising the sequence $YSSNLX_1X_2$ (SEQ ID NO:35), wherein $X_1$ is H or Q and $X_2$ is S or T, and (iii) a light chain CDR3 comprising the sequence $QQSX_1KLPX_2T$ (SEQ ID NO:36), wherein $X_1$ is I or N and $X_2$ is F or L.

In a further aspect, the invention provides a polypeptide, such as an antibody, comprising: (a) one or more (e.g., one, two, or three) heavy chain CDRs that each have at least about 80% identity to a CDR selected from the group consisting of (i) a heavy chain CDR1 selected from the group consisting of GFSLTTYGVH (SEQ ID NO:55), GFSLSTYGVH (SEQ ID NO:56), and GYSLTTYGVH (SEQ ID NO:57), (ii) a heavy chain CDR2 selected from the group consisting of VIWGDGRTDYDAAFMS (SEQ ID NO:58) and VIWGDGRTDYDSSFMS (SEQ ID NO:59), and (iii) a heavy chain CDR3 sequence NRHDWFDY (SEQ ID NO:60); and/or (b) one or more (e.g., one, two, or three) light chain CDRs that each have at least about 80% identity to a CDR selected from the group consisting of (i) a light chain CDR1 selected from the group consisting of RASQDIRNNLN (SEQ ID NO:61), RASQGIRNNLN (SEQ ID NO:62), and SASQDIRNSLN (SEQ ID NO:63), (ii) a light chain CDR2 selected from the group consisting of YSSNLHS (SEQ ID NO:64), YSSNLQS (SEQ ID NO:65) and YSSNLHT (SEQ ID NO:66), and (iii) a light chain CDR3 selected from the group consisting of QQSIKLPLT (SEQ ID NO:67), QQSIKLPFT (SEQ ID NO:68), and QQSNKLPLT (SEQ ID NO:69).

In still another aspect, the invention provides a polypeptide comprising: (a) a heavy chain FR1 comprising the sequence $EVQLVX_1SGX_2X_3X_4X_5QPGX_6X_7LRLX_8CX_9AS$ (SEQ ID NO:37), wherein $X_1$ is E or Q, $X_2$ is A or G, $X_3$ is G or E, $X_4$ is L or V, Xs is V, K, or E, $X_6$ is G or E, $X_7$ is T or S, $X_8$ is T or S, and $X_9$ is T or K; (b) a heavy chain FR2 comprising the sequence $WVRQAPGKGLEWX_1G$ (SEQ ID NO:38), wherein $X_1$ is V or M; (c) a heavy chain FR3 comprising the sequence $RVTISX_1DX_2SKX_3TX_4YLQX_5NSLRAEDTAVYYCX_6R$ (SEQ ID NO:39), wherein $X_1$ is K or R, $X_2$ is N or T, $X_3$ is S or N, $X_4$ is V or A, $X_5$ is M or L, and $X_6$ is V, M, or T; and/or (d) a heavy chain FR4 comprising the sequence WGQGTTVTVSS (SEQ ID NO:40). In some embodiments, the polypeptide is an antibody.

In a further aspect, the invention provides a polypeptide comprising: (a) a light chain FR1 comprising the sequence $X_1IX_2X_3TQSPSSLSX_4X_5X_6GX_7RX_8TIX_9C$ (SEQ ID NO:41), wherein $X_1$ is D or E, $X_2$ is L or E, $X_3$ is M or L, $X_4$ is A or V, $X_5$ is S or T, $X_6$ is L, P, or A, $X_7$ is D or E, $X_8$ is V or A, and $X_9$ is T or S; (b) a light chain FR2 comprising the sequence WYQQKPGQAPRLLIY (SEQ ID NO: 42); (c) a light chain FR3 comprising the sequence $GVPX_1RFSGSGSGTDFTLTISRLX_2X_3EDX_4AX_5YYC$ (SEQ ID NO: 43), wherein $X_1$ is S, D, or A, $X_2$ is E or Q, $X_3$ is P or A, $X_4$ is F or V, and $X_5$ is T, A, or I; and/or (d) a light chain FR4 comprising the sequence FGSGTKVEIK (SEQ ID NO:44). In some embodiments, the polypeptide is an antibody.

In an additional aspect, the invention provides a polypeptide, such as an antibody, comprising: (a) one or more (e.g., one, two, three, or four) heavy chain framework regions selected from the group consisting of (i) a heavy chain FR1 comprising the sequence $EVQLVX_1SGX_2X_3X_4X_5QPGX_6X_7LRLX_8CX_9AS$ (SEQ ID NO:37), wherein $X_1$ is E or Q, $X_2$ is A or G, $X_3$ is G or E, $X_4$ is L or V, $X_5$ is V, K, or E, $X_6$ is G or E, $X_7$ is T or S, $X_8$ is T or S, and $X_9$ is T or K; (ii) a heavy chain FR2 comprising the sequence $WVRQAPGKGLEWX_1G$ (SEQ ID NO:38), wherein $X_1$ is V or M, (iii) a heavy chain FR3 comprising the sequence $RVTISX_1DX_2SKX_3TX_4YLQX_5NSLRAEDTAVYYCX_6R$ (SEQ ID NO:39), wherein $X_1$ is K or R, $X_2$ is N or T, $X_3$ is S or N, $X_4$ is V or A, X is M or L, and $X_6$ is V, M, or T, and (iv) a heavy chain FR4 comprising the sequence WGQGT-TVTVSS (SEQ ID NO:40); and/or (b) one or more (e.g., one, two, three, or four) light chain framework regions selected from the group consisting of (i) a light chain FR1 comprising the sequence $X_1IX_2X_3$TQSPSSLS$X_4X_5X_6$G$X_7$R$X_8$TI$X_9$C (SEQ ID NO:41), wherein $X_1$ is D or E, $X_2$ is L or E, $X_3$ is M or L, $X_4$ is A or V, X is S or T, $X_6$ is L, P, or A, $X_7$ is D or E, $X_8$ is V or A, and $X_9$ is T or S, (ii) a light chain FR2 comprising the sequence WYQQKPGQAPRLLIY (SEQ ID NO: 42), (iii) a light chain FR3 comprising the sequence GVP$X_1$RFSGSGSGTDFTLTISRL$X_2X_3$ED$X_4$A$X_5$YYC (SEQ ID NO: 43), wherein X is S, D, or A, $X_2$ is E or Q, $X_3$ is P or A, $X_4$ is F or V, and $X_5$ is T, A, or I, and (iv) a light chain FR4 comprising the sequence FGSGTKVEIK (SEQ ID NO:44).

In another aspect, the invention provides a polypeptide comprising one or more of the heavy chain CDRs described herein and/or one or more of the heavy chain FRs described herein (e.g., above or elsewhere herein, such as in FIGS. 3 and 5). In some embodiments, the invention provides a polypeptide comprising a heavy chain variable region comprising one or more of the heavy chain CDRs described herein and/or one or more of the heavy chain FRs described herein. In addition, the invention also provides a polypeptide comprising one or more of the light chain CDRs described herein and/or one or more of the light chain FRs described herein. In some embodiments, the polypeptide comprises a light chain variable region comprising one or more of the light chain CDRs described herein and/or one or more of the light chain FRs described herein. In some embodiments, the polypeptide comprises the following: (1) one or more of the heavy chain CDRs described herein and/or one or more of the heavy chain FRs described herein; and (2) one or more of the light chain CDRs described herein and/or one or more of the light chain FRs described herein. In some embodiments, the polypeptide comprises a heavy chain variable region comprising one or more heavy chain CDRs described herein and/or a light chain variable region comprising one or more of the light chain CDRs described herein.

The invention further provides a heavy chain variable region comprising one or more of the heavy chain CDRs described herein and/or one or more of the heavy chain FRs described herein. In addition, the invention also provides a light chain variable region comprising one or more of the light chain CDRs described herein and/or one or more of the light chain FRs described herein.

In another aspect, the invention provides a polypeptide comprising the amino acid sequence EVQLV$X_1$SG$X_2X_3X_4X_5$QPG$X_6X_7$LRL$X_8$C$X_9$ASG$X_{10}$-$X_{11}$L$X_{12}$TYGVHWVRQAPGKGLEW$X_{13}$GVIWG$X_{14}$GR-TDYD$X_{15}X_{16}$FMSRVTIS$X_{17}$D$X_{18}$SK$X_{19}$T$X_{20}$YLQ$X_{21}$N-SLRAEDTAVYYC$X_{22}$R$X_{23}$RHDWFDYWGQGTTVTVSS (SEQ ID NO:29), wherein $X_1$ is E or Q, $X_2$ is A or G, $X_3$ is G or E, $X_4$ is L or V, $X_5$ is V, K, or E, $X_6$ is G or E, $X_7$ is T or S, $X_8$ is T or S, $X_9$ is T or K, $X_{10}$ is F or Y, $X_{11}$ is S or T, $X_{12}$ is T, N, or S, $X_{13}$ is V or M, $X_{14}$ is G or D, $X_{15}$ is A or S, $X_{16}$ is A or S, $X_{17}$ is K or R, $X_{18}$ is N or T, $X_{19}$ is S or N, $X_{20}$ is V or A, $X_{21}$ is M or L, $X_{22}$ is V, M, or T, and $X_{23}$ is N or S. In some embodiments, the polypeptide is an antibody.

In an additional aspect, the invention provides a polypeptide comprising the amino acid sequence $X_1IX_2X_3$TQSPSSLS$X_4X_5X_6$G$X_7$R$X_8$TI$X_9$C$X_{10}$ASQ$X_{11}$I-RN$X_{12}$LNWYQQKPGQAPRLLIYYSS NL$X_{13}X_{14}$GVP$X_{15}$RFSGSGSGTDFTLTISRL$X_{16}X_{17}$ED-$X_{18}$A$X_{19}$YYCQQS$X_{20}$KLP$X_{21}$TFGSGT KVEIK (SEQ ID NO:30), wherein $X_1$ is D or E, $X_2$ is L or E, $X_3$ is M or L, $X_4$ is A or V, $X_5$ is S or T, $X_6$ is L, P, or A, $X_7$ is D or E, $X_8$ is V or A, $X_9$ is T or S, $X_{10}$ is S or R, $X_{11}$ is G or D, $X_{12}$ is S or N, $X_{13}$ is H or Q, $X_{14}$ is S or T, $X_{15}$ is S, D, or A, $X_{16}$ is E or Q, $X_{17}$ is P or A, $X_{18}$ is F or V, $X_{19}$ is T, A, or I, $X_{20}$ is I or N and $X_{21}$ is F or L. In some embodiments, the polypeptide further comprises the amino acid sequence EVQLV$X_1$SG$X_2X_3X_4$-$X_5$QPG$X_6X_7$LRL$X_8$C$X_9$ASG$X_{10}X_{11}$L$X_{12}$TYGVHWVR-QAPGKGLEW$X_{13}$GVIWG$X_{14}$GRTDYD$X_{15}X_{16}$FMSRV-TIS$X_{17}$D$X_{18}$SK$X_{19}$T$X_{20}$YLQ$X_{21}$NSLRAEDTAVYYC-$X_{22}$R$X_{23}$RHDWFDYWGQGTTVTVSS (SEQ ID NO:29), wherein $X_1$ is E or Q, $X_2$ is A or G, $X_3$ is G or E, $X_4$ is L or V, $X_5$ is V, K, or E, $X_6$ is G or E, $X_7$ is T or S, $X_8$ is T or S, $X_9$ is T or K, $X_{10}$ is F or Y, $X_{11}$ is S or T, $X_{12}$ is T, N, or S, $X_{13}$ is V or M, $X_{14}$ is G or D, $X_{15}$ is A or S, $X_{16}$ is A or S, $X_{17}$ is K or R, $X_{18}$ is N or T, $X_{19}$ is S or N, $X_{20}$ is V or A, $X_{21}$ is M or L, $X_{22}$ is V, M, or T, and $X_{23}$ is N or S. In some embodiments, the polypeptide is an antibody.

In another aspect, the invention provides an antibody that is a humanized form of the murine antibody 14D10.

In another aspect, the invention provides a polypeptide, such as an antibody, that binds to one or more peptides selected from the group consisting of YSLRWISDHEYLY (SEQ ID NO:45; peptide 6), LEYNYVKQWRHSY (SEQ ID NO:46; peptide 35), TWSPVGHKLAYVW (SEQ ID NO:47; peptide 55), LWWSPNGTFLAYA (SEQ ID NO:48; peptide 84), RISLQWLRRIQNY (SEQ ID NO:49; peptide 132), YVKQWRHSYTASY (SEQ ID NO:50; peptide 37), EEEVFSAYSALWW (SEQ ID NO:51; peptide 79), DYS-ISPDGQFILL (SEQ ID NO:52; peptide 29), SISPDGQFIL-LEY (SEQ ID NO:53; peptide 30), and IYVKIEPNLPSYR (SEQ ID NO:54; peptide 63).

In an additional aspect, the invention provides a polypeptide, comprising (a) an amino acid sequence having at least about 80% identity to an amino acid sequence selected from the group consisting of SEQ ID NOS:15-21 or to a fragment of an amino acid sequence selected from the group consisting of SEQ ID NOS:15-21, and/or (b) an amino acid sequence having at least about 80% identity to an amino acid sequence selected from the group consisting of SEQ ID NOS:22-28 or to a fragment of to an amino acid sequence selected from the group consisting of SEQ ID NOS:22-28. In another aspect, the invention provides a polypeptide, comprising (a) an amino acid sequence having at least about 80% identity to an amino acid sequence selected from the group consisting of SEQ ID NOS:15-21, and/or (b) an amino acid sequence having at least about 80% identity to an amino acid sequence selected from the group consisting of SEQ ID NOS:22-28.

In a further aspect, the invention provides a polypeptide, such as an antibody, comprising a light chain variable region comprising an amino acid sequence having at least about 80% identity to an amino acid sequence selected from the group consisting of the following sequences shown in FIG. 3: X376, X377, X378, X379, X380, X381, and X394 (SEQ ID NOS: 15-21, respectively).

In another aspect, the invention provides a polypeptide, such as an antibody, comprising a heavy chain variable region comprising an amino acid sequence having at least about 80% identity to an amino acid sequence selected from the group consisting of the following sequences shown in FIG. 5: X384, X385, X386, X387, X388, X399, and X420 (SEQ ID NOS: 22-28, respectively).

In still another aspect, the invention provides a polypeptide, such as an antibody, comprising an amino acid sequence selected from the group consisting of each of the following sequences shown in FIG. 3 or FIG. 5: X376, X377, X378, X379, X380, X381, X394, X384, X385, X386, X387, X388, X399, and X420 (SEQ ID NOS:15-28).

In yet another aspect, the invention provides a polypeptide (e.g., an antibody) comprising SEQ ID NO:217, or a fragment or variant thereof.

In another aspect, the invention provides a polypeptide (e.g., an antibody) comprising SEQ ID NO:218, or a fragment or variant thereof.

In some embodiments of each of the aforementioned aspects, as well as other aspects described herein, the polypeptide is an antibody. In some embodiments, the polypeptide is a monoclonal antibody. In some embodiments, of each of the aforementioned aspects, as well as other aspects described herein, the polypeptide is a humanized antibody. In some embodiments of each of the aforementioned aspects, as well as other aspects described herein, the polypeptide is not a murine monoclonal antibody. In some embodiments of each of the aforementioned aspects, as well as other aspects described herein, the polypeptide is not a mouse monoclonal antibody. In some embodiments of each of the aforementioned aspects, as well as other aspects described herein, the polypeptide is not the murine monoclonal antibody 14D10. In some embodiments of each of the aforementioned aspects, as well as other aspects described herein, the polypeptide does not comprise a heavy chain variable region of the sequence QVKLQESGPGLVQPSQTLSITCTVSGFS-LTTYGVHWVRQSPGKGLEWLGVIWGGGRTD YDAAFISRLSISKDNSKSQVFFK-MNSLQANDTAIYYCVRNRHDWFDYWGQGTTVTVSS (SEQ ID NO:90). In some embodiments of each of the aforementioned aspects, as well as other aspects described herein, the polypeptide does not comprise a light chain variable region of the sequence DIQMTQSPSSLSASLGDRVTITC-SASQGIRNSLNWYQQKPD-GAVKLLIYYSSNLHSGVPS RFSGSGSGTDFSLTISNLE-PEDIATYYCQQSIKLPFTFGSGTKLEIK (SEQ ID NO:91). In some embodiments of each of the aforementioned aspects, as well as other aspects described herein, the polypeptide does not comprise both a heavy chain variable region of the sequence QVKLQESGPGLVQPSQTL-SITCTVSGFSLTTYGVHWVRQSPGK-GLEWLGVIWGGGRTD YDAAFISRLSISKDN-SKSQVFFKMNSLQANDTAIYYCVRNRHDWFDYWG-QGTTVTVSS (SEQ ID NO:90) and a light chain variable region of the sequence DIQMTQSPSSLSASLGDRVTITC-SASQGIRNSLNWYQQKPD-GAVKLLIYYSSNLHSGVPS RFSGSGSGTDFSLTISNLE-PEDIATYYCQQSIKLPFTFGSGTKLEIK (SEQ ID NO:91). In some embodiments of each of the aforementioned aspects, as well as other aspects described herein, the polypeptide is not the mouse monoclonal antibody 1F7. In some embodiments of each of the aforementioned aspects, the polypeptide has one or more of the following characteristics: binds CD26; modulates CD26 activity, causes cell cycle arrest of CD26+ cells at the G1/S checkpoint; inhibits proliferation of cells expressing CD26, and/or is useful in the treatment of a condition (such as a disease or disorder) associated with CD26 expression. In some embodiments of each of the aforementioned aspects, as well as other aspects described herein, the polypeptide binds human CD26.

Methods of making each of the aforementioned polypeptides are also provided. For instance, the invention provides methods of producing the antibodies described herein, comprising expressing one or more polynucleotides in a host cell, wherein each chain of the antibody is encoded by at least one of the polynucleotides.

The invention further provides kits comprising each of the aforementioned polypeptides.

The invention further provides compositions, such as pharmaceutical compositions, comprising each of the aforementioned polypeptides, as well as other polypeptides described herein. The use of each of these polypeptides in the manufacture of a pharmaceutical composition or medicament is likewise provided. The compositions may be used in any of the methods described herein.

The invention provides methods of inhibiting proliferation of a cell expressing CD26, comprising contacting the cell with a polypeptide described herein (typically with an amount of the polypeptide effective to effect the desired inhibition). In addition, the invention provides methods of treating a condition associated with CD26 expression in a subject, comprising administering an effective amount of a composition comprising a polypeptide described herein to the subject. The compositions described herein may be used in the treatment of a variety of diseases or conditions, such as graft versus host disease, autoimmune disease, or cancer. In some embodiments, the cancer is a hematological malignancy. In some embodiments, the cancer is a solid tumor. The invention also provides the use of the compositions described herein for inhibiting progression of a CD26+ cancer, inhibiting growth of a CD26-expressing tumor, inducing regression of a CD26-expressing tumor, and/or inhibiting metastasis of cancer cells that express CD26.

In some aspects, the invention provides polynucleotides encoding the polypeptides described herein. In some aspects, the invention provides a polynucleotide comprising a nucleic acid sequence selected from the group consisting of each of the sequences shown in FIG. 2 and FIG. 4 (SEQ ID NOS:1-14). In further aspects, the invention provides a polynucleotide comprising a nucleic acid sequence that is at least about 80% identical to a nucleic acid selected from the group consisting of each of the sequences shown in FIG. 2 and FIG. 4 (SEQ ID NOS:1-14). In other aspects, the invention further provides a polynucleotide comprising a polynucleotide encoding an amino acid sequence selected from the group consisting of each of the following amino acid sequences shown in FIG. 3 or FIG. 5: X376, X377, X378, X379, X380, X381, X394, X384, X385, X386, X387, X388, X399, and X420 (SEQ ID NOS:15-28). Vectors and host cells comprising the polynucleotides of each of the aforementioned aspects are also provided.

In some embodiments, the polypeptides (e.g., antibodies) of the invention do not include the exclusions described herein.

With respect to the sequences herein which comprise amino acid substituents, as is evident to the one skilled in the art, each amino acid substituent may be independently selected. The invention also provides sequences comprising amino acid substituents in which one or more of the amino acid substituents are eliminated.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

BRIEF DESCRIPTION OF THE DRAWINGS

FIG. 1 shows the sequence of VH of CM03 (SEQ ID NO:90) and VL of CM03 (SEQ ID NO:91).

FIG. 2 shows DNA sequences for humanized VL variants X376 (SEQ ID NO:1), X377 (SEQ ID NO:2), X378 (SEQ ID NO:3), X379 (SEQ ID NO:4), X380 (SEQ ID NO:5), X381 (SEQ ID NO:6), and X394 (SEQ ID NO:7).

FIG. 3 shows the amino acid sequences of CM03 VL (SEQ ID NO:91) and humanized VL variants X376 (SEQ ID NO:15), X377 (SEQ ID NO:16), X378 (SEQ ID NO:17), X379 (SEQ ID NO:18), X380 (SEQ ID NO:19), X381 (SEQ ID NO:20), and X394 (SEQ ID NO:21). Kabat and sequential numbering schemes are identical for the light chain variable regions.

FIG. 4 shows DNA sequences for humanized VH variants X384 (SEQ ID NO:8), X385 (SEQ ID NO:9), X386 (SEQ ID NO:10), X387 (SEQ ID NO:11) and X388 (SEQ ID NO:12), X399 (SEQ ID NO:13) and X420 (SEQ ID NO:14).

FIG. 5 shows the amino acid sequences of CM03 VH (SEQ ID NO:90) and humanized VH variants X384 (SEQ ID NO:22), X385 (SEQ ID NO:23), X386 (SEQ ID NO:24), X387 (SEQ ID NO:25) and X388 (SEQ ID NO:26), X399 (SEQ ID NO:27) and X420 (SEQ ID NO:28). Both the sequential and Kabat numbering schemes are shown. The Kabat numbering scheme includes 82a, 82b, and 82c.

FIG. 6 shows the amino acid sequences of the VH and VL of Fabs comprising selected variant VH and variant VL: X389, X390, X391, X392, X393, X394, X395, X396, X399, X420, and X429. Fab X389 comprises X384 VH (SEQ ID NO:22) and X376 VL (SEQ ID NO:15), Fab X390 comprises X385 VH (SEQ ID NO:23) and X376 VL (SEQ ID NO:15), Fab X391 comprises X388 VH (SEQ ID NO:26) and X376 VL (SEQ ID NO:15), Fab X392 comprises X384 VH (SEQ ID NO:22) and X379 VL (SEQ ID NO:18), Fab X393 comprises X385 VH (SEQ ID NO:23) and X379 VL (SEQ ID NO:18), Fab X394 comprises X384 VH (SEQ ID NO:22) and X394 VL (SEQ ID NO:21), Fab X395 comprises X384 VH (SEQ ID NO:22) and X380 VL (SEQ ID NO:19), Fab X396 comprises X385 VH (SEQ ID NO:23) and X380 VL (SEQ ID NO:19), Fab X399 comprises X399 VH (SEQ ID NO:27) and X380 VL (SEQ ID NO:19), Fab X420 comprises X420 VH (SEQ ID NO:28) and X380 VL (SEQ ID NO:19), and Fab X429 comprises X399 VH (SEQ ID NO:27) and X394 VL (SEQ ID NO:21).

FIG. 17A shows an exemplary heavy chain linked to a leader sequence. The heavy chain constant region amino acid sequence (human IgG1) is shown (SEQ ID NO:87).

FIG. 17B shows an exemplary light chain linked to a leader sequence. The light chain constant region amino acid sequence (human kappa) is shown (SEQ ID NO:88).

DETAILED DESCRIPTION OF THE INVENTION

Figure 7:
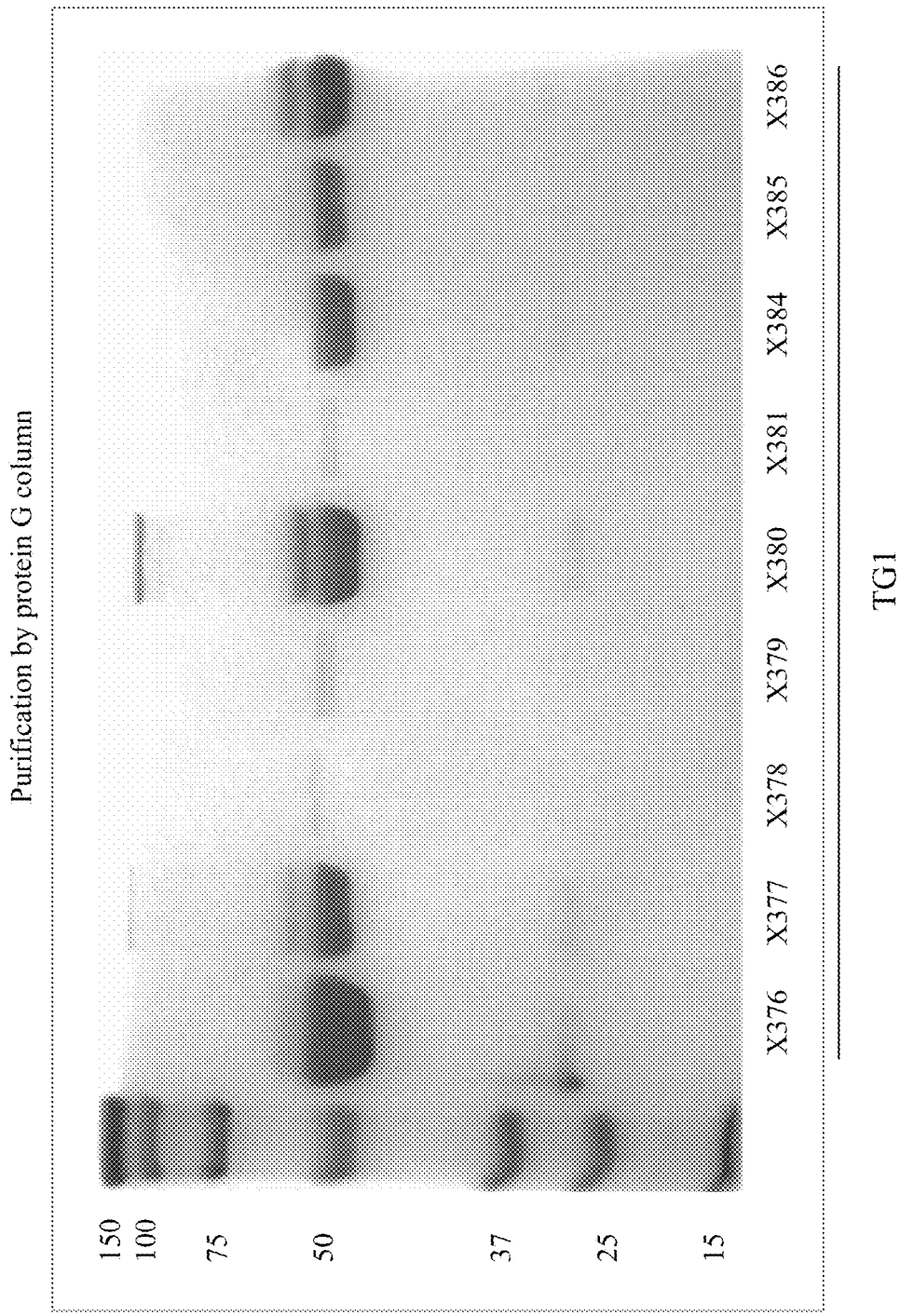
FIG. 7 shows a gel loaded with protein samples containing Fabs comprising CM03 VL variants X376, X377, X378, X379, X380, or X381 paired with CM03 VH, as well as Fabs comprising CM03 VH variants X384, X385, X386, paired with CM03 VL, expressed in *E. coli* strain TG1.

The present invention provides a variety of novel polypeptides including those comprising one or more CDRs or FRs of an anti-CD26 antibody or comprising a heavy chain variable region or light chain variable region (or fragment thereof) of an anti-CD26 antibody. In some embodiments, the polypeptides bind CD26. In particular, a variety of novel anti-CD26 antibodies are provided, including, but not limited to, humanized anti-CD26 antibodies. Compositions, such as pharmaceutical compositions comprising the polypeptides are also provided. Polynucleotides encoding the polypeptides and vectors and host cells comprising the polynucleotides are also provided. Methods of making and using the polypeptides are also provided. In some instances, the polypeptides of the invention are useful as intermediates for making, for example, polypeptides (such as antibodies) that bind CD26.

It is understood that wherever embodiments are described herein with the language "comprising," otherwise analogous embodiments described in terms of "consisting of" and/or "consisting essentially of" are also provided.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refers to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Some humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Some humanized antibodies comprise at least one, and typically two, variable domains that are generally derived from a non-human species (donor antibody) such as a mouse, rat, or rabbit having the desired specificity, affinity, and/or capacity, but in which one or more Fv framework region residues and/or one or more Fv CDR residues have been replaced by a corresponding human residue (i.e., a residue derived from a human antibody sequence). Most typically, at least a plurality of Fv framework region residues will have been replaced in one or more of the variable domains of the humanized antibody. Furthermore, the humanized antibody may comprise residues that are found neither in the recipient antibody nor in the imported CDR or framework sequences, but are included to further refine and optimize antibody performance. Some humanized antibodies will comprise substantially all of at least one, and typically two, variable domains, in which all or substantially all of the CDRs correspond to those of a non-human immunoglobulin and all or substantially all of the FRs are those of a human immunoglobulin consensus sequence. Some humanized antibodies will comprise substantially all of at least one, and typically two, variable domains, in which the majority of the amino acid residues of the CDRs correspond to those of a non-human immunoglobulin and one or more of the amino acid residues of the FRs are those of a human immunoglobulin consensus sequence. A humanized antibody optimally also will comprise at least a portion of an immunoglobulin constant region or domain (Fc), typically that of a human immunoglobulin. Some humanized antibodies have Fc regions modified as described in WO 99/58572. Some forms of humanized antibodies have one or more (e.g., one, two, three, four, five, six) CDRs which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373. In some embodiments, a human antibody is "fully human," meaning the antibody contains human heavy chain and light chain polypeptides.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD26 epitope is an antibody that binds this CD26 epitope with greater affinity, avidity, more readily, and/or with greater duration than it binds to other CD26 epitopes or non-CD26 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "treatment" is an approach for obtaining beneficial or desired clinical results. For purposes of this invention, beneficial or desired clinical results include, but are not limited to, alleviation of one or more symptoms associated with a disease, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. In some embodiments, "treatment" of a disease can encompass, but is not limited to, curing a disease. In some embodiments, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival. In those embodiments where the compositions described herein are used for treatment of cancer, the beneficial or desired results can include, but are not limited to, one or more of the following: reducing the proliferation of (or destroying) neoplastic or cancerous cells, inhibiting metastasis of neoplastic cells, shrinking the size of a tumor, inhibiting the growth of a tumor, regression of a tumor, remission of a cancer, decreasing symptoms resulting from the cancer, increasing the quality of life of those suffering from cancer, decreasing the dose of other medications required to treat the cancer, delaying the progression of cancer, and/or prolonging survival of patients having cancer.

An "effective amount" is an amount sufficient to effect beneficial or desired clinical results including clinical results. An effective amount can be administered in one or more administrations. For purposes of this invention, an effective amount of a polypeptide, such as an anti-CD26 antibody, described herein is an amount sufficient to ameliorate, stabilize, reverse, slow and/or delay progression of a condition associated with CD26 expression. As is understood in the art, an effective amount of, for example, an anti-CD26 antibody may vary, depending on, inter alia, patient history as well as other factors such as the type (and/or dosage) of an anti-CD26 antibody used. As evident by this disclosure to one skilled in the art, these principles apply to polypeptide embodiments.

An "individual," also referred to herein as a "subject," is a vertebrate, preferably a mammal, more preferably a human. Mammals include, but are not limited to, farm animals (such as cows), sport animals, pets (such as cats, dogs, and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutically acceptable excipient" includes any material which, when combined with an active ingredient, allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{off}$", as used herein, is intended to refer to the off rate constant for dissociation of an antibody from the antibody/antigen complex.

The term "$K_D$", as used herein, is intended to refer to the dissociation constant of an antibody-antigen interaction.

As used herein, "substantially pure" refers to material which is at least 50% pure (i.e., free from contaminants), more preferably at least 90% pure, more preferably at least 95% pure, more preferably at least 98% pure, more preferably at least 99% pure.

Polypeptides

The invention provides a variety of novel polypeptides comprising one or more heavy chain and/or light chain complementarity determining regions (CDRs), heavy chain and/or light chain framework regions (FRs), and/or heavy chain and/or light chain variable regions (VHs and VLs, respectively). In some embodiments, the polypeptides are antibodies. In some embodiments, the polypeptides are isolated. The invention also encompasses polypeptides which are substantially pure. In some embodiments, the antibodies are monoclonal antibodies. In some embodiments, the antibodies are chimeric antibodies. In some embodiments, the antibodies are humanized antibodies. In some embodiments, the antibodies are human antibodies. In some embodiments, the polypeptides are not (i.e., are other than) murine monoclonal antibodies. In some embodiments, the polypeptides are not (i.e., are other than) mouse monoclonal antibodies. In some embodiments, the polypeptides are not (i.e., are other than) the 14D10 antibody (Dong et al. (1998) Mol. Immunol. 35(1):13-21 and U.S. Pat. Pub. No. 2003/0031665). In some embodiments, the polypeptides do not comprise the VH or the VL (or both the VH and VL) or a particular CDR, FR, set of CDRs, or set of FRs of the 14D10 antibody. In some embodiments, the polypeptides do not comprise one or more of the CDRs and/or one or more of the FRs of the 14D10 antibody. In some embodiments, the polypeptides do not comprise all of the CDRs and/or all of the FRs of the 14D10 antibody. In some embodiments, the polypeptides do not comprise both the VH and VL of the 14D10 antibody. (The VH and VL and the CDRs and FRs of the 14D10 antibody are identified in FIGS. 3 and 5.) In some embodiments, the polypeptide does not comprise a heavy chain variable region of the sequence QVKLQESGPGLVQPSQTLSITCTVSGFSLTTYGVHWVRQSPGKGLEWLGVIWGGGRTD YDAAFISRLSISKDNSKSQVFFK-MNSLQANDTAIYYCVRNRHDWFDYWGQGTTVTVSS (CM03 VH; SEQ ID NO:90). In some embodiments, the polypeptide does not comprise a light chain variable region of the sequence DIQMTQSPSSLSASLGDRVTITCSASQ-GIRNSLNWYQQKPDGAVKLLIYYSSNLHSGVPS RFSGSGSGTDFSLTISNLEPEDIATYYC-QQSIKLPFTFGSGTKLEIK (CM03 VL; SEQ ID NO:91). In some embodiments, the polypeptide does not comprise both a heavy chain variable region of the sequence QVKLQESG-PGLVQPSQTLSITCTVSGFSLTTYGVH-WVRQSPGKGLEWLGVIWGGGRTD YDAAFISRL-SISKDNSKSQVFFKMNSLQANDTAIYYCVRNRHDW-FDYWGQGTTVTVSS (SEQ ID NO:90) and a light chain variable region of the sequence DIQMTQSPSSL-SASLGDRVTITCSASQGIRNSLNWYQQK-PDGAVKLLIYYSSNLHSGVPS RFSGSGSGTDFS-LTISNLEPEDIATYYCQQSIKLPFTFGSGTKLEIK (SEQ ID NO:91). In some embodiments of each of the aforementioned aspects, as well as other aspects described herein, the polypeptide is not the mouse monoclonal antibody 1F7 (U.S. Pat. No. 5,120,642; PCT Publication No. WO 91/07985 (Schlossman et al.); Morimoto et al. (1989) J. Immunology, 143:3430-3439). In some embodiments, the polypeptides do not comprise both the VH and VL of the 1F7 antibody. In some embodiments, the polypeptides do not comprise one or more of the CDRs and/or one or more of the FRs of the 1F7 antibody. In some embodiments, the polypeptides do not comprise all of the CDRs and/or all of the FRs of the 1F7 antibody. In some embodiments, the polypeptides are affinity matured antibodies. In some embodiments, a polypeptide described herein is an antibody chain, such as a heavy chain or light chain. In some embodiments, the polypeptide comprises a light chain variable region (e.g., a light chain variable region comprising one or more of the light chain CDRs described herein and/or one or more of the light chain FRs described herein). In some embodiments, the polypeptide comprises a heavy chain variable region (e.g., a heavy chain variable region comprising one or more of the heavy chain complementarity determining regions (CDRs) described herein and/or one or more of the light chain framework regions (FRs) described herein). In some embodiments, the invention encompasses polypeptides which each comprise both a light chain variable region and a heavy chain variable region. The invention further encompasses polypeptides which are intermediates in the synthesis of antibodies or other CD26-binding polypeptides.

In some embodiments, the polypeptides, such as antibodies, described herein bind CD26. In some embodiments, the polypeptides described herein preferentially bind CD26. In some embodiments, the polypeptides bind human CD26. In some embodiments, the polypeptides preferentially bind human CD26. In some embodiments, the polypeptides cross-react with human CD26 and CD26 of another species. In some embodiments, a polypeptide described herein binds human CD26 with a $K_D$ of about 200 nM or less, about 60 nM or less, about 30 nM or less, about 12 nM or less, about 6 nM or less, or about 3 nM, or about 1 nM or less. In some embodiments, the polypeptide binds human CD26 with a $K_D$ of about 10 nM or less. In some embodiments, the polypeptide binds human CD26 with a $K_D$ of about 6 nM or less. In some embodiments, the polypeptide binds human CD26 with a $K_D$ of about 3 nM or less. In some embodiments, the polypeptide binds human CD26 with a $K_D$ of about 1 nM or less. In some embodiments, the polypeptide (e.g., antibody) binds human CD26 with a $K_D$ of about 0.1 nM to about 10 nM, about 0.1 nM to about 6 nM, about 0.1 nM to about 3 nM, or about 0.1 nM to about 1 nM.

In some embodiments, the polypeptides (e.g., antibodies) described herein bind to one or more peptides selected from the group consisting of YSLRWISDHEYLY (SEQ ID NO:45; peptide 6), LEYNYVKQWRHSY (SEQ ID NO:46; peptide 35), TWSPVGHKLAYVW (SEQ ID NO:47; peptide 55), LWWSPNGTFLAYA (SEQ ID NO:48; peptide 84), RISLQWLRRIQNY (SEQ ID NO:49; peptide 132), YVKQWRHSYTASY (SEQ ID NO:50; peptide 37), EEEVFSAYSALWW (SEQ ID NO:51; peptide 79), DYS-ISPDGQFILL (SEQ ID NO:52; peptide 29), SISPDGQFIL-LEY (SEQ ID NO:53; peptide 30), and IYVKIEPNLPSYR (SEQ ID NO:54; peptide 63). In some embodiments, the polypeptides described herein preferentially bind to the one or more peptides. These peptides are regions of human CD26. In some embodiments, the polypeptides described herein bind to the same epitope as the mouse monoclonal antibody 14D10. In some embodiments, the polypeptides described herein are capable of blocking the binding of mouse monoclonal antibody 14D10 to human CD26 in a competition assay. In some embodiments, the polypeptides described herein are capable of blocking the binding of mouse monoclonal antibody 1F7 to human CD26 in a competition assay.

Methods of determining affinity are known in the art. For instance, binding affinity may be determined using a BIAcore biosensor, a KinExA biosensor, scintillation proximity assays, ELISA, ORIGEN immunoassay (IGEN), fluorescence quenching, fluorescence transfer, and/or yeast display. Binding affinity may also be screened using a suitable bioassay.

One way of determining binding affinity of antibodies to CD26 is by measuring affinity of monofunctional Fab fragments of the antibodies. To obtain monofunctional Fab fragments, antibodies, for example, IgGs can be cleaved with papain or expressed recombinantly. Affinities of anti-CD26 Fab fragments of monoclonal antibodies can be determined by Surface Plasmon Resonance (SPR) system (BIAcore 3000™, BIAcore, Inc., Piscaway, N.J.). SA chips (streptavidin) are used according to the supplier's instructions. Biotinylated CD26 can be diluted into HBS-EP (100 mM HEPES pH 7.4, 150 mM NaCl, 3 mM EDTA, 0.005% P20) and injected over the chip at a concentration of 0.005 mg/mL. Using variable flow time across the individual chip channels, two ranges of antigen density are achieved: 10-20 response units (RU) for detailed kinetic studies and 500-600 RU for concentration. A mixture of Pierce elution buffer and 4 M NaCl (2:1) effectively removes the bound Fab while keeping the activity of CD26 on the chip for over 200 injections. HBS-EP buffer can be used as running buffer for all the BIAcore assays. Serial dilutions (0.1-10× estimated $K_D$) of purified Fab samples are injected for 2 min at 100 µL/min and dissociation times of up to 30 h min are generally allowed. The concentrations of the Fab proteins can be determined by ELISA and/or SDS-PAGE electrophoresis using a standard Fab of known concentration (determined by amino acid analysis). Kinetic association rates ($k_{on}$) and dissociation rates ($k_{off}$) are obtained simultaneously by fitting the data to a 1:1 Langmuir binding model (Lofas & Johnsson, 1990) using the BIAevaluation program. Equilibrium dissociation constant ($K_D$) values are calculated as $k_{off}/k_{on}$.

In some embodiments, the invention encompasses polypeptides, such as antibodies, which inhibit proliferation of cells expressing CD26. The invention also encompasses embodiments where the polypeptides are useful in the treatment of a condition (such as a disease or disorder) associated with CD26 expression (e.g., a T-cell malignancy). In some embodiments, the polypeptides (e.g., antibodies) of the invention may have one or more of the following characteristics: (a) bind CD26; (b) modulate CD26 activity, (c) cause cell cycle arrest of CD26+ cells at the G1/S checkpoint; (d) inhibit proliferation of cells expressing CD26, and/or (e) are useful in the treatment of a condition associated with CD26 expression. In some embodiments, the polypeptides are useful in inhibiting growth of a CD26-expressing tumor, inducing regression of a CD26-expressing tumor, and/or inhibiting metastasis of CD26 expressing cancer cells. In some embodiments, the condition associated with CD26 expression is a disease or disorder associated with CD26 overexpression. In some embodiments, the condition associated with CD26 expression is mediated, at least in part, by CD26. In some embodiments, the condition associated with CD26 expression is a condition associated with the proliferation of cells expressing CD26. In some embodiments, the disease or disorder is a cancer (e.g., a solid tumor cancer, pancreatic cancer, kidney cancer, or lymphoma), an autoimmune disease or disorder, graft versus host disease (GVHD), or an inflammatory disease or disorder.

In one aspect, the invention provides a polypeptide comprising one or more (e.g., one, two, three, four, five or six) complementarity determining regions (CDRs) described herein. In another aspect, the invention provides a polypeptide comprising one or more (e.g., one, two, or three) heavy chain complementarity determining regions (CDRs) described herein and/or one or more (e.g., one, two, or three) light chain CDRs described herein. In some of the embodiments, the polypeptide further comprises one or more (e.g., one, two, three, or four) heavy chain framework regions (FRs) described herein and/or one or more (e.g., one, two, three, or four) light chain FRs described herein. In another aspect, the invention provides a polypeptide comprising a heavy chain variable region comprising one or more (e.g., one, two, or three) heavy chain complementarity determining regions (CDRs) described herein and/or a light chain variable region comprising one or more (e.g., one, two, or three) light chain CDRs described herein. In some of the embodiments, the heavy chain variable region further comprises one or more (e.g., one, two, three, or four) heavy chain framework regions (FRs) described herein and/or the light chain variable region further comprises one or more (e.g., one, two, three, or four) light chain FRs described herein.

It is understood that reference to "heavy chain CDR(s)" or "light chain CDR(s)" does not mean that all embodiments of these CDRs are contained in a heavy chain or light chain, respectively. These terms are used for convenience to indicate their origin. The invention, however, does include embodiments in which one or more CDRs are contained within (a) heavy chain variable region(s) and/or light chain variable region(s), and/or (b) heavy chain(s) and/or light chain(s). The same principles apply to framework designations.

The invention provides a polypeptide, such as an antibody, comprising: (a) one or more (e.g., one, two, or three) heavy chain CDRs that each have at least about 80% identity to a CDR selected from the group consisting of (i) a heavy chain CDR1 selected from the group consisting of GFSLTTYGVH (SEQ ID NO:55), GFSLSTYGVH (SEQ ID NO:56), and GYSLTTYGVH (SEQ ID NO:57), (ii) a heavy chain CDR2 selected from the group consisting of VIWGDGRTDYDAAFMS (SEQ ID NO:58) and VIWGDGRTDYDSSFMS (SEQ ID NO:59), and (iii) a heavy chain CDR3 sequence NRHDWFDY (SEQ ID NO:60); and/or (b) one or more (e.g., one, two, or three) light chain CDRs that each have at least about 80% identity to a CDR selected from the group consisting of (i) a light chain CDR1 selected from the group consisting of RASQDIRNNLN (SEQ ID NO:61), RASQGIRNNLN (SEQ ID NO:62), and SASQDIRNSLN (SEQ ID NO:63), (ii) a light chain CDR2 selected from the group consisting of YSSNLHS (SEQ ID NO:64), YSSNLQS (SEQ ID NO:65) and YSSNLHT (SEQ ID NO:66), and (iii) a light chain CDR3 selected from the group consisting of QQSIKLPLT (SEQ ID NO:67), QQSIKLPFT (SEQ ID NO:68), and QQSNKLPLT (SEQ ID NO:69). In some embodiments, the CDR(s) have at least about 85%, at least about 90%, at least about 95%, at least about 98%, or 100% identity to the indicated sequence(s). In some embodiments, the polypeptide binds CD26. In some embodiments, the polypeptide is not a murine monoclonal antibody. In some embodiments, the polypeptide is an antibody that comprises: (i) a heavy chain CDR1 that has at least about 80% identity to GFSLTTYGVH (SEQ ID NO:55), (ii) a heavy chain CDR2 that has at least about 80% identity to VIWGDGRTDYDAAFMS (SEQ ID NO:58), and (iii) a heavy chain CDR3 that has at least about 80% identity to NRHDWFDY (SEQ ID NO:60). In some embodiments, the polypeptide is an antibody that comprises (i) a light chain CDR1 that has at least about 80% identity to RASQGIRNNLN (SEQ ID NO:62), (ii) a light chain CDR2 that has at least about 80% identity to YSSNLQS (SEQ ID NO:65), and (iii) a light chain CDR3 that has at least about 80% identity to QQSIKLPFT (SEQ ID NO:68).

In some embodiments, the polypeptide comprises one or more (e.g., one, two, or three) CDRs, wherein each of the CDRs comprises a CDR of a heavy chain variable region (VH) X384, X385, X386, X387, X388, X399, or X420 shown in FIG. 5. In some embodiments, the polypeptide comprises one or more (e.g., one, two, or three) CDRs, wherein each of the CDRs comprises a CDR of a light chain variable region (VL) shown in FIG. 3 as any of the sequences X376, X377, X378, X379, X380, X381, or X394. In some embodiments, the one or more CDRs are CDR1, CDR2, or CDR3 of the light chain variable region or heavy chain variable region shown in FIG. 3 or 5, respectively (e.g., CDR-L1, CDR-L2, CDR-L3, CDR-H1, CDR-H2, and/or CDR-H3). Some embodiments include polypeptides (such as antibodies) that comprise one or more CDRs of a heavy chain variable region (VH) sequence X384, X385, X386, X387, X388, X399, or X420 shown in FIG. 5, as well as one or more CDRs of a light chain variable region sequence X376, X377, X378, X379, X380, X381, or X394 shown in FIG. 3.

In some embodiments, the invention provides a polypeptide, such as an antibody, which comprises at least one CDR that is at least about 80% identical to at least one CDR, at least two CDRs, or at least three CDRs of a VH shown in FIG. 5 as any of the sequences X384, X385, X386, X387, X388, X399, or X420 or of a light chain variable region (VL) shown in FIG. 3 as any of the sequences X376, X377, X378, X379, X380, X381, or X394. Other embodiments include polypeptides which comprise at least two or three CDR(s) that are at least about 80% identical to at least two or three CDRs of a VH shown in FIG. 5 as any of the sequences X384, X385, X386, X387, X388, X399, or X420 or a VL shown in FIG. 3 as any of the sequences X376, X377, X378, X379, X380, X381, or X394. In some embodiments, one or more CDRs substantially homologous to at least one CDR, at least two, or at least three CDRs of a VH or VL shown in FIG. 5 or 3 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical to at least one, at least two, or at least three CDRs of a VH or VL shown in FIG. 5 as any of the sequences X384, X385, X386, X387, X388, X399, or X420 or shown in FIG. 3 in any of the sequences X376, X377, X378, X379, X380, X381, or X394. In some embodiments, the CDR is a CDR-L1, CDR-L2, CDR-L3, CDR-H1, CDR-H2, and/or CDR-H3.

Determination of CDRs is well within the skill of the art. In some embodiments, the CDRs are Kabat CDRs. In other embodiments, the CDRs are Chothia CDRs. In still further embodiments, one or more of the CDRs are defined by a combination of the Kabat and Chothia definitions.

In one aspect, the invention provides a polypeptide comprising: (a) a heavy chain CDR1 comprising the sequence GX$_1$X$_2$LX$_3$TYGVH (SEQ ID NO:31), wherein X$_1$ is F or Y, X$_2$ is S or T, and X$_3$ is T, N, or S; (b) a heavy chain CDR2 comprising the sequence VIWGX$_1$GRTDYDX$_2$X$_3$FMS (SEQ ID NO:32), wherein X$_1$ is G or D, X$_2$ is A or S, and X$_3$ is A or S; and/or (c) a heavy chain CDR3 comprising the sequence X$_1$RHDWFDY (SEQ ID NO:33), wherein X$_1$ is N or S. In some embodiments, the polypeptide comprises the CDR1. In some embodiments, the polypeptide comprises the CDR2. In some embodiments, the polypeptide comprises the CDR3. In some embodiments, the polypeptide comprises the CDR1, the CDR2, and the CDR3. In some embodiments, the polypeptide comprises a heavy chain variable region comprising the CDR1, the CDR2, and/or the CDR3. In some embodiments, the polypeptide further comprises a light chain variable region (e.g., a light chain variable region described herein).

In some embodiments, the polypeptide comprises heavy chain CDRs comprising (i) a CDR1 comprising the sequence GX$_1$X$_2$LX$_3$TYGVH (SEQ ID NO:31), wherein X$_1$ is F or Y, X$_2$ is S or T, and X$_3$ is T, N, or S; (ii) a CDR2 comprising the sequence VIWGX$_1$GRTDYDX$_2$X$_3$FMS (SEQ ID NO:32), wherein X$_1$ is G or D, X$_2$ is A or S, and X$_3$ is A or S; and (iii) a CDR3 comprising the sequence X$_1$RHDWFDY (SEQ ID NO:33), wherein X$_1$ is N or S. In some embodiments, the polypeptide comprises a heavy chain variable region comprising the heavy chain CDRs.

In some embodiments, the polypeptide comprises a heavy chain CDR1 comprising a sequence selected from the group consisting of GFSLTTYGVH (SEQ ID NO:55), GFSLSTYGVH (SEQ ID NO:56), and GYSLTTYGVH (SEQ ID NO:57). In some embodiments, the polypeptide comprises a heavy chain CDR2 comprising a sequence selected from the group consisting of VIWGDGRTDYDAAFMS (SEQ ID NO:58) and VIWGDGRTDYDSSFMS (SEQ ID NO:59). In some embodiments, the polypeptide comprises a heavy chain CDR3 comprising the sequence NRHDWFDY (SEQ ID NO:60). In some embodiments, the polypeptide comprises a heavy chain variable region comprising the heavy chain CDR(s).

Again, where any aspect or embodiment of the invention is described herein in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

In some embodiments, the polypeptide comprises heavy chain CDRs comprising: (a) a CDR1 comprising the sequence GFSLTTYGVH (SEQ ID NO:55); (b) a CDR2 comprising the sequence VIWGDGRTDYDAAFMS (SEQ ID NO:58); and (c) a CDR3 comprising the sequence NRHDWFDY (SEQ ID NO:60). In some embodiments, the polypeptide comprises heavy chain CDRs comprising: (a) a CDR1 comprising the sequence GFSLSTYGVH (SEQ ID NO:56); (b) a CDR2 comprising the sequence VIWGDGRTDYDAAFMS (SEQ ID NO:58); and (c) a CDR3 comprising the sequence NRHDWFDY (SEQ ID NO:60). In some embodiments, the polypeptide comprises heavy chain CDRs comprising: (a) a CDR1 comprising the sequence GYSLTTYGVH (SEQ ID NO:57); (b) a CDR2 comprising the sequence VIWGDGRTDYDSSFMS (SEQ ID NO:59); and (c) a CDR3 comprising the sequence NRHDWFDY (SEQ ID NO:60). In some embodiments of each of the above, the polypeptide comprises a heavy chain variable region that comprises the specified CDR1, CDR2, and CDR3.

In another aspect, the invention provides a polypeptide comprising: (a) a light chain CDR1 comprising the sequence X$_1$ASQX$_2$IRNX$_3$LN (SEQ ID NO:34), wherein X$_1$ is S or R, X$_2$ is G or D, and X$_3$ is S or N; (b) a light chain CDR2 comprising the sequence YSSNLX$_1$X$_2$ (SEQ ID NO:35), wherein X$_1$ is H or Q and X$_2$ is S or T; and/or (c) a light chain CDR3 comprising the sequence QQSX$_1$KLPX$_2$T (SEQ ID NO:36), wherein X$_1$ is I or N and X$_2$ is F or L. In some embodiments, the polypeptide is an antibody. In some embodiments, the polypeptide comprises the CDR1. In some embodiments, the polypeptide comprises the CDR2. In some embodiments, the polypeptide comprises the CDR3. In some embodiments, the polypeptide comprises the CDR1, the CDR2, and the CDR3. In some embodiments, the polypeptide comprises a light chain variable region comprising CDR1, the CDR2, and/or the CDR3. In some embodiments, the polypeptide further comprises a heavy chain variable region (e.g., a heavy chain variable region described herein).

In some embodiments, the polypeptide comprises light chain CDRs comprising (i) a CDR1 comprising the sequence $X_1ASQX_2IRNX_3LN$ (SEQ ID NO:34), wherein $X_1$ is S or R, $X_2$ is G or D, and $X_3$ is S or N; (ii) a CDR2 comprising the sequence $YSSNLX_1X_2$ (SEQ ID NO:35), wherein $X_1$ is H or Q and $X_2$ is S or T; and (iii) a CDR3 comprising the sequence $QQSX_1KLPX_2T$ (SEQ ID NO:36), wherein $X_1$ is I or N and $X_2$ is F or L. In some embodiments, the polypeptide comprises a light chain variable region comprising the light chain CDRs.

In some embodiments, the polypeptide comprises a light chain CDR1 comprising an amino acid sequence selected from the group consisting of RASQDIRNNLN (SEQ ID NO:61), RASQGIRNNLN (SEQ ID NO:62), and SASQDIRNSLN (SEQ ID NO:63). In some embodiments, the polypeptide comprises a light chain CDR2 comprising an amino acid sequence selected from the group consisting of YSSNLHS (SEQ ID NO:64), YSSNLQS (SEQ ID NO:65) and YSSNLHT (SEQ ID NO:66). In some embodiments, the polypeptide comprises a light chain CDR3 comprising an amino acid sequence selected from the group consisting of QQSIKLPLT (SEQ ID NO:67), QQSIKLPFT (SEQ ID NO:68), and QQSNKLPLT (SEQ ID NO:69). In some embodiments, the polypeptide comprises a light chain variable region comprising the light chain CDRs.

In some embodiments, the polypeptide comprises light chain CDRs comprising (a) a CDR1 comprising the sequence RASQDIRNNLN (SEQ ID NO:61), (b) a CDR2 comprising the sequence YSSNLHS (SEQ ID NO:64), and (c) a CDR3 comprising the sequence QQSIKLPLT (SEQ ID NO:67). In some embodiments, the polypeptide comprises light chain CDRs comprising (a) a CDR1 comprising the sequence RASQGIRNNLN (SEQ ID NO:62), (b) a CDR2 comprising the sequence YSSNLQS (SEQ ID NO:65), and (c) a CDR3 comprising the sequence QQSIKLPFT (SEQ ID NO:68). In some other embodiments, the polypeptide comprises light chain CDRs comprising (a) a CDR1 comprising the sequence SASQDIRNSLN (SEQ ID NO:63), (b) a CDR2 comprising the sequence YSSNLHT (SEQ ID NO:66), and (c) a CDR3 comprising the sequence QQSNKLPLT (SEQ ID NO:69). In some embodiments of each of the above, the polypeptide comprises a light chain variable region that comprises the specified CDR1, CDR2, and CDR3.

In some embodiments, the polypeptide comprises heavy chain CDRs comprising (a) a CDR1 comprising the sequence GFSLTTYGVH (SEQ ID NO:55), (b) a CDR2 comprising the sequence VIWGDGRTDYDAAFMS (SEQ ID NO:58), and (c) a CDR3 comprising the sequence NRHDWFDY (SEQ ID NO:60), and/or light chain CDRs comprising (a) a CDR1 comprising the sequence RASQGIRNNLN (SEQ ID NO:62), (b) a CDR2 comprising the sequence YSSNLQS (SEQ ID NO:65), and (c) a CDR3 comprising the sequence QQSIKLPFT (SEQ ID NO:68). In some embodiments, the polypeptide is an antibody.

In some embodiments, the polypeptide comprises a heavy chain CDR1 comprising the sequence $GX_1X_2LX_3TYGVH$ (SEQ ID NO:31), wherein $X_1$ is F or Y, $X_2$ is S or T, and $X_3$ is T, N, or S, a heavy chain CDR2 comprising the sequence $VIWGX_1GRTDYDX_2X_3FMS$ (SEQ ID NO:32), wherein $X_1$ is G or D, $X_2$ is A or S, and $X_3$ is A or S, and/or a heavy chain CDR3 comprising the sequence $X_1RHDWFDY$ (SEQ ID NO:33), wherein $X_1$ is N or S, and further comprises a light chain CDR1 comprising the sequence $X_1ASQX_2IRNX_3LN$ (SEQ ID NO:34), wherein $X_1$ is S or R, $X_2$ is G or D, and $X_3$ is S or N, a light chain CDR2 comprising the sequence $YSSNLX_1X_2$ (SEQ ID NO:35), wherein $X_1$ is H or Q and $X_2$ is S or T, and/or a light chain CDR3 comprising the sequence $QQSX_1KLPX_2T$ (SEQ ID NO:36), wherein $X_1$ is I or N and $X_2$ is F or L. For instance, in some embodiments, the polypeptide comprises the three heavy chain CDRs CDR1, CDR2, and CDR3, as well as the three light chain CDRs CDR1, CDR2, and CDR3.

The invention also encompasses polypeptides comprising one or more CDRs described herein, wherein the polypeptides further comprise one or more FRs described herein.

In some embodiments, the CDRs and/or FRs are in a sequential order.

The invention further provides a heavy chain variable region comprising one or more (e.g., one, two, or three) of the heavy chain CDRs described herein. In some embodiments, the heavy chain variable region further comprises one or more (e.g., one, two, three, or four) of the heavy chain FRs described herein. In addition, the invention also provides a light chain variable region comprising one or more (e.g., one, two, or three) of the light chain CDRs described herein. In some embodiments, the light chain variable region further comprises one or more (e.g., one, two, three, or four) of the light chain FRs described herein.

In another aspect, the invention provides a polypeptide, comprising one or more heavy chain framework regions (FRs) described herein and/or one or more light chain framework regions described herein. In some embodiments, the polypeptide comprises a heavy chain variable region comprising one or more heavy chain FRs described herein and/or a light chain variable region comprising one or more of the light chain FRs described herein.

In some embodiments, the polypeptide comprises one or more (e.g., one, two, three, or four) FRs, wherein each FR comprises an FR of a heavy chain variable region (VH) shown in FIG. 5 as any of the sequences X384, X385, X386, X387, X388, X399, or X420. In some embodiments, the FR of a heavy chain variable region in FIG. 5 is FR1, FR2, FR3, or FR4. In some embodiments, the polypeptide comprises one or more (e.g., one, two, three, or four) FRs, wherein each FR comprises an FR of a light chain variable region (VL) shown in FIG. 3 as any of the sequences X376, X377, X378, X379, X380, X381, or X394. In some embodiments, the FR of a light chain variable region in FIG. 3 is FR1, FR2, FR3, or FR4. Some embodiments include polypeptides (e.g., antibodies) that comprise one or more FRs of a heavy chain variable region (VH) shown in FIG. 5 as any of the sequences X384, X385, X386, X387, X388, X399, or X420 as well as one or more FRs of a light chain variable region shown in shown in FIG. 3 in any of the sequences X376, X377, X378, X379, X380, X381, or X394.

In some embodiments, the invention provides a polypeptide (such as an antibody) which comprises at least one FR that is substantially homologous to at least one FR, at least two FRs, at least three FRs, or at least four FRs of a VH shown in FIG. 5 as any of the sequences X384, X385, X386, X387, X388, X399, or X420 or a VL shown in FIG. 3 in any of the sequences X376, X377, X378, X379, X380, X381, or X394. In some embodiments, one or more FRs substantially homologous to at least one FR, at least two, at least three, or at least four FRs of a VH or VL shown in FIG. 5 or 3 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical to at least one, at least two, at least three, or at least four FRs of a VH or VL shown in FIG. 5 as any of the sequences X384, X385, X386, X387, X388, X399, or X420 or shown in FIG. 3 as any of the sequences X376, X377, X378, X379, X380, X381, or X394.

In still another aspect, the invention provides a polypeptide comprising: (a) a heavy chain FR1 comprising the sequence EVQLVX$_1$SGX$_2$X$_3$X$_4$X$_5$QPGX$_6$X$_7$LRLX$_8$CX$_9$AS (SEQ ID NO:37), wherein X$_1$ is E or Q, X$_2$ is A or G, X$_3$ is G or E, X$_4$ is L or V, X$_5$ is V, K, or E, X$_6$ is G or E, X$_7$ is T or S, X$_8$ is T or S, and X$_9$ is T or K; (b) a heavy chain FR2 comprising the sequence WVRQAPGKGLEWX$_1$G (SEQ ID NO:38), wherein X$_1$ is V or M; (c) a heavy chain FR3 comprising the sequence RVTISX$_1$DX$_2$SKX$_3$TX$_4$YLQX$_5$NSLRAEDTAVYYCX$_6$R (SEQ ID NO:39), wherein X$_1$ is K or R, X$_2$ is N or T, X$_3$ is S or N, X$_4$ is V or A, X$_5$ is M or L, and X$_6$ is V, M, or T; and/or (d) a heavy chain FR4 comprising the sequence WGQGTTVTVSS (SEQ ID NO:40). In some embodiments, the polypeptide comprises the FR1. In some embodiments, the polypeptide comprises the FR2. In some embodiments, the polypeptide comprises the FR3. In some embodiments, the polypeptide comprises the FR1, the FR2, the FR3, and the FR4. In some embodiments, the polypeptide comprises a heavy chain variable region comprising the FR1, the FR2, the FR3, and/or the FR4. In some embodiments, the polypeptide further comprises a light chain variable region.

In some embodiments, the polypeptide comprises a heavy chain FR1 comprising the sequence EVQLVESGAGVKQPGGTLRLTCTAS (SEQ ID NO:70), EVQLVQSGGGVKQPGETLRLTCTAS (SEQ ID NO:71), EVQLVQSGGGLKQPGETLRLSCTAS (SEQ ID NO:72), or EVQLVESGGGVKQPGETLRLTCTAS (SEQ ID NO:73). In other embodiments, the polypeptide comprises a heavy chain FR2 comprising the sequence WVRQAPGKGLEWVG (SEQ ID NO:74) or WVRQAPGKGLEWMG (SEQ ID NO:75). In other embodiments, the polypeptide comprises a heavy chain FR3 comprising the sequence RVTISKDTSKSTVYLQMNSLRAEDTAVYYCMR (SEQ ID NO:76), RVTISKDTSKSTAYLQMNSLRAEDTAVYYCMR (SEQ ID NO:77), or RVTISKDTSKSTAYLQLNSLRAEDTAVYYCTR (SEQ ID NO:78). In some embodiments, the polypeptide comprises a heavy chain FR4 comprising the sequence WGQGTTVTVSS (SEQ ID NO:40).

In some embodiments, the polypeptide comprises heavy chain framework regions comprising (a) an FR1 comprising the sequence EVQLVESGAGVKQPGGTLRLTCTAS (SEQ ID NO:70), (b) an FR2 comprising the sequence WVRQAPGKGLEWVG (SEQ ID NO:74), (c) an FR3 comprising the sequence RVTISKDTSKSTVYLQMNSLRAEDTAVYYCMR (SEQ ID NO:76), and (d) an FR4 comprising the sequence WGQGTTVTVSS (SEQ ID NO:40). In other embodiments, the polypeptide comprises heavy chain framework regions comprising (a) an FR1 comprising the sequence EVQLVQSGGGVKQPGETLRLTCTAS (SEQ ID NO:71), (b) an FR2 comprising the sequence WVRQAPGKGLEWVG (SEQ ID NO:74), (c) an FR3 comprising the sequence RVTISKDTSKSTAYLQMNSLRAEDTAVYYCMR (SEQ ID NO:77), and (d) an FR4 comprising the sequence WGQGTTVTVSS (SEQ ID NO:40). In still other embodiments, the polypeptide comprises heavy chain framework regions comprising (a) an FR1 comprising the sequence EVQLVQSGGGLKQPGETLRLSCTAS (SEQ ID NO:72), (b) an FR2 comprising the sequence WVRQAPGKGLEWMG (SEQ ID NO:75), (c) an FR3 comprising the sequence RVTISKDTSKSTAYLQLNSLRAEDTAVYYCTR (SEQ ID NO:78), and (d) an FR4 comprising the sequence WGQGTTVTVSS (SEQ ID NO:40). In some alternative embodiments, the polypeptide comprises heavy chain framework regions comprising (a) an FR1 comprising the sequence EVQLVESGGGVKQPGETLRLTCTAS (SEQ ID NO:73), (b) an FR2 comprising the sequence WVRQAPGKGLEWVG (SEQ ID NO:74), (c) an FR3 comprising the sequence RVTISKDTSKSTVYLQMNSLRAEDTAVYYCMR (SEQ ID NO:76), and (d) an FR4 comprising the sequence WGQGTTVTVSS (SEQ ID NO:40). In some embodiments, the heavy chain framework regions are contained within a heavy chain variable region.

In a further aspect, the invention provides a polypeptide, comprising (a) a light chain FR1 comprising the sequence X$_1$IX$_2$X$_3$TQSPSSLSX$_4$X$_5$X$_6$GX$_7$RX$_8$TIX$_9$C (SEQ ID NO:41), wherein X$_1$ is D or E, X$_2$ is L or E, X$_3$ is M or L, X$_4$ is A or V, X$_5$ is S or T, X$_6$ is L, P, or A, X$_7$ is D or E, X$_8$ is V or A, and X$_9$ is T or S; (b) a light chain FR2 comprising the sequence WYQQKPGQAPRLLIY (SEQ ID NO: 42); (c) a light chain FR3 comprising the sequence GVPXIRFSGSGSGTDFTLTISRLX$_2$X$_3$EDX$_4$AX$_5$YYC (SEQ ID NO: 43), wherein X$_1$ is S, D, or A, X$_2$ is E or Q, X$_3$ is P or A, X$_4$ is F or V, and X$_5$ is T, A, or I; and/or (d) a light chain FR4 comprising the sequence FGSGTKVEIK (SEQ ID NO:44). In some embodiments, the polypeptide comprises the FR1. In some embodiments, the polypeptide comprises the FR2. In some embodiments, the polypeptide comprises the FR3. In some embodiments, the polypeptide comprises the FR4. In some embodiments, the polypeptide comprises the FR1, the FR2, the FR3, and the FR4. In some embodiments, the polypeptide comprises a light chain variable region comprising the FR1, FR2, FR3, and/or FR4. In some embodiments, the polypeptide further comprises a heavy chain variable region.

In some embodiments, the polypeptide comprises a light chain FR1 comprising the sequence DILMTQSPSSLSASPGDRVTISC (SEQ ID NO:79), DILLTQSPSSLSATPGERATITC (SEQ ID NO:80), or EIEMTQSPSSLSVSAGERATISC (SEQ ID NO:81). In some embodiments, the polypeptide comprises a light chain FR2 comprising the sequence WYQQKPGQAPRLLIY (SEQ ID NO:42). In some embodiments, the polypeptide comprises a light chain FR3 comprising the sequence GVPDRFSGSGSGTDFTLTISRLEPEDFAAYYC (SEQ ID NO:82), GVPSRFSGSGSGTDFTLTISRLQPEDVAAYYC (SEQ ID NO:83), or GVPARFSGSGSGTDFTLTISRLEPEDVAIYYC (SEQ ID NO:84). In some embodiments, the polypeptide comprises a light chain FR4 comprising the sequence FGSGTKVEIK (SEQ ID NO:44).

In some embodiments, the polypeptide comprises light chain framework regions comprising (a) an FR1 comprising the sequence DILMTQSPSSLSASPGDRVTISC (SEQ ID NO:79), (b) an FR2 comprising the sequence WYQQKPGQAPRLLIY (SEQ ID NO:42), c) an FR3 comprising the sequence GVPDRFSGSGSGTDFTLTISRLEPEDFAAYYC (SEQ ID NO:82), and (d) an FR4 comprising the sequence FGSGTKVEIK (SEQ ID NO:44). In some embodiments, the polypeptide comprises light chain framework regions comprising (a) an FR1 comprising the sequence DILLTQSPSSLSATPGERATITC (SEQ ID NO:80), (b) an FR2 comprising the sequence WYQQKPGQAPRLLIY (SEQ ID NO:42), (c) an FR3 comprising the sequence GVPSRFSGSGSGTDFTLTISRLQPEDVAAYYC (SEQ ID NO:83), and (d) an FR4 comprising the sequence FGSGTKVEIK (SEQ ID NO:44). In some embodiments, the polypeptide comprises light chain framework regions comprising (a) an FR1 comprising the sequence EIEMTQSPSSLSVSAGERATISC (SEQ ID NO:81), (b) an FR2 comprising the sequence WYQQK-PGQAPRLLIY (SEQ ID NO:42), (c) an FR3 comprising the sequence GVPARFSGSGSGTDFTLTISRLEPEDVAIYYC (SEQ ID NO:84), and (d) an FR4 comprising the sequence FGSGTKVEIK (SEQ ID NO:44). In some embodiments, the light chain framework regions are contained within a light chain variable region.

The invention further provides a heavy chain variable region comprising one or more (e.g., one, two, three, or four) of the heavy chain FRs described herein. In addition, the invention also provides a light chain variable region comprising one or more (e.g., one, two, three, or four) of the light chain FRs described herein.

The invention further provides a polypeptide comprising one or more of the heavy chain variable regions described herein and/or one of the light chain variable regions described herein. In some embodiments, the polypeptide comprises a heavy chain variable region comprising one or more of the heavy chain CDRs described herein and/or one or more of the heavy chain FRs described herein. In some embodiments, the polypeptide comprises a light chain variable region comprising one or more of the light chain CDRs described herein and/or one or more of the light chain FRs described herein.

In another aspect, the invention provides a polypeptide comprising the amino acid sequence EVQLVX$_1$SGX$_2$X$_3$X$_4$X$_5$QPGX$_6$X$_7$LRLX$_8$CX$_9$ASGX$_{10}$-X$_{11}$LX$_{12}$TYGVHWVRQAPGKGLEWX$_{13}$GVIWGX$_{14}$GR-TDYDX$_{15}$X$_{16}$FMSRVTISX$_{17}$DX$_{18}$SKX$_{19}$TX$_{20}$YLQX$_{21}$N-SLRAEDTAVYYCX$_{22}$RX$_{23}$RHDWFDYWGQGTTVTVSS (SEQ ID NO:29), wherein X$_1$ is E or Q, X$_2$ is A or G, X$_3$ is G or E, X$_4$ is L or V, X$_5$ is V, K, or E, X$_6$ is G or E, X$_7$ is T or S, X$_8$ is T or S, X$_9$ is T or K, X$_{10}$ is F or Y, X$_{11}$ is S or T, X$_{12}$ is T, N, or S, X$_{13}$ is V or M, X$_{14}$ is G or D, X$_{15}$ is A or S, X$_{16}$ is A or S, X$_{17}$ is K or R, X$_{18}$ is N or T, X$_{19}$ is S or N, X$_{20}$ is V or A, X$_{21}$ is M or L, X$_{22}$ is V, M, or T, and X$_{23}$ is N or S. In some embodiments, the polypeptide comprises a heavy chain variable region comprising the sequence EVQLVX$_1$SGX$_2$-X$_3$X$_4$X$_5$QPGX$_6$X$_7$LRLX$_8$CX$_9$ASGX$_{10}$X$_{11}$LX$_{12}$TYGVH-WVRQAPGKGLEWX$_{13}$GVIWGX$_{14}$GRTDYDX$_{15}$X$_{16}$FM-SRVTISX$_{17}$DX$_{18}$SKX$_{19}$TX$_{20}$YLQX$_{21}$NSLRAEDTAVYY-CX$_{22}$RX$_{23}$RHDWFDYWGQGTTVTVSS (SEQ ID NO:29), wherein X$_1$ is E or Q, X$_2$ is A or G, X$_3$ is G or E, X$_4$ is L or V, X$_5$ is V, K, or E, X$_6$ is G or E, X$_7$ is T or S, X$_8$ is T or S, X$_9$ is T or K, X$_{10}$ is F or Y, X$_{11}$ is S or T, X$_{12}$ is T, N, or S, X$_{13}$ is V or M, X$_{14}$ is G or D, X$_{15}$ is A or S, X$_{16}$ is A or S, X$_{17}$ is K or R, X$_{18}$ is N or T, X$_{19}$ is S or N, X$_{20}$ is V or A, X$_{21}$ is M or L, X$_{22}$ is V, M, or T, and X$_{23}$ is N or S. In some embodiments, the polypeptide is an antibody. In some embodiments, the polypeptide further comprises a light chain variable region.

The CDRs (CDR1, CDR2, and CDR3) of the heavy chain variable region are underlined (and positioned in sequential order) in the following sequence: EVQLVX$_1$SGX$_2$X$_3$X$_4$X$_5$QPGX$_6$X$_7$LRLX$_8$CX$_9$AS GX$_{10}$X$_{11}$LX$_{12}$TYGVHWVRQAPGKGLEWX$_{13}$G <u>VIWGX$_{14}$GRTDYDX$_{15}$</u>X$_{16}$FMSRVTISX$_{17}$DX$_{18}$SKX$_{19}$T-X$_{20}$YLQX$_{21}$NSLRAEDTAVYYC X$_{22}$RX$_{23}$RHDWFDYWGQGTTVTVSS (SEQ ID NO:29), wherein X$_1$ is E or Q, X$_2$ is A or G, X$_3$ is G or E, X$_4$ is L or V, X$_5$ is V, K, or E, X$_6$ is G or E, X$_7$ is T or S, X$_8$ is T or S, X$_9$ is T or K, X$_{10}$ is F or Y, X$_{11}$ is S or T, X$_{12}$ is T, N, or S, X$_{13}$ is V or M, X$_{14}$ is G or D, X$_{15}$ is A or S, X$_{16}$ is A or S, X$_{17}$ is K or R, X$_{18}$ is N or T, X$_{19}$ is S or N, X$_{20}$ is V or A, X$_{21}$ is M or L, X$_{22}$ is V, M, or T, and X$_{23}$ is N or S. CDR2 and CDR3 of the heavy chain variable region (CDR-H2 and CDR-H3) were defined according to the Kabat definition (Kabat et al., *Sequences of Proteins of Immunological Interest*, 4$^{th}$ edit., National Institutes of Health, Bethesda, Md. (1987)). CDR1 of the heavy chain variable region (CDR-H1) was defined according to a combination of the Kabat and Chothia definitions (Chothia et al., *J. Mol. Biol.*, 196:901-917). Such methods are known in the art for defining antibody CDRs. See, e.g., Chen et al., *J. Mol. Biol.*, 293:865-881 (1999) and Muller et al., *Structure*, 6:1153-1167 (1998). Within the sequence shown in SEQ ID NO:29, the position of CDR1 is H26-35, the position of CDR2 is H50-65, and the position of CDR3 is H95-102, based on Kabat numbering. According to sequential numbering, the position of CDR1 is H26-35, the position of CDR2 is H50-65, and the position of CDR3 is H98-105. (See, e.g., FIG. 5 for an illustration of the position of the CDRs and FRs of the heavy chain variable region on selected, exemplary heavy chain variable region sequences.)

In some embodiments, the polypeptide comprises an amino acid sequence selected from the group consisting of EVQLVESGAGVKQPGGTLRLTCTASGFS-LTTYGVHWVRQAPGKGLEWVGVIWGDGRT DYDAAFMSRVTISKDTSKSTVYLQMNSL-RAEDTAVYYCMRNRHDWFDYWGQGTTVT VSS (SEQ ID NO:22; X384), EVQLVQSGGGVKQPGETLRLTCTAS-GFSLTTYGVHWVRQAPGKGLEWVGVIWGDGRT DYDAAFMSRVTISKDTSKSTAYLQMNSL-RAEDTAVYYCMRNRHDWFDYWGQGTTVT VSS (SEQ ID NO:23; X385), EVQLVQSGGGLKQPGETLRLSCTAS-GYSLTTYGVHWVRQAPGKGLEWMGVIWGDGRT DYDSSFMSRVTISKDTSKSTAYLQLNSL-RAEDTAVYYCTRNRHDWFDYWGQGTTVTVS S (SEQ ID NO:26; X388), and EVQLVESGGGVKQPGETLR-LTCTASGFSLSTYGVHWVRQAPGK-GLEWVGVIWGDGRT DYDAAFM-SRVTISKDTSKSTVYLQMNSLRAEDTAVYYCMRNRH-DWFDYWGQGTTVT VSS (SEQ ID NO:28; X420). In some embodiments, the polypeptide (e.g., an antibody) comprises a heavy chain variable region comprising an amino acid sequence selected from the group consisting of SEQ ID NO:22 (X384), SEQ ID NO:23 (X385), SEQ ID NO:26 (X388), and SEQ ID NO:28 (X420).

In an additional aspect, the invention provides a polypeptide comprising the sequence X$_1$IX$_2$X$_3$TQSPSSLSX$_4$X$_5$X$_6$GX$_7$RX$_8$TIX$_9$CX$_{10}$ASQX$_{11}$I-RNX$_{12}$LNWYQQKPGQAPRLLIYYSS NLX$_{13}$X$_4$GVPX$_{15}$RFSGSGSGTDFTLTISRLX$_{16}$X$_{17}$ED-X$_{18}$AX$_{19}$YYCQQSX$_{20}$KLPX$_{21}$TFGSGT KVEIK (SEQ ID NO:30), wherein X$_1$ is D or E, X$_2$ is L or E, X$_3$ is M or L, X$_4$ is A or V, X$_5$ is S or T, X$_6$ is L, P, or A, X$_7$ is D or E, X$_8$ is V or A, X$_9$ is T or S, X$_{10}$ is S or R, X$_{11}$ is G or D, X$_{12}$ is S or N, X$_{13}$ is H or Q, X$_{14}$ is S or T, X$_{15}$ is S, D, or A, X$_{16}$ is E or Q, X$_{17}$ is P or A, X$_{18}$ is F or V, X$_{19}$ is T, A, or I, X$_{20}$ is I or N and X$_{21}$ is F or L. In some embodiments, the polypeptide comprises a light chain variable region comprising an amino acid sequence of X$_1$IX$_2$X$_3$TQSPSSLSX$_4$X$_5$X$_6$GX$_7$RX$_8$TI-X$_9$CX$_{10}$ASQX$_{11}$IRNX$_{12}$LNWYQQKPGQAPRLLIYYSS NLX$_{13}$X$_{14}$GVPX$_{15}$RFSGSGSGTDFTLTISRLX$_{16}$X$_{17}$E-DX$_{18}$AX$_{19}$YYCQQSX$_{20}$KLPX$_{21}$TFGSGT KVEIK (SEQ ID NO:30), wherein X$_1$ is D or E, X$_2$ is L or E, X$_3$ is M or L, X$_4$ is A or V, X$_5$ is S or T, X$_6$ is L, P, or A, X$_7$ is D or E, X$_8$ is V or A, X$_9$ is T or S, X$_{10}$ is S or R, X$_{11}$ is G or D, X$_{12}$ is S or N, X$_{13}$ is H or Q, X$_{14}$ is S or T, X$_{15}$ is S, D, or A, X$_{16}$ is E or Q, X$_{17}$ is P or A, X$_{18}$ is F or V, X$_{19}$ is T, A, or I, X$_{20}$ is I or N and X$_{21}$ is F or L. In some embodiments, the polypeptide is an antibody. In some embodiments, the polypeptide further comprises a heavy chain variable region.

The CDRs (CDR1, CDR2, and CDR3) of the light chain variable region are underlined (and positioned in sequential order) in the following sequence:
$X_1IX_2X_3TQSPSSLSX_4X_5X_6GX_7RX_8TIX_9C$
$X_{10}ASQX_{11}IRNX_{12}LNWYQQKPGQAPRLLIY$
$YSSNLX_{13}X_{14}GVPX_{15}RFSGSGSGTDFTLTISRLX_{16}X_{17}$
$EDX_{18}AX_{19}YYCQQSX_{20}KLPX_{21}TFGSGT$ KVEIK (SEQ
ID NO:30), wherein $X_1$ is D or E, $X_2$ is L or E, $X_3$ is M or L,
$X_4$ is A or V, $X_5$ is S or T, $X_6$ is L, P, or A, $X_7$ is D or E, $X_8$ is
V or A, $X_9$ is T or S, $X_{10}$ is S or R, $X_1$, is G or D, $X_{12}$ is S or
N, $X_{13}$ is H or Q, $X_{14}$ is S or T, $X_{15}$ is S, D, or A, $X_{16}$ is E or
Q, $X_{17}$ is P or A, $X_{18}$ is F or V, $X_{19}$ is T, A, or I, $X_{20}$ is I or N
and $X_{21}$ is F or L. The CDR1, CDR2, and CDR3 of the light
chain variable region (CDR-L1, CDR-L2, and CDR-L3,
respectively) shown were defined according to the Kabat
definition (Kabat et al., *Sequences of proteins of Immunological Interest*, 4th edit., National Institutes of Health, Bethesda,
Md. (1987)). The position of the CDR1 in the light chain
variable region is L24-34, the position of the CDR2 in the
light chain variable region is L50-56, and the position of the
CDR3 in the light chain variable region is L89-97 (under both
sequential and Kabat numbering schemes). (See, e.g., FIG. 3
for an illustration of the position of the CDRs and FRs of the
light chain variable region on selected, exemplary light chain
variable region sequences.)

In some embodiments, the polypeptide comprises an
amino acid sequence selected from the group consisting of

```
                                         (SEQ ID NO: 15; X376)
DILMTQSPSSLSASPGDRVTISCRASQDIRNNLNWYQQKPGQAPRLLIYY

SSNLHSGVPDRFSGSGSGTDFTLTISRLEPEDFAAYYCQQSIKLPLTFGS

GTKVEIK, (SEQ ID NO: 18; X379)
DILLTQSPSSLSATPGERATITCRASQGIRNNLNWYQQKPGQAPRLLIYY

SSNLQSGVPSRFSGSGSGTDFTLTISRLQPEDVAAYYCQQSIKLPFTFGS

GTKVEIK,
and (SEQ ID NO: 19; X380)
EIEMTQSPSSLSVSAGERATISCSASQDIRNSLNWYQQKPGQAPRLLIYY

SSNLHTGVPARFSGSGSGTDFTLTISRLEPEDVAIYYCQQSNKLPLTFGS

GTKVEIK.
```

In some embodiments, the polypeptide (e.g., an antibody)
comprises a light chain variable region comprising an amino
acid sequence selected from the group consisting of SEQ ID
NO:15 (X376), SEQ ID NO:18 (X379), and SEQ ID NO:19
(X380).

In some embodiments, the polypeptide comprises both (a)
an amino acid sequence selected from the group consisting of
SEQ ID NO:22 (X384), SEQ ID NO:23 (X385), SEQ ID
NO:26 (X388), and SEQ ID NO:28 (X420) and (b) an amino
acid sequence selected from the group consisting of SEQ ID
NO:15 (X376), SEQ ID NO:18 (X379), and SEQ ID NO:19
(X380). In some embodiments, the polypeptide (e.g., an antibody) comprises both (a) a heavy chain variable region comprising an amino acid sequence selected from the group consisting of SEQ ID NO:22 (X384), SEQ ID NO:23 (X385),
SEQ ID NO:26 (X388), and SEQ ID NO:28 (X420) and (b) a
light chain variable region comprising an amino acid
sequence selected from the group consisting of SEQ ID
NO:15 (X376), SEQ ID NO:18 (X379), and SEQ ID NO:19
(X380).

In some embodiments, the polypeptide comprises an
amino acid sequence SEQ ID NO:26 (X388) and an amino
acid sequence SEQ ID NO:15 (X376). In some embodiments,
the polypeptide comprises an amino acid sequence SEQ ID
NO:22 (X384) and an amino acid sequence SEQ ID NO:18
(X379). In some embodiments, the polypeptide comprises an
amino acid sequence SEQ ID NO:28 (X420) and an amino
acid sequence SEQ ID NO:19 (X380). In some embodiments,
the polypeptide comprises an amino acid sequence SEQ ID
NO:23 (X385) and an amino acid sequence SEQ ID NO:19
(X380). In some embodiments, the polypeptide is an antibody.

In some embodiments, the polypeptide comprises a heavy
chain variable region comprising an amino acid sequence
SEQ ID NO:26 (X388) and a light chain variable region
comprising an amino acid sequence SEQ ID NO:15 (X376).
In some embodiments, the polypeptide comprises a heavy
chain variable region comprising an amino acid sequence
SEQ ID NO:22 (X384) and a light chain variable region
comprising an amino acid sequence SEQ ID NO:18 (X379).
In some embodiments, the polypeptide comprises a heavy
chain variable region comprising an amino acid sequence
SEQ ID NO:28 (X420) and a light chain variable region
comprising an amino acid sequence SEQ ID NO:19 (X380).
In some embodiments, the polypeptide comprises a heavy
chain variable region comprising an amino acid sequence
SEQ ID NO:23 (X385) and a light chain variable region
comprising an amino acid sequence SEQ ID NO:19 (X380).
In some embodiments, the polypeptide comprising the heavy
chain variable region and the light chain variable region is an
antibody.

The invention provides a polypeptide, such as an antibody,
comprising (a) an amino acid sequence having at least about
80% identity to an amino acid sequence selected from the
group consisting of SEQ ID NOS:15-21 or to a fragment of an
amino acid sequence selected from the group consisting of
SEQ ID NOS:15-21, and/or (b) an amino acid sequence having at least about 80% identity to an amino acid sequence
selected from the group consisting of SEQ ID NOS:22-28 or
to a fragment of an amino acid sequence selected from the
group consisting of SEQ ID NOS:22-28. In some embodiments the amino acid sequences have at least about 85%, at
least about 90%, at least about 95%, at least about 97%, at
least about 99% identity, or 100% identity to the indicated
sequences. In some embodiments, the polypeptide comprises
(a) an amino acid sequence having at least about 90% identity
to SEQ ID NO:18 or to a fragment of amino acid sequence
SEQ ID NO:18, and/or (b) an amino acid sequence having at
least about 90% identity to an amino acid sequence SEQ ID
NO:22 or to a fragment of to an amino acid sequence SEQ ID
NO:22. In some embodiments, the fragment comprises at
least about 10 amino acids, at least about 25 amino acids, at
least about 50 amino acids, or at least about 100 amino acids.
In some embodiments, the polypeptide binds CD26. In some
embodiments, the polypeptide is not a murine monoclonal
antibody.

In another aspect, the invention provides a polypeptide
comprising an amino acid sequence having at least about 80%
identity to an amino acid sequence selected from the group
consisting of the following sequences shown in FIG. 5: X384,
X385, X386, X387, X388, X399, and X420 (SEQ ID NOS:
22-28, respectively). The invention also provides a polypeptide, such as an antibody, comprising a heavy chain variable
region comprising an amino acid sequence having at least
about 80% identity to an amino acid sequence selected from
the group consisting of the following sequences shown in
FIG. 5: X384, X385, X386, X387, X388, X399, and X420
(SEQ ID NOS:22-28, respectively). For instance, in some
embodiments, the heavy chain variable region comprises an amino acid sequence having at least about 80% identity to an amino acid sequence having at least about 80% identity to SEQ ID NO:22 (X384). In some embodiments, the heavy chain variable region comprises an amino acid sequence having at least about 80% identity to SEQ ID NO:23 (X385). In some embodiments, the heavy chain variable region comprises an amino acid sequence having at least about 80% identity to SEQ ID NO:26 (X388). In some embodiments, the heavy chain variable region comprises an amino acid sequence having at least about 80% identity to SEQ ID NO:28 (X420). In some embodiments, the heavy chain variable region comprises an amino acid sequence having at least about 85%, at least about 90%, at least about 95%, at least about 97%, at least about 99% identity, or 100% identity to an amino acid sequence selected from the group consisting of the following sequences shown in FIG. 5: X384, X385, X386, X387, X388, X399, and X420 (SEQ ID NOS:22-28, respectively). For instance, in some embodiments, the heavy chain variable region comprises at least about 95% identity to an amino acid sequence selected from the group consisting of SEQ ID NOS:22-28. In some other embodiments, the heavy chain variable region comprises an amino acid sequence selected from the group consisting of SEQ ID NOS:22-28.

In a further aspect, the invention provides a polypeptide comprising an amino acid sequence having at least about 80% identity to an amino acid sequence selected from the group consisting of the following sequences shown in FIG. 3: X376, X377, X378, X379, X380, X381, and X394 (SEQ ID NOS: 15-21, respectively). The invention further provides a polypeptide, such as an antibody, comprising a light chain variable region comprising an amino acid sequence having at least about 80% identity to an amino acid sequence selected from the group consisting of the following sequences shown in FIG. 3: X376, X377, X378, X379, X380, X381, and X394 (SEQ ID NOS:15-21, respectively). For instance, in some embodiments, the light chain variable region comprises an amino acid sequence having at least about 80% identity to an amino acid sequence of SEQ ID NO:15 (X376). In some embodiments, the light chain variable region comprises an amino acid sequence having at least about 80% identity to an amino acid sequence of SEQ ID NO:18 (X379). In some embodiments, the light chain variable region comprises an amino acid sequence having at least about 80% identity to an amino acid sequence of SEQ ID NO:19 (X380). In some embodiments, the light chain variable region comprises an amino acid sequence having at least about 85%, at least about 90%, at least about 95%, at least about 97%, at least about 99% identity, or 100% identity to an amino acid sequence selected from the group consisting of the following sequences shown in FIG. 3: X376, X377, X378, X379, X380, X381, and X394 (SEQ ID NOS:15-21, respectively). For instance, in some embodiments, the light chain variable region comprises at least about 95% identity to an amino acid sequence selected from the group consisting of SEQ ID NOS:15-21. In other embodiments, the light chain variable region comprises an amino acid sequence selected from the group consisting of SEQ ID NOS:15-21.

In some embodiments, the antibody comprises both a heavy chain variable region comprising an amino acid sequence having at least about 80% identity to an amino acid sequence selected from the group consisting of SEQ ID NOS: 22-28 and a light chain variable region comprising an amino acid sequence having at least about 80% identity to an amino acid sequence selected from the group consisting of SEQ ID NOS:15-21. In some embodiments, the antibody comprises a light chain variable region comprising an amino acid sequence selected from the group consisting of SEQ ID NOS: 15-21 and a heavy chain variable region comprising an amino acid sequence selected from the group consisting of SEQ ID NOS:22-28.

In some embodiments, the polypeptide comprises at least 5 contiguous amino acids, at least 8 contiguous amino acids, at least about 10 contiguous amino acids, at least about 15 contiguous amino acids, at least about 20 contiguous amino acids, at least about 30 contiguous amino acids, or at least about 50 contiguous amino acids of an amino acid sequence of any one of SEQ ID NOS:15-28.

In another aspect, the invention provides a polypeptide comprising an amino acid sequence selected from the group consisting of SEQ ID NOS:15-28.

An *E. coli* sample containing a plasmid encoding the heavy and light chains of rhuMAb 411 has been deposited under the name "DH5α *Escherichia coli* with plasmid having insert of heavy and light chain of a humanized monoclonal antibody against human CD26 cDNA," and with the strain designation "S604069.YST-pABMC148 (x411)," with the American Type Culture Collection (ATCC), P.O. Box 1549, Manassas, Va., 20108, United States of America (10801 University Blvd., Manassas, Va. 20110-2209, United States of America) on Jun. 30, 2006, under the provisions of the Budapest Treaty on the International Recognition of the Deposit of Microorganisms for the Purposes of a Patent Procedure, and designated with accession number PTA-7695. Accordingly, the invention provides a polypeptide comprising the heavy chain and/or the light chain of the antibody encoded by the plasmid in *E. coli* in the sample named "DH5α *Escherichia coli* with plasmid having insert of heavy and light chain of a humanized monoclonal antibody against human CD26 cDNA," having strain designation "5604069.YST-pABMC148 (x411)," deposited with the American Type Culture Collection (ATCC) under the provisions of the Budapest Treaty on the International Recognition of the Deposit of Microorganisms for the Purposes of a Patent Procedure. The invention further provides a polypeptide comprising the heavy chain variable region and/or the light chain variable region of the antibody encoded by the plasmid in *E. coli* in the sample named "DH5α *Escherichia coli* with plasmid having insert of heavy and light chain of a humanized monoclonal antibody against human CD26 cDNA," having strain designation "5604069.YST-pABMC148 (x411)," deposited with the ATCC on Jun. 30, 2006, under the provisions of the Budapest Treaty on the International Recognition of the Deposit of Microorganisms for the Purposes of a Patent Procedure, and designated with accession number PTA-7695. The invention also provides an antibody encoded by the plasmid deposited with the ATCC in *E. coli* as accession number PTA-7695.

The invention further provides polypeptides comprising fragments of the polypeptide sequences described herein (e.g., any one of SEQ ID NOS:15-21, SEQ IDS NOS: 22-28, SEQ IDS NO:29, or SEQ IDS NO:30). In some embodiments, the polypeptide comprises a fragment of a polypeptide sequence described herein, wherein the fragment is at least about 10 amino acids in length, at least about 25 amino acids in length, at least about 50 amino acids in length, at least about 75 amino acids in length, or at least about 100 amino acids in length.

The invention further provides a polypeptide (e.g., an antibody) comprising SEQ ID NO:217 (see Example 4, below), or a fragment or variant thereof. In some embodiments, the polypeptide comprises SEQ ID NO:217. In some embodiments, the polypeptide comprises SEQ ID NO:217 except for the signal sequence. (One of ordinary skill in the art will readily appreciate that in some embodiments, the signal sequence of a polypeptide is cleaved off of the polypeptide.)

In some embodiments, the polypeptide comprises the variable region of SEQ ID NO:217. In some embodiments, the polypeptide comprises a polypeptide having at least about 80%, at least about 85%, at least about 90%, at least about 95%, or at least about 98% identity to SEQ ID NO:217 (or a fragment thereof). In some embodiments, the polypeptide comprises a fragment of SEQ ID NO:217 (or of its variable region), wherein the fragment is at least about 10 amino acids in length, at least about 25 amino acids in length, at least about 50 amino acids in length, at least about 75 amino acids in length, or at least about 100 amino acids in length. In some embodiments, the polypeptide binds human CD26.

The invention further provides a polypeptide (e.g., an antibody) comprising SEQ ID NO:218 (see Example 4, below), or a fragment or variant thereof. In some embodiments, the polypeptide comprises SEQ ID NO:218. In some embodiments, the polypeptide comprises SEQ ID NO:218 except for the signal sequence. (One of ordinary skill in the art will readily appreciate that in some embodiments, the signal sequence of a polypeptide is cleaved off of the polypeptide.) In some embodiments, the polypeptide comprises the variable region of SEQ ID NO:218. In some embodiments, the polypeptide comprises a polypeptide having at least about 80%, at least about 85%, at least about 90%, at least about 95%, or at least about 98% identity to SEQ ID NO:218 (or a fragment thereof). In some embodiments, the polypeptide comprises a fragment of SEQ ID NO:218 (or of its variable region), wherein the fragment is at least about 10 amino acids in length, at least about 25 amino acids in length, at least about 50 amino acids in length, at least about 75 amino acids in length, or at least about 100 amino acids in length. In some embodiments, the polypeptide further comprises SEQ ID NO:218 (see Example 4, below), or a fragment or variant thereof. In some embodiments, the polypeptide binds human CD26. For instance, in some embodiments, the polypeptide is an antibody comprising at least one heavy chain (e.g., two heavy chains), each of which comprises SEQ ID NO:217 without the signal sequence, and at least one light chain (e.g., two light chains), each of which comprises SEQ ID NO:218 without the signal sequence.

The invention further provides a polypeptide comprising the polypeptide of SEQ ID NO:219 and/or SEQ ID NO:220 (shown in Example 13, below), or a fragment thereof, or a variant thereof.

In another aspect, the invention provides a polypeptide, such as an antibody, that binds to one or more peptides selected from the group consisting of YSLRWISDHEYLY (SEQ ID NO:45; peptide 6), LEYNYVKQWRHSY (SEQ ID NO:46; peptide 35), TWSPVGHKLAYVW (SEQ ID NO:47; peptide 55), LWWSPNGTFLAYA (SEQ ID NO:48; peptide 84), RISLQWLRRIQNY (SEQ ID NO:49; peptide 132), YVKQWRHSYTASY (SEQ ID NO:50; peptide 37), EEEVFSAYSALWW (SEQ ID NO:51; peptide 79), DYSISPDGQFILL (SEQ ID NO:52; peptide 29), SISPDGQFILLEY (SEQ ID NO:53; peptide 30), and IYVKIEPNLPSYR (SEQ ID NO:54; peptide 63). In some embodiments, the polypeptide preferentially binds to the one or more peptides. These peptides are regions of human CD26. In some embodiments, the polypeptide preferentially binds to one or more peptides selected from the group consisting of YSLRWISDHEYLY (SEQ ID NO:45; peptide 6), LEYNYVKQWRHSY (SEQ ID NO:46; peptide 35), TWSPVGHKLAYVW (SEQ ID NO:47; peptide 55), LWWSPNGTFLAYA (SEQ ID NO:48; peptide 84), RISLQWLRRIQNY (SEQ ID NO:49; peptide 132), YVKQWRHSYTASY (SEQ ID NO:50; peptide 37), EEEVFSAYSALWW (SEQ ID NO:51; peptide 79), DYSISPDGQFILL (SEQ ID NO:52; peptide 29), SISPDGQ-FILLEY (SEQ ID NO:53; peptide 30), and IYVKIEPNLPSYR (SEQ ID NO:54; peptide 63), relative to one or more peptides corresponding to other regions of human CD26.

In some embodiments, the polypeptide (e.g., antibody) binds to each of the following peptides: YSLRWISDHEYLY (SEQ ID NO:45; peptide 6); LEYNYVKQWRHSY (SEQ ID NO:46; peptide 35); TWSPVGHKLAYVW (SEQ ID NO:47; peptide 55); LWWSPNGTFLAYA (SEQ ID NO:48; peptide 84); and RISLQWLRRIQNY (SEQ ID NO:49; peptide 132). In some other embodiments, the polypeptide binds to each of the following peptides: YSLRWISDHEYLY (SEQ ID NO:45; peptide 6); TWSPVGHKLAYVW (SEQ ID NO:47; peptide 55); RISLQWLRRIQNY (SEQ ID NO:49; peptide 132); YVKQWRHSYTASY (SEQ ID NO:50; peptide 37); and EEEVFSAYSALWW (SEQ ID NO:51; peptide 79). In some embodiments, the polypeptide binds to each of the following peptides: DYSISPDGQFILL (SEQ ID NO:52; peptide 29); SISPDGQFILLEY (SEQ ID NO:53; peptide 30); and TWSPVGHKLAYVW (SEQ ID NO:47; peptide 55). In some other embodiments, the polypeptide binds to each of the following peptides: DYSISPDGQFILL (SEQ ID NO:52; peptide 29); SISPDGQFILLEY (SEQ ID NO:53; peptide 30); TWSPVGHKLAYVW (SEQ ID NO:47; peptide 55); and IYVKIEPNLPSYR (SEQ ID NO:54; peptide 63). In some embodiments, the polypeptides preferentially bind to the specified peptides.

Competition assays can be used to determine whether two antibodies bind the same epitope by recognizing identical or sterically overlapping epitopes. See, e.g., Dong et al. (1998) and the specificity experiments in the Examples below. Typically, antigen is immobilized on a multi-well plate and the ability of unlabeled antibodies to block the binding of labeled antibodies is measured. Common labels for such competition assays are radioactive labels or enzyme labels. In addition, epitope mapping techniques known to those in the art can be used to determine the epitopes with which antibodies bind. See, e.g., Example 3(e) below.

In some embodiments, a polypeptide described herein comprises one or more constant regions. In some embodiments, a polypeptide described herein comprises a human constant region. In some embodiments, the constant region is a constant region of the heavy chain. In other embodiments, the constant region is a constant region of the light chain. In some embodiments, the polypeptide comprises a constant region which has at least about 80%, at least about 85%, at least about 90%, at least about 95%, at least about 98%, or 100% identity to a human constant region. In some embodiments, a polypeptide (e.g., an antibody) described herein comprises an Fc region. In some embodiments, the polypeptide comprises a human Fc region. In some embodiments, a polypeptide described herein comprises an Fc region which has at least about 80%, at least about 85%, at least about 90%, at least about 95%, at least about 98%, or 100% identity to a human Fc region.

In some embodiments, an antibody described herein is an IgG antibody. In some embodiments, the antibody is an IgG1 antibody. In some other embodiments, the antibody is an IgG2 antibody. In some embodiments, the antibody is a human IgG antibody.

The invention provides antibodies in monomeric, dimeric and multivalent forms. For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

In certain embodiments, an antibody described herein is an antibody fragment. For instance, in some embodiments, the antibody is selected from the group consisting of Fab, Fab', Fab'-SH, Fv, scFv and F(ab')$_2$. In some embodiments, the antibody is a Fab. Various techniques have been developed for the production of antibody fragments. These fragments can be derived via proteolytic digestion of intact antibodies (see, e.g., Morimoto et al., 1992, J. Biochem. Biophys. Methods 24:107-117 and Brennan et al., 1985, Science 229:81), or produced directly by recombinant host cells. For example, Fab'-SH fragments can be directly recovered from *E. coli* and chemically coupled to form F(ab')$_2$ fragments (Carter et al., 1992, Bio/Technology 10:163-167). In another embodiment, the F(ab')$_2$ is formed using the leucine zipper GCN4 to promote assembly of the F(ab')$_2$ molecule. According to another approach, Fv, Fab or F(ab')$_2$ fragments are isolated directly from recombinant host cell culture.

In some embodiments, the antibodies of the invention are single chain (ScFv), mutants thereof, fusion proteins comprising an antibody portion, humanized antibodies, chimeric antibodies, diabodies linear antibodies, single chain antibodies, and any other modified configuration of the immunoglobulin molecule.

Single chain variable region fragments are made by linking light and/or heavy chain variable regions by using a short linking peptide. Bird et al. (1988) Science 242:423-426. An example of a linking peptide is (GGGGS)$_3$ (SEQ ID NO:85), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The invention encompasses modifications to antibodies or other polypeptides described herein, including functionally equivalent antibodies which do not significantly affect their properties and variants which have enhanced or decreased activity. It is understood that the principles of modification apply to polypeptides as well as antibodies. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions or additions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody or other polypeptide sequence removed and a different residue inserted in its place. The sites of greatest interest for substitutional mutagenesis include the CDRs, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
 (1) Hydrophobic: Norleucine, Met, Ala, Val, Leu, Ile;
 (2) Neutral hydrophilic: Cys, Ser, Thr;
 (3) Acidic: Asp, Glu;
 (4) Basic: Asn, Gln, His, Lys, Arg;
 (5) Residues that influence chain orientation: Gly, Pro; and
 (6) Aromatic: Trp, Tyr, Phe.

Non-conservative substitutions are made by exchanging a member of one of these classes for another class. More conservative substitutions involve exchanging one member of a class for another member of the same class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR3 domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetyl-glucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

In some embodiments, the polypeptides of the invention are conjugates. For instance, in some embodiments, the polypeptide is conjugated to another agent such as a chemotherapeutic agent, a radionuclide, an immunotherapeutic agent, a cytokine, a chemokine, an imaging agent, a toxin, a biological agent, an enzyme inhibitor, or an antibody.

In some embodiments the polypeptides, such as antibodies, are conjugated to water-soluble polymer moieties. The polypeptides may be conjugated to polyethylene glycol (PEG), monomethoxy-PEG, ethylene glycol/propylene glycol copolymers, carboxymethylcellulose, dextran, polyvinyl alcohol or the like. The polypeptides may be modified at random positions with the molecule, or at predetermined positions with the molecule and may include one, two, three or more attached moieties. The polymer may be of any molecular weight, and may be branched or unbranched. In some embodiments, the moiety is attached to the polypeptide via a linker. In some embodiments, the attached moiety increases the circulating half-life of the polypeptide in an animal. Methods of attaching polymers such as PEG to polypeptides including antibodies are well known in the art. In some embodiments, the polypeptides are PEGylated polypeptides, such as PEGylated antibodies.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184). Candidate affinity matured antibodies may be screened or selected for improved and/or altered binding affinity using any method known in the art, including screening using BIAcore surface plasmon resonance analysis, and selection using any method known in the art for selection, including phage display, yeast display, and ribosome display.

Monoclonal antibodies may be prepared using hybridoma methods, such as those described by Kohler and Milstein, 1975, Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies (as well as other polypeptides) of the invention may also be made by recombinant DNA methods, such as those described in U.S. Pat. No. 4,816,567. Methods of preparing polypeptides and monoclonal antibodies are well known in the art. In some embodiments, DNA encoding the monoclonal antibodies is isolated, sequenced, and/or amplified using conventional procedures, such as by using oligonucleotide probes or primers that are capable of binding specifically to genes or polynucleotides encoding the heavy and light chains of the monoclonal antibodies. Sequences encoding polypeptides, such as antibodies, of a desired sequence may also readily be prepared using a combination of synthetic DNA methods, PCR methods, and recombinant techniques well known in the art. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

In some embodiments, the polypeptides of the invention (e.g., antibodies) are expressed in any organism, or cells derived from any organism, including, but not limited to bacteria, yeast, plant, insect, and mammal. Particular types of cells include, but are not limited to, *Drosophila melanogaster* cells, *Saccharomyces cerevisiae* and other yeasts, *E. coli, Bacillus subtilis*, SF9 cells, HEK-293 cells, Neurospora, BHK cells, CHO cells, COS cells, HeLa cells, fibroblasts, Schwannoma cell lines, immortalized mammalian myeloid and lymphoid cell lines, Jurkat cells, mast cells and other endocrine and exocrine cells, and neuronal cells.

A variety of protein expression systems, vectors, and cell media useful in the production of polypeptides are known to those of ordinary skill in the art. See, e.g., International Patent Publication Nos. WO 03/054172, WO 04/009823, and WO 03/064630, as well as U.S. Patent Publication Nos. US 2005/0170454, US 2005/0084928, and US 2006/0003405, each of which is incorporated herein by reference in its entirety. In some embodiments, a glutamine synthetase (GS) expression system is used for expression of the polypeptides (e.g., antibodies).

The polypeptide may be purified or isolated after expression according to methods known to those skilled in the art. Examples of purification methods include electrophoretic, molecular, immunological and chromatographic techniques, including ion exchange, hydrophobic affinity, and reverse-phase HPLC chromatography, and chromatofocusing. The degree of purification necessary will vary depending on the use of the polypeptide. In some instances, no purification will be necessary.

The DNA can be modified, for example, by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody disclosed herein. Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for one surface epitope CD26 and another antigen-combining site having specificity for a different antigen or CD26 epitope.

The invention also encompasses humanized antibodies. Therapeutic antibodies often elicit adverse effects, in part due to triggering of an immune response directed against the administered antibody. This can result in reduced drug efficacy, depletion of cells bearing the target antigen, and an undesirable inflammatory response. To circumvent the above, recombinant anti-CD26 humanized antibodies may be generated. The general principle in humanizing an antibody involves retaining the basic sequence of the antigen-binding portion of the antibody, while swapping at least portions of the non-human remainder of the antibody with human antibody sequences. Four traditional, but non-limiting, general steps to humanize a monoclonal antibody include: (1) determining the nucleotide and predicted amino acid sequence of the starting antibody light and heavy variable domains (2) designing the humanized antibody, i.e., deciding which antibody framework region or residues and/or CDR residues to use during the humanizing process (3) the actual humanizing methodologies/techniques and (4) the transfection and expression of the humanized antibody. The constant region may also be engineered to more resemble human constant regions to avoid immune response if the antibody is used in clinical trials and treatments in humans. See, for example, U.S. Pat. Nos. 5,997,867 and 5,866,692.

In the recombinant humanized antibodies, the Fcγ portion can be modified to avoid interaction with Fcγ receptor and the complement immune system. Techniques for preparation of such antibodies are described in WO 99/58572.

A number of "humanized" antibody molecules comprising an antigen-binding site derived from a non-human immunoglobulin have been described, including chimeric antibodies having rodent V regions and their associated complementarity determining regions (CDRs) fused to human constant domains. See, for example, Winter et al. *Nature* 349:293-299 (1991); Lobuglio et al. *Proc. Nat. Acad. Sci. USA* 86:4220-4224 (1989); Shaw et al. *J Immunol.* 138:4534-4538 (1987); and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988); Verhoeyen et al. *Science* 239:1534-1536 (1988); and Jones et al. *Nature* 321:522-525 (1986). Another reference describes rodent CDRs supported by recombinantly veneered rodent framework regions. See, for example, European Patent Publication No. 519,596. These types of "humanized" molecules are designed to minimize unwanted immunological response toward rodent antihuman antibody molecules which limits the duration and effectiveness of therapeutic applications of those moieties in human recipients. Other methods of humanizing antibodies that may also be utilized are disclosed by Daugherty et al., *Nucl. Acids Res.,* 19:2471-2476 (1991) and in U.S. Pat. Nos. 6,180,377; 6,054,297; 5,997,867; 5,866,692; 6,210,671; 6,350,861; and PCT WO 01/27160.

Additional exemplary methods of humanizing antibodies are described in International Publication No. WO 02/084277 and U.S. Publication No. US 2004/0133357, both of which are incorporated by reference herein in their entirety.

In yet another alternative, fully human antibodies may be obtained by using commercially available mice which have been engineered to express specific human immunoglobulin proteins. Transgenic animals which are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In another alternative, antibodies may be made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT patent application PCT WO 9306213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines and bovines.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Iliades et al., 1997, FEBS Letters, 409:437-441. Coupling of such single chain fragments using various linkers is described in Kortt et al., 1997, Protein Engineering, 10:423-433. A variety of techniques for the recombinant production and manipulation of antibodies are well known in the art.

In one aspect, the invention provides methods of producing the polypeptides described herein. In some embodiments, the method comprises expressing a polynucleotide in a host cell, wherein the polynucleotide encodes the polypeptide. In some embodiments, the method is a method of producing an antibody and comprises expressing one or more polynucleotides in a host cell (e.g., in cell culture), wherein each chain of the antibody is encoded by at least one of the polynucleotides. In some embodiments, the one or more polynucleotides are on the same vector. In other embodiments, the one or more polynucleotides are located on separate vectors. In some embodiments, the methods of producing polypeptides described herein further comprise the step of isolating the polypeptides from the host cells in which they are expressed (e.g., isolated from the cell culture in which the host cells are grown).

Polynucleotides, Variant Sequences, Vectors, and Host Cells

The invention further provides polynucleotides encoding the polypeptides, such as antibodies, described herein. In some embodiments, the polynucleotides encode a polypeptide comprising a heavy chain variable region or light chain variable region described herein. Vectors, such as expression vectors, comprising the polynucleotides are also provided. Host cells comprising the vectors and/or polynucleotides of the invention are further provided. In some embodiments, the polynucleotides are isolated.

In one aspect, the invention provides a polynucleotide comprising a nucleic acid sequence selected from the group consisting of each of the sequences shown in FIG. 2 and FIG. 4 (SEQ IDS NOS:1-14), or a fragment thereof. The invention further provides a polynucleotide that hybridizes under moderately stringent conditions to a polynucleotide selected from the group consisting of those polynucleotides shown in FIG. 2 and FIG. 4 (SEQ IDS NOS:1-14). In some embodiments, the polynucleotide hybridizes under highly stringent conditions to a polynucleotide shown in FIG. 2 and FIG. 4 (SEQ IDS NOS:1-14).

In another aspect, the invention provides a polynucleotide comprising a polynucleotide encoding an amino acid sequence selected from the group consisting of each of the following sequences shown in FIG. 3 or FIG. 5: X376, X377, X378, X379, X380, X381, X394, X384, X385, X386, X387, X388, X399, and X420 (SEQ ID NOS:15-28).

The invention further provides a polynucleotide comprising a polynucleotide of the sequence SEQ ID NO:215 and/or SEQ ID NO:216 (see Example 4, below), or a fragment thereof. In some embodiments, the fragment comprises at least 12, at least 20, at least 50, at least 75, or at least 100 nucleotides. In some embodiments, the polynucleotide comprises a polynucleotide comprising the sequence of SEQ ID NO:215 that encodes the heavy chain. In some embodiments, the polynucleotide comprises a polynucleotide comprising the sequence of SEQ ID NO:216 that encodes the light chain. In some embodiments, the polynucleotide comprises the fragment of the sequence of SEQ ID NO:215 that encodes the heavy chain. In some embodiments, the polynucleotide comprises a polynucleotide that comprises the fragment of SEQ ID NO:216 that encodes the light chain. In some embodiments, the polynucleotide comprises the fragment of the sequence of SEQ ID NO:215 that encodes the heavy chain variable region. In some embodiments, the polynucleotide comprises a polynucleotide that comprises the fragment of SEQ ID NO:216 that encodes the light chain variable region.

The invention also provides a polynucleotide (e.g., an antibody) encoding a polypeptide comprising the heavy chain and/or the light chain of the antibody encoded by the plasmid in *E. coli* in the sample named "DH5α *Escherichia coli* with plasmid having insert of heavy and light chain of a humanized monoclonal antibody against human CD26 cDNA," having strain designation "S604069.YST-pABMC148 (x411)," deposited with the American Type Culture Collection (ATCC) on Jun. 30, 2006, under the provisions of the Budapest Treaty on the International Recognition of the Deposit of Microorganisms for the Purposes of a Patent Procedure, and designated with accession number PTA-7695. The invention further provides a polynucleotide encoding a polypeptide comprising the heavy chain variable region and/or the light chain variable region of the antibody encoded by the plasmid in *E. coli* in the sample named "DH5 α *Escherichia coli* with plasmid having insert of heavy and light chain of a humanized monoclonal antibody against human CD26 cDNA," having strain designation "S604069.YST-pABMC148 (x411)," deposited with the ATCC on Jun. 30, 2006, under the provisions of the Budapest Treaty on the International Recognition of the Deposit of Microorganisms for the Purposes of a Patent Procedure, and designated with accession number PTA-7695. In some embodiments, the polynucleotide comprises the heavy and/or light chain coding sequences of the deposited sequence.

Expression systems comprising expression vectors and host cells can be used in a method of producing a polypeptide, such as an antibody, of the invention, wherein the host cell is cultured and the polypeptide produced by the cultured host cell is recovered. Polynucleotides encoding antibodies of the invention can also be delivered to a host subject for expression of the antibody by cells of the host subject.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Variants of the polynucleotides and polypeptides described herein are also provided. The polynucleotide and polypeptide variants may contain one or more substitutions, additions, deletions and/or insertions. In some embodiments, the variants are such that the binding of the encoded polypeptide to human CD26 is not substantially diminished, relative to the polypeptide encoded by the original polynucleotide or the polypeptide. The effect on the immunoreactivity of the encoded polypeptide may generally be assessed as described herein. Variants preferably exhibit at least about 70% identity, more preferably at least about 80% identity and most preferably at least about 90% identity to the original sequence or a portion thereof. In some embodiments, where a sequence is being compared to a CDR or a small fragment, the comparison window may be smaller, e.g., at least 7 amino acids or at least 10 amino acids.

Two polynucleotide or polypeptide sequences are said to be "identical" or have "identity" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Alternatively, the % (amino acid) identity may be obtained using one of the publicly available BLAST or BLAST-2 programs. The WU-BLAST-2 computer program (Altschul et al., Methods in Enzymology 266:460-480 (1996)). Percent (amino acid) sequence identity may also be determined using the sequence comparison program NCBI-BLAST2 (Altschul et al., Nucleic Acids Res. 25:3389-3402 (1997)). The BLAST program is based on the alignment method of Karlin and Altschul. Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997).

In some embodiments, the "percentage of identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity. In some embodiments, the comparison window may be smaller (e.g., 7 or 10 amino acids).

Variants may also, or alternatively, be substantially homologous to a polynucleotide described herein, or a portion or complement thereof. Such polynucleotide variants are capable of hybridizing under moderately stringent conditions to a naturally occurring DNA sequence encoding a native antibody (or a complementary sequence). In some embodiments, the variants are capable of hybridizing under highly stringent conditions to the original sequence.

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Nonetheless, polynucleotides that vary due to differences in codon usage are specifically contemplated by the present invention.

Polynucleotides may be prepared using any of a variety of techniques known in the art. DNA encoding an antibody may be obtained from a cDNA library prepared from tissue expressing antibody mRNA. The antibody-encoding gene may also be obtained from a genomic library or by oligonucleotide synthesis. Libraries can be screened with probes (such as binding partners or oligonucleotides of at least about 20-80 bases) designed to identify the gene of interest or the protein encoded by it. Illustrative libraries include human liver cDNA library (human liver 5' stretch plus cDNA, Clontech Laboratories, Inc.) and mouse kidney cDNA library (mouse kidney 5'-stretch cDNA, Clontech laboratories, Inc.). Screening the cDNA or genomic library with the selected probe may be conducted using standard procedures, such as those described in Sambrook et al., Molecular Cloning: A Laboratory Manual, New York: Cold Spring Harbor Laboratory Press, 1989. Alternatively, one can isolate the gene encoding antibody using PCR methodology (Sambrook et al., supra; Dieffenbach et al., PCR Primer: A Laboratory Manual, Cold Spring Harbor Laboratory Press, 1995).

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding an antibody, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding the polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Pharmaceutical Compositions and Kits

The present invention further provides compositions comprising the polypeptides (e.g., antibodies) and/or polynucleotides described herein. For instance, the invention provides pharmaceutical compositions comprising the polypeptides described herein. Kits comprising the polypeptides are also provided.

The compositions of the invention include bulk drug compositions useful in the manufacture of non-pharmaceutical compositions (e.g., impure or non-sterile compositions) and pharmaceutical compositions (i.e., compositions that are suitable for administration to a subject or patient) which can be used in the preparation of unit dosage forms.

In some embodiments, the pharmaceutical composition comprises a polypeptide described herein and a pharmaceutically acceptable excipient (also referred to herein as a "pharmaceutically acceptable carrier"). In some embodiments, the polypeptide in the pharmaceutical composition is an antibody. In some embodiments, the polypeptide in the pharmaceutical composition is a humanized antibody.

Pharmaceutical compositions within the scope of the present invention may also contain other compounds that may be biologically active or inactive.

A pharmaceutical composition can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal).

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., 1991, Science 252: 431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749, and reviewed by Cohen, 1993, Science 259:1691-1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextran), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated.

In some embodiments, the polypeptide also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000. To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The antibodies disclosed herein may also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. In addition, Fab' fragments of the antibody of the present invention can be conjugated to the liposomes as described in Martin et al., 1982, *J. Biol. Chem.* 257:286-288, via a disulfide interchange reaction.

Kits and articles of manufacture comprising the polypeptides, polynucleotides, vectors, or host cells described herein are also provided.

In some embodiments, the article of manufacture comprises a container with a label. Suitable containers include, for example, bottles, vials, and test tubes. The containers may be formed from a variety of materials such as glass or plastic. In some embodiments, the container holds a composition useful in the identification or quantitation of cells expressing CD26, the inhibition of proliferation of cells expressing CD26, or the treatment of a disease associated with expression of CD26. In some embodiments, the label on the container indicates the composition is useful for the identification or quantitation of cells expressing CD26, the inhibition of proliferation of cells expressing CD26, or the treatment of a disease associated with expression of CD26.

In some embodiments, the kit of the invention comprises the container described above. In other embodiments, the kit of the invention comprises the container described above and a second container comprising a buffer. In some embodiments, the kit comprises a package insert with instructions for use of a polypeptide, polynucleotide, vector or host cell contained therein.

Methods of Using the Polypeptides

The polypeptides (such as antibodies) of the present invention are useful in a variety of applications including, but not limited to, diagnostic methods and therapeutic treatment methods. Methods of inhibiting proliferation of cells expressing CD26 are also provided.

Antibodies and polypeptides of the invention can be used in the detection, diagnosis and/or monitoring of a condition (such as a disease or disorder) associated with CD26 expression. In some embodiments, the condition associated with CD26 expression is a condition associated with abnormal CD26 expression. For instance, in some embodiments, the condition associated with CD26 expression is a condition associated with altered or aberrant CD26 expression (in some embodiments, increased or decreased CD26 expression (relative to a normal sample), and/or inappropriate expression, such as presence of expression in tissue(s) and/or cell(s) that normally lack CD26 expression, or absence of CD26 expression in tissue(s) or cell(s) that normally possess CD26 expression). In some embodiments, the condition associated with CD26 expression is a condition associated with CD26 overexpression. Overexpression of CD26 is understood to include both an increase in expression of CD26 in cell(s) or tissue(s) which normally expresses CD26 relative to the normal level of expression of CD26 in those cell(s) or tissue(s), as well as the presence of expression of CD26 in tissue(s) or cell(s) that normally lack CD26 expression. In some embodiments, the condition associated with CD26 expression is mediated, at least in part, by CD26. In some embodiments, the condition associated with CD26 expression is a condition associated with cells expressing CD26. In some embodiments, the condition associated with CD26 expression is a condition associated with the proliferation of cells expressing CD26. In some embodiments, the proliferation of the cells expressing CD26 is an abnormal proliferation. The diagnostic method may be in vitro or in vivo.

Exemplary reference is made in this discussion to antibodies, with the understanding that this discussion also pertains to the polypeptides of the invention.

For diagnostic applications, the antibody typically will be labeled with a detectable moiety including but not limited to radioisotopes, fluorescent labels, and various enzyme-substrate labels. Methods of conjugating labels to an antibody are known in the art. In other embodiment of the invention, antibodies of the invention need not be labeled, and the presence thereof can be detected using a labeled antibody which binds to the antibodies of the invention.

The antibodies of the present invention may be employed in any known assay method, such competitive binding assays, direct and indirect sandwich assays, and immunoprecipitation assays. Zola, Monoclonal Antibodies: A Manual of Techniques, pp. 147-158 (CRC Press, Inc. 1987).

The antibodies may also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized using immunoscintiography.

The antibody may also be used as staining reagent in pathology, following techniques well known in the art.

In another aspect, the invention provides a method of inhibiting proliferation of a cell expressing CD26. Inhibition of proliferation of a cell expressing CD26 encompasses any observable level of inhibition, including partial to complete inhibition of proliferation. In some embodiments, proliferation of the cells is inhibited at least about 10%, at least about 25%, at least about 50%, at least about 75%, at least about 90%, or at least about 95%, or at least about 98%, or about 100%. The method may be in vitro or in vivo. In some embodiments, the method comprises contacting the cell with a polypeptide (e.g., antibody) described herein. Generally, the cell will be contacted with an amount of the polypeptide sufficient to inhibit proliferation of the cell.

A number of cancer cells have been identified as expressing CD26. For instance, CD26 has been identified as being overexpressed in each of the following cancer cells: T cell lymphoma (Ruiz et al. (1998) Cytometry, 34:30-5); B Chronic lymphocytic leukemia (B-CLL) (Bauvois et al. (1999) Br. J. Cancer, 79:1042-8); thyroid carcinoma (Aratake et al. (1991) Am. J. Clin. Pathol., 47:43-7); basal cell carcinoma (Moehrle et al. (1995) J. Cutan. Pathol. 22:241-7); breast cancer (Dixon et al. (1994) Clin. Pathol., 47:43-7); hepatocellular carcinoma (Stecca et al. (1997) 27:337-45); and lung tumors (Sedo et al. (1991) 40:359-62). Experimental results indicating that CD26 is expressed in a variety of cancer cell lines are also provided in the specific example, Example 12, below.

In some embodiments of the aspects described herein, a cell expressing CD26 is a human cell. In some embodiments, a cell expressing CD26 is a cancer cell. In some embodiments, a cell expressing CD26 is a hematological cancer cell, a T-cell cancer cell, a pancreatic cancer cell, a kidney cancer cell, a lymphoma cell, a B-cell cancer cell, a thyroid cancer cell, a breast cancer cell, an ovarian cancer cell, a prostate cancer cell, a colon cancer cell, a bladder cancer cell, a lung cancer cell, a liver cancer cell, a stomach cancer cell, a testicular cancer cell, an uterine cancer cell, a brain cancer cell, a lymphatic cancer cell, a skin cancer cell, a bone cancer cell, a rectal cancer cell, a sarcoma cell, a T-cell lymphoma cell, a lung adenocarcinoma cell, a thyroid carcinoma cell, a B-cell chronic lymphocytic leukemia cell, or a B-cell lymphoma cell. In some embodiments, the cancer cell is a lymphoma cell, a kidney cancer cell, a prostate cancer cell, or a lung cancer cell. In some embodiments, a cell expressing CD26 is a tumor cell, such as a cell in a solid tumor. In some embodiments, the tumor cell is malignant or benign. In some embodiments, a cell expressing CD26 is a T-cell. In some embodiments, the cell is a human T-cell. In some embodiments, the cell is a malignant T-cell. In some embodiments, a cell expressing CD26 is a hyperactive immune cell. In some embodiments, a cell expressing CD26 is an activated T-cell. In some embodiments, the cells are human. In some embodiments, the cancer cell that expresses CD26 overexpresses CD26 relative to a noncancerous cell of the same type. In some embodiments, the cancer cell that overexpresses CD26 is a breast cancer cell, a prostate cancer cell, colorectal cancer cell, ovarian cancer cell, renal cancer cell, T-cell lymphoma, B chronic lymphocytic leukemia (B-CLL), basal cell carcinoma, hepatocellular carcinoma, or a lung cancer cell.

Methods of assessing the inhibition of proliferation of a cell are known in the art and include MTT assays. (See, e.g., Aytac et al. (2003) British Journal of Cancer 88:455-462, Ho et al. (2001) Clinical Cancer Research 7:2031-2040, Hansen et al. (1989) J. Immunol. Methods, 119:203-210, and Aytac et al. (2001) Cancer Res. 61:7204-7210.) Examples of MTT assays are also provided in the specific examples Examples 2(G), 3(D), and 5 below.

The invention further provides methods for treating a condition associated with CD26 expression in a subject. In some embodiments, the method of treating a condition associated with CD26 expression in a subject, comprises administering an effective amount of a composition comprising a polypeptide, such as an antibody, described herein to the subject. In some embodiments, the condition associated with CD26 expression is associated with abnormal expression of CD26. In some embodiments, the condition associated with CD26 expression is a condition associated with altered or aberrant CD26 expression (in some embodiments, increased or decreased CD26 expression (relative to a normal sample), and/or inappropriate expression, such as presence of expression in tissue(s) and/or cell(s) that normally lack CD26 expression, or absence of CD26 expression in tissue(s) or cell(s) that normally possess CD26 expression). In some embodiments, the condition associated with CD26 expression is a condition associated with CD26 overexpression. In some embodiments, the condition associated with CD26 expression is mediated, at least in part, by CD26. In some embodiments, the condition associated with CD26 expression is a condition associated with cells expressing CD26. In some embodiments, the condition associated with CD26 expression is a condition associated with the proliferation of cells expressing CD26. In some embodiments, the proliferation of CD26-expressing cells is abnormal. In some embodiments, the cell expressing CD26 is a T-cell. In some embodiments, the cell expressing CD26 is a tumor cell, which may be malignant or benign. In some embodiments, the condition associated with CD26 expression is a cancer in which the cancer cells are CD26+ cancer cells or express CD26 (i.e., a CD26-expressing cancer). (Additional cells expressing CD26 are described above.)

In some embodiments, the condition associated with CD26 expression in a subject is a proliferative disorder. In some embodiments, the condition associated with CD26 expression in a subject is a cancer. In some embodiments, the cancer is a CD26+ hematological malignancy. In some embodiments, the cancer is a T-cell cancer, such as a T-cell lymphoma. For instance, in some embodiments, the cancer is a T-cell lymphoblastic lymphoma or acute lymphoblastic leukemia. In other embodiments, the cancer is a T-cell CD30+ anaplastic large cell lymphoma. In some embodiments, the cancer is a peripheral T-cell lymphoma, a T-cell chronic lymphocytic leukemia, an angioimmunoblastic T-cell lymphoma, an angiocentric T-cell lymphoma, an HTLV-related T-cell leukemia, or an adult T-cell leukemia. In some embodiments, the cancer is a solid tumor. In some embodiments, the cancer is pancreatic cancer, kidney cancer, or lymphoma. In some embodiments, the cancer is a B-cell cancer, thyroid cancer, breast cancer, ovarian cancer, prostate cancer, colon cancer, bladder cancer, lung cancer, liver cancer, stomach cancer, testicular cancer, uterine cancer, brain cancer, lymphatic cancer, skin cancer, bone cancer, rectal cancer, sarcoma, lung cancer, B-cell chronic lymphocytic leukemia, or a B-cell lymphoma. In some embodiments, the cancer is associated with overexpression of CD26. In some embodiments, the cancer is not mesothelioma. In some embodiments, the cancer is not melanoma. In some embodiments, the cancer is lymphoma, kidney cancer, prostate cancer, or lung cancer. In some embodiments, the cancer is lymphoma. In some embodiments, the cancer is kidney carcinoma. In some embodiments, the cancer is prostate carcinoma. In some embodiments, the cancer is lung carcinoma.

In some embodiments, the condition associated with CD26 expression is an inflammatory disease or disorder. In some embodiments, the inflammatory disease is associated with overexpression of CD26.

In other embodiments, the condition associated with CD26 expression is angiogenesis.

In further embodiments, the condition associated with CD26 expression is a condition involving an activated immune status such as, but not limited to, graft versus host disease and autoimmune diseases or disorders. In some embodiments, the condition is Addison's disease, alopecia, ankylosing spondylitis, antiphospholipid syndrome, Behcet's disease, chronic fatigue syndrome, Crohn's disease, ulcerative colitis, diabetes, fibromyalgia, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vasculitis, vitiligo, or Wegener's granulomatosis. In some embodiments, the condition involving an activated immune status is associated with overexpression of CD26.

In one aspect, the invention provides a method of treating cancer. In some embodiments, the invention provides a method of inhibiting progression of a cancer in a subject that has cancer, comprising administering an effective amount of a composition described herein to the subject. The invention further provides a method of inhibiting tumor growth in a subject, comprising administering an effective amount of a composition comprising the polypeptide to the subject. In some embodiments, the subject has a CD26-expressing tumor or has had a CD26-expressing tumor removed. In some embodiments, regression of the tumor is induced. The invention further provides a method of inhibiting metastasis of cancer cells (e.g., CD26-expressing cancer cells) in a subject, comprising administering an effective amount of a composition described herein to the subject.

In some embodiments, the methods described herein further comprise the step of treating the subject with an additional form of therapy. In some embodiments, the additional form of therapy is an additional anti-cancer therapy. In some embodiments the methods described herein further comprise the step of treating the subject with chemotherapy, radiation, surgery, hormone therapy, and/or additional immunotherapy. In some embodiments, the radiation is external beam radiation or teletherapy. In some alternative embodiments, the radiation is administered as internal therapy or brachytherapy. In some embodiments, the additional form of therapy comprises administration of one or more therapeutic agents, such as inhibitors of kinases. In some embodiments, the therapeutic agent is a therapeutic antibody, such as Avastin®, which is an anti-VEGF antibody, Herceptin® (Trastuzumab) (Genentech, California), which is an anti-HER2 antibody, Zenapax® (daclizumab) (Roche Pharmaceuticals, Switzerland), which is an anti-CD25 antibody, and Rituxan™ (IDEC Pharm./Genentech, Roche/Zettyaku), which is an anti-CD20 antibody. In some embodiments, the additional therapeutic agent is an angiogenesis inhibitor. In some embodiments, the additional therapeutic agent is a cytotoxic agent. In some embodiments the additional therapeutic agent is an anti-cancer agent. In some embodiments, the addition therapeutic agent is an antinflammatory agent. In some embodiments, the additional agent comprises an agent selected from the group consisting of paclitaxel (Taxol®), docetaxel (Taxotere®), prednisone, cisplatin, mitomycin, progesterone, tamoxifen citrate, fluorousacil, and doxorubicin hydrochloride.

The methods described herein (including therapeutic methods) can be accomplished by a single direct injection at a single time point or multiple time points to a single or multiple sites. Administration can also be nearly simultaneous to multiple sites. Frequency of administration may be determined and adjusted over the course of therapy, and is base on accomplishing desired results. In some cases, sustained continuous release formulations of polypeptides (including antibodies), polynucleotides, and pharmaceutical compositions of the invention may be appropriate. Various formulations and devices for achieving sustained release are known in the art.

Patients, subjects, or individuals include mammals, such as human, bovine, equine, canine, feline, porcine, and ovine animals. The subject is preferably a human, and may or may not be afflicted with disease or presently show symptoms. In some embodiments, the subject has cancer. In some embodiments, the subject has a tumor or has had a tumor removed. It is understood that even if a tumor has been removed from a subject, tumor cells may nevertheless, in some instances, remain in the subject. For instance, although a tumor from one site may have been removed, the tumor may have metastasized and spread to other locations in the body. Also, although a tumor may have been removed from a subject, a portion of the tumor or some tumor cells may have been inadvertently or unavoidably left behind in the subject due to limitations in the surgical procedure or the like. In some embodiments, the subject is at risk of developing a tumor (or cancer). In some embodiments, the subject is undergoing or has undergone additional treatment (e.g., chemotherapy, surgery, hormone therapy, radiation, or additional immunotherapy).

The antibody is preferably administered to the mammal in a carrier; preferably a pharmaceutically-acceptable carrier. Suitable carriers and their formulations are described in *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., systemic, intravenous, intraperitoneal, subcutaneous, intramuscular, intraportal), or by other methods, such as infusion, which ensure its delivery to the bloodstream in an effective form. The antibody may also be administered by isolated perfusion techniques, such as isolated tissue perfusion, to exert local therapeutic effects. Intravenous injection is preferred.

Effective dosages and schedules for administering the polypeptide (e.g., antibody) may be determined empirically, and making such determinations is within the skill in the art. Those skilled in the art will understand that the dosage of antibody that must be administered will vary depending on, for example, the mammal that will receive the antibody, the route of administration, the particular type of antibody used and other drugs being administered to the mammal. Guidance in selecting appropriate doses for antibody is found in the literature on therapeutic uses of antibodies, e.g., *Handbook of Monoclonal Antibodies*, Ferrone et al., eds., Noges Publications, Park Ridge, N.J., 1985, ch. 22 and pp. 303-357; Smith et al., *Antibodies in Human Diagnosis and Therapy*, Haber et al., eds., Raven Press, New York, 1977, pp. 365-389. A typical daily dosage of the antibody used alone might range from about 1 μg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 μg/kg body weight; at least about 500 μg/kg body weight; at least about 250 μg/kg body weight; at least about 100 μg/kg body weight; at least about 50 μg/kg body weight; at least about 10 μg/kg body weight; at least about 1 μg/kg body weight, or more, is administered. In some embodiments, a dose of a polypeptide (e.g., antibody) provided herein is between about 0.01 mg/kg and about 50 mg/kg, between about 0.05 mg/kg and about 40 mg/kg, between about 0.1 mg and about 30 mg/kg, between about 0.1 mg and about 20 mg/kg, between about 0.5 mg and about 15 mg, or between about 1 mg and 10 mg. In some embodiments, the dose is between about 1 mg and 5 mg. In some alternative embodiments, the dose is between about 5 mg and 10 mg.

In some embodiments, more than one antibody may be present. Such compositions may contain at least one, at least two, at least three, at least four, at least five different antibodies (including polypeptides) of the invention.

The polypeptide may also be administered to the mammal in combination with effective amounts of one or more other therapeutic agents. The polypeptide may be administered sequentially or concurrently with the one or more other therapeutic agents. The amounts of polypeptide and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner.

The above principles of administration and dosage can be adapted for polypeptides described herein.

A polynucleotide encoding an polypeptide (including an antibody) of the invention may also be used for delivery and expression of the antibody or the polypeptide in a desired cell. It is apparent that an expression vector can be used to direct expression of the antibody. The expression vector can be administered systemically, intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding a polypeptide or antibody of the invention can also be used. Receptor-mediated DNA delivery techniques are described in, for example, Findeis et al., *Trends Biotechnol.* (1993) 11:202; Chiou et al., *Gene Therapeutics. Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. (USA)* (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, *Mol. Cell. Biol.* (1994) 14:2411, and in Woffendin, *Proc. Natl. Acad. Sci.* (1994) 91:1581.

The following examples are provided to illustrate, but not to limit, the invention.

EXAMPLES

It is understood that the examples and embodiments described herein are for illustrative purposes only and that various modifications or changes in light thereof will be suggested to persons skilled in the art and are to be included within the spirit and purview of this application.

Example 1

Binding Affinity and VH and VL Sequences of CM03 Fab

CM03 (also referred to herein as 14D10) is a mouse monoclonal antibody raised against human CD26. The VH and VL sequences of CM03 were used as leads for designing the variants in the examples below. A Fab was also produced that comprised a light chain variable region (VL) and a heavy chain variable region (VH) corresponding to the VL and VH sequences, respectively, of the mouse monoclonal antibody CM03. This CM03 Fab is often referred to herein as "X369" or "CM03X369" or the like.

Biacore® technology (surface plasmon resonance, or "SPR") was used to determine the affinity of CM03 Fab for CD26. Generally, SPR-based biosensors monitor interactions by measuring the concentration of biomolecules close to a surface. The surface has one of the interacting partners immobilized thereon. Sample containing the other partner(s) flows over the surface. When molecules from the sample bind to the interactant attached to the surface, an SPR response is measured. The response is proportional to the mass of molecules that bind to the surface.

These affinity measurements were taken at 25° C. according to the manufacturer's manual. Purified recombinant human CD26 (rhDipeptidyl peptidase IV) purchased from R&D Systems, CAT# 1180-SE) was prepared as stock in PBS, and diluted in a concentration of ~0.05 mg/ml in 10 mM Sodium Acetate buffer pH 5 before it was immobilized onto a CM5 chip (BiaCore Inc., CAT# BR-1000-14). Fabs produced in E. coli as described below were diluted in PBS in a concentration of ~0.5 µM for the assay. A typical recording included a 3 minute period of injection of the Fab followed by a period of 15 minutes of dissociation, and analysis was performed based on the raw data of the binding curves accordingly.

Affinity is the strength of binding of one molecule to another at a single site. $K_D$ is the dissociation constant, a measure of the rate at which the antibody dissociates from the antigen. Generally, antibodies with lower $K_D$s have higher affinity.

Biacore® technology was used to determine affinity of the Fab comprising CM03 VH and VL for the human CD26 antigen. From this data, the $K_D$ of CM03 Fab ($1.63 \times 10^{-9}$) was determined. This indicates a relatively high affinity. Additional affinity data for the CM03 Fab is shown in Table 2, below.

TABLE 2

| | $K_{on}$/SE ($M^{-1} \cdot sec^{-1}$) | $K_{off}$/SE ($sec^{-1}$) | $K_D$ (M) |
|---|---|---|---|
| CM03 (X369) | 5.09E+05/1.19E+04 | 8.29E-04/3.40E-06 | 1.63e-9 |

FIG. 1 shows the sequences of the heavy chain variable region (VH) and light chain variable region (VL) of CM03 mouse Ab and CM03 Fab.

Example 2

Fabs of Humanized CM03 Variants

A. Sequences

The heavy and light chain variable regions of the CM03 antibody were used for humanization to produce a variety of variant heavy and light chain variable regions.

The nucleic acid sequences of humanized VL variants X376 (SEQ ID NO:1), X377 (SEQ ID NO:2), X378 (SEQ ID NO:3), X379 (SEQ ID NO:4), X380 (SEQ ID NO:5), X381 (SEQ ID NO:6), and X394 (SEQ ID NO:7) are shown in FIG. 2. The amino acid of humanized VL variants X376 (SEQ ID NO:15), X377 (SEQ ID NO:16), X378 (SEQ ID NO:17), X379 (SEQ ID NO:18), X380 (SEQ ID NO:19), X381 (SEQ ID NO:20), and X394 (SEQ ID NO:21) are shown in FIG. 3.

The nucleic acid sequences for humanized VH variants X384 (SEQ ID NO:8), X385 (SEQ ID NO:9), X386 (SEQ ID NO:10), X387 (SEQ ID NO:11), X388 (SEQ ID NO:12), X399 (SEQ ID NO:13) and X420 (SEQ ID NO:14) are shown in FIG. 4. The amino acid sequences for humanized VH variants X384 (SEQ ID NO:22), X385 (SEQ ID NO:23), X386 (SEQ ID NO:24), X387 (SEQ ID NO:25), X388 (SEQ ID NO:26), X399 (SEQ ID NO:27) and X420 (SEQ ID NO:28) are shown in FIG. 5.

FIG. 6 shows the amino acid sequences of selected pairs of variant heavy and light chain variable regions used to make Fabs comprising both VH and VL variants.

B. Expression

E. coli cell lines were used to express the heavy and light chain Fab variants shown in FIGS. 7-10.

For expression, individual E. coli cell lines were inoculated in 2×YT medium containing 100 µg/ml Carbenicilline to grow at 37° C. until OD600=~1 before IPTG was added to a final concentration of 0.5 mM, the culture was then induced for Fab production at 30° C. for 4-5 hours. Cells were harvested and periplasmic extracts were prepared according to a standard protocol (Phage Display, A Laboratory Manual, Carlos Barbas III et al., Cold Spring Harbor Laboratory Press, 2001). The crude extract was purified in protein affinity G column (Amerham-Pharmacia, CAT# 17-0404-01) according to the manufacturer's instruction, and eluted by 0.1 M glycine pH. 2.7, followed by immediate neutralization by 1 M Tris pH 8. The samples were dialyzed against PBS extensively and eventually determined for protein concentration using OD280 before use for Biacore analysis and other assays.

Figure 8:
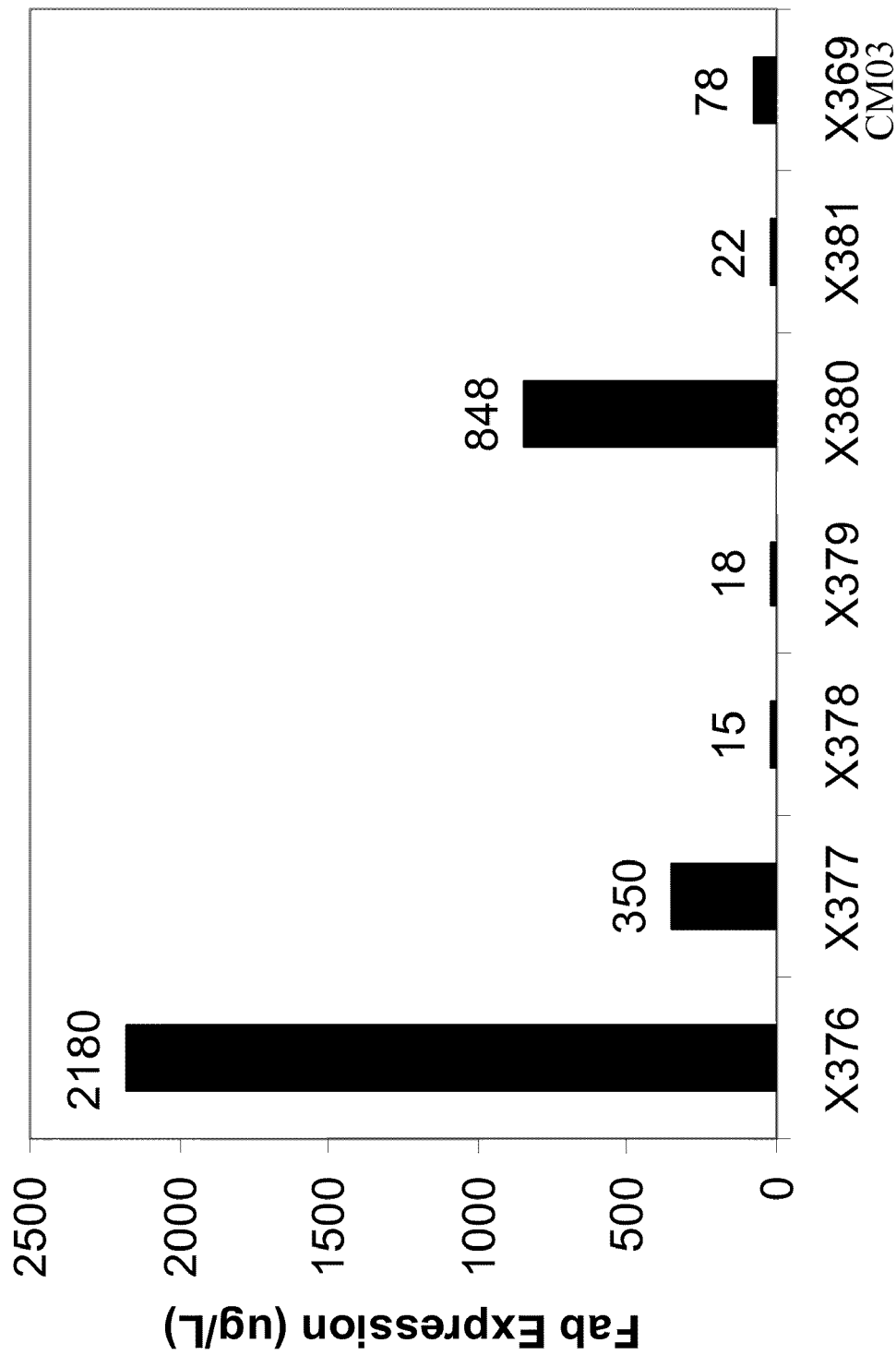
FIG. 8 shows a quantitative representation of accumulation of protein containing Fabs comprising CM03 VL variants X376, X377, X378, X379, X380, or X381 paired with CM03 VH, as well as the Fab X369 (comprising CM03 VH and CM03 VL), expressed in *E. coli*.
Figure 11:
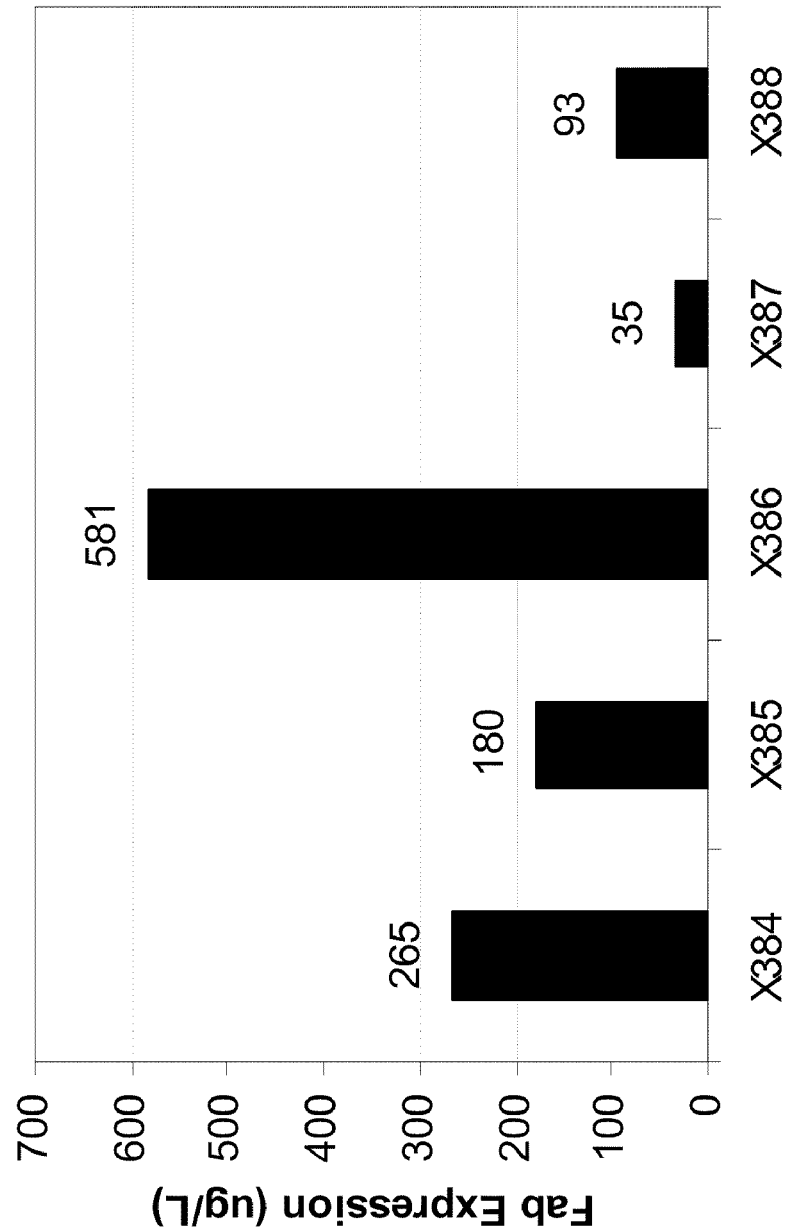
FIG. 11 shows a quantitative representation of accumulation of Fabs comprising a CM03 VH variant X384, X385, X386, X387 or X388 paired with CM03 VL in *E. coli*.

FIG. 7 shows an SDS-PAGE gel under non-reducing conditions loaded with samples purified by protein G column of Fabs of CM03 VL variants X376, X377, X378, X379, X380, X381, as well as Fabs of VH variants X384, X385, X386 expressed in E. coli strain TG1. The VL variants were paired with CM03 VH in the Fabs; the VH variants were paired with CM03 VL in the Fabs. In each sample a protein band was seen around 50 kDa, but yields were highest in X376, X377, X380, X384, X385, and X386. FIG. 8 shows a quantitative representation of accumulation of protein of Fabs of CM03 VL variants X376, X377, X378, X379, X380, X381, as well as Fab X369 (CM03), expressed in E. coli. Samples X376, X377, and X380 had higher levels of Fab protein than the CM03 murine Fab. FIG. 11 shows the quantitative protein yield of Fabs comprising VH variants X384, X385, X386, X387 or X388 paired with CM03 VL, expressed in E. coli.

Figure 9:
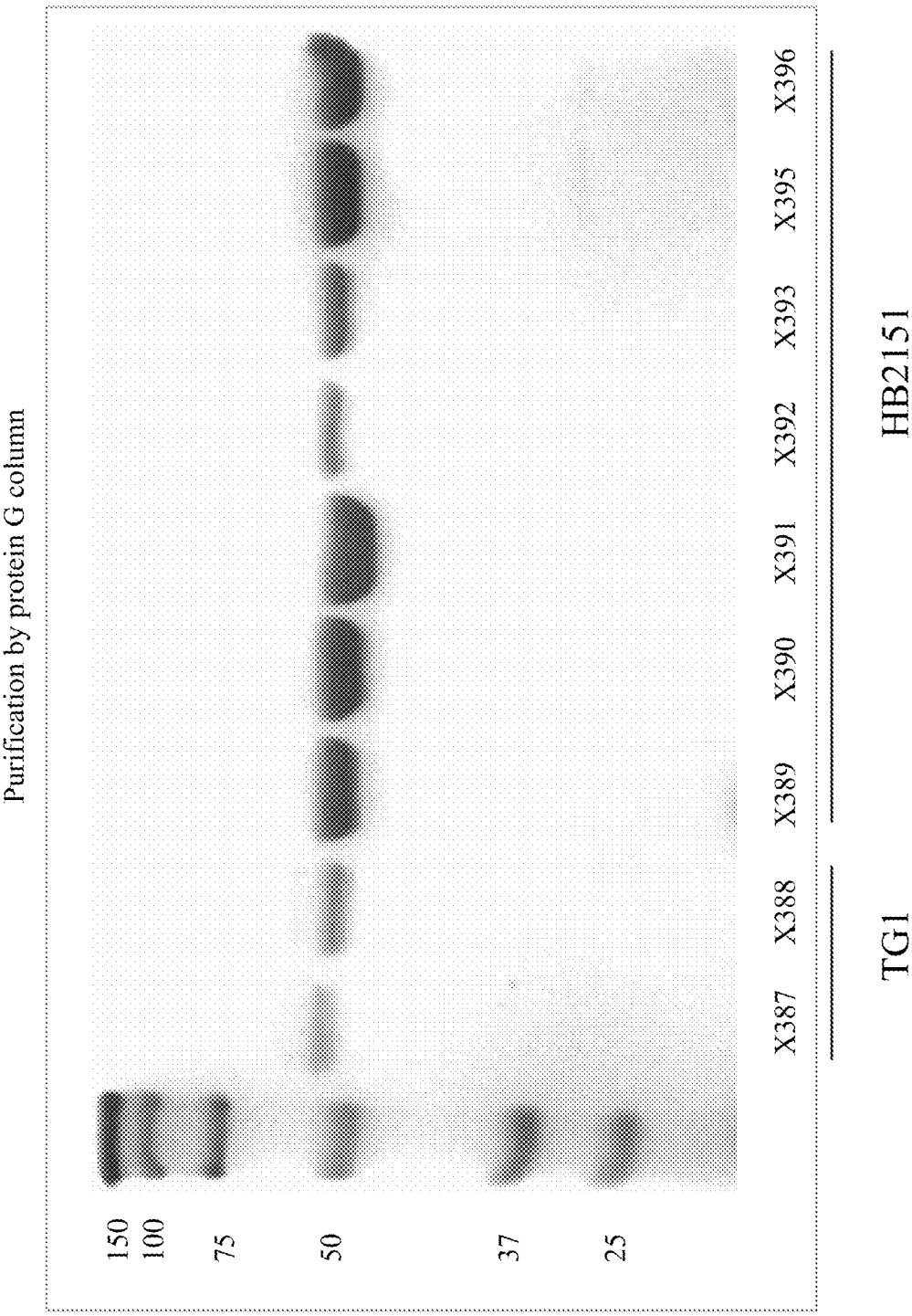
FIG. 9 shows a gel loaded with protein samples containing Fabs comprising CM03 VH variants X387 or X388 paired with CM03 VL, expressed in *E. coli* strain TG1, as well as the Fab X389, X390, X391, X392, X393, X395 and X396 (comprising VH and VL variant pairs) expressed in *E. coli* strain HB2151.
Figure 10:
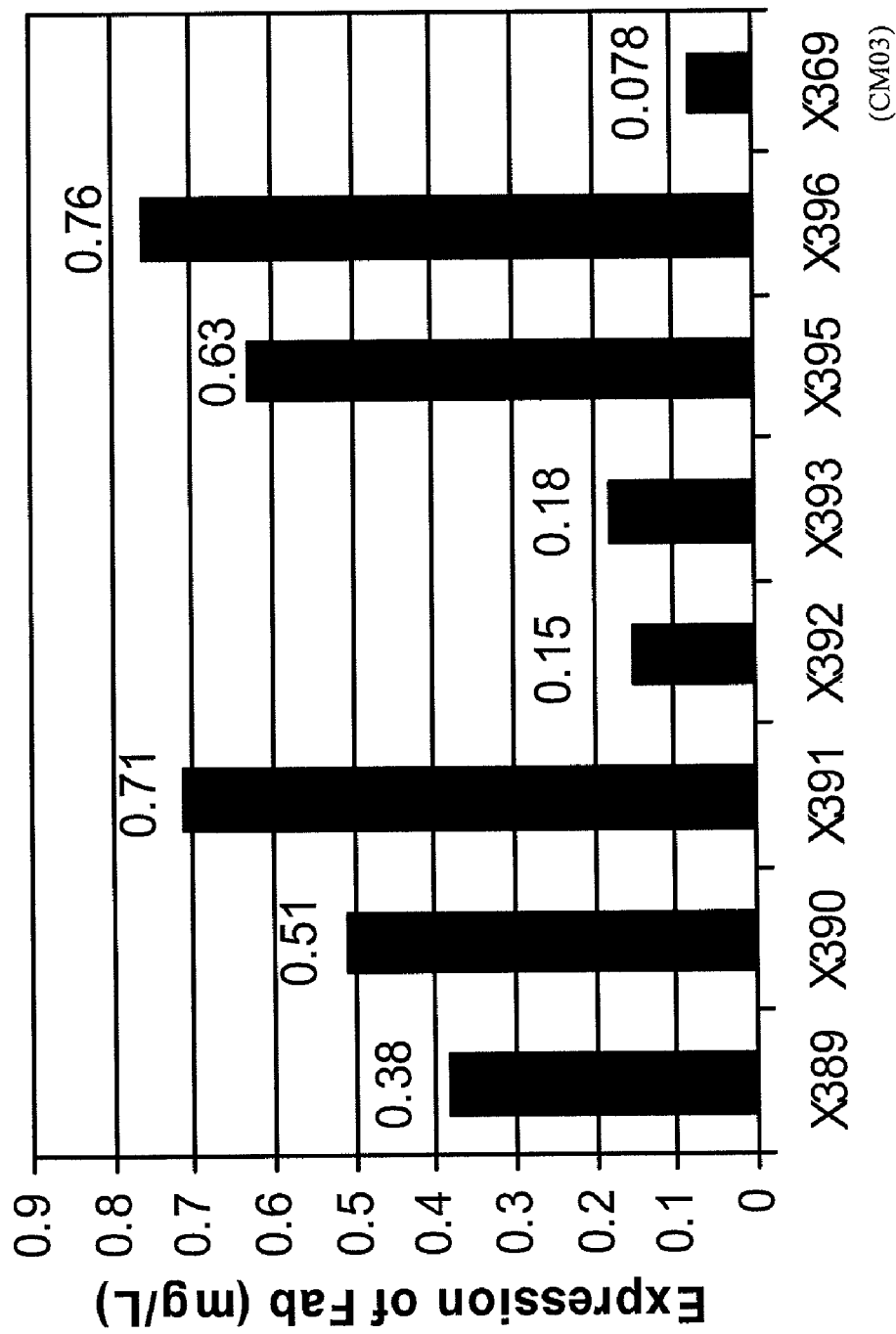
FIG. 10 shows a quantitative representation of accumulation of the Fab of CM03×369 and the following Fabs comprising CM03 VH and VL variant pairs, expressed in *E. coli* strain HB2151: X389, X390, X391, X392, X393, X395 and X396.

FIG. 9 shows an SDS-PAGE gel under non-reducing conditions loaded with samples purified by protein G column from expression of Fabs of CM03 VH variants X387 and X388 in E. coli strain TG1, as well as from expression of Fabs X389, X390, X391, X392, X393, X395 and X396, each comprising a pair of a VL variant and VH variant, in E. coli HB2151. (The X387 and X388 VH variants were paired with CM03 VL.) The VL and VH pairs of the Fabs X389, X390, X391, X392, X393, X395 and X396 are shown in FIG. 6. In each sample a protein band was seen around 50 kDa, but yields were highest in X389, X390, X391, X395 and X396. FIG. 10 shows a quantitative representation of accumulation of protein from Fab VH variant and VL variant pairs X389, X390, X391, X392, X393, X395 and X396, as well as CM03x369, expressed in E. coli strain HB2151. In all cases the Fab variant pair samples had higher levels of protein than the CM03 murine Fab.

C. Fab Properties

Table 3, below, shows a summary of various theoretical physical characteristics of Fabs X369 (CM03 VH and VL), X391, X392, X396 and X399. For instance, the molecular weight, number of charged residues, hydrophobic residues, isoelectric point, and overall charge are shown.

TABLE 3

| Fab | Properties |
|---|---|
| X369 | Molecular Weight 49596.31 Daltons |
|  | 458 Amino Acids |
|  | 38 Strongly Basic(+) Amino Acids (K, R) |
|  | 35 Strongly Acidic(−) Amino Acids (D, E) |
|  | 134 Hydrophobic Amino Acids (A, I, L, F, W, V) |
|  | 176 Polar Amino Acids (N, C, Q, S, T, Y) |
|  | 7.992 Isoelectric Point |
|  | 4.937 Charge at PH 7.0 |
| X391 | Molecular Weight 49809.46 Daltons |
|  | 458 Amino Acids |
|  | 41 Strongly Basic(+) Amino Acids (K, R) |
|  | 39 Strongly Acidic(−) Amino Acids (D, E) |
|  | 129 Hydrophobic Amino Acids (A, I, L, F, W, V) |
|  | 172 Polar Amino Acids (N, C, Q, S, T, Y) |
|  | 7.822 Isoelectric Point |
|  | 3.943 Charge at PH 7.0 |
| X392 | Molecular Weight 49634.45 Daltons |
|  | 458 Amino Acids |
|  | 41 Strongly Basic(+) Amino Acids (K, R) |
|  | 36 Strongly Acidic(−) Amino Acids (D, E) |
|  | 134 Hydrophobic Amino Acids (A, I, L, F, W, V) |
|  | 170 Polar Amino Acids (N, C, Q, S, T, Y) |
|  | 8.272 Isoelectric Point |
|  | 6.776 Charge at PH 7.0 |
| X396 | Molecular Weight 49664.36 Daltons |
|  | 458 Amino Acids |
|  | 40 Strongly Basic(+) Amino Acids (K, R) |
|  | 39 Strongly Acidic(−) Amino Acids (D, E) |
|  | 132 Hydrophobic Amino Acids (A, I, L, F, W, V) |
|  | 170 Polar Amino Acids (N, C, Q, S, T, Y) |
|  | 7.625 Isoelectric Point |
|  | 2.950 Charge at PH 7.0 |
| X399 | Molecular Weight 49678.39 Daltons |
|  | 458 Amino Acids |
|  | 40 Strongly Basic(+) Amino Acids (K, R) |
|  | 39 Strongly Acidic(−) Amino Acids (D, E) |
|  | 132 Hydrophobic Amino Acids (A, I, L, F, W, V) |
|  | 170 Polar Amino Acids (N, C, Q, S, T, Y) |
|  | 7.625 Isoelectric Point |
|  | 2.950 Charge at PH 7.0 |

D. Specificity of a Fab Comprising a Variant Light Chain Variable Region

Figure 12A:
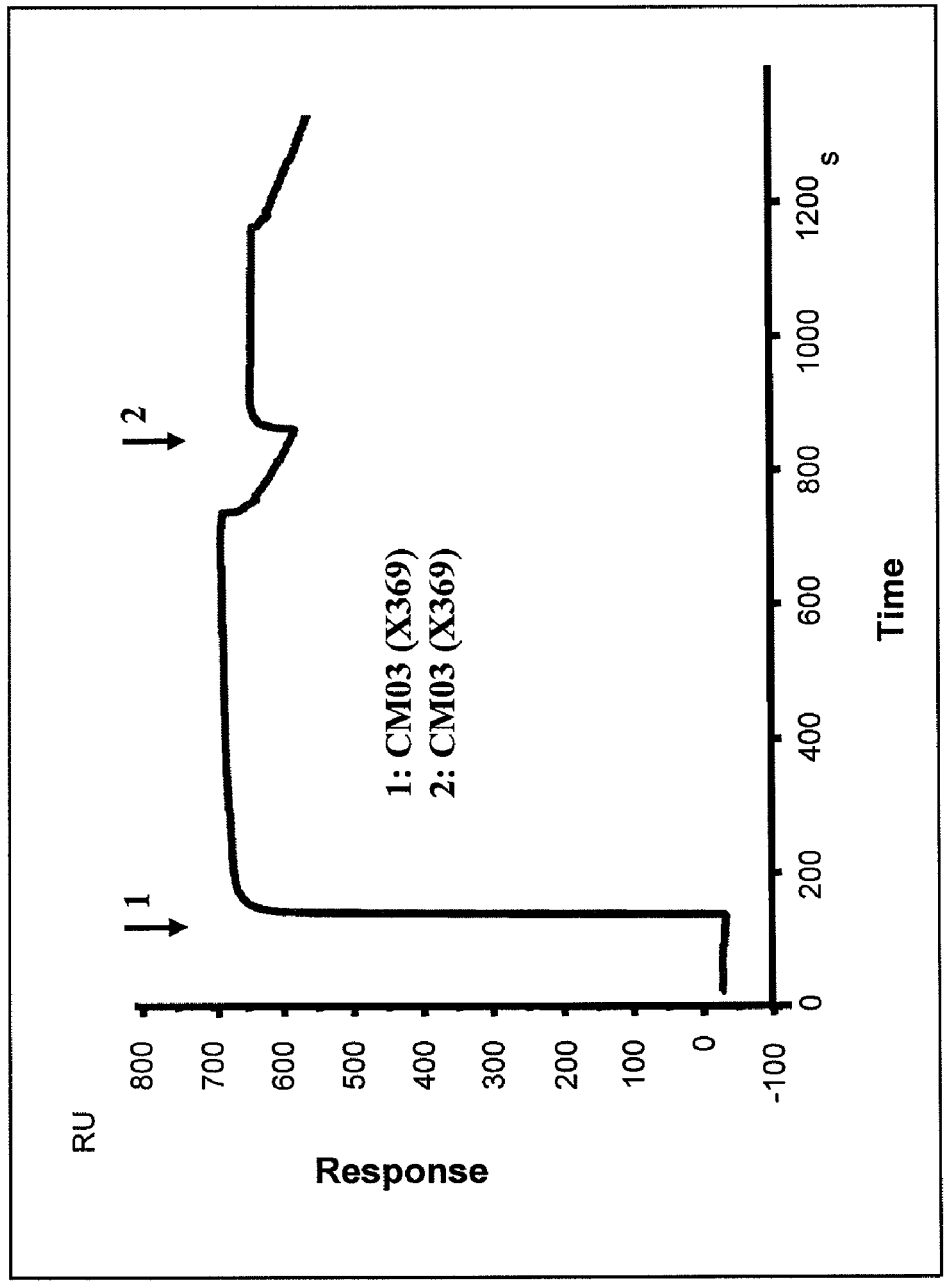
FIG. 12A shows the CM03 Fab X369 bound to human CD26 and response after introduction of additional X369.
Figure 12B:
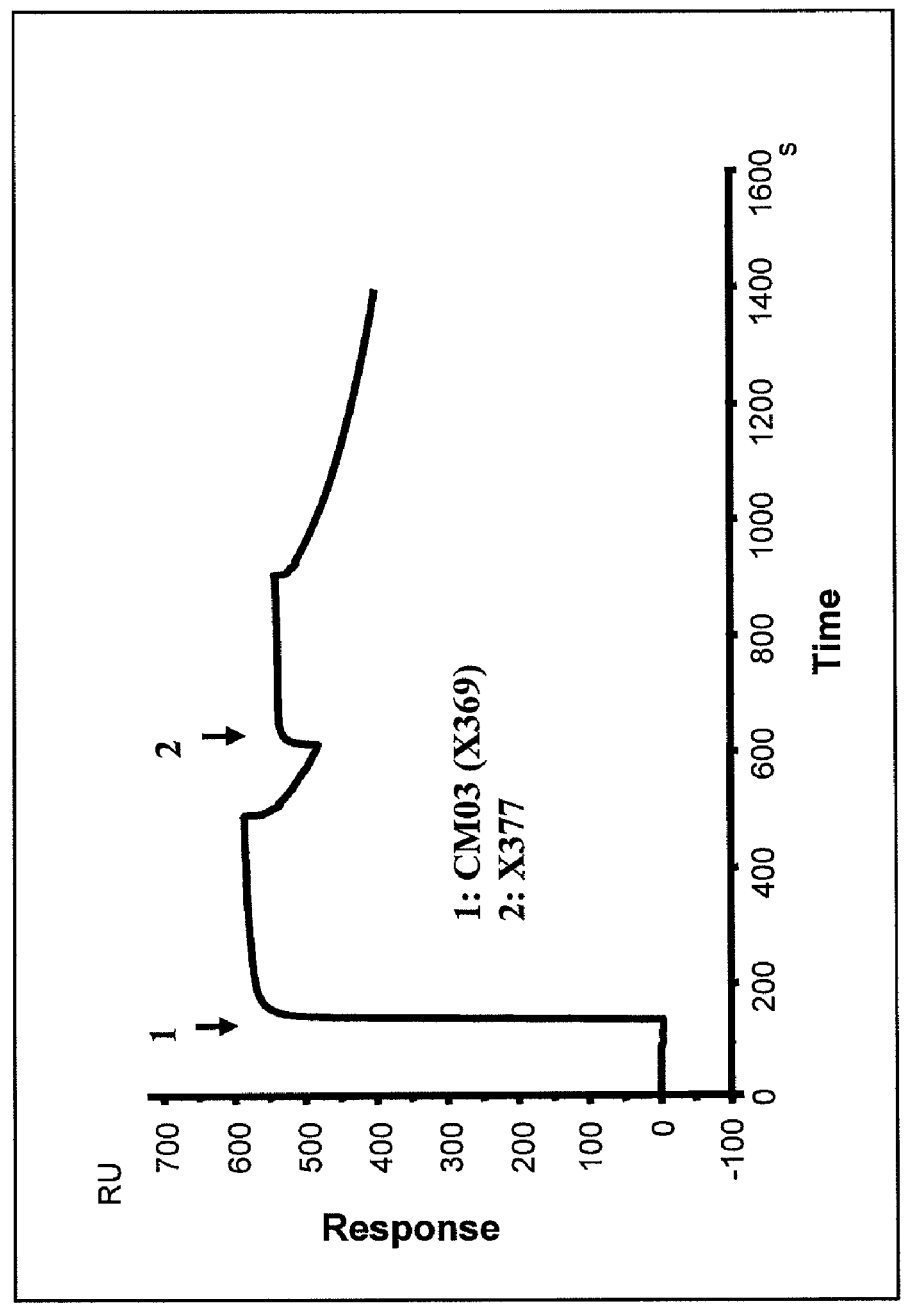
FIG. 12B shows the CM03 Fab X369 bound to human CD26 and response after introduction of a Fab comprising X377 VL and CM03 VH.
Figure 12C:
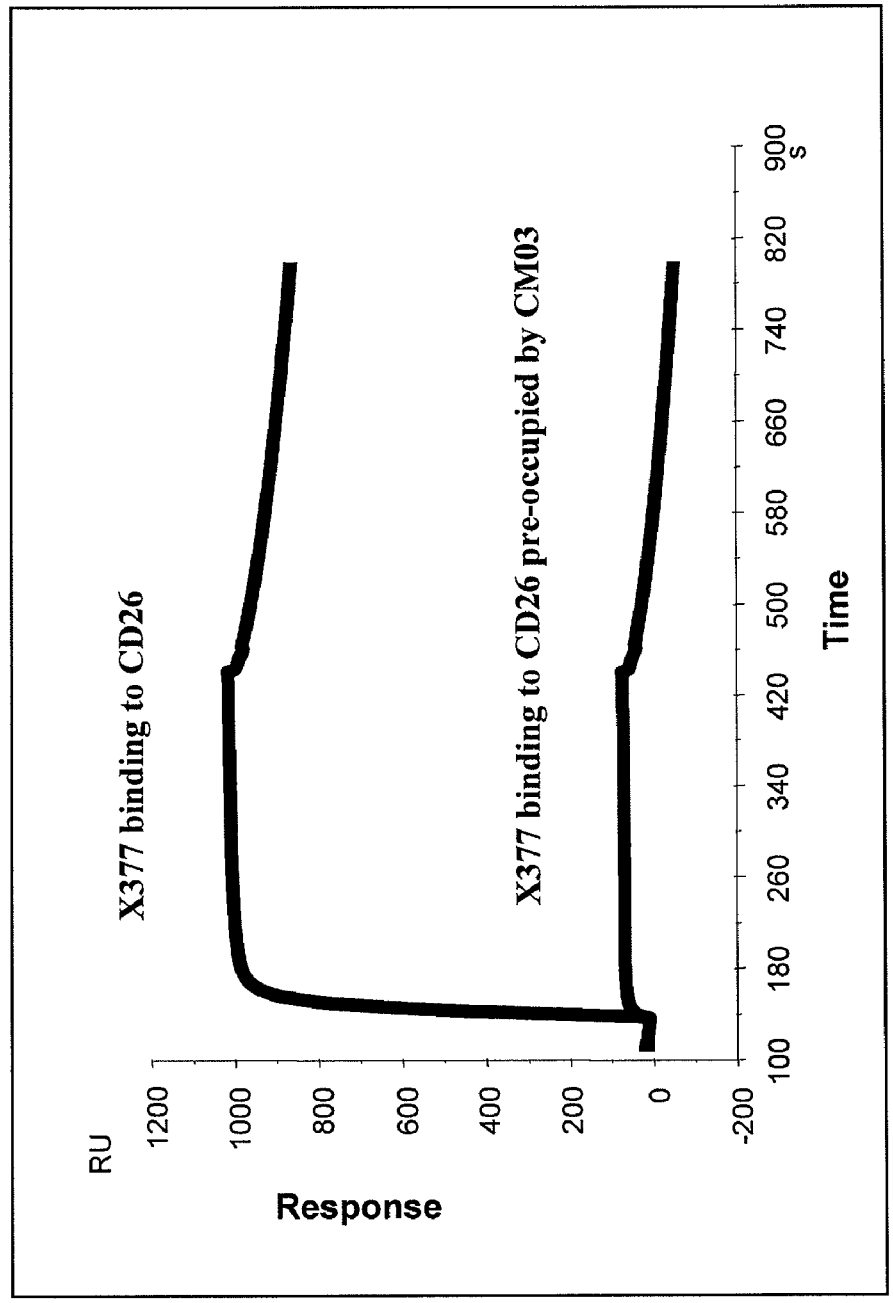
FIG. 12C shows the binding of X377 Fab to human CD26 and the binding of the X377 Fab to human CD26 which has previously been bound to CM03 Fab X369.

A specificity analysis of CM03 Fab X369 and a Fab comprising an X377 VL variant linked to the CM03 VH was done. The data is shown in FIGS. 12A, 12B, and 12C. The data was generated using the Biacore® technology. The CD26 binding partner was as described below.

FIG. 12A shows X369 (CM03 Fab) bound to human CD26. Also shown is the response after introduction of additional CM03 at approximately 800 seconds. FIG. 12B shows X369 (CM03 Fab) bound to human CD26. Also shown is the response after introduction of a Fab comprising the X377 VL variant paired with CM03 VH at approximately 600 seconds. FIG. 12C shows the X377 Fab bound to human CD26 versus the X377 Fab bound to CD26 pre-occupied by the CM03 Fab X369. A diminished level of X377 Fab binding with CD26 which has previously been bound by X369, as compared to X377 Fab bound to previously unbound CD26, indicates that X377 Fab and the CM03 Fab X369 have similar or at least overlapping sites of interaction with CD26.

E. Affinity of Fab Variants to Human CD26

Table 4, below, shows a summary of affinity analyses, including $K_D$, of CM03×369 as well as of Fabs comprising the CM03 VH combined with each of the CM03 VL variants X376, X377, X378, X379, X380, or X381. This data was generated using Biacore® technology. The CD26 binding partner was as shown below.

TABLE 4

| Variants | $K_{on}$/SE (M$^{-1}$·sec$^{-1}$) | $K_{off}$/SE (sec$^{-1}$) | $K_D$ (M) | Ki2 |
|---|---|---|---|---|
| X369 | 5.09E+05/1.19E+04 | 8.29E−04/3.40E−06 | 1.63e−9 | 7.03 |
| X376 | 2.58E+05/1.71E+03 | 5.96E−04/3.49E−06 | 2.31e−9 | 12.2 |
| X377 | 3.17E+05/2.28E+03 | 5.96E−04/3.48E−06 | 1.88e−9 | 12.7 |
| X378 | 2.85E+05/1.85E+03 | 8.30E−04/6.02E−06 | 2.92e−9 | 10.7 |
| X379 | 5.78E+05/4.67E+03 | 6.70E−04/3.82E−06 | 1.16e−9 | 8.89 |
| X380 | 2.94E+05/2.84E+03 | 6.87E−04/4.54E−06 | 2.33e−9 | 10.5 |
| X381 | 2.93E+05/1.76E+03 | 6.01E−04/4.04E−06 | 2.10e−9 | 4.44 |

X369: murine CM03 Fab

Table 5, below, shows a summary of affinity analyses, including $K_D$, of CM03×369 and of Fabs comprising a CM03 VL paired with one of the CM03 VH variants X384, X385, X386, X387 or X388.

TABLE 5

| Variants | $K_{on}$/SE (M$^{-1}$·sec$^{-1}$) | $K_{off}$/SE (sec$^{-1}$) | $K_D$ (M) | Ki2 |
|---|---|---|---|---|
| X369 | 5.09E+05/1.19E+04 | 8.29E−04/3.40E−06 | 1.63e−9 | 7.03 |
| X384 | 2.62E+05/1.84E+03 | 3.12E−04/6.26E−06 | 1.19e−9 | 23.9 |
| X385 | 2.56E+05/1.84E+03 | 3.75E−04/6.47E−06 | 1.47e−9 | 50.1 |
| X386 | 1.84E+05/4.32E+03 | 4.98E−04/3.27E−06 | 2.71e−9 | 68.3 |
| X387 | 1.96E+05/1.10E+04 | 1.00E−02/1.96E−04 | 5.11e−8 | 819 |
| X388 | 2.35E+05/2.37E+03 | 6.98E−04/5.00E−06 | 2.98e−9 | 27.5 |

X369: murine CM03 Fab

Figure 13:
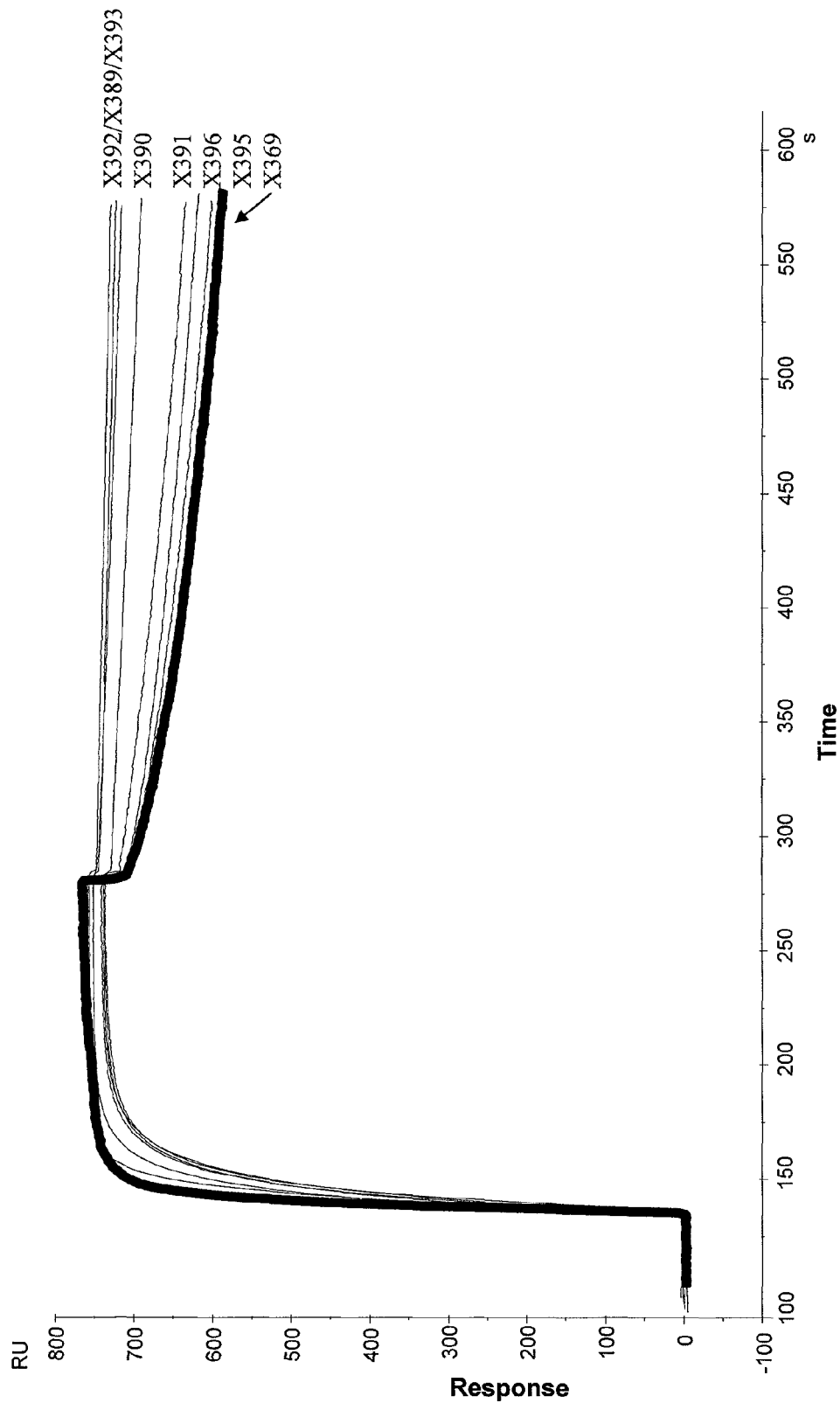
FIG. 13 shows an affinity analysis of CM03×369 and the following Fabs comprising CM03 VH variants and VL variants: X389, X390, X391, X392, X393, X395 and X396.

FIG. 13 shows an affinity analysis of X369 Fab (CM03 VH and VL) and the following Fabs comprising pairs of humanized CM03 VH and VL variants: X389, X390, X391, X392, X393, X395 and X396. See FIG. 6 for the amino acid sequences of the pairs of the variant heavy and light chain variable regions. The analysis was done using Biacore® as described in Example 1, excepting the CD26 binding partner was as shown in the figure.

Table 6, below, shows a summary of Tables 4 and 5, as well as expression yields of the indicated Fabs. It also shows the variant heavy and light chains used to make selected Fabs, $K_D$, yield, and ratios of $K_D$ and yield of selected Fabs comprising pairs of VH and VL variants, as compared to CM03 Fab.

TABLE 6

|  | VH | | | VL | |
|---|---|---|---|---|---|
|  | Kd (nM) | Yield (µg/l) |  | Kd (nM) | Yield (µg/l) |
| X384 | 1.2 | 260 | X376 | 2.3 | 2180 |
| X385 | 1.5 | 180 | X377 | 1.9 | 350 |
| X386 | 2.7 | 581 | X378 | 2.9 | 15 |
| X387 | 51 | 50 | X379 | 1.2 | 18 |
| X388 | 3 | 93 | X380 | 2.3 | 848 |
|  |  |  | X381 | 2.1 | 22 |
| CM03 | 1.6 | 78 | CM03 | 1.6 | 78 |

| Fab | VH | VL | Yield (µg/l) | Ratio# | Kd (nM) | Ratio## |
|---|---|---|---|---|---|---|
| X389 | X384 | X376 | 380 | 4.87 | 0.38 | 4.29 |
| X390 | X385 | X376 | 500 | 6.41 | 0.96 | 1.70 |
| X391 | X388 | X376 | 760 | 9.74 | 2.12 | 0.77 |
| X392 | X384 | X379 | 150 | 1.92 | 0.24 | 6.79 |
| X393 | X385 | X379 | 180 | 2.31 | 0.33 | 4.94 |
| X394 | X384 | X394 | 235 | 3.01 | 0.58 | 2.81 |
| X395 | X384 | X380 | 630 | 8.08 | 3.26 | 0.50 |
| X396 | X385 | X380 | 760 | 9.74 | 2.53 | 0.64 |
| X399 | X399 | X380 | 453 | 5.81 | 2.85 | 0.57 |

TABLE 6-continued

| | | | | | | |
|---|---|---|---|---|---|---|
| X431 | X420 | X380 | 1110 | 14.23 | 0.92 | 1.77 |
| X430 | X399 | X394 | 1290 | 16.54 | 1.19 | 1.37 |
| CM03 | Murine | Murine | 78 | 1.00 | 1.63 | 1.00 |

Murine CM03 Fab is X369
The ratio of the yield of each individual clone to the yield of murine CM03
The ratio of the Kd of CM03 Fab to the Kd of individual clone F. Specificity of Fabs Comprising Variant VH and VL Pairs for Binding to Human CD26

Figure 14:
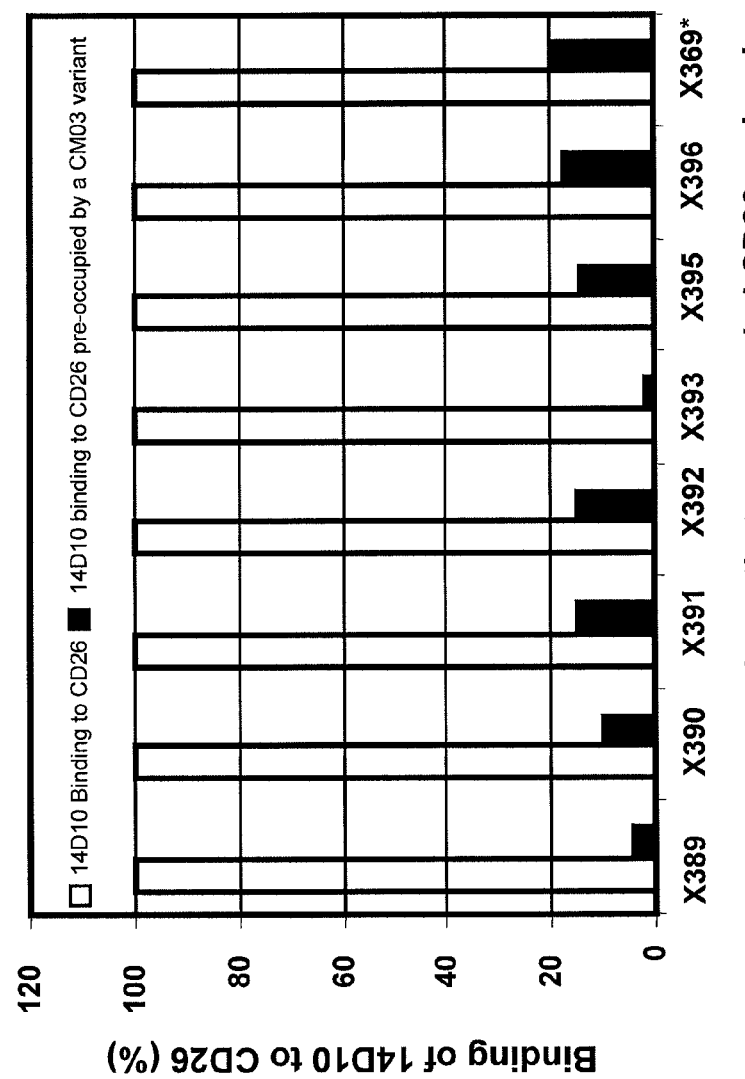
FIG. 14 shows CM03 X369 Fab and humanized CM03 Fabs X389, X390, X391, X392, X393, X395 and X396 competing with unpurified ascites murine MAb CM03 (14D10) for binding to human CD26.

A specificity analysis of selected Fabs comprising pairs of variant VH and VL sequences was done. FIG. 14 shows CM03X369 Fab and humanized CM03 Fabs X389, X390, X391, X392, X393, X395 and X396 that competed with unpurified ascites murine MAb CM03 (14D10) for binding to CD26. Binding of 14D10 to CD26 was compared to binding of 14D10 to C26 that was preoccupied by a CM03 variant. The recombinant Fab of cloned CM03 was used as a positive control. The analysis was done using Biacore) as described in Example 1. All Fabs result in at least an 80% decrease in binding of 14D10 to CD26, indicating the Fab variant pairs have a similar, or at least overlapping, binding site as 14D10.

G. Biological Activity

Fabs comprising various pairs of humanized heavy and light chain variable regions were analyzed for their ability to inhibit cell proliferation.

The effect of the various Fab variants was analyzed in Jurkat CD26+ cells for growth inhibitory effect. The 3-4,5-Dimethylthiazol-2-yl-2,5-diphenyltetrazolium bromide ("MTT") assay, which is well known in the art, was used. This assay is a quantitative method used to determine cell proliferation. Generally, the MTT assay is based on the ability of a mitochondrial dehydrogenase enzyme from viable cells to cleave MTT and form dark blue formazan crystals. The number of surviving cells is proportional to the level of the formazan product created. The color can be quantified using a simple calorimetric assay.

To perform the MTT assay, briefly, 50 μl of exponentially growing Jurkat CD26+ cells were placed in Microtitre plate (50,000 cells in 50 μl well). CM03 Fab X369 and Fab variants X389, X390, X391, X392, X393, X395 and X396 (comprising pairs of VH and VL variants), as well as the Fab comprising VL variant X376 and CM03 VH were added at 0.1, 0.5, 1, 5 and 10 μg/ml of growth medium and mixed. Cells were incubated for 48 hours in a sealed CO$_2$ incubator at 37° C. MTT was added to approximately 1 mg/ml. Cells were incubated for 2 hours at 37° C. Extraction of formazan took place overnight in a CO$_2$ incubator. Absorbance at 570 nm was measured.

Figure 15:
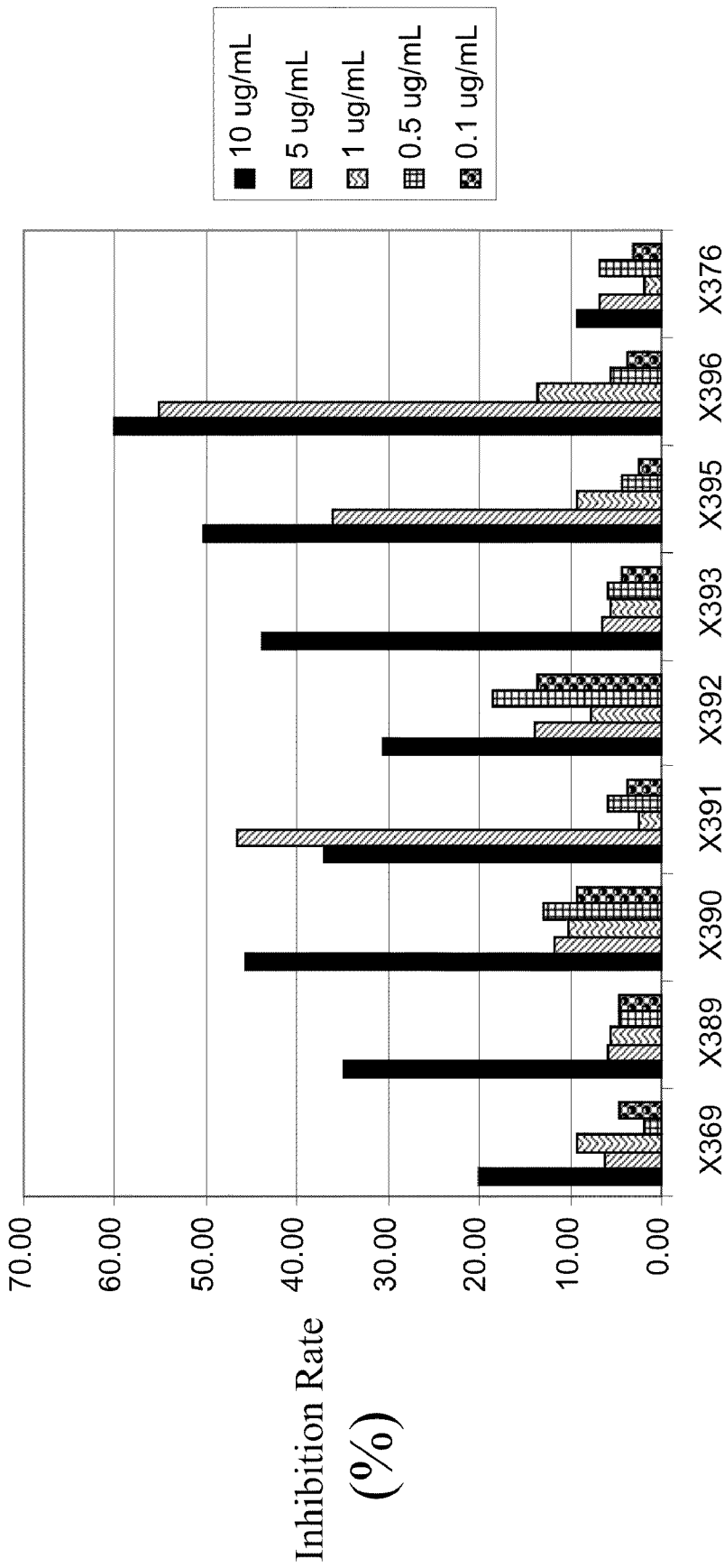
FIG. 15 shows the percent inhibition of JKT/CD26+ cell proliferation by CM03 Fab X369 and Fabs comprising VH/VL variant pairs (X389, X390, X391, X392, X393, X395 and X396), as well as a Fab comprising variant X376 and CM03 VH.

FIG. 15 shows the percent inhibition of JKT/CD26+ cell proliferation by CM03 Fab X369 and Fabs X389, X390, X391, X392, X393, X395 and X396 (comprising pairs of VH and VL variants), as well as a Fab comprising the VL variant X376 and CM03 VH.

All Fabs caused inhibition of cell proliferation, with highest inhibition at the 5 or 10 μg/ml level.

Example 3

Humanized CM03 IgG1 Antibodies

A. Sequences

Figure 16:
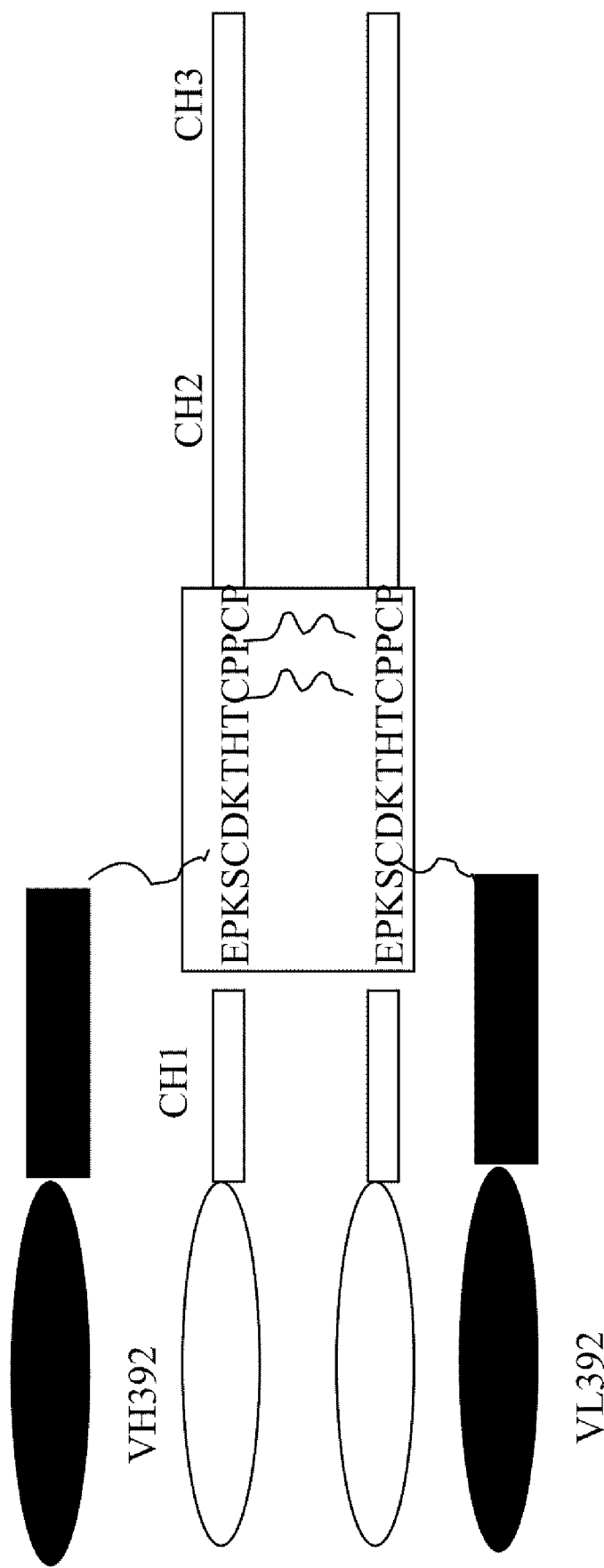
FIG. 16 shows a diagram of an IgG1 antibody including the IgG1 chain-chain interaction. The indicated hinge sequence is SEQ ID NO:86.

Full-length humanized antibodies were generated using selected VH and VL pairs, the human IgG1 heavy chain constant region, and the human kappa light chain constant region. FIG. 16 shows the IgG1 chain-chain interaction and hinge region. FIG. 17A shows the heavy chain constant region amino acid sequence. It also shows the position of the VH variant in the heavy chain, and the leader sequence. FIG. 17B shows the light chain constant region amino acid sequence. It also shows the position of the VL variant in the light chain, and the leader sequence.

Table 7 and Table 8, below, match the identity of the VH and VL pairs used to make the recombinant humanized monoclonal antibodies (rhuMAbs) 409, 410, 411, 412, 420 and 429 with those of some of the Fabs previously tested. The VH and VL variants used to make the Fabs comprising VH and VL variant pairs are shown in Table 8, below. For instance, rhuMab410, also referred to herein as "X410," comprises X388 VH and X376 VL sequences, just as Fab X391 does. FIG. 6 shows the amino acid sequences of selected pairs of variant heavy and light chains, as described above, excepting that of X369 (CM03 Fab). The CM03 VH and CM03 VL sequences of X369 (CM03 Fab) were used to generate rhuMAb409.

TABLE 7

Nomenclature of the

| Fabs | MAb |
|---|---|
| X369 (CM03) | rhuMAb409 |
| X391 | rhuMAb410 |
| X392 | rhuMAb411 |
| X396 | rhuMAb412 |
| X420 | rhuMAb420 |
| X429 | rhuMAb429 |

TABLE 8

| IgG1 | Fab | VH | VL | Fab Yield (ug/l) | CHO Yield (ug/l) | Fab Kd (nM) |
|---|---|---|---|---|---|---|
| | X389 | X384 | X376 | 380 | 650 | 0.38 |
| | X390 | X385 | X376 | 500 | 700 | 0.96 |
| X410 | X391 | X388 | X376 | 760 | 229 | 2.12 |
| X411 | X392 | X384 | X379 | 150 | 720 | 0.24 |
| | X393 | X385 | X379 | 180 | 1,580 | 0.33 |
| | X394 | X384 | X394 | 235 | 250 | 0.58 |
| | X395 | X384 | X380 | 630 | 310 | 3.26 |
| X412 | X396 | X385 | X380 | 760 | 1,370 | 2.53 |
| X427 | X399 | X399 | X380 | 453 | 1,420 | 2.85 |
| X420 | X431 | X420 | X380 | 1110 | 1,100 | 0.92 |
| X429 | X430 | X399 | X394 | 1290 | 4,300 | 1.19 |
| X409 | CM03 | Murine | Murine | 78 | 470 | 1.63 |

Murine CM03 Fab is X369

B. Expression

Figure 18:
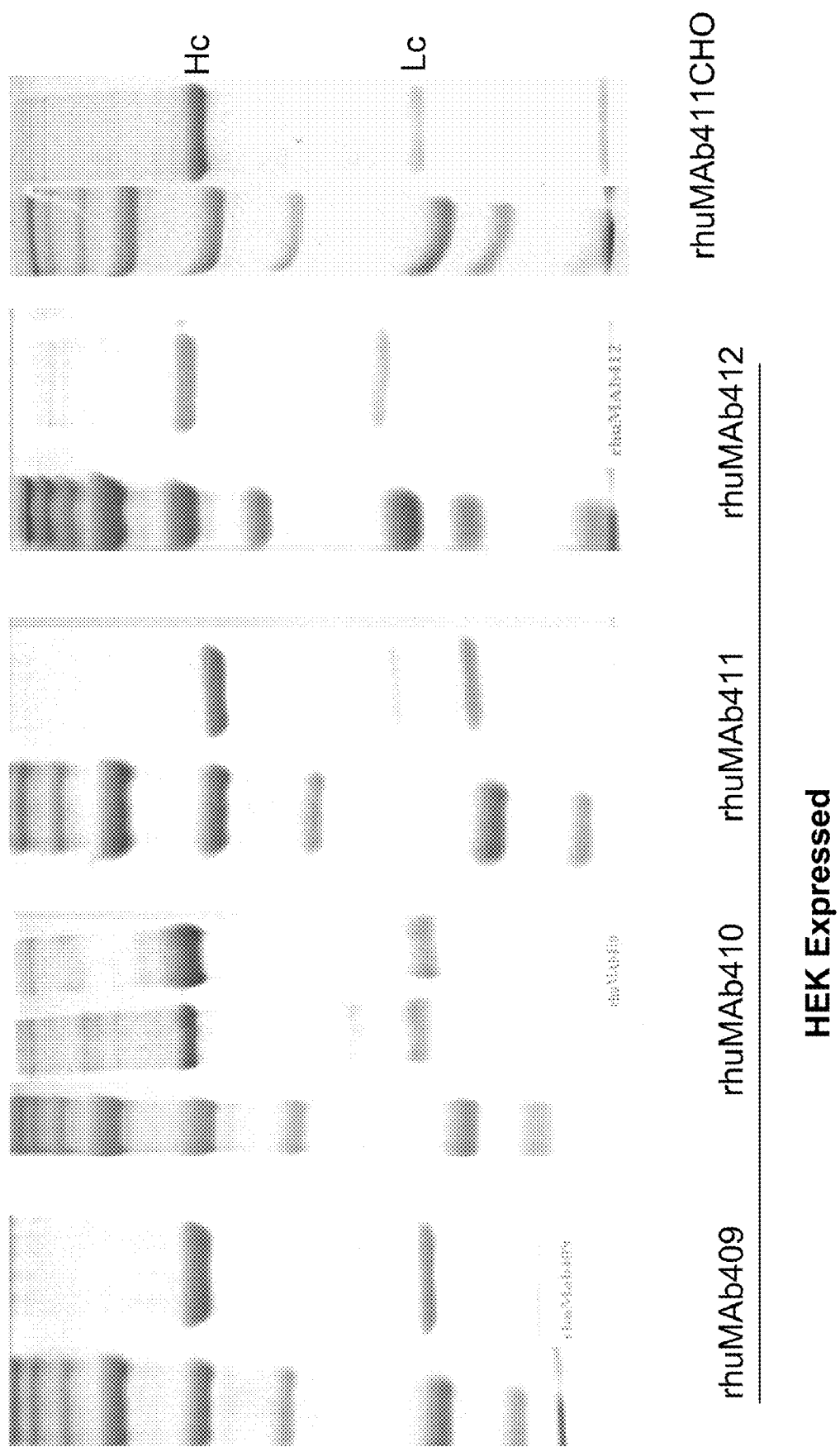
FIG. 18 shows recombinant humanized monoclonal antibodies (rhuMAbs) 409, 410, 411, and 412 expressed in HEK cells, and rhuMAb 411 expressed in CHO cells.

FIG. 18 shows full-length recombinant humanized monoclonal antibodies (rhuMAbs) 409, 411, 410 and 412 transiently expressed in HEK293 cells and purified via a protein A affinity column (Procep-A, Millipore, CAT# 113111827) according to the manufacturer's manual. The antibody was eluted by 100 mM Sodium Acetate pH 3.0 followed by immediate neutralization by 2 M Tris pH 9.0. The samples were then spun in JS4.2 rotor at 4,000 rpm for 30 minutes to remove insoluble material and filtered through a 0.2 μm filter for sterilization before storage. FIG. 18 also shows rhuMAb 411 stably expressed in Chinese hamster ovarian (CHO-DG44) cells. In each case, transfection was performed via lipofectomin.

FIG. 18 shows a Coomassie blue-stained SDS polyacrylamide gel run under reducing conditions. Two major bands with migration points consistent with that expected for free heavy and light chains were seen. Table 7, above, shows the yields of the various indicated full-length antibodies expressed in CHO cells.

C. Affinity of rhuMAbs for Human CD26

The CD26 binding affinities of rhuMAbs 409, 410, 411 and 412 to CD26 are shown in Table 9, below. Analyses thereof were performed using Biacore® as described in Example 1, excepting the binding partners were the rhuMAbs noted above. RhuMAb 411 had 3.7-fold the $K_D$ of rhuMAb 409. RhuMAbs 410 and 412 had 0.5- and 0.4-fold the $K_D$ of rhuMAb 409, respectively.

TABLE 9

Affinity of rhuMABs to YSCMA Antigen Detected by Biacore ®

| Construct | µM | $K_{on}$/SE | $K_{off}$/SE | $K_D$ | nM | -fold |
|---|---|---|---|---|---|---|
| X409 | 0.2 | 5.77E+05/1.56E+04 | 4.73E−04/7.78E−06 | 8.19e−10 | 0.82 | 1 |
| X411 | 0.2 | 4.85E+05/3.67E+03 | 1.08E−04/8.59E−07 | 2.22e−10 | 0.22 | 3.7 |
| X410 | 0.1 | 1.58E+05/2.42E+03 | 2.68E−04/9.95E−06 | 1.69e−9 | 1.69 | 0.5 |
| X412 | 0.12 | 2.03E+05/2.21E+03 | 4.23E−04/9.66E−06 | 2.09e−9 | 2.09 | 0.4 |

Figure 19:
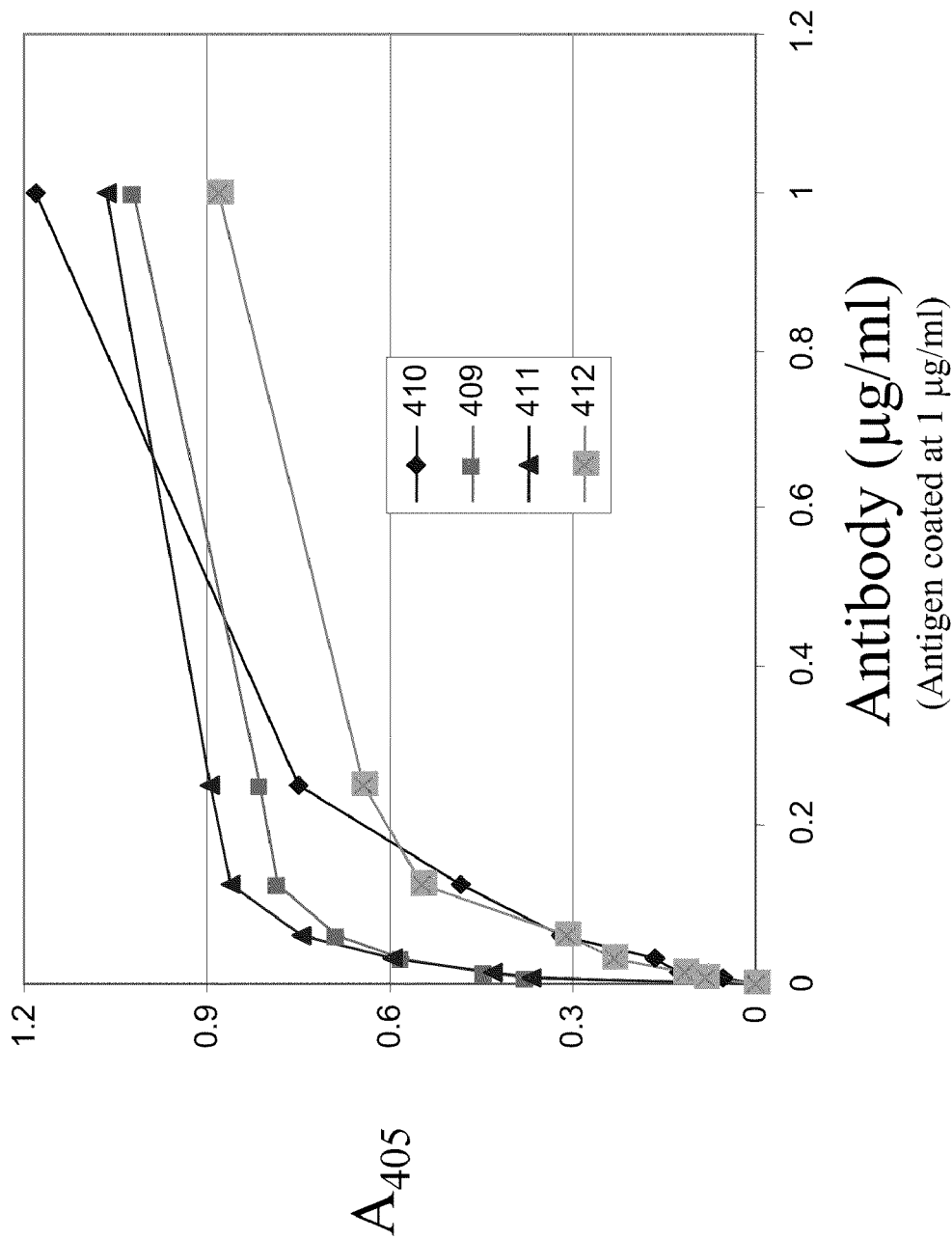
FIG. 19 shows rhuMAbs 409, 410, 411, and 412 specifically binding to human CD26.
Figure 20:
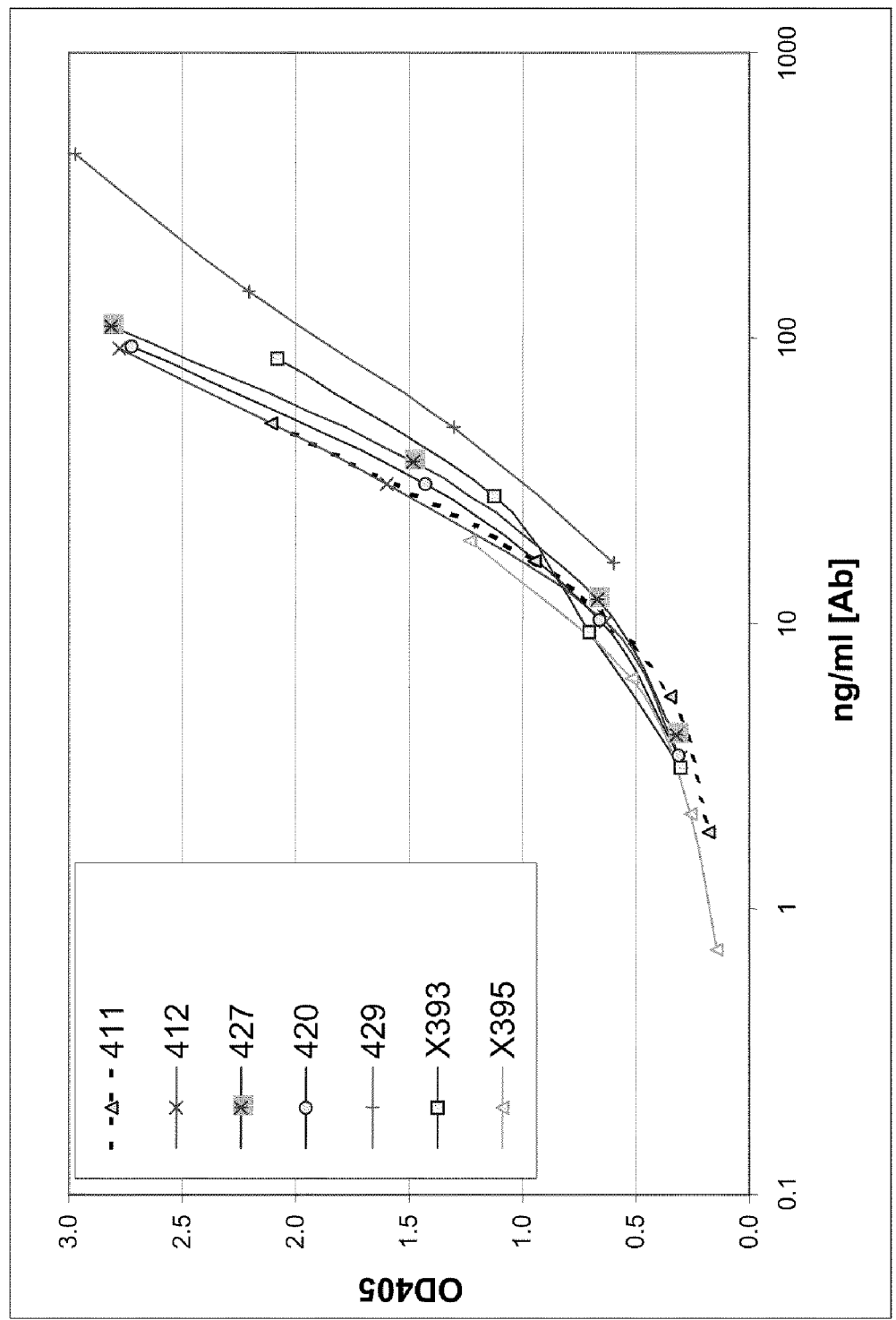
FIG. 20 shows ELISA data showing CD26-binding by rhuMAb variants.

FIG. 19 shows data showing rhuMAbs 409, 411, 410 and 412 specifically bound to human CD26. FIG. 20 shows data of an ELISA using a standard protocol ((Phage Display, A Laboratory Manual, Carlos Barbas III et al., Cold Spring Harbor Laboratory Press, 2001) showing the binding of additional transiently expressed rhuMAb variants to human CD26 (1 µg/ml human CD26 coating and goat anti-human-kappa HRP conjugate (SouthernBiotech, Birmingham, Ala., CAT# 2060-05) as a detection secondary antibody).

D. Biological Activity

Figure 21:
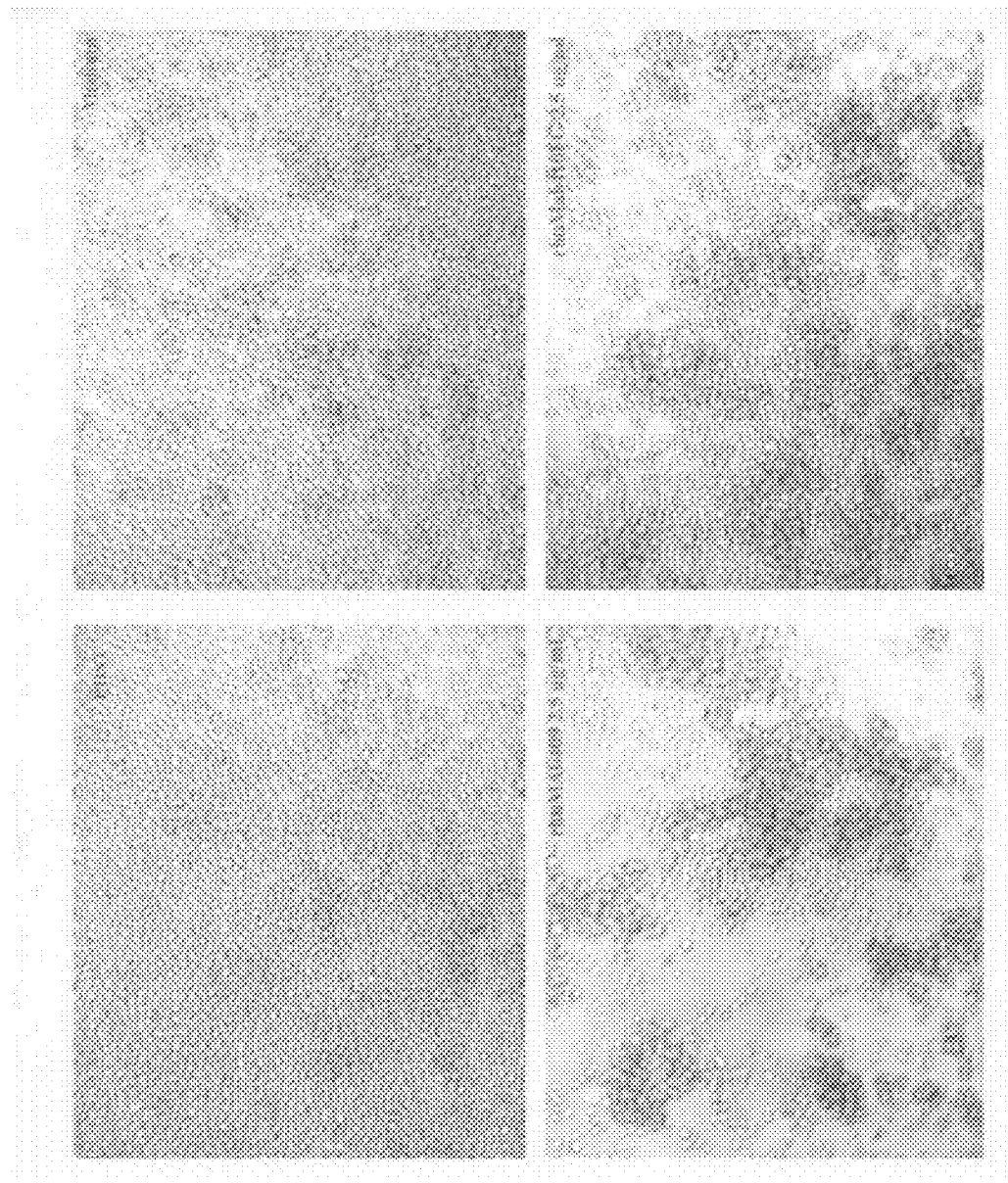
FIG. 21 shows the effect of 2.5 μg/ml of rhuMAbs 409 and 410 on JKT/CD26+ cells at 48 hours.

The anti-proliferative effect of specified recombinant human MAbs was analyzed in Jurkat CD26+ cells in a morphological assay that assessed aggregation induced by the antibodies. FIG. 21 shows images of cells treated with rhuMAb 409 (lower left image) and rhuMAb 410 (lower right image) relative to control treatments (upper images). Both rhuMAbs produced evidence of inhibition of cell proliferation relative to the control treatments.

Figure 22:
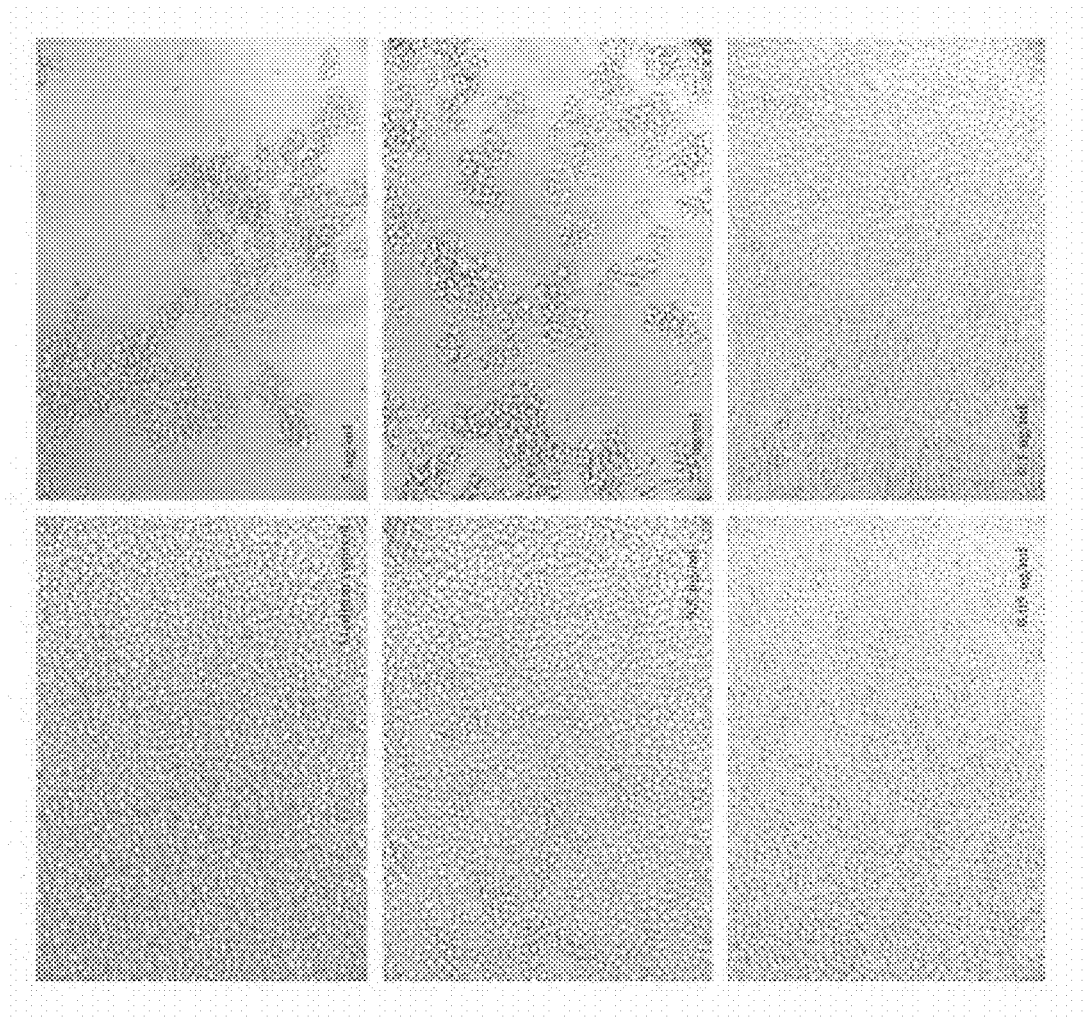
FIG. 22 shows the effect of 0.05, 0.1, 0.5, 2.5, and 5 μg/ml of rhuMAb 411 on JKT/CD26+ cells at 48 hours.

FIG. 22 shows the results of treatment with 0.05 µg/ml (lower left image), 0.1 µg/ml (lower right image), 0.5 µg/ml (middle left image), 2.5 µg/ml (middle right image), and 5 µg/ml (upper right image) of rhuMAb 411 relative to control (upper left image). Evidence of inhibition of cell proliferation was observed at higher levels of the antibody. The evidence of an inhibitory effect was higher with increasing rhuMAb 411; the most inhibitory concentration was at 5 µg/ml of rhuMAb 411.

The effect of specified recombinant human MAbs was also analyzed in Jurkat CD26+ cells for growth inhibitory effect using an MTT assay. The rhuMAbs 409, 410, 411, 412, 420 and 429 were each tested at various different concentrations. Table 10, below, shows the percent inhibition observed in the MTT assay for various recombinant human Mabs.

Figure 23A:
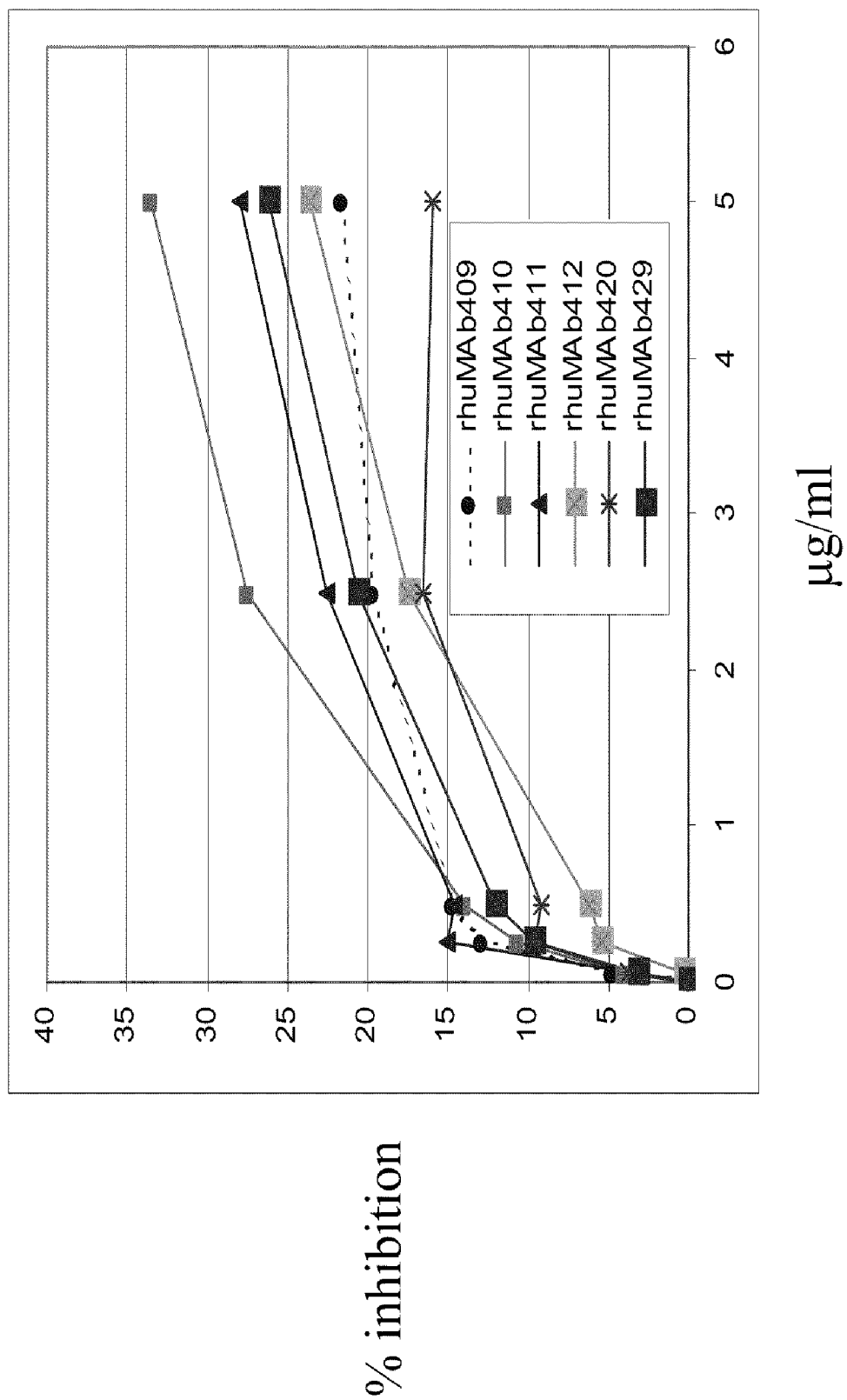
FIGS. 23A and 23B show MTT data (% inhibition) of rhuMAbs 409, 410, 411, 412, 420 and 429 produced in HEK293 cells.
Figure 23B:
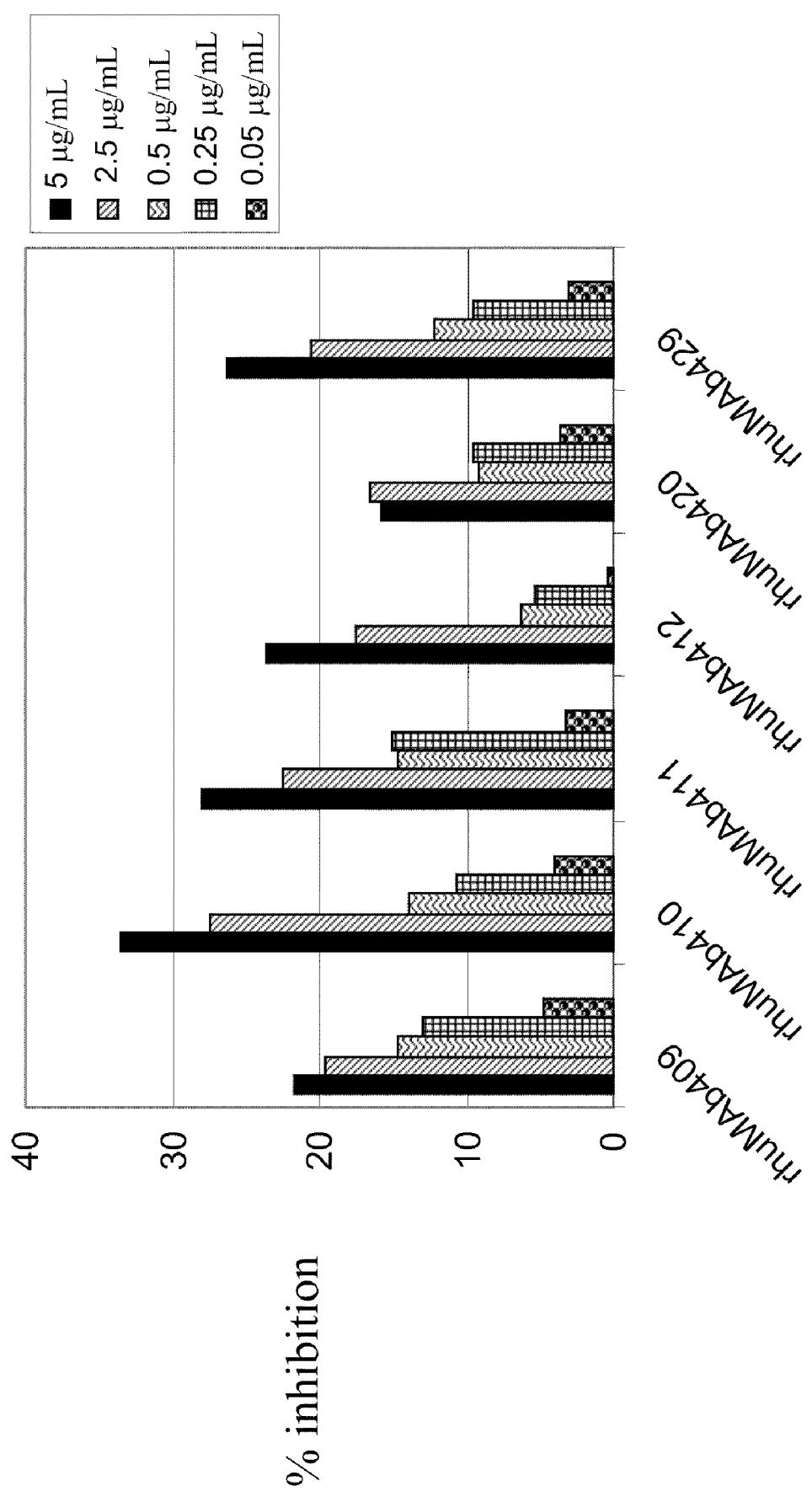

FIGS. 23A and 23B also show the MTT assay results of rhuMAbs 409, 410, 411, 412, 420 and 429. FIG. 23A shows a line chart representation of the percent inhibition, while FIG. 23B shows a bar chart representation thereof. Treatment with all of the antibodies shown resulted in inhibition of cell proliferation. Treatment with increased concentrations of the antibodies resulted in an increasing percentage of inhibition in all cases, with the exception of rhuMAb420, which showed a slight decrease in the 5 µg/ml treatment as opposed to the 2.5 µg/ml treatment.

E. Epitope Mapping

Epitope mapping experiments were performed to determine likely binding sites of the humanized monoclonal antibodies on CD26. Epitope mapping was performed using peptide microarrays.

Generally, this method of mapping requires the synthesis of peptides of overlapping sequence that collectively corresponds to all or a part of the amino acid sequence of the antigen (here, human CD26). The peptides are then reacted with the antibody of interest. Excess, or unbound, antibody is washed off. Reacted or bound antibody is detected. Since the sequence of each peptide on reactive pins is known, reactive regions of the antigen are deduced from the microarray reactivity profile.

The microarray was composed of 144 overlapping human CD26-derived 13mer peptides. Shown below is the 766 amino acid sequence of human CD26 (Dipeptidyl peptidase IV membrane form; SEQ ID NO:89).

TABLE 10

| ug/ml | rhuMAb409 | rhuMAb410 | rhuMAb411 | rhuMAb412 | rhuMAb420 | rhuMAb429 |
|---|---|---|---|---|---|---|
| 5 | 21.7 | 33.5 | 28 | 23.6 | 15.9 | 26.2 |
| 2.5 | 19.7 | 27.5 | 22.5 | 17.5 | 16.6 | 20.6 |
| 0.5 | 14.7 | 14 | 14.6 | 6.2 | 9.2 | 12.1 |
| 0.25 | 12.9 | 10.7 | 15 | 5.4 | 9.6 | 9.6 |
| 0.05 | 4.8 | 4 | 3.3 | 0.3 | 3.7 | 3.1 |
| 0 | 0 | 0 | 0 | 0 | 0 | 0 |
| Test # | 5 | 4 | 3 | 3 | 2 | 2 |

```
  1 MKTPWKVLLG LLGAAALVTI ITVPVVLLNK GTDDATADSR KTYTLTDYLK
 51 NTYRLKLYSL RWISDHEYLY KQENNILVFN AEYGNSSVFL ENSTFDEFGH
101 SINDYSISPD GQFILLEYNY VKQWRHSYTA SYDIYDLNKR QLITEERIPN
151 NTQWVTWSPV GHKLAYVWNN DIYVKIEPNL PSYRITWTGK EDIIYNGITD
201 WVYEEEVFSA YSALWWSPNG TFLAYAQFND TEVPLIEYSF YSDESLQYPK
251 TVRVPYPKAG AVNPTVKFFV VNTDSLSSVT NATSIQITAP ASMLIGDHYL
301 CDVTWATQER ISLQWLRRIQ NYSVMDICDY DESSGRWNCL VARQHIEMST
351 TGWVGRFRPS EPHFTLDGNS FYKIISNEEG YRHICYFQID KKDCTFITKG
401 TWEVIGIEAL TSDYLYYISN EYKGMPGGRN LYKIQLSDYT KVTCLSCELN
451 PERCQYYSVS FSKEAKYYQL RCSGPGLPLY TLHSSVNDKG LRVLEDNSAL
501 DKMLQNVQMP SKKLDFIILN ETKFWYQMIL PPHFDKSKKY PLLLDVYAGP
551 CSQKADTVFR LNWATYLAST ENIIVASFDG RGSGYQGDKI MHAINRRLGT
601 FEVEDQIEAA RQFSKMGFVD NKRIAIWGWS YGCYVTSMVL GSGSGVFKCG
651 IAVAPVSRWE YYDSVYTERY MGLPTPEDNL DHYRNSTVMS RAENFKQVEY
701 LLIHGTADDN VHFQQSAQIS KALVDVGVDF QAMWYTDEDH GIASSTAHQH
751 IYTHMSHFIK QCFSLP
```

Only amino acid residues 48-324 were represented on the microarray. The 13mers were offset by two amino acids. Therefore, peptide 1 represented amino acid residues 48-60, peptide 2 represented amino acid residues 50-62, and so on, finishing with peptide 133 representing amino acid residues 312-324. Table 11, below, shows the signal data for rhuMAbs 409, 411, 412, and 420. It also shows the amino acids represented by each of the peptide numbers shown in FIG. 24. Rows 134-144 represent background controls.

Note that the antibodies described may react with other peaks outside of the amino acid sequences used in the microarrays. Additionally, there may be association with amino acid residues not identified as being most reactive. This may be, in part, due to the disparity between the linear nature of the short peptides bound to the microarray, and the three-dimensional context of the antigen in its full length state.

The 13 mers were immobilized on a modified glass surface. The immobilized peptide derivatives had the following general structure: modified glass surface—linker—13 mer peptide.

The microarrays were pre-treated with blocking buffer for 4 hours at room temperature, followed by 3 washes each with PBS buffer pH 7.5 and water. Each pre-treated microarray was scanned using ArrayWorx-Microarray Scanner for background signal. No signals were detected.

As a control, one microarray was incubated with fluorescein-labelled human anti IgG antibody (SIGMA #F9512, anti-human IgG (Fc specific)—FITC antibody produced in goat, 1:1000) for 2 hours at room temperature, followed by three washings each with PBS buffer pH 7.5 and water. The microarrays were then scanned using an ArrayWorx-Microarray Scanner.

Microarrays were incubated overnight at 6° C. with rhuMAbs 409, 411, 412 and 420, using 10 µg antibody in 250 µl of assay buffer (PBS-T, 0.1% NaN$_3$). The overnight incubation was followed by three washings with each of PBS buffer pH 7.5 and water. The microarrays were then scanned using ArrayWorx-Microarray Scanner.

Figure 24:
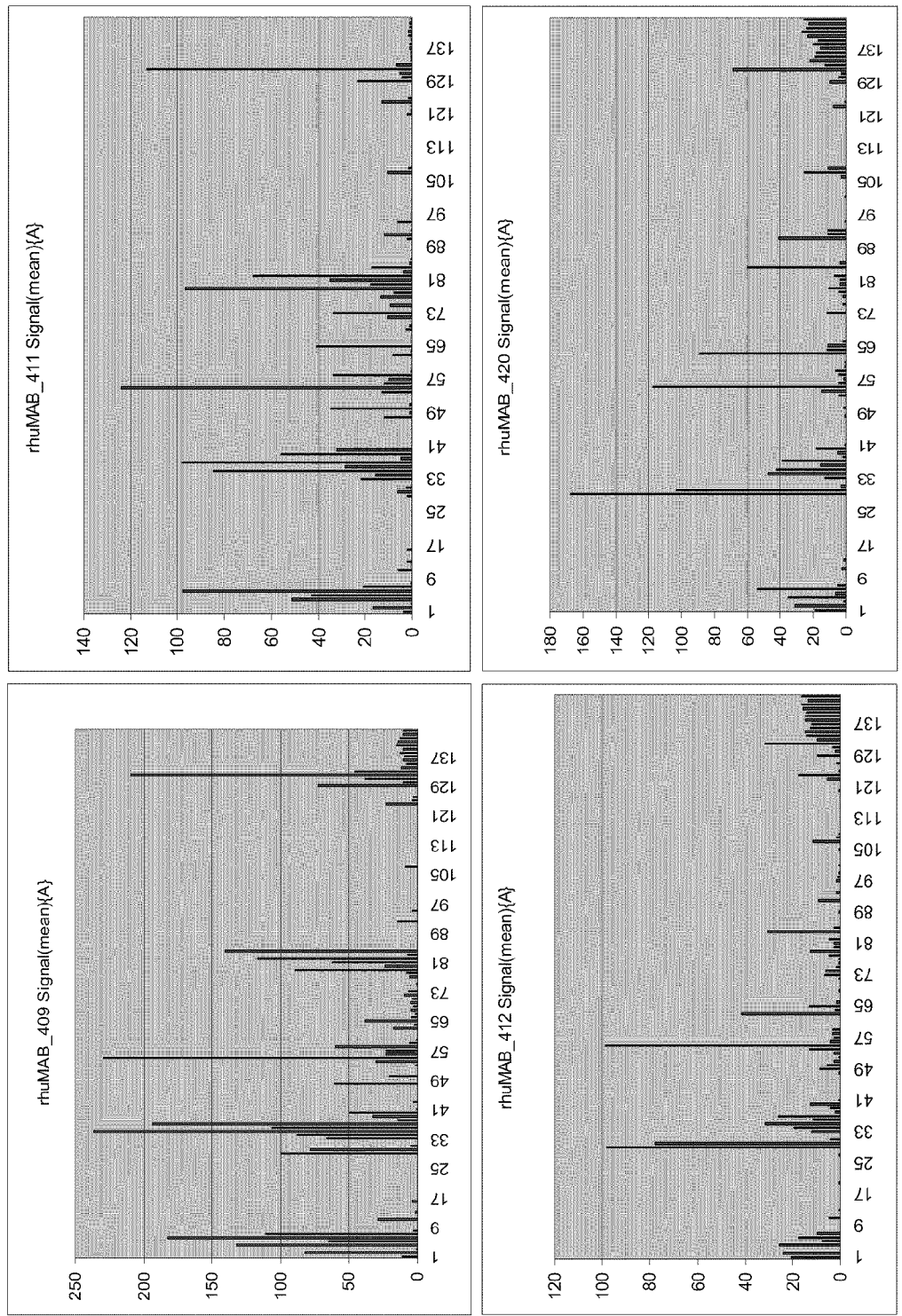
FIG. 24 shows 13mer peptides reactive with the rhuMAbs 409, 411, 412 and 420 humanized antibodies.

The SPOT recognition software package ArrayPro was used for data analysis. The mean of signal intensities from 3 identical subarrays on each microarray image was used for data evaluation. Table 11, below, shows the signal intensity data for rhuMAbs 409, 411, 412, and 420 to the 13mer peptides. FIG. 24 shows a bar chart representation of signal data for rhuMAbs 409, 411, 412, and 420.

TABLE 11

| Peptide No. | Amino Acids | Mean Signal Value rhuMAb409 | Mean Signal Value rhuMAb411 | Mean Signal Value rhuMAb412 | Mean Signal Value rhuMAb420 |
|---|---|---|---|---|---|
| 1 | YLKNTYRLKLYSL (SEQ ID NO: 92) | 11.331731 | 3.504808 | 20.307692 | 18.951923 |
| 2 | KNTYRLKLYSLRW (SEQ ID NO: 93) | 82.432692 | 16.480769 | 23.764423 | 31.028846 |
| 3 | TYRLKLYSLRWIS (SEQ ID NO: 94) | 0.663462 | 0.725962 | 0.033654 | 1.125 |
| 4 | RLKLYSLRWISDH (SEQ ID NO: 95) | 132.076923 | 51.326923 | 25.629808 | 35.057692 |
| 5 | KLYSLRWISDHEY (SEQ ID NO: 96) | 64.798077 | 43.125 | 7.591346 | 6.634615 |
| 6 | YSLRWISDHEYLY (SEQ ID NO: 45) | 183.028846 | 97.456731 | 17.629808 | 53.947115 |

TABLE 11-continued

| Peptide No. | Amino Acids | Mean Signal Value rhuMAb409 | Mean Signal Value rhuMAb411 | Mean Signal Value rhuMAb412 | Mean Signal Value rhuMAb420 |
|---|---|---|---|---|---|
| 7 | LRWISDHEYLYKQ (SEQ ID NO: 97) | 110.764423 | 20.586538 | 9.485577 | 5.115385 |
| 8 | WISDHEYLYKQEN (SEQ ID NO: 98) | 3.283654 | 0.735577 | 0.004808 | 0.009615 |
| 9 | SDHEYLYKQENNI (SEQ ID NO: 99) | 0 | 0.067308 | 0 | 0 |
| 10 | HEYLYKQENNILV (SEQ ID NO: 100) | 0.033654 | 0.019231 | 0 | 0.024038 |
| 11 | YLYKQENNILVFN (SEQ ID NO: 101) | 28.870192 | 5.783654 | 4.235577 | 2.649038 |
| 12 | YKQENNILVFNAE (SEQ ID NO: 102) | 0 | 0 | 0.086538 | 0.009615 |
| 13 | QENNILVFNAEYG (SEQ ID NO: 103) | 1.341346 | 1.942308 | 0.682692 | 1.432692 |
| 14 | NNILVFNAEYGNS (SEQ ID NO: 104) | 0 | 0.009615 | 0.043269 | 0 |
| 15 | ILVFNAEYGNSSV (SEQ ID NO: 105) | 0.105769 | 0 | 0 | 0.009615 |
| 16 | VFNAEYGNSSVFL (SEQ ID NO: 106) | 3.865385 | 1.918269 | 0.177885 | 0 |
| 17 | NAEYGNSSVFLEN (SEQ ID NO: 107) | 0.110577 | 0.0625 | 0.004808 | 0.067308 |
| 18 | EYGNSSVFLENST (SEQ ID NO: 108) | 0 | 0 | 0 | 0 |
| 19 | GNSSVFLENSTFD (SEQ ID NO: 109) | 0 | 0 | 0.072115 | 0 |
| 20 | SSVFLENSTFDEF (SEQ ID NO: 110) | 0 | 0.057692 | 0.379808 | 0.009615 |
| 21 | VFLENSTFDEFGH (SEQ ID NO: 111) | 0 | 0.197115 | 0 | 0 |
| 22 | LENSTFDEFGHSI (SEQ ID NO: 112) | 0 | 0.019231 | 0 | 0 |
| 23 | NSTFDEFGHSIND (SEQ ID NO: 113) | 0 | 0.004808 | 0 | 0 |
| 24 | TFDEFGHSINDYS (SEQ ID NO: 114) | 0 | 0.009615 | 0 | 0 |
| 25 | DEFGHSINDYSIS (SEQ ID NO: 115) | 0 | 0 | 0 | 0 |
| 26 | FGHSINDYSISPD (SEQ ID NO: 116) | 0 | 0.033654 | 0 | 0 |
| 27 | HSINDYSISPDGQ (SEQ ID NO: 117) | 0 | 0.004808 | 0.298077 | 0 |
| 28 | INDYSISPDGQFI (SEQ ID NO: 118) | 0.004808 | 0.221154 | 0 | 0.163462 |
| 29 | DYSISPDGQFILL (SEQ ID NO: 52) | 99.745192 | 2.163462 | 97.918269 | 167.634615 |
| 30 | SISPDGQFILLEY (SEQ ID NO: 53) | 78.033654 | 6.264423 | 77.4375 | 103.365385 |
| 31 | SPDGQFILLEYNY (SEQ ID NO: 119) | 4.9375 | 2.331731 | 3.807692 | 3.254808 |
| 32 | DGQFILLEYNYVK (SEQ ID NO: 120) | 0.019231 | 0.019231 | 0.004808 | 0 |
| 33 | QFILLEYNYVKQW (SEQ ID NO: 121) | 66.586538 | 21.817308 | 12.168269 | 12.769231 |
| 34 | ILLEYNYVKQWRH (SEQ ID NO: 122) | 87.649038 | 15.658654 | 19.451923 | 47.341346 |
| 35 | LEYNYVKQWRHSY (SEQ ID NO: 46) | 236.774038 | 84.745192 | 31.442308 | 42.360577 |
| 36 | YNYVKQWRHSYTA (SEQ ID NO: 123) | 106.850962 | 28.245192 | 11.456731 | 15.4375 |
| 37 | YVKQWRHSYTASY (SEQ ID NO: 50) | 193.5625 | 98.201923 | 25.764423 | 39.245192 |
| 38 | KQWRHSYTASYDI (SEQ ID NO: 125) | 14.519231 | 4.769231 | 1.865385 | 1.793269 |
| 39 | WRHSYTASYDIYD (SEQ ID NO: 126) | 32.307692 | 55.6875 | 4.144231 | 5.447115 |
| 40 | HSYTASYDIYDLN (SEQ ID NO: 127) | 49.552885 | 32.163462 | 12.586538 | 17.990385 |
| 41 | YTASYDIYDLNKR (SEQ ID NO: 128) | 0.980769 | 0.067308 | 0.408654 | 0.423077 |
| 42 | ASYDIYDLNKRQL (SEQ ID NO: 129) | 0 | 0 | 0.043269 | 0.014423 |
| 43 | YDIYDLNKRQLIT (SEQ ID NO: 130) | 2.889423 | 0 | 0 | 0.048077 |

TABLE 11-continued

| Peptide No. | Amino Acids | Mean Signal Value rhuMAb409 | Mean Signal Value rhuMAb411 | Mean Signal Value rhuMAb412 | Mean Signal Value rhuMAb420 |
|---|---|---|---|---|---|
| 44 | IYDLNKRQLITEE (SEQ ID NO: 131) | 0 | 0 | 0 | 0 |
| 45 | DLNKRQLITEERI (SEQ ID NO: 132) | 0 | 0 | 0 | 0 |
| 46 | NKRQLITEERIPN (SEQ ID NO: 133) | 0 | 0 | 0 | 0 |
| 47 | RQLITEERIPNNT (SEQ ID NO: 134) | 0 | 0 | 0 | 0 |
| 48 | LITEERIPNNTQW (SEQ ID NO: 135) | 60.288462 | 12.057692 | 0.360577 | 0.971154 |
| 49 | TEERIPNNTQWVT (SEQ ID NO: 136) | 0 | 0.961538 | 8.235577 | 0.139423 |
| 50 | ERIPNNTQWVTWS (SEQ ID NO: 137) | 20.644231 | 34.629808 | 5.360577 | 1.331731 |
| 51 | IPNNTQWVTWSPV (SEQ ID NO: 138) | 0 | 0.855769 | 2.701923 | 0.201923 |
| 52 | NNTQWVTWSPVGH (SEQ ID NO: 139) | 0.129808 | 0.120192 | 0.504808 | 0.120192 |
| 53 | TQWVTWSPVGHKL (SEQ ID NO: 140) | 1.639423 | 0.004808 | 2.567308 | 4.25 |
| 54 | WVTWSPVGHKLAY (SEQ ID NO: 141) | 30.326923 | 13.004808 | 12.980769 | 15.149038 |
| 55 | TWSPVGHKLAYVW (SEQ ID NO: 47) | 229.370192 | 123.735577 | 98.365385 | 117.5625 |
| 56 | SPVGHKLAYVWNN (SEQ ID NO: 142) | 23.254808 | 11.745192 | 3.754808 | 4.826923 |
| 57 | VGHKLAYVWNNDI (SEQ ID NO: 143) | 23.048077 | 9.668269 | 2.456731 | 1.528846 |
| 58 | HKLAYVWNNDIYV (SEQ ID NO: 144) | 59.721154 | 33.754808 | 3.206731 | 4.235577 |
| 59 | LAYVWNNDIYVKI (SEQ ID NO: 145) | 6.163462 | 0.682692 | 3.197115 | 6.730769 |
| 60 | YVWNNDIYVKIEP (SEQ ID NO: 146) | 0.975962 | 0.076923 | 0 | 0.524038 |
| 61 | WNNDIYVKIEPNL (SEQ ID NO: 147) | 0 | 0.038462 | 0 | 0.451923 |
| 62 | NDIYVKIEPNLPS (SEQ ID NO: 148) | 0.004808 | 0.004808 | 0 | 0.259615 |
| 63 | IYVKIEPNLPSYR (SEQ ID NO: 54) | 17.649038 | 8.125 | 41.081731 | 88.706731 |
| 64 | VKIEPNLPSYRIT (SEQ ID NO: 149) | 2.5625 | 0.4375 | 2.201923 | 11.995192 |
| 65 | IEPNLPSYRITWT (SEQ ID NO: 150) | 38.826923 | 40.802885 | 13.134615 | 11.346154 |
| 66 | PNLPSYRITWTGK (SEQ ID NO: 151) | 4.447115 | 0.110577 | 1.716346 | 2.240385 |
| 67 | LPSYRITWTGKED (SEQ ID NO: 152) | 1.745192 | 0.009615 | 0 | 0.014423 |
| 68 | SYRITWTGKEDII (SEQ ID NO: 153) | 4.543269 | 0 | 0.216346 | 0.192308 |
| 69 | RITWTGKEDIIYN (SEQ ID NO: 154) | 3.25 | 2.451923 | 0.283654 | 0.043269 |
| 70 | TWTGKEDIIYNGI (SEQ ID NO: 155) | 5.533654 | 1.004808 | 0.009615 | 0.081731 |
| 71 | TGKEDIIYNGITD (SEQ ID NO: 156) | 4.057692 | 0 | 0 | 0 |
| 72 | KEDIIYNGITDWV (SEQ ID NO: 157) | 9.889423 | 10.134615 | 0.379808 | 0.125 |
| 73 | DIIYNGITDWVYE (SEQ ID NO: 158) | 6.932692 | 33.557692 | 6.341346 | 11.5 |
| 74 | IYNGITDWVYEEE (SEQ ID NO: 159) | 0 | 0 | 6.173077 | 0.293269 |
| 75 | NGITDWVYEEEVF (SEQ ID NO: 160) | 0.961538 | 9.384615 | 1.538462 | 1.870192 |
| 76 | ITDWVYEEEVFSA (SEQ ID NO: 161) | 0.144231 | 0.033654 | 0.274038 | 0.25 |
| 77 | DWVYEEEVFSAYS (SEQ ID NO: 162) | 5.923077 | 13.658654 | 0.509615 | 2.038462 |
| 78 | VYEEEVFSAYSAL (SEQ ID NO: 163) | 7.956731 | 7.855769 | 4.355769 | 4.596154 |
| 79 | EEEVFSAYSALWW (SEQ ID NO: 51) | 89.245192 | 96.394231 | 12.625 | 10.533654 |
| 80 | EVFSAYSALWWSP (SEQ ID NO: 164) | 23.548077 | 17.735577 | 2.278846 | 4.100962 |

TABLE 11-continued

| Peptide No. | Amino Acids | Mean Signal Value rhuMAb409 | Mean Signal Value rhuMAb411 | Mean Signal Value rhuMAb412 | Mean Signal Value rhuMAb420 |
|---|---|---|---|---|---|
| 81 | FSAYSALWWSPNG (SEQ ID NO: 165) | 62.177885 | 35.370192 | 2.278846 | 4.201923 |
| 82 | AYSALWWSPNGTF (SEQ ID NO: 166) | 117.192308 | 67.831731 | 4.663462 | 7.091346 |
| 83 | SALWWSPNGTFLA (SEQ ID NO: 167) | 7.413462 | 3.644231 | 0.048077 | 0.033654 |
| 84 | LWWSPNGTFLAYA (SEQ ID NO: 48) | 140.740385 | 17.225962 | 30.399038 | 59.620192 |
| 85 | WSPNGTFLAYAQF (SEQ ID NO: 168) | 0.033654 | 1.024038 | 2.721154 | 4.216346 |
| 86 | PNGTFLAYAQFND (SEQ ID NO: 169) | 0.038462 | 0.524038 | 0.067308 | 0.004808 |
| 87 | GTFLAYAQFNDTE (SEQ ID NO: 170) | 0.134615 | 0.028846 | 0 | 0 |
| 88 | FLAYAQFNDTEVP (SEQ ID NO: 171) | 0 | 0 | 0 | 0.014423 |
| 89 | AYAQFNDTEVPLI (SEQ ID NO: 172) | 0 | 0 | 0.4375 | 0.182692 |
| 90 | AQFNDTEVPLIEY (SEQ ID NO: 173) | 0 | 0 | 0 | 0.009615 |
| 91 | FNDTEVPLIEYSF (SEQ ID NO: 174) | 0.019231 | 2.302885 | 0.134615 | 40.956731 |
| 92 | DTEVPLIEYSFYS (SEQ ID NO: 175) | 14.447115 | 11.865385 | 9.043269 | 10.764423 |
| 93 | EVPLIEYSFYSDE (SEQ ID NO: 176) | 0.004808 | 0.269231 | 0.014423 | 11.201923 |
| 94 | PLIEYSFYSDESL (SEQ ID NO: 177) | 0.067308 | 0.043269 | 1.524038 | 0.038462 |
| 95 | IEYSFYSDESLQY (SEQ ID NO: 178) | 3.903846 | 6.139423 | 0.048077 | 0.336538 |
| 96 | YSFYSDESLQYPK (SEQ ID NO: 179) | 0 | 0.014423 | 0 | 0.004808 |
| 97 | FYSDESLQYPKTV (SEQ ID NO: 180) | 0.014423 | 0.014423 | 1.317308 | 0.052885 |
| 98 | SDESLQYPKTVRV (SEQ ID NO: 181) | 0.014423 | 0.004808 | 1.014423 | 0.197115 |
| 99 | ESLQYPKTVRVPY (SEQ ID NO: 182) | 0 | 0.086538 | 0.725962 | 0.0625 |
| 100 | LQYPKTVRVPYPK (SEQ ID NO: 183) | 0 | 0.009615 | 0 | 0.004808 |
| 101 | YPKTVRVPYPKAG (SEQ ID NO: 184) | 0.024038 | 0.004808 | 0.480769 | 0.846154 |
| 102 | KTVRVPYPKAGAV (SEQ ID NO: 185) | 0 | 0.019231 | 0 | 0.048077 |
| 103 | VRVPYPKAGAVNP (SEQ ID NO: 186) | 0 | 0 | 0 | 0 |
| 104 | VPYPKAGAVNPTV (SEQ ID NO: 187) | 0 | 0.004808 | 0 | 0.168269 |
| 105 | YPKAGAVNPTVKF (SEQ ID NO: 188) | 0 | 0 | 0.509615 | 0 |
| 106 | KAGAVNPTVKFFV (SEQ ID NO: 189) | 0 | 0.245192 | 0.014423 | 3.235577 |
| 107 | GAVNPTVKFFVVN (SEQ ID NO: 190) | 8.730769 | 10.5625 | 11.230769 | 25.057692 |
| 108 | VNPTVKFFVVNTD (SEQ ID NO: 191) | 0 | 1.331731 | 1.283654 | 11.1875 |
| 109 | PTVKFFVVNTDSL (SEQ ID NO: 192) | 0 | 0 | 0.408654 | 0.004808 |
| 110 | VKFFVVNTDSLSS (SEQ ID NO: 193) | 0 | 0.024038 | 0 | 0 |
| 111 | FFVVNTDSLSSVT (SEQ ID NO: 194) | 0 | 0 | 0 | 0 |
| 112 | VVNTDSLSSVTNA (SEQ ID NO: 195) | 0 | 0 | 0 | 0.043269 |
| 113 | NTDSLSSVTNATS (SEQ ID NO: 196) | 0 | 0.028846 | 0.168269 | 0.004808 |
| 114 | DSLSSVTNATSIQ (SEQ ID NO: 197) | 0 | 0.004808 | 0.033654 | 0 |
| 115 | LSSVTNATSIQIT (SEQ ID NO: 198) | 0 | 0.067308 | 0.0625 | 0.004808 |
| 116 | SVTNATSIQITAP (SEQ ID NO: 199) | 0 | 0.038462 | 0 | 0 |
| 117 | TNATSIQITAPAS (SEQ ID NO: 200) | 0 | 0.009615 | 0 | 0.120192 |

TABLE 11-continued

| Peptide No. | Amino Acids | Mean Signal Value rhuMAb409 | Mean Signal Value rhuMAb411 | Mean Signal Value rhuMAb412 | Mean Signal Value rhuMAb420 |
|---|---|---|---|---|---|
| 118 | ATSIQITAPASML (SEQ ID NO: 201) | 0 | 0 | 0 | 0 |
| 119 | SIQITAPASMLIG (SEQ ID NO: 202) | 0 | 0.024038 | 0 | 0 |
| 120 | QITAPASMLIGDH (SEQ ID NO: 203) | 0 | 0.033654 | 0.466346 | 0 |
| 121 | TAPASMLIGDHYL (SEQ ID NO: 204) | 0.019231 | 2.081731 | 0.168269 | 0.096154 |
| 122 | PASMLIGDHYLCD (SEQ ID NO: 205) | 0 | 0.307692 | 0 | 0.014423 |
| 123 | SMLIGDHYLCDVT (SEQ ID NO: 206) | 0.009615 | 0.4375 | 5.254808 | 7.514423 |
| 124 | LIGDHYLCDVTWA (SEQ ID NO: 207) | 23.269231 | 12.663462 | 17.538462 | 0.913462 |
| 125 | GDHYLCDVTWATQ (SEQ ID NO: 208) | 3.769231 | 1.798077 | 0.620192 | 0.057692 |
| 126 | HYLCDVTWATQER (SEQ ID NO: 209) | 3.072115 | 0.033654 | 0.009615 | 0.245192 |
| 127 | LCDVTWATQERIS (SEQ ID NO: 210) | 0.009615 | 0.009615 | 1.283654 | 0.024038 |
| 128 | DVTWATQERISLQ (SEQ ID NO: 211) | 0.278846 | 0.105769 | 0.043269 | 0.125 |
| 129 | TWATQERISLQWL (SEQ ID NO: 212) | 72.225962 | 23.307692 | 9.456731 | 9.807692 |
| 130 | ATQERISLQWLRR (SEQ ID NO: 213) | 10.014423 | 4.302885 | 1.855769 | 4.427885 |
| 131 | QERISLQWLRRIQ (SEQ ID NO: 214) | 38.365385 | 5.254808 | 2.9375 | 2.778846 |
| 132 | RISLQWLRRIQNY (SEQ ID NO: 49) | 209.283654 | 113.028846 | 31.177885 | 69.014423 |
| 133 | SLQWLRRIQNYSV (SEQ ID NO: 124) | 45.5 | 6.509615 | 9.288462 | 12.918269 |
| 134 | control | 11.682692 | 0.538462 | 13.995192 | 22.1875 |
| 135 | Control | 8.269231 | 0.572115 | 14.625 | 18.903846 |
| 136 | Control | 10.235577 | 0.581731 | 12.245192 | 18.4375 |
| 137 | Control | 9.600962 | 0.923077 | 11.855769 | 15.903846 |
| 138 | Control | 12.75 | 1.096154 | 14.259615 | 20.375 |
| 139 | Control | 10.3125 | 0.264423 | 14.586538 | 16.600962 |
| 140 | Control | 15.485577 | 1.461538 | 14.004808 | 23.466346 |
| 141 | Control | 13.721154 | 1.596154 | 15.317308 | 26.552885 |
| 142 | Control | 12.259615 | 1.086538 | 15.908654 | 24.144231 |
| 143 | Control | 10.322115 | 0.899038 | 13.5 | 22.610577 |
| 144 | Control | 10.572115 | 0.600962 | 16.177885 | 25.081731 |

FIG. 24 shows that rhuMAB 409 (comprising CM03 VH and VL) had highest reactivity against peptides 6 (YSLRWIS-DHEYLY (SEQ ID NO:45)), 35 (LEYNYVKQWRHSY (SEQ ID NO:46)), 55 (TWSPVGHKLAYVW (SEQ ID NO:47)), 84 (LWWSPNGTFLAYA (SEQ ID NO:48)) and 132 (RISLQWLRRIQNY (SEQ ID NO:49)). Each of these peaks had associated smaller peaks with overlapping 13 mer peptides.

Figure 25:
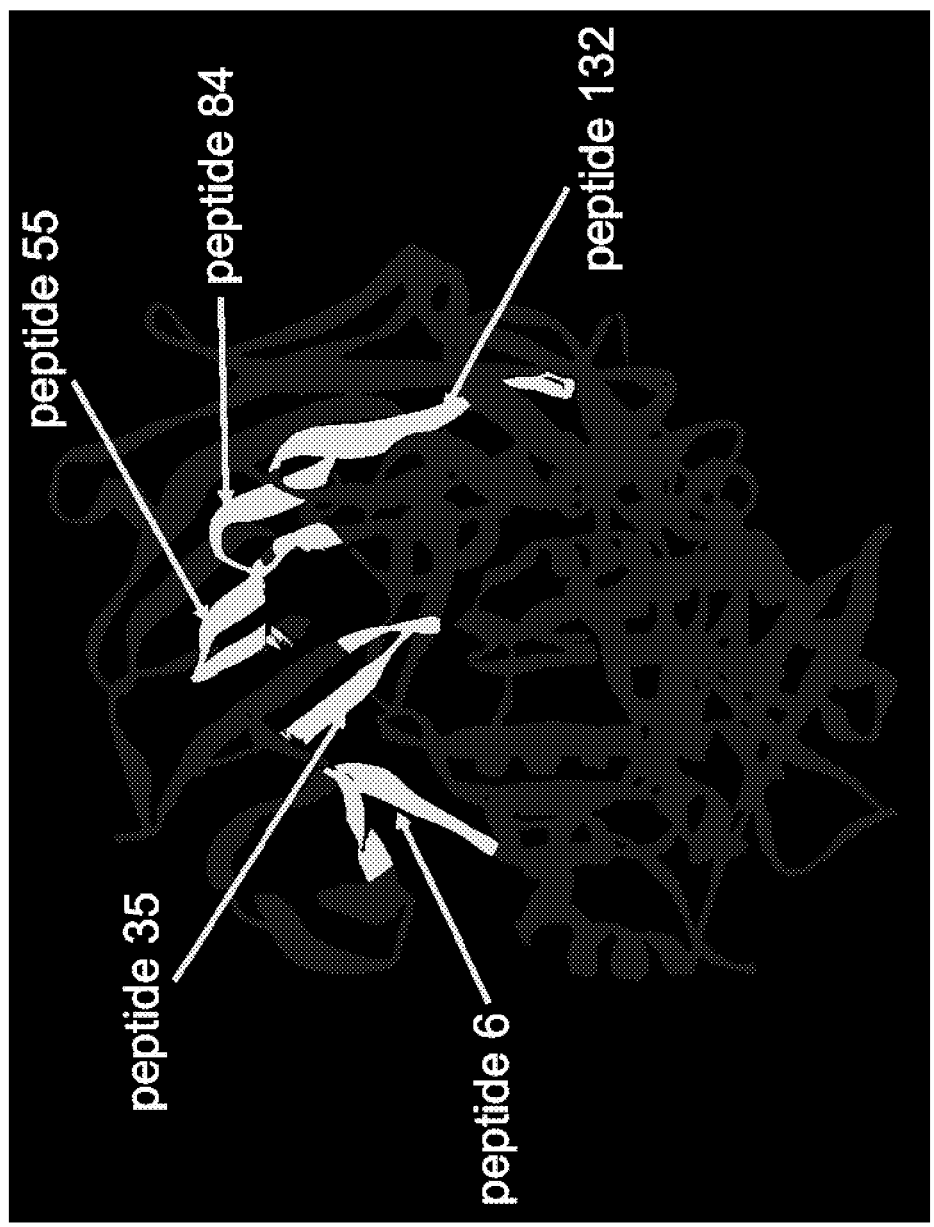
FIG. 25 shows a ribbon diagram of the crystal structure of human CD26-1J2E. The peptides most reactive in the epitope mapping experiments with rhuMAb 409 are lighter in color.

Reactivity with discontinuous sequences suggested a discontinuous, or conformational, epitope. FIG. 25 shows a ribbon diagram of the crystal structure of human CD26_1 J2E, with the reactive peptides identified above in lighter color. The coordinates of human CD26 are publicly available Reference: PubMed; MMDB: 25581; PDB: IJ2E; Description: Crystal Structure of Human Dipeptidyl Peptidase IV; Deposition: H. Hiramatsu et al.). The three-dimensional structure as depicted showed that these linear, discontinuous sequences were arranged near to one another when the antigen is in its three-dimensional state. This further confirms that this is likely a discontinuous, or conformational, epitope. Again, note that because only amino acids 48-324 were represented in these experiments, there may be other areas of reactivity outside of these sequences.

RhuMAB 411 had highest reactivity against peptides 6 (YSLRWISDHEYLY (SEQ ID NO:45)), 37 (YVKQWRH-SYTASY (SEQ ID NO:50)), 55 (TWSPVGHKLAYVW (SEQ ID NO:47)), 79 (EEEVFSAYSALWW (SEQ ID NO:51)) and 132 (RISLQWLRRIQNY (SEQ ID NO:49)). Each of these peaks also had associated smaller peaks with overlapping 13mer peptides.

Figure 26:
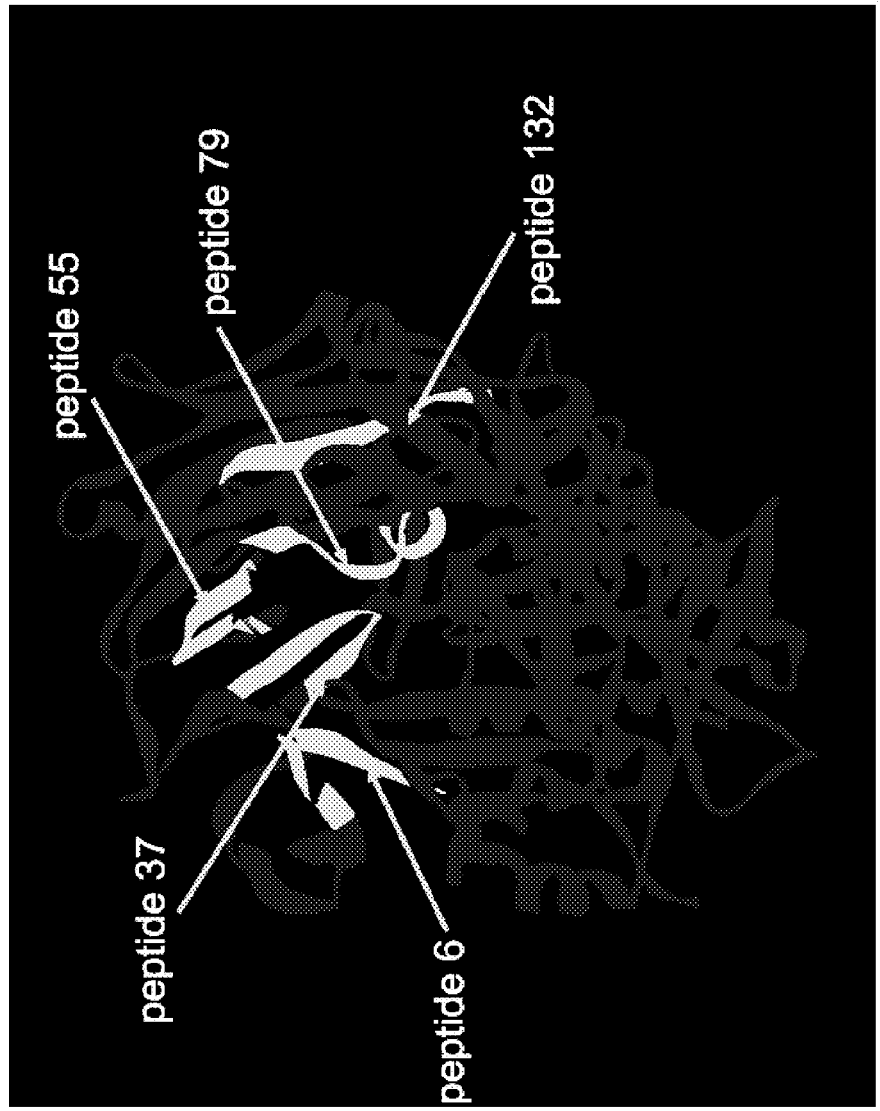
FIG. 26 shows a ribbon diagram of the crystal structure of human CD26-1J2E. The peptides most reactive in the epitope mapping experiments with rhuMAb 411 are lighter in color.

Reactivity with discontinuous sequences again suggested a discontinuous, or conformational, epitope. FIG. 26 shows a ribbon diagram of the crystal structure of CD26_1J2E, with the reactive peptides identified above highlighted. The three-dimensional structure showed that these linear, discontinuous sequences are arranged near to one another when the antigen is in its three-dimensional state, confirming the discontinuous nature of this epitope.

Figure 27:
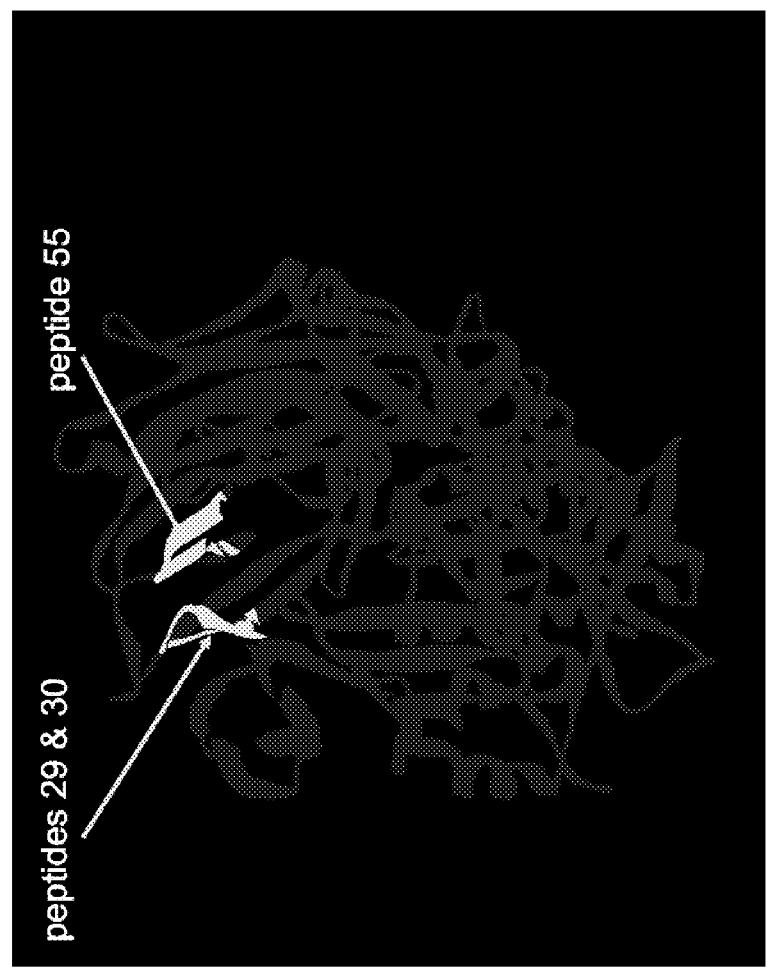
FIG. 27 shows a ribbon diagram of the crystal structure of human CD26-1J2E. The peptides most reactive in the epitope mapping experiments with rhuMAb 412 are lighter in color.

RhuMAB 412 had highest reactivity against peptides 29 (DYSISPDGQFILL (SEQ ID NO:52)), 30 (SISPDGQFILLEY (SEQ ID NO:53)) and 55 (TWSPVGHKLAYVW (SEQ ID NO:47)). Each of these peaks had associated smaller peaks with overlapping 13mer peptides. FIG. 27 shows a ribbon diagram of the crystal structure of CD26_1J2E, with the reactive peptides identified above highlighted. The three-dimensional structure showed that these linear, discontinuous sequences were arranged near to one another when the antigen is in its three-dimensional state, suggesting a discontinuous, or conformational, epitope.

Figure 28:
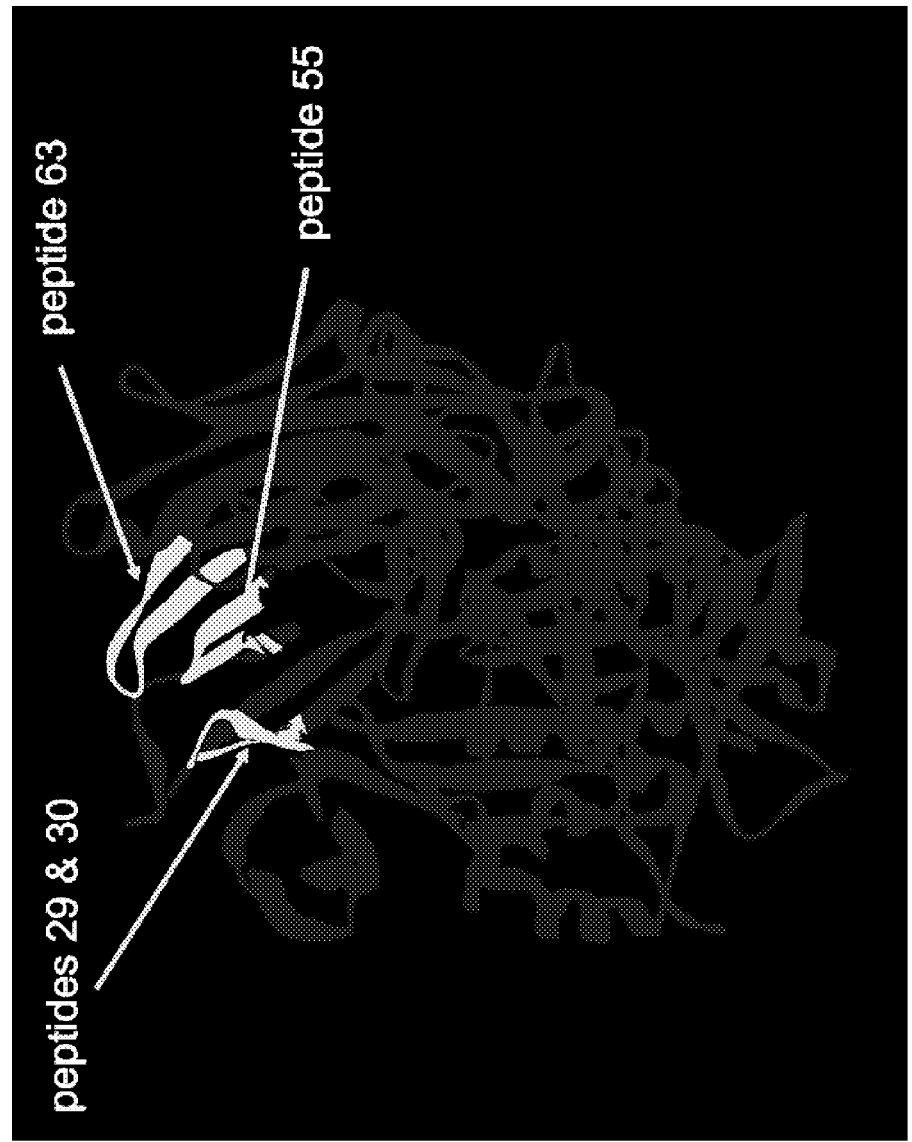
FIG. 28 shows a ribbon diagram of the crystal structure of human CD26-1J2E. The peptides most reactive in the epitope mapping experiments with rhuMAb 420 are lighter in color.

RhuMAB 420 had highest reactivity against peptides 29 (DYSISPDGQFILL (SEQ ID NO:52)), 30 (SISPDGQFILLEY (SEQ ID NO:53)), 55 (TWSPVGHKLAYVW (SEQ ID NO:47)) and 63 (IYVKIEPNLPSYR (SEQ ID NO:54)). Each of these peaks had associated smaller peaks with overlapping 13 mer peptides. FIG. 28 shows a ribbon diagram of the crystal structure of CD26_1J2E, with the reactive peptides identified above highlighted. The three-dimensional structure showed that these linear, discontinuous sequences were arranged near to one another when the antigen is in its three-dimensional state, again suggesting a discontinuous, or conformational, epitope.

Example 4

Exemplary Recombinant Heavy Chain and Light Chain Antibody Sequences

Humanized IgG1 antibodies comprising the VH and VL of the X392 Fab or other VH and/or VL sequences described herein can be produced in cells such as Chinese hamster ovary (CHO) cells using methods known to those of ordinary skill in the art. Some exemplary sequences for a humanized IgG1 antibody comprising the VH and VL of the X392 Fab are provided below.

A. DNA Sequences Coding for an Exemplary Heavy Chain and Light Chain

Exemplary nucleotide sequences encoding a heavy chain or light chain of a humanized antibody comprising the VH and VL of the X392 Fab are provided below. The encoded proteins include signal sequences fused to the VH and VL sequences. (Sequences encoding signal sequences are indicated as underlined, and sequences encoding variable regions are indicated in bold italics.)

```
                                                        (SEQ ID NO: 215)
Heavy chain:
ATGGAATGGAGCTGGGTCTTTCTCTTCTTCCTGTCAGTAACTACAGGTGTCCACTCCG

AAGTGCAGCTGGTGGAAAGCGGTGCTGGAGTGAAGCAGCCGGGTGGAACCCTGCGTC

TGACCTGCACGGCTAGCGGTTTCAGCCTGACCACATACGGTGTGCACTGGGTGCGTCA

GGCGCCCGGGAAAGGTCTGGAATGGGTGGGTGTAATCTGGGGCGATGGTCGTACCGA

TTACGATGCTGCTTTCATGAGCCGGGTGACCATCAGCAAAGATACCAGCAAAAGCACC

GTGTACTTGCAGATGAACAGCCTGCGTGCGGAAGATACTGCAGTGTACTACTGCATGC

GTAATCGTCATGATTGGTTCGATTACTGGGGCCAAGGAACCACCGTGACCGTCTCGAG

CGCAAGCACCAAAGGCCCATCGGTATTCCCCCTGGCACCCTCCTCCAAGAGCACCTC

TGGGGGCACAGCGGCCCTGGGCTGCCTGGTCAAGGACTACTTCCCCGAACCGGTGA

CGGTGTCGTGGAACTCAGGCGCCCTGACCAGCGGCGTGCACACCTTCCCGGCTGTCC

TACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTG

GACAAGAAAGTTGAGCCCAAATCTTGTGACAAAACTCACACATGCCCACCGTGCCC

AGCACCTGAACTCCTGGGGGGACCGTCAGTCTTCCTCTTCCCCCCAAAACCCAAGGA

CACCCTCATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGCATAATG

CCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCAAGGTCTC

CAACAAAGCCCTCCCAGCCCCCATCGAGAAAACCATCTCCAAAGCCAAAGGGCAGC

CCCGAGAACCACAGGTGTACACCCTGCCCCCATCCCGGGATGAGCTGACCAAGAAC

CAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGA

CTCCGACGGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACCACTACAC

GCAGAAGAGCCTCTCCCTGTCTCCGGGTAAATGA
```

Light chain (SEQ ID NO:216):

ATGAGTGTGCCCACTCAGGTCCTGGGGTTGCTGCTGCTGTGGCTTACAGATGCCAGA

TGT *GACATCCTGCTGACCCAGTCTCCATCTTCTCTGTCTGCTACTCCTGGCGAACGTG*

*CTACCATCACCTGTCGTGCCTCTCAGGGCATCCGTAACAACCTGAACTGGTATCAGCA*

*GAAACCAGGTCAGGCCCCACGTCTGCTGATCTACTACTCTTCTAATTTGCAGTCCGGT*

*GTGCCATCCCGTTTCTCCGGATCTGGTTCTGGCACCGACTTCACCCTGACCATCTCTA*

*GACTGCAACCTGAAGACGTTGCCGCCTACTACTGCCAGCAGTCTATCAAGCTGCCATT*

*TACCTTCGGTTCTGGTACCAAAGTGGAGATCAAA*CGTACGGTGGCTGCAC-
CATCTGTC

TTCATCTTCCCGCCATCTGATGAGCAGTTGAAATCTGGAACTGCCTCTGTTGTGTGCC

TGCTGAATAACTTCTATCCCAGAGAGGCCAAAGTACAGTGGAAGGTGGATAACGCC

CTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAG

TCTACGCCTGCGAAGTCACCCATCAGGGCCTGAGCTCGCCCGTCACAAAGAGCTTCA

ACAGGGGAGAGTGTTAG

B. Protein Sequences for an Exemplary Heavy Chain and Light Chain

Exemplary protein sequences of a heavy chain or light chain of a humanized antibody comprising the VH and VL of the X392 Fab are provided below. The heavy chain and light chain sequences are shown fused to signal sequences. (Signal sequences are indicated as underlined, and variable regions are indicated in bold italics.)

Heavy chain (SEQ ID NO:217):

MEWSWVFLFFLSVTTGVHS *EVQLVESGAGVKQPGGTLRLTCTASGFSLTTYGVHWVRQ*

*APGKGLEWVGVIWGDGRTDYDAAFMSRVTISKDTSKSTVYLQMNSLRAEDTAVYYCMR*

*NRHDWFDYWGQGTTVTVSS* ASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

Light chain (SEQ ID NO:218):

MSVPTQVLGLLLLWLTDARC *DILLTQSPSSLSATPGERATITCRASQGIRNNLNWYQQKP*

*GQAPRLLIYYSSNLQSGVPSRFSGSGSGTDFTLTISRLQPEDVAAYYCQQSIKLPFTFGSG*

*TKVEIK* RTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

Example 5

Exemplary MTT Assay Protocol

An exemplary MTT assay protocol is as follows:

Jurkat cells are transfected with plasmid encoding the full length of human CD26 and selected under 200 μg/ml G418. Cells are passaged at 1:5 for every three days to maintain viability at >95%. Approximately 48 hours prior to assay, the spinning medium is completely replaced with fresh growth medium (37° C.) by spinning 1100 rpm for 5 min. (The assay medium is the same as the growth medium: 87 mL RPMI-1640 liquid medium (Hyclone: SH30027-02); 10 mL FCS (56° C. 30 min treated); 0.5 mL Penicillin/Streptomycin (100 μg/mL); 2 mL G418 (Calbiochem, 100 mg/ml in PBS); and 2 mL L-glutamine (200 mM, Hyclone, #SH30034.01).) By the approach, cell viability can be 97-99% when the assay takes place. Cell viability must be at least 95%.

The cells are spun down at 1100 rpm, 5 min (Beckman Benchtop Centrifuge) and the medium thoroughly removed. The cells are resuspended into 5-10 ml complete medium for T75 flask culture. 0.01 mL of cell suspension is mixed with 0.01 mL of trypan blue (0.125% (1×), VWR, #VWb721-0).

0.01 mL is placed into a hemacytometer and the total cells and dead cells are counted. The cell number per ml is calculated as follows: Total cells/4× dilution factor×10,000=cells/mL. Viable cells %=(total cells-dead cells)/total cells×100. The cells are then diluted with complete growth medium at ~$10^6$ viable cells per mL. Seed cells, 0.05 mL/well, are transferred into the center 60 wells of a 96-well plate, and the edge wells are filled with growth medium, 0.1 mL/well.

Antibody samples are diluted with growth medium at 0, 0.1, 0.2, 1.0, 5, and 10 μg/mL in a total of 0.2 mL. For each plate, there are negative control, antibody formulation buffer (usually PBS or PBS-T, or other buffers) and positive antibody (murine) control in triplicates. If the antibody sample is diluted in growth medium for >10-fold, antibody formulation buffer is not needed. The surrounding wells are filled with growth medium to maintain homogeneous microenvironment in the plate. The plate is incubated in a 5% $CO_2$ incubator, at 37° C.+/−0.5° C., 90% humidity for 48 hr.

25 μL of MTT solution (5 mg/mL MTT) is added to each well and the incubation is continued for 2 hr. (To prepare the MTT solution, 50 mg of MTT (tetrazolium salt MTT, 3-(4,5-dimethylthiazolyl-2)-2,5-diphenyltetrazolium bromide, Calbiochem, #475989)) powder is dissolved into 10 mL of PBS at room temperature and filtered through a 0.2 μM membrane after completely solubilized.)

0.1 mL of extraction buffer per well is added and the plate is incubated at 37° C. for 12 hr or overnight. (To prepare the extraction buffer, 20 g of SDS (W/V) powder is weighed and dissolved in 50 mL MQ water and 50 mL of N,N-dimethyl formamide at 37° C. After temperature is equilibrated to ambient, pH is adjusted to 4.7 with 1M HCl. Finally CHX (cycloheximide, Calbiochem, 239764-100MG)) is added to a final concentration of 20 μg/mL.) The extracts in the plate are mixed by pipeting up and down for 5 times and completely discharging solution in the tips. The plate is read at 570 nm. The inhibition rate (tumor cell proliferation inhibition) is generally calculated as follows: Inhibition rate (%)=1−(Abs of Mab treated wells/Abs of medium control wells).

See also Ho et al., (2001). Clinical Cancer Res. Vol 7, 2031-2040.

Example 6

Efficacy of rhuMAb 411 in Karpas 299 T-Cell Lymphoma Xenograft-Bearing NCR Nude Mice The objective of this study was to examine the ability of rhuMAb 411 to inhibit the growth of a Karpas 299 T-cell lymphoma xenograft. The effect of rhuMAb 411 alone was compared to Taxol® alone and Taxol® plus rhuMAb 411 when given seven days following tumor cell implantation.

Materials: Cell line: Karpas 299 is a human CD26-positive T-cell lymphoma line and was obtained from DSMZ German Collection of Microorganisms and Cell Cultures, Braunschweig, Germany, and banked at and shipped from Cell & Molecular Technologies, Inc., Phillipsburg, N.J.

Animals: Female NCR athymic mice, having a body weight of 18-22 g and being approximately 5-6 weeks of age, were obtained from Taconic (Germantown, N.Y.).

RhuMAb 411: BDS (Bulk Drug Substance), 1.0 ml/vial, 10.3 mg/ml. lot#D0679 in PBS, pH 7.0, was manufactured at Lonza Biologics, Slough, UK.

Medium and buffers: RPMI-1640 medium (Cat# 15-040-CV) and Phosphate buffered saline (PBS, Cat# 21-040-CV) were purchased from Mediatech, Inc., Herndon, Va.

Paclitaxel (Taxol®, Cat# T7402) and Dimethylsulfoxide (DMSO, Cat# D2438) were obtained from Sigma, St. Louis, Mo.

Methods: One hundred animals were implanted subcutaneously on right flank with 4-6×$10^6$ Karpas 299 cells in 100 μl of RPMI-1640 medium. When tumor size reaching 100 $mm^3$, mice were grouped and administered 100 μl i.v. of solutions as follows:

Group 1, received vehicle (PBS); Group 2 received 10 mg/kg paclitaxel (as 10 mg/ml solution in PBS with 20% DMSO); Groups 3, 4 and 5 received 3, 10 and 30 mg/Kg rhuMAb 411 antibody respectively. Group 6 received a combination of 10 mg/kg rhuMAb 411 and 10 mg/kg paclitaxel. 10 mice of each group were treated three times a week for 5 weeks by bolus intravenous injection via the tail vein.

Tumor volumes were measured twice a week and body weights were measured once per week. Signs of toxicity or distress were noted and animals euthanized if necessary. Any animal exhibiting 20% or greater body weight loss was euthanized for humane purposes.

Figure 29:
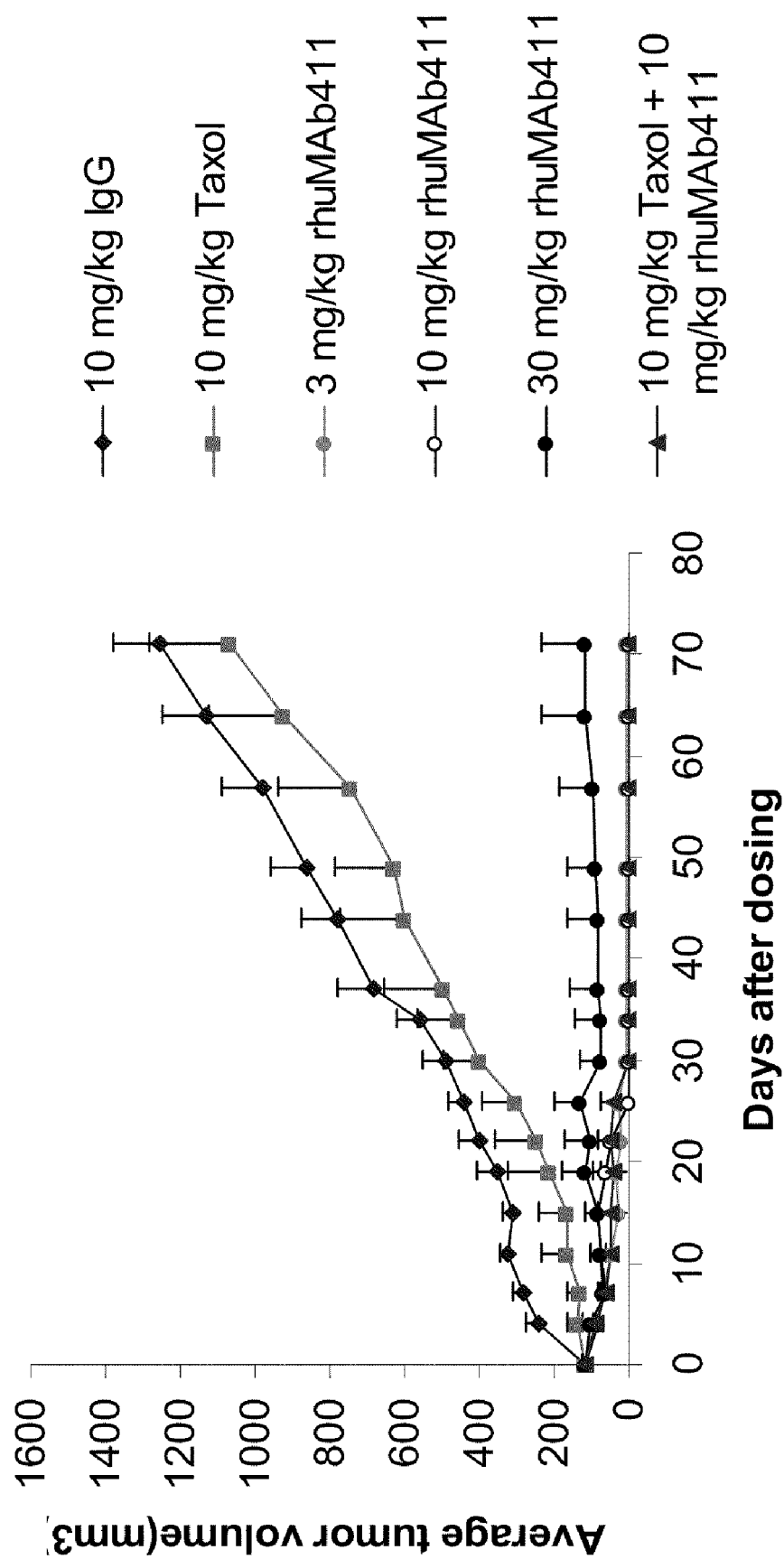
FIG. 29 shows that rhuMAb 411 treatment induces Karpas299 (T-cell lymphoma) tumor regression in mouse xenograft model. Data represent the mean±SEM values of 10 animals.

Results: As shown in the FIG. 29, dosing with rhuMAb 411 resulted in shrinkage and in many cases complete disappearance of the tumors at all dosages used, while steady tumor growth was observed in animals dosed with a control antibody (human IgG) or Taxol®, a therapeutic routinely used in current standard of care in oncology. Body weight was maintained during rhuMAb 411 treatment and no apparent toxicity was observed. (Data not shown.) This killing of tumor is CD26 dependent and is assumed to be mediated by antibody-dependent cellular cytotoxicity (ADCC), apoptosis via induction of intracellular signaling pathways (cytolytic activity), complement-dependent cytotoxicity (CDC), or a combination of these mechanisms.

By contrast, rhuMAb 411 was found to have no efficacy in a xenograft mouse model implanted with A375, a human melanoma cell line, which does not express significant levels of CD26 protein. (Data not shown.)

Example 7

Efficacy of rhuMAb 411 in 786-O (Kidney Carcinoma) Xenograft-Bearing SCID Mice

The objective of this study was to examine the ability of rhuMAb 411 to inhibit the growth of a 786-O kidney carcinoma xenograft. The effect of rhuMAb 411 alone was compared to PBS and typical anti-cancer compounds (cisplatin and Taxol®) plus rhuMAb 411.

Materials: Cell line: 786-O is a human CD26-positive kidney carcinoma line and was obtained from ATCC.

Animals: Female CB17 SCID mice, having a body weight of 18-22 g and being approximately 5-6 weeks of age, were obtained from Taconic (Germantown, N.Y.).

Cisplatin was purchased from Sigma (Cat# P9394).

Matrigel was obtained from BD Biosciences (Cat# 356237).

HBSS was obtained from ATCC (Cat# 30-2213).

All other materials in this study were the same as described above in Example 6.

Methods: Seventy animals were implanted subcutaneously on the right flank with 5×$10^6$ 786-O cells in 100 μl of HBSS and matrigel (HBSS: matrigel=1:1). When tumor size reached 100 $mm^3$, mice were grouped and administered 100 μl i.p. of solutions as follows:

Group 1, received vehicle (PBS); Group 2, 3 and 4 received 3, 10 and 30 mg/Kg rhuMAb 411 antibody respectively; Group 5 received a combination of 30 mg/kg rhuMAb 411, 10 mg/kg paclitaxel and 2 mg/Kg cisplatin. 10 mice of each group were treated twice a week for 3 weeks by intraperitoneal injection (i.p.) except that cisplatin was given only once.

Tumor volumes were measured twice a week and body weights were measured once per week. Signs of toxicity or distress were noted and animals euthanized if necessary. Any animal exhibiting 20% or greater body weight loss was euthanized for humane purposes.

Figure 30:
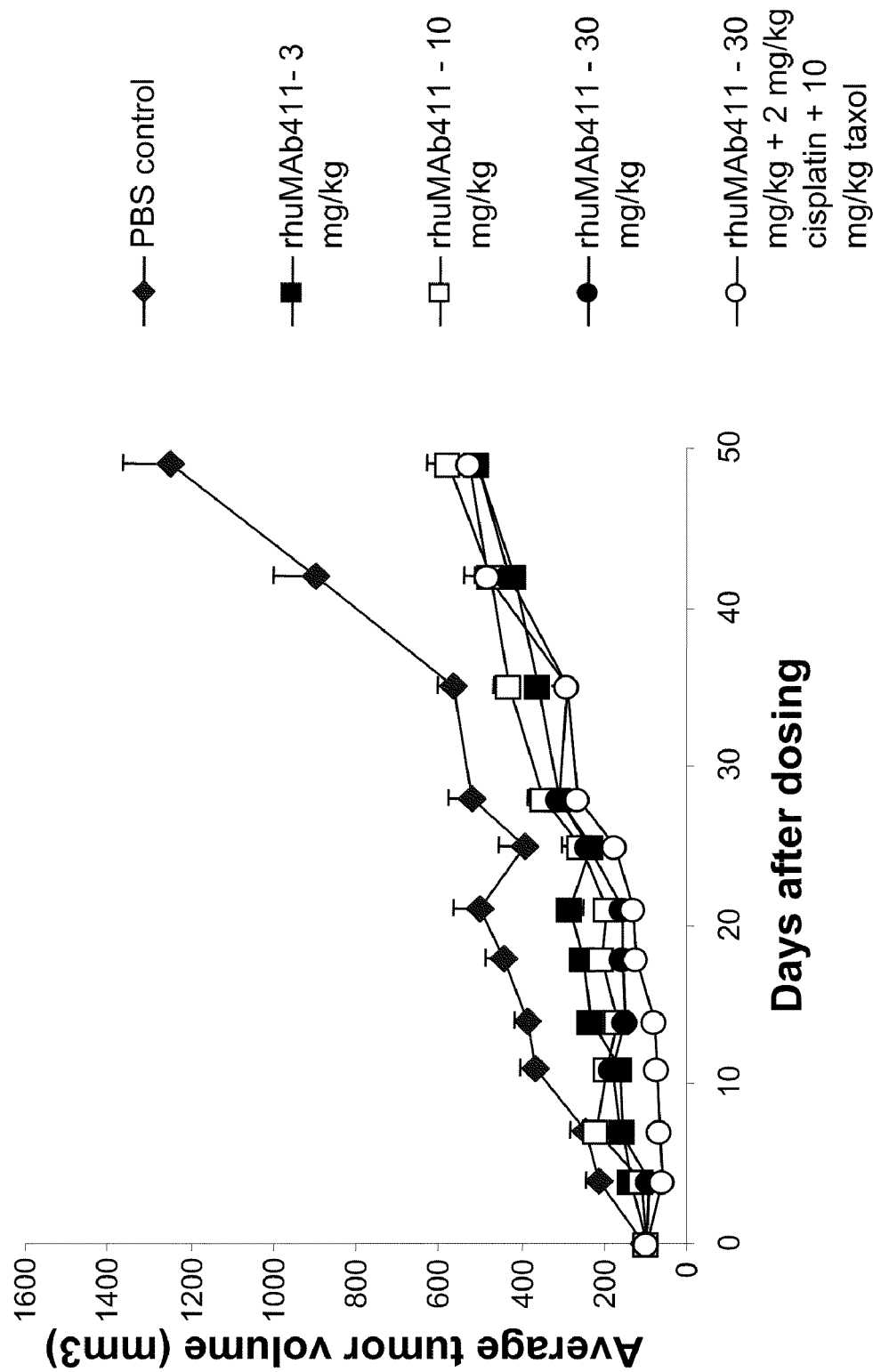
FIG. 30 shows that rhuMAb 411 treatment significantly delays 786-O (kidney carcinoma) tumor growth in mouse xenograft model. Data represent the mean±SEM values of 10 animals.

Results: As shown in the FIG. 30, growth of 786-O tumors was significantly inhibited in rhuMAb 411-treated animals as compared to vehicle treated animals. Although 786-O tumors were not completely cleared in our study, there was a significant growth delay with the treatment of rhuMAb 411. In addition, high dose rhuMAb 411 (30 mg/Kg) alone played the same effect as with the combination of cisplatin and Taxol. Body weight was maintained during rhuMAb 411 treatment and no apparent toxicity was observed. (Data not shown.)

Example 8

Efficacy and Dose-Ranging of rhuMAb 411 in Caki-2 (Kidney Carcinoma) Xenograft-Bearing NCR Nude Mice The objective of this study was to examine the ability of rhuMAb 411 to inhibit the growth of a Caki-2 kidney carcinoma xenograft in a dose-dependent manner. The effect of rhuMAb 411 was compared to vehicle control as well as combination of chemotherapy compounds.

Materials: Cell line: Caki-2 is a human CD26-positive kidney carcinoma line and was obtained from ATCC.

Animals: Female NCR Nude mice, having a body weight of 18-22 g and being approximately 5-6 weeks of age, were obtained from Taconic (Germantown, N.Y.).

Docetaxel (cat# 01885) and doxorubicin (Cat# D515) were obtained from Sigma.

All other materials in this study were the same as described above in Example 6-7.

Methods: 100 animals were implanted subcutaneously on right flank with $1 \times 10^6$ Caki2 cells in 100 µl of HBSS and matrigel (HBSS:matrigel=1:1). When tumor size reached 100 mm$^3$, mice were grouped and administered 100 µl i.p. of solutions as follows:

Group 1, received vehicle (PBS); Group 2, 3, 4 and 5 received 1, 3, 10 and 30 mg/kg rhuMAb 411 antibody respectively; Group 6 received a combination of 30 mg/kg rhuMAb 411, 10 mg/kg paclitaxel, 2 mg/kg cisplatin, 2 mg/kg docetaxel and 8 mg/kg Doxurubicin. Group 7 with no rhuMAb 411, all the others same as Group 6. 10 mice of each group were treated twice a week for 3 weeks by i.p. except that chemotherapy compounds (cisplatin, taxol, docetaxel and doxurobicin) were given only once by i.p. during the study.

Tumor volumes were measured twice a week and body weights were measured once per week. Signs of toxicity or distress were noted and animals euthanized if necessary. Any animal exhibiting 20% or greater body weight loss was euthanized for humane purposes.

Figure 31:
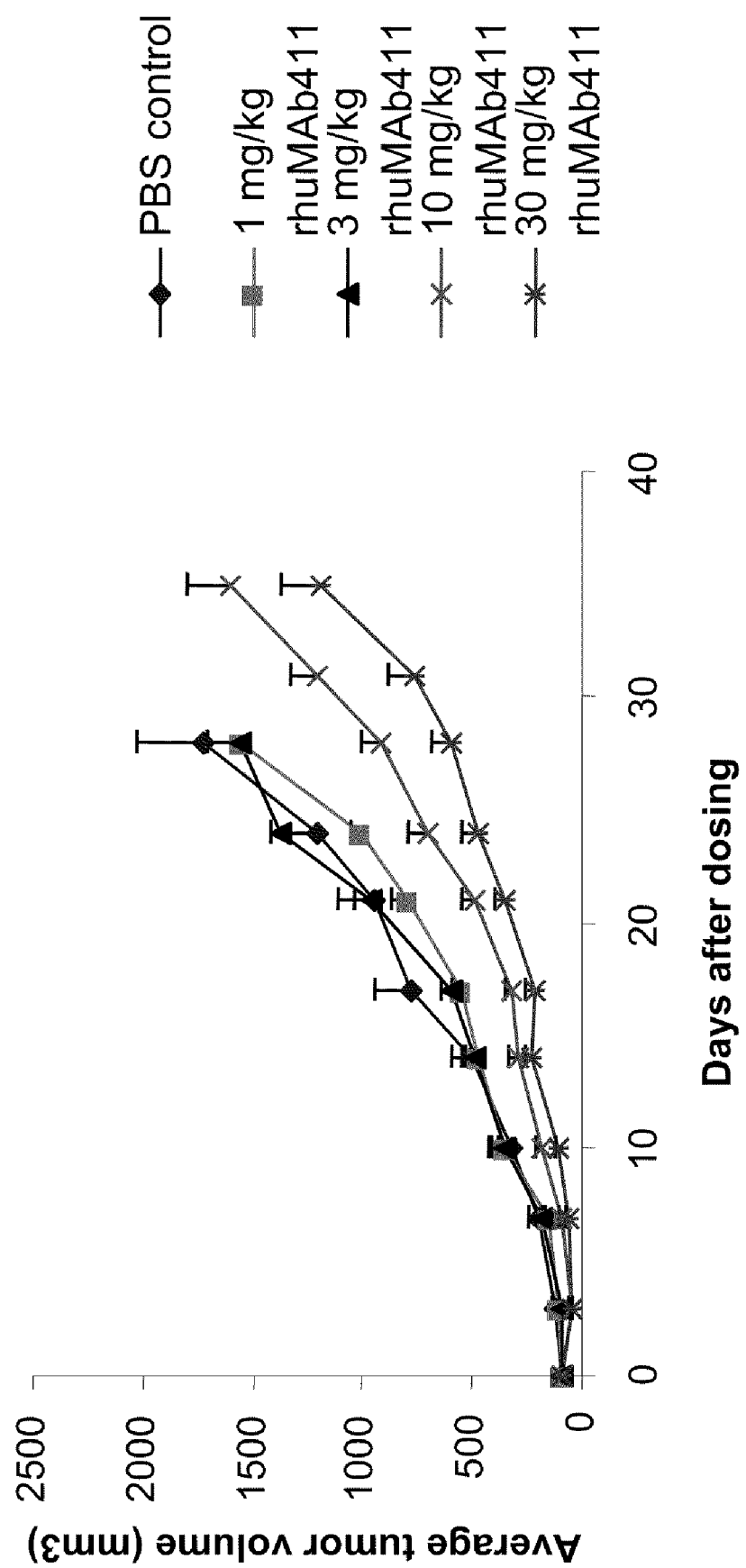
FIG. 31 shows that rhuMAb 411 treatment reduces Caki-2 (kidney carcinoma) xenograft tumor growth in a dose-dependent manner. Data represent the mean±SEM values of 10 animals.
Figure 32:
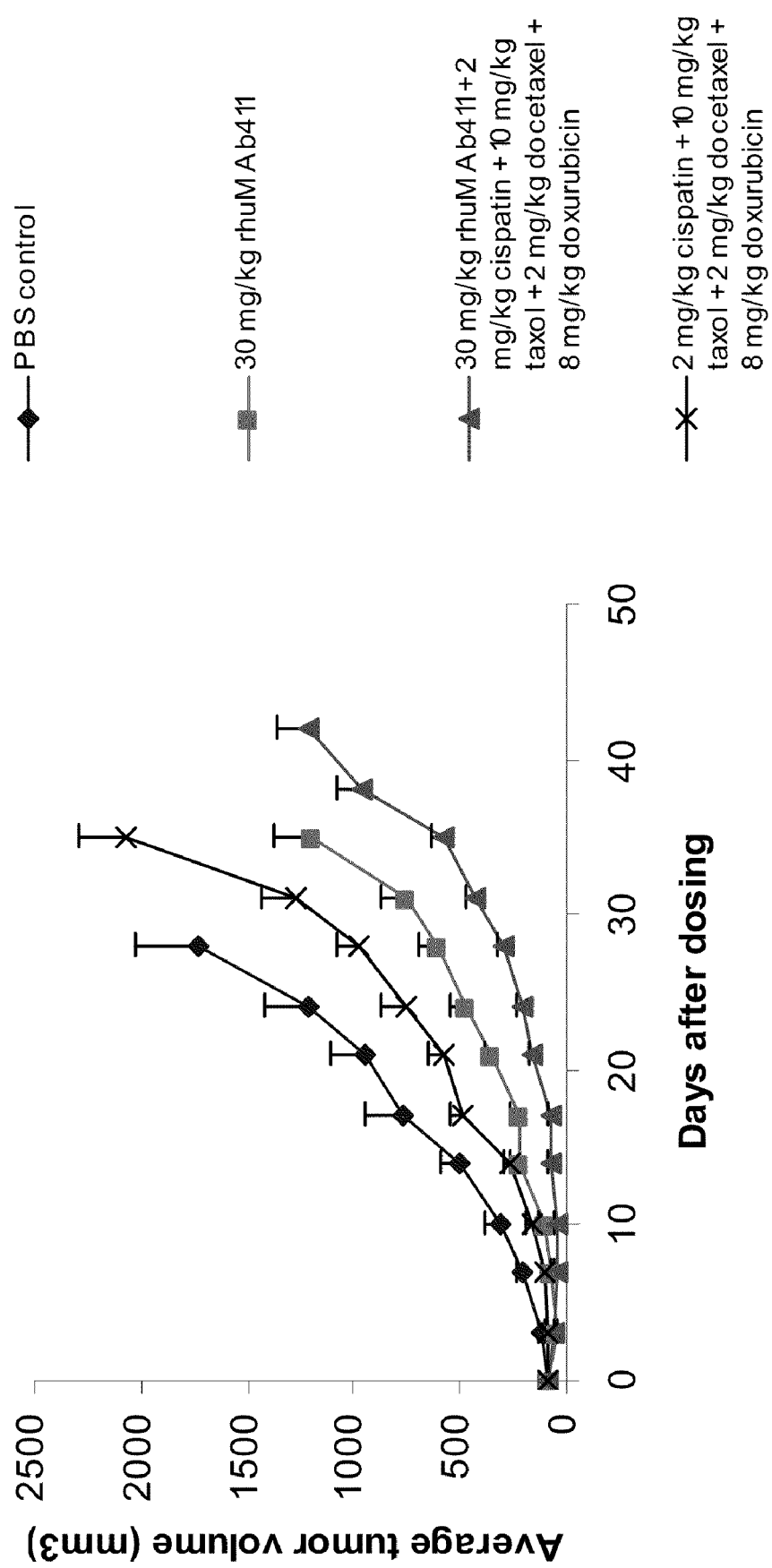
FIG. 32 shows that rhuMAb 411 treatment reduces Caki-2 (kidney carcinoma) xenograft tumor growth with added efficacy by using combination therapy. Data represent the mean±SEM values of 10 animals.

Results: As shown in the FIG. 31, growth of Caki-2 tumors was significantly inhibited in rhuMAb 411-treated animals as compared to vehicle treated animals, moreover, the inhibition of rhuMAb 411 showed a dose-dependent manner. As shown in FIG. 32, rhuMAb 411 plus chemotherapy compounds presented much stronger inhibitory effect when compared to compounds alone, which suggested the added efficacy using combination therapy. Body weight was maintained during rhuMAb 411 treatment and no apparent toxicity was observed. (Data not shown.)

Example 9

Efficacy of rhuMAb 411 in PC-3 (Prostate Carcinoma) Xenograft-Bearing SCID Mice

The objective of this study was to examine the ability of rhuMAb 411 to inhibit the growth of a PC-3 prostate carcinoma xenograft. The effect of rhuMAb 411 was compared to vehicle control as well as combination of chemotherapy compounds.

Materials: Cell line: PC-3 a human CD26-positive prostate carcinoma line and was obtained from ATCC.

Animals: Male CB17 SCID mice, having a body weight of 18-22 g and being approximately 5-6 weeks of age, were obtained from Taconic (Germantown, N.Y.).

All other materials in this study were the same as described above in Examples 6-8.

Methods: 80 animals were implanted subcutaneously on right flank with $3 \times 10^6$ PC3 cells in 100 µl of HBSS and matrigel (HBSS:matrigel=1:1). When tumor size reached 100 mm$^3$, mice were grouped and administered 100 µl i.p. of solutions as follows:

Group 1, received vehicle (PBS); Group 2, 3 and 4 received 3, 10 and 30 mg/kg rhuMAb 411 antibody respectively; Group 5 received a combination of 2 mg/kg cisplatin and 10 mg/kg docetaxel. Group 6 with 30 mg/kg rhuMAb 411, all the others same as Group 5. 10 mice of each group were treated 3 times a week for 3 weeks by intraperitoneal injection (i.p.) except that chemotherapy compounds (cisplatin and docetaxel) were given only once a week for 2 weeks by ip.

Tumor volumes were measured twice a week and body weights were measured once per week. Signs of toxicity or distress were noted and animals euthanized if necessary. Any animal exhibiting 20% or greater body weight loss was euthanized for humane purposes.

Figure 33:
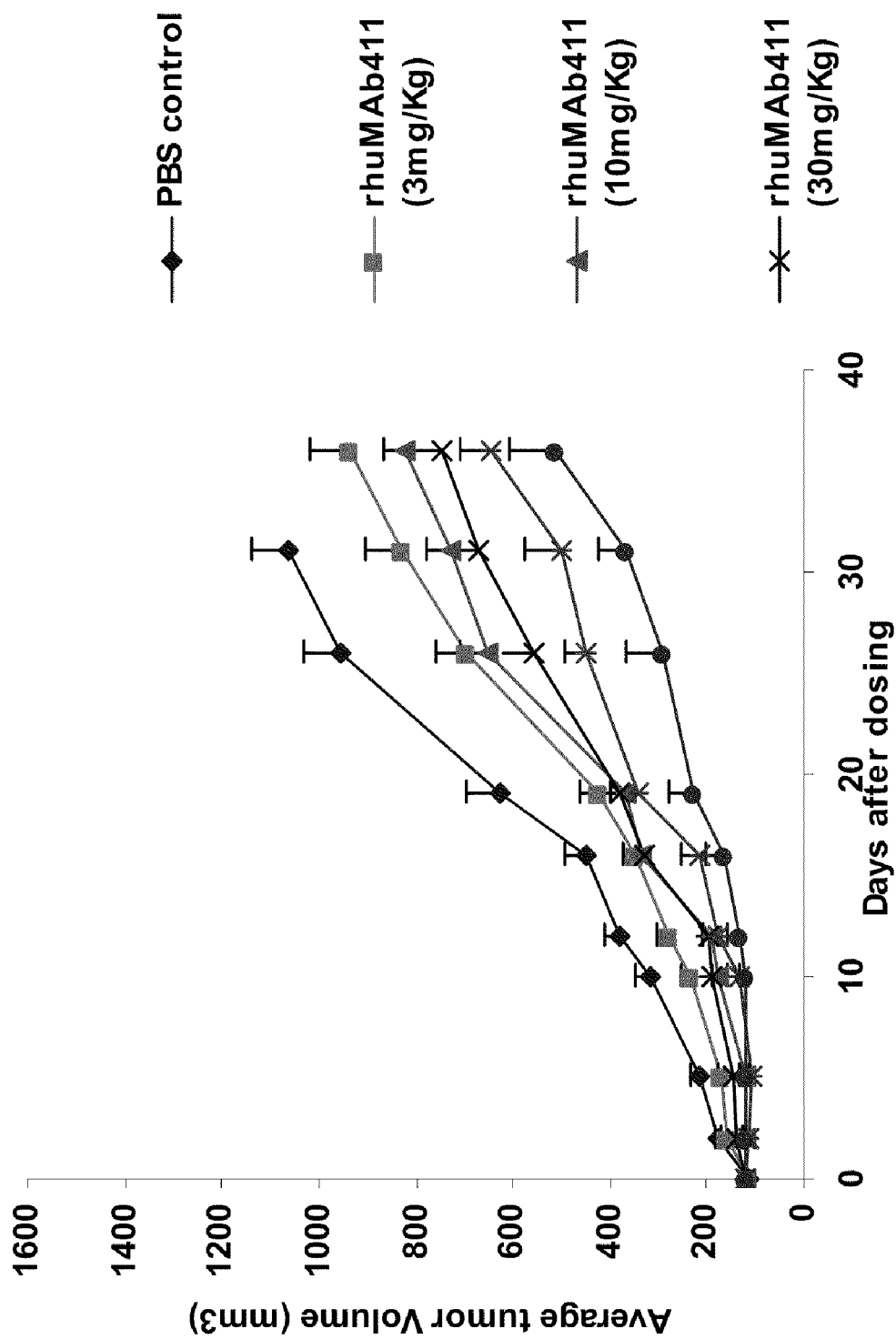
FIG. 33 shows that rhuMAb 411 treatment reduces PC-3 (prostate carcinoma) xenograft tumor growth in SCID mouse. Data represent the mean±SEM values of 10 animals.
Figure 34:
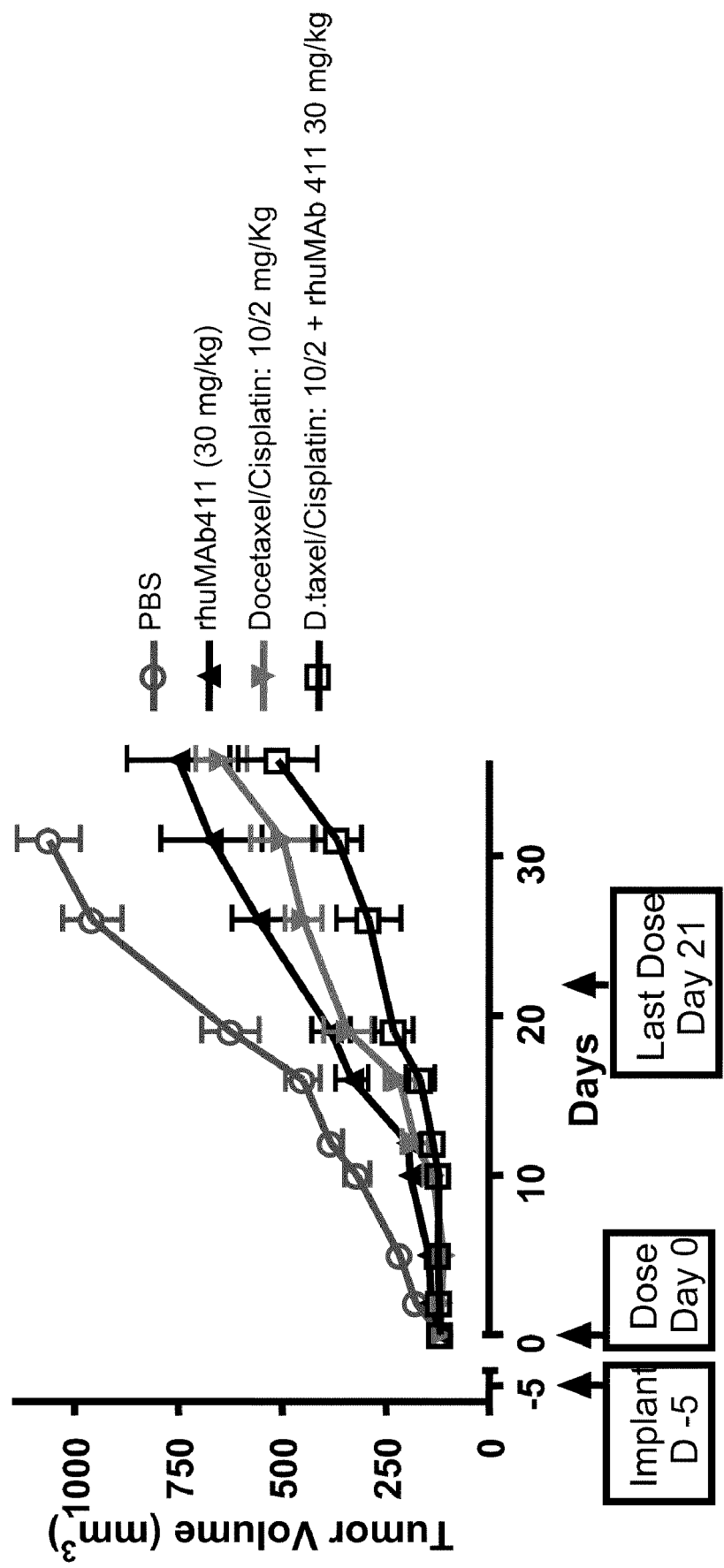
FIG. 34 shows that rhuMAb 411 reduces PC-3 tumor growth with added efficacy using combination therapy.

Results: As shown in the FIG. 33, growth of PC-3 tumors was significantly inhibited in rhuMAb 411-treated animals as compared to vehicle treated animals. In addition, as shown in FIG. 34, rhuMAb 411 plus chemotherapy compounds presented much stronger inhibitory effect when comparing to compounds alone, which suggested the added efficacy using combination therapy. Body weight was maintained during rhuMAb 411 treatment and no apparent toxicity was observed. (Data was not shown.)

Example 10

Efficacy of rhuMAb 411 in DU-145 (Prostate Carcinoma) Xenograft-Bearing NCR Nude Mice The objective of this study was to examine the ability of rhuMAb 411 to inhibit the growth of a DU-145 prostate carcinoma xenograft. The effect of rhuMAb 411 was compared to a vehicle control.

Materials: Cell line: DU-145 a human CD26-positive prostate carcinoma line and was obtained from ATCC.

Animals: Male NCR Nude mice, having a body weight of 18-22 g and being approximately 5-6 weeks of age, were obtained from Taconic (Germantown, N.Y.).

All other materials in this study were the same as described above in Examples 6-10.

Methods: 30 animals were implanted subcutaneously on right flank with $3 \times 10^6$ DU145 cells in 100 µl of HBSS and matrigel (HBSS:matrigel=1:1). When tumor size reached 100 mm$^3$, mice were grouped and administered 100 µl i.p. of solutions as follows:

Group 1, received vehicle (PBS); Group 2 received 30 mg/kg rhuMAb 411 antibody. 10 mice of each group were treated twice a week for 3 weeks by intraperitoneal injection (i.p.).

Tumor volumes were measured twice a week and body weights were measured once per week. Signs of toxicity or distress were noted and animals euthanized if necessary. Any animal exhibiting 20% or greater body weight loss was euthanized for humane purposes.

Figure 35:
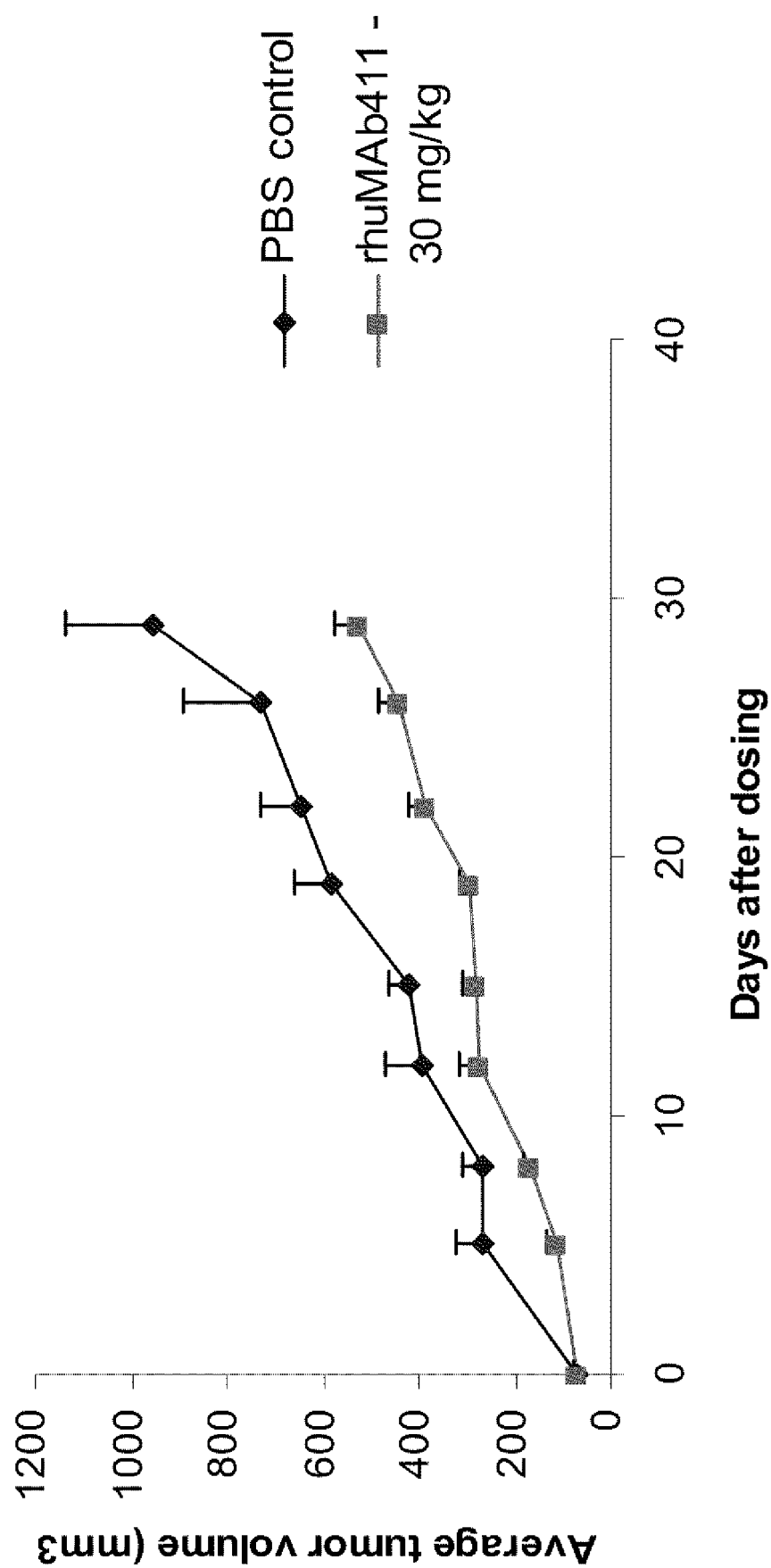
FIG. 35 shows that rhuMAb 411 treatment delays DU-145 (prostate carcinoma) tumor growth in mouse xenograft model. Data represent the mean±SEM values of 10 animals.

Results: As shown in the FIG. 35, growth of DU-145 tumors was significantly delayed in rhuMAb 411-treated animals as compared to vehicle treated animals. Body weight was maintained during rhuMAb 411 treatment and no apparent toxicity was observed. (Data not shown.)

Example 11

Efficacy of rhuMAb 411 in H226 Lung Carcinoma Metastasis Model

The objective of this study was to examine the ability of rhuMAb 411 to inhibit the metastasis induced by H226, a lung carcinoma cell line. The effect of rhuMAb 411 was compared to vehicle control.

Materials: Cell line: H226, a human CD26-positive lung carcinoma line and was obtained from ATCC.

Animals: Female NCR Nude mice, having a body weight of 18-22 g and being approximately 5-6 weeks of age, were obtained from Taconic (Germantown, N.Y.).

All other materials in this study were the same as described above in Examples 6-10.

Methods: Sixteen animals were in injected with $1 \times 10^4$ H226 cells via the tail vein and then divided into 2 groups, with 8 mice per group. Group 1, received 100 μl vehicle (PBS); Group 2 received same volume of 30 mg/kg rhuMAb 411 antibody. Both groups were treated twice a week for 3 weeks by ip injection. 4 weeks after the start of dosing, animals were euthanized and the lungs were taken out. The total number of metastasis in both lungs of each mouse was counted.

Figure 36:
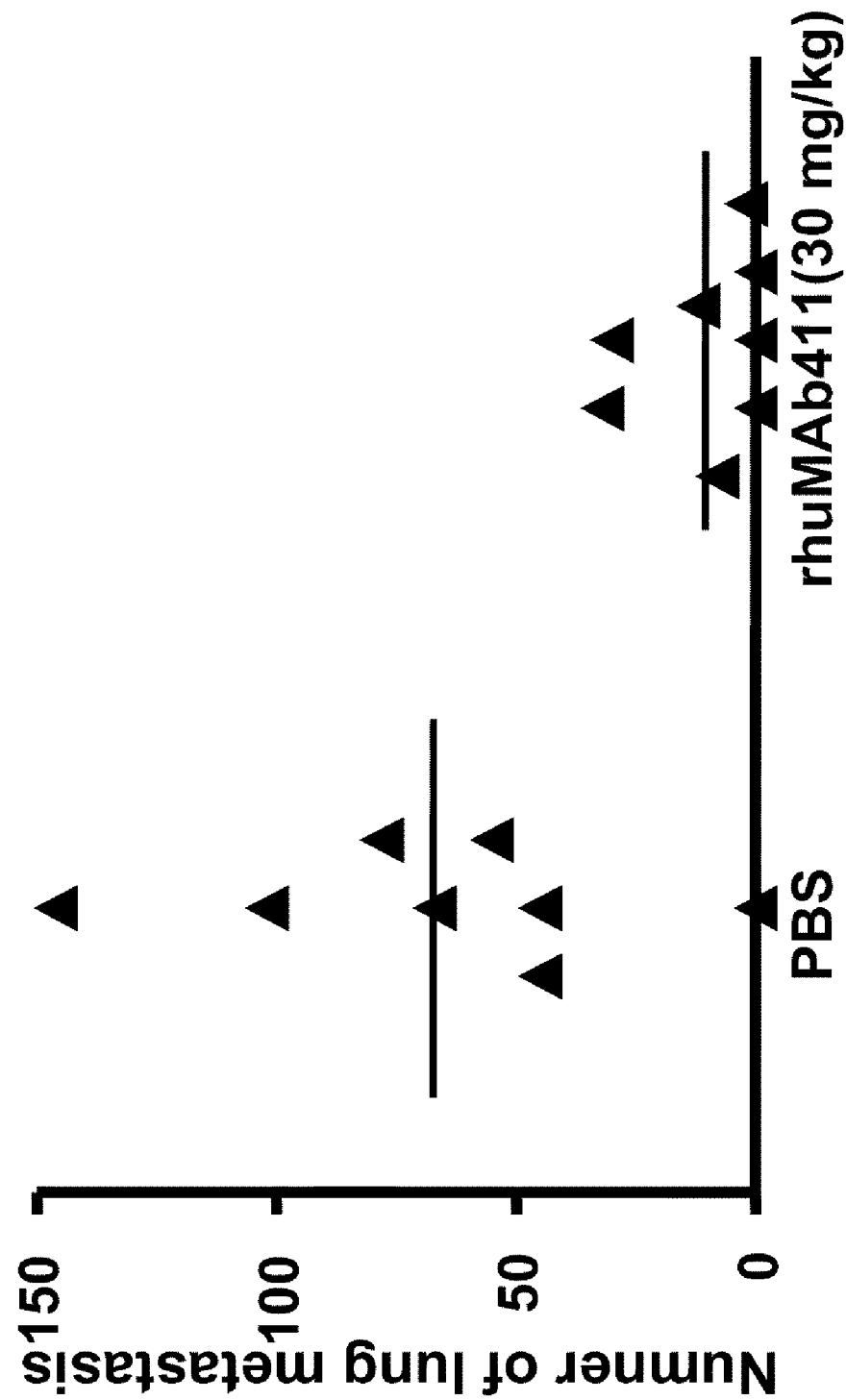
FIG. 36 shows that rhuMAb 411 treatment significantly attenuates H226 (lung carcinoma) induced lung metastasis in NCR nude mice. Line in each group represents the mean value.

Results: As shown in the FIG. 36, dosing with rhuMAb 411 resulted in much lower metastasis occurrence as compared to vehicle control. Mean value was 67.25 in PBS group vs. 10.5 in rhuMAb 411 treatment group. Body weight was maintained during rhuMAb 411 treatment and no apparent toxicity was observed. (Data not shown.)

Example 11

Binding Affinity of rhuMAb 411

RhuMAb 411 was produced by fermentation in mammalian cell (Chinese hamster ovary) suspension culture with Glutamine Synthetase Expression System (GS System; Lonza Biologics, Slough, UK). The binding affinity of RhuMab 411 to human CD26 (hu-CD26) was determined using a standard Biacore® protocol. The binding affinity of the murine monoclonal antibody 14D10 to human CD26 was also determined. The results of these binding studies are presented in Table 12, below.

TABLE 12

| Antibody | $K_{on}$/SE (M$^{-1}$ sec$^{-1}$) | $K_{off}$/SE (sec$^{-1}$) | $K_D$ (M) |
|---|---|---|---|
| 14D10 | 5.09E+05/1.19E+04 | 8.29E-04/3.40E-06 | 1.63e$^{-9}$ |
| rhuMAb411 | 2.72E+05/1.11E+03 | 6.63E-05/1.91E-07 | 2.44e$^{-10}$ |

In a whole cell binding assay, rhuMAb 411 was found to bind to endogenous CD26 in the membrane of Karpas-299 and soluble human CD26 with similar affinity. (Data not shown.)

Example 12

Expression of CD26 in Cancer Cell Lines

The level and percentage of CD26 cell surface expression was measured in a variety of cancer cell lines by flow cytometry. The cancer cell lines tested in this study are listed below in Table 13.

TABLE 13

| name | tumor source | vendor | cat# |
|---|---|---|---|
| K562 | Leukemia cell | ATCC | CLL-243 |
| MDA-MD-231 | Breaset cancer cell | ATCC | HTB-26 |
| HT-29 | Colorectal cell line | ATCC | HTB-38 |
| DU145 | Prostate cell | ATCC | HTB-81 |
| PC-3 | Prostate cell | ATCC | CRL-1435 |
| C3A | liver cancer | ATCC | CRL-10741 |
| Caki1 | kidney cancer cell | ATCC | HTB-46 |
| Caki2 | kidney cancer cell | ATCC | HTB-47 |
| 786O | kidney cancer cell | ATCC | CRL-1932 |
| Karpas 299 | T-cell lymphoma | DSMZ | ACC31 |
| H226 | lung cancer | ATCC | CRL-5826 |
| J82 | blader cell line | ATCC | HTB-1 |

Materials and methods: RhuMAb 411 was conjugated with Alex-488 using a kit provided by Invitrogen (Carlsbad, Calif.). Suspension cells were used as is, while adherent cell lines were dissociated with enzyme-free reagent. All cells were 90-100% confluent. Cells were washed with phosphate-buffered saline (PBS) with 10% bovine serum albumin (BSA) by centrifugation (1200 rpm for 5 min). Cells (100,000) were resuspended in 40 μl of PBS/BSA, 4 nM rhuMAb411-Alexa-488 in replicates. For negative control, rhuMAb411-Alexa-488 was replaced with human IgG1. Cells were incubated for 1-2 hr at room temperature with mild agitation. 200l of PBS/BSA was added to dilute the cells to 500,000/ml. Cells in 96 well plates were then analyzed with Guava EasyCyte™ flow cytometer (Guava Technologies, Hayward, Calif.). Data analysis was performed with Guava Express™ Plus software.

Figure 37:
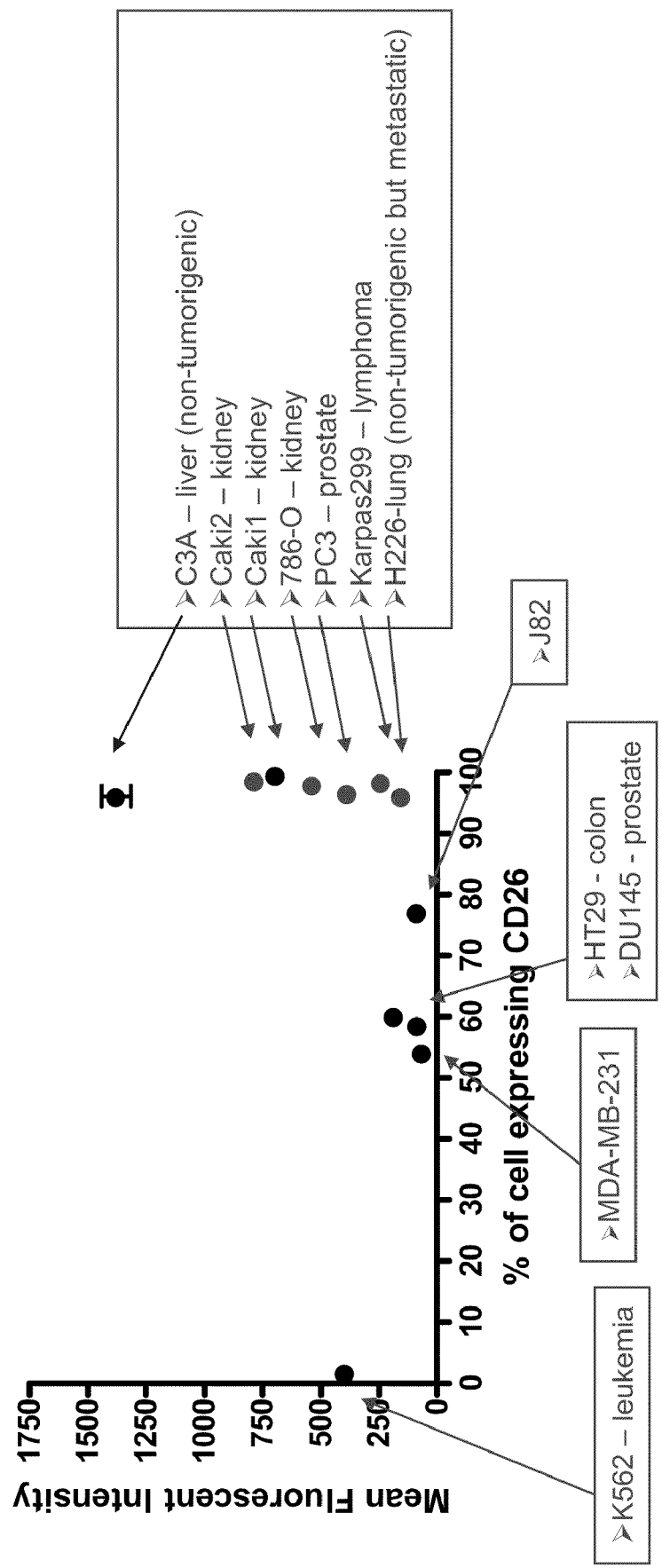
FIG. 37 shows the level and percentage of CD26 cell surface expression in various cancer cells lines.

Results: The results of the flow analysis of the Alexa-488 conjugated rhuMAb 411 are shown in FIG. 37. Significant levels and percentages of CD26 cell surface expression were evident in several cancer cell types, especially the kidney, prostate, lung, and Karpas 299 cancer cell lines.

Example 13

An Additional Exemplary Method for Production and Purification of a rhuMAb 411

A non-limiting example of the production of the recombinant antibody rhuMAb 411 by fermentation in mammalian cell (Chinese hamster ovary) suspension culture with a Glutamine Synthetase (GS) Expression Systems created at Lonza Biologics, Inc., as well as of its subsequent purification, is provided below. The antibody is an IgG1 kappa with a molecular weight of 144672 daltons.

Sequences: The polypeptide sequence of the heavy chain of the rhuMAb 411 is as follows:

(SEQ ID NO: 219)
EVQLVESGAGVKQPGGTLRLTCTASGFSLTTYGVHWVRQAPGKGLEWV

GVIWGDGRTDYDAAFMSRVTISKDTSKSTVYLQMNSLRAEDTAVYYCMRN

RHDWFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.

The polypeptide sequence of the light chain of the rhuMAb 411 is as follows:

(SEQ ID NO: 220)
DILLTQSPSSLSATPGERATITCRASQGIRNNLNWYQQKPGQAPRLLIYY

SSNLQSGVPSRFSGSGSGTDFTLTISRLQPEDVAAYYCQQSIKLPFTFGS

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Figure 38:
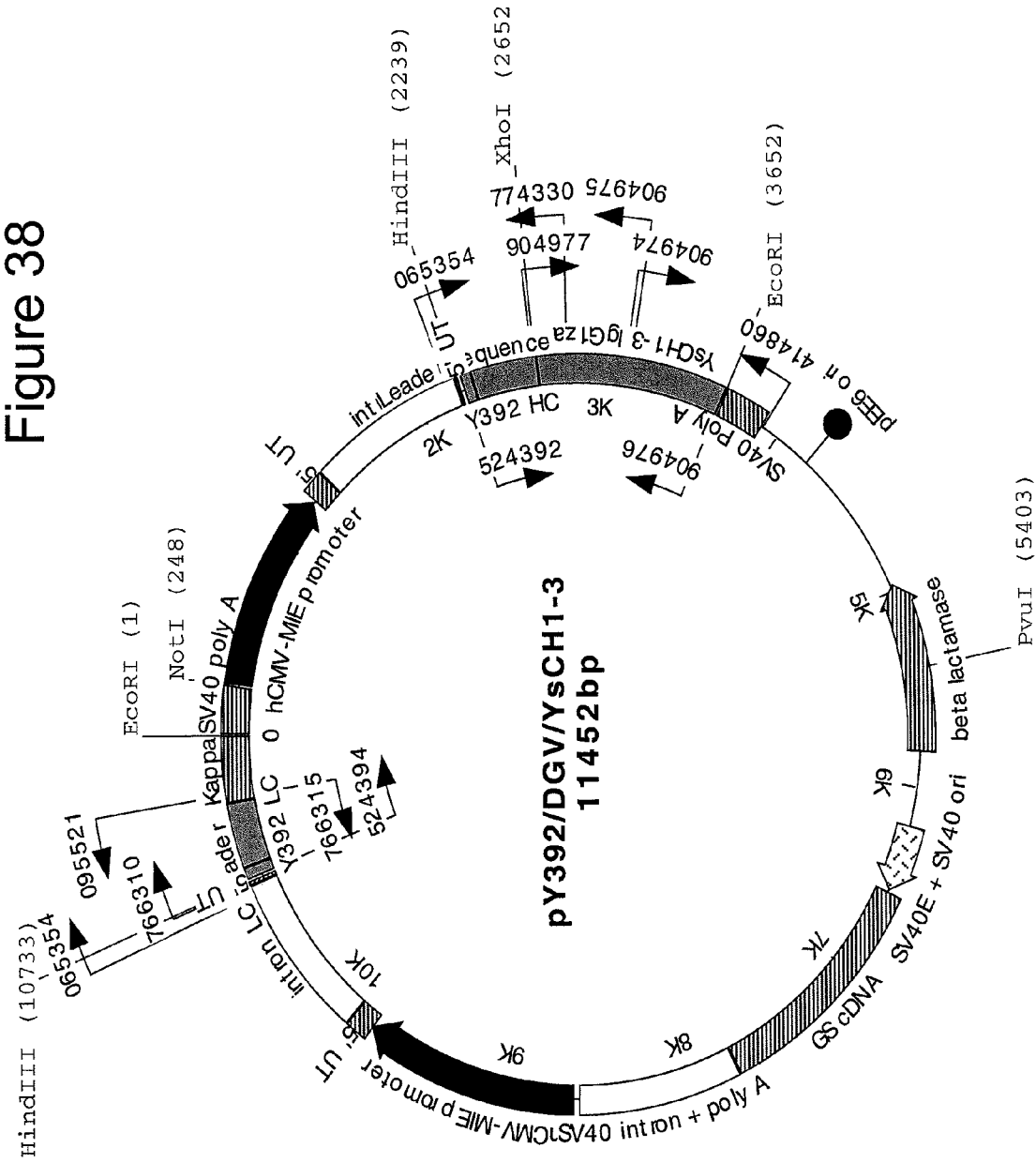
FIG. 38 shows the double-gene vector clone pY392/DGV/YsCH1-3.

Construction of vector: The heavy chain variable region of rhuMAb 411 was combined with a cDNA sequence coding for IgG1za constant region to produce the heavy chain single-gene vector (SGV). The light chain variable region was cloned into Lonza's proprietary vector pConKappa to form the light chain single-gene vector. A double-gene vector was constructed by ligating the complete expression cassette from the heavy chain vector into the light chain vector to generate a single vector expressing both the complete heavy and light chains of rhuMAb 411. The double-gene vector (DGV) was prepared in bulk and linearized with restriction enzyme Pvu I for transfection into CHO cells. The cloned fragments of the heavy chain and light chain genes within the vector were sequenced to verify the construct and were found to match the expected sequences. The double-gene vector was tested for antibody expression in a transient transfection system using CHO cells, and was shown to express correctly folded and secreted antibody. A double-gene vector clone was identified for further use and was renamed pY392/DGV/YsCH1-3 (FIG. 38).

Construction and selection of GS-CHO cell lines expressing the IgG1/kappa antibody rhuMAb 411: GS-CHO, a CHOK1SV cell line of Lonza Biologics, Inc. (Slough, UK), was used to produce the antibody rhuMAb 411. A GS-CHO cell line transfected with a double gene vector, containing the heavy and light chain genes encoding the IgG1 antibody rhuMAb 411, was constructed.

CHOK1SV cells were transfected with the double gene vector using electroporation, and plated out in multiple 96-well plates. Four of these transfections were performed in the protein containing medium CM25/10% dialysed fetal calf serum (dFCS) (Lonza Biologics, Inc.). The remaining two transfections were performed using a protein free transfection protocol, in the chemically defined, animal component free (CDACF) medium CD-CHO. The day after transfection, the selective agent L-methionine sulphoximine (MSX) was added to each well of the 96-well plates to give a final concentration of 50 µM.

Supernatants from the resultant transfectants were screened for assembled antibody using a semi-quantitative ELISA method. All screened transfectants produced detectable levels of antibody. From these data, some of the transfectants (derived from the protein-containing and protein-free transfections) were selected for further evaluation based on a ranking of their relative antibody concentrations and a visual assessment of growth. A second screening was performed based on productivity data. Twenty eight protein-containing transfectants were successfully adapted to grow in the protein-free medium. The four protein-free transfectants selected did not require any adaptation.

After review of the growth and productivity data from the fed batch shake-flask cultures, cell lines were selected using the following selection criteria: high harvest antibody concentration, a high specific production rate, and acceptable growth characteristics. Product quality of purified antibody was analyzed by SDS-PAGE and IEF.

The integrity of the gene sequences encoding the rhuMAb 411 antibody in the selected cell line (referred to herein as "rhuMAb411M") was verified by comparing them with the gene sequences of the DNA vector with which the cell line was constructed. Total RNA was isolated from cell line rhuMAb411M and used as a template to synthesize cDNA. The sequences coding for the light chain (LC) and heavy chain (HC) were specifically amplified by the PCR method using primers annealing to the 5'-untranslated region (UTR) and 3'-UTR of chain-coding sequences. The resultant DNA products were sequenced using a set of primers chosen to permit the entire cDNA segments of both LC and HC PCR products to be sequenced in both forward and reverse directions. The transcripts encoding for the LC of the rhuMAb 411 antibody present in the cell line rhuMAb411M are identical to the sequences within the rhuMAb 411-encoding vector (pY392/DGV/YsCH1-3) used to generate the rhuMAb411M cell line. For the HC, the major RNA species detected encoded an identical HC sequence as present in the rhuMAb 411-encoding vector (pY392/DGV/YsCH1-3).

Method of production of rhuMAb 411: RhuMAb 411 is produced from the master cell bank in GS-CHO cells. Bioreactors are inoculated at a viable cell concentration using well-defined culture media and the fermentation is maintained under stable and controlled conditions. Harvests are fed into a continuous stacked disc centrifuge and the filtrate is then collected into bioprocess containers (BPCs) and stored at 4° C. prior to purification.

The fermentation and isolation process comprises the following, in the order listed: thawing of ampule; inoculation of shake flask; inoculate Wave Bioreactor®; inoculation of air-lift fermenter; fermentation; fermentation harvest; disk stack centrifugation (Westfalia SA1); post centrifuge filtration (2-stage lenticular filtration); 0.22 micrometer filtration; and purification.

Purification of rhuMAb 411: The antibody purification process comprises the following, in the order listed: protein A-affinity chromatography; viral inactivation (low pH (pH 3.7+/−0.1) hold); hydrophobic interaction chromatography; anion-exchange chromatography, virus reduction filtration (Pall DV20); concentration and diafiltration; filtration (0.2 micron); and filling into containers for storage (−20° C.).

Example 14

An Additional Exemplary Formulation of rhuMAb 411

An exemplary formulation of rhuMAb is provided in Table 14, below. The drug product can be provided in a a liquid parenteral dosage form (10 mg/mL±1.0 mg/mL) that can easily be administered to patients.

TABLE 14

| Ingredient | Quantity per mL |
| --- | --- |
| rhuMAb 411 | 10 mg |
| Sodium citrate, USP | 139 mg |
| Citric acid, anhydrous, USP | 5.38 mg |
| Sucrose, granular, USP | 600 mg |
| NaOH or HCl | as needed for pH |
| Water for injection (WFI) | q.s. to 1 mL |

What is claimed is:

1. An isolated polynucleotide comprising a nucleic acid sequence selected from the group consisting of SEQ ID NOS: 1-14.

2. An isolated host cell comprising the polynucleotide of claim 1.

* * * * *